(12) United States Patent
Bower et al.

(10) Patent No.: US 8,710,224 B2
(45) Date of Patent: *Apr. 29, 2014

(54) HETEROCYCLIC COMPOUNDS AS CCR2B ANTAGONISTS

(71) Applicant: AstraZeneca AB, Sodertalje (SE)

(72) Inventors: Justin Fairfield Bower, Cheshire (GB); Jeffrey Philip Poyser, Cheshire (GB); Paul Turner, Cheshire (GB); David Waterson, Cheshire (GB); Jon James Gordon Winter, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/025,939

(22) Filed: Sep. 13, 2013

(65) Prior Publication Data

US 2014/0038978 A1 Feb. 6, 2014

Related U.S. Application Data

(60) Continuation of application No. 13/490,765, filed on Jun. 7, 2012, now abandoned, which is a continuation of application No. 13/018,783, filed on Feb. 1, 2011, now abandoned, which is a division of application No. 11/793,606, filed as application No. PCT/GB2005/004895 on Dec. 19, 2005, now Pat. No. 7,906,645.

(30) Foreign Application Priority Data

Dec. 24, 2004 (GB) .................................. 0428327.1
Oct. 6, 2005 (GB) .................................. 0520325.2

(51) Int. Cl.
*C07D 241/02* (2006.01)
*A61K 31/495* (2006.01)

(52) U.S. Cl.
USPC ..................................... 544/357; 514/252.11

(58) Field of Classification Search
USPC ..................................... 544/357; 514/252.11
See application file for complete search history.

(56) References Cited

U.S. PATENT DOCUMENTS

| | | |
|---|---|---|
| 5,442,064 A | 8/1995 | Pieper et al. |
| 6,492,368 B1 | 12/2002 | Dorsch et al. |
| 6,506,751 B1 | 1/2003 | Justus et al. |
| 7,906,645 B2 | 3/2011 | Bower |
| 2004/0077655 A1 | 4/2004 | Dartois et al. |
| 2004/0082589 A1 | 4/2004 | Farina et al. |
| 2004/0147502 A1 | 7/2004 | Bisacchi et al. |
| 2006/0063767 A1 | 3/2006 | Javaid et al. |
| 2007/0179126 A1 | 8/2007 | Casellas et al. |
| 2008/0287453 A1 | 11/2008 | Bower |
| 2010/0152197 A1 | 6/2010 | Cumming |
| 2011/0136820 A1 | 6/2011 | Bower |
| 2012/0264762 A1 | 10/2012 | Bower |

FOREIGN PATENT DOCUMENTS

| | | |
|---|---|---|
| EP | 0264865 | 4/1988 |
| EP | 0519449 | 12/1992 |
| EP | 0592949 | 4/1994 |
| EP | 0563345 | 7/2002 |
| FR | 2872813 | 1/2007 |
| JP | 53031669 | 3/1978 |
| WO | 9405628 | 3/1994 |
| WO | 9916751 | 4/1994 |
| WO | 9715576 | 5/1997 |
| WO | 0125200 | 4/2001 |
| WO | 02079151 | 10/2002 |
| WO | 03072197 | 9/2003 |
| WO | 2004041777 | 5/2004 |
| WO | 2004050024 | 6/2004 |
| WO | 2004094381 | 11/2004 |
| WO | 2006016039 | 2/2006 |
| WO | 2007071952 | 6/2007 |
| WO | 2010071567 | 6/2010 |

OTHER PUBLICATIONS

CAPLUS abstract of Bisacchi et al., PG Pub 2004/0147502; Jul. 2004.
Shiozawa et al., Chemical & Pharmaceutical Bulletin, vol. 32(2), pp. 553-563, 1984.
Nagasawa et al., Journal of Organic Chemistry, vol. 37(3), pp. 516-519, 1972.
Registry 851787-98-9, "1-Piperidinecarboxamide, 4-(4-morpholinylcarbonyl)-N-phenyl", Jun. 7, 2005.
Registry 332423-87-7, 1-Pyrrolidinecarboxamide, 2-[(4-ethyl-1-piperazinyl)carbonyl]-N-(2-fluorophenyl) Apr. 25, 2001.
English abstract of EP 0264865, Apr. 27, 1988.
English abstract of JP 53-031669, Mar. 25, 1978.
McDermott et al., Synlett, vol. 6, pp. 875-879, 2008.
Non-final OA issued for U.S. Appl. No. 12/158,248 on Apr. 29, 2010.
International Search Report and Written Opinion issued for corresponding PCT/GB2005/004895 on Apr. 18, 2006.
International Preliminary Report on Patentability issued for corresponding PCT/GB2005/004895 on Jul. 5, 2007.

*Primary Examiner* — Robert Havlin
(74) *Attorney, Agent, or Firm* — Rebecca Barrett

(57) ABSTRACT

Compounds of formula (I)

Q-L-W—C(=X)—Z—P wherein
Q is an amine of the formula —N($R^1$)($R^2$);
L is an alkyl or heterocyclyl-alkyl linker;
W is a 6- or 7-membered aliphatic ring comprising ring atoms $Y^1$ and $Y^2$ which are linked to groups L and C(X) respectively and $Y^1$ and $Y^2$ are independently selected from N and C;
X is O, N, N—CN or S;
Z is $NR^3$;
P is an optionally substituted monocyclic or bicyclic aryl or heteroaryl group;
and pharmaceutically acceptable salts or solvates thereof, are useful in the treatment of C—C chemokine mediated conditions.

8 Claims, No Drawings

HETEROCYCLIC COMPOUNDS AS CCR2B ANTAGONISTS

CROSS-REFERENCE TO RELATED APPLICATIONS

This application is a continuation of U.S. application Ser. No. 13/490,765, filed Jun. 7, 2013, which is a continuation of U.S. application Ser. No. 13/018,783, filed Feb. 1, 2011, which is a divisional of U.S. application Ser. No. 11/793,606, filed Jun. 20, 2007, pending, which is a US National Stage under 35 U.S.C §371 of International Application No. PCT/GB2005/004895, filed 19 Dec. 2005, which claims priority under 35 U.S.C. §119(a)-(d) to United Kingdom Application Nos. 0428327.1 filed 24 Dec. 2004 and 0520325.2 filed 6 Oct. 2005.

The present invention relates to pharmaceutical compositions which comprise compounds that act via antagonism of the CCR2b receptor for which MCP-1 is one of the known ligands and so may be used to treat inflammatory disease which is mediated by these receptors. These compounds contain a cyclic aromatic moiety. The invention further relates to novel compounds for use in the compositions, to processes for their preparation, to intermediates useful in their preparation and to their use as therapeutic agents.

Chemokines play an important role in immune and inflammatory responses in various diseases and disorders, including rheumatoid arthritis, chronic obstructive pulmonary disease, atherosclerosis and other autoimmune pathologies such as inflammatory bowel disease, diabetes, asthma and allergic diseases. Chemokines also have a role in angiogenesis and modulation of chemokines may be beneficial in the treatment of cancer. Chemokines are small secreted molecules belonging to a growing superfamily of 8-14 kDa proteins characterised by a conserved four cysteine motif. The chemokine superfamily can be divided into two main groups exhibiting characteristic structural motifs, the Cys-X-Cys (C—X—C) and Cys-Cys (C—C) families. These are distinguished on the basis of a single amino acid insertion between the NH-proximal pair of cysteine residues and sequence similarity.

The C—C chemokines include potent chemoattractants of monocytes and lymphocytes such as monocyte chemoattractant proteins 1-3 (MCP-1, MCP-2 and MCP-3), RANTES (Regulated on activation, Normal T expressed and Secreted), eotaxin and the macrophage inflammatory proteins 1α and 1β (MIP-1α and MIP-1β).

The C—X—C chemokines include several potent chemoattractants and activators of neutrophils such as interleukin-8 (IL-8) and neutrophil-activating peptide 2 (NAP-2).

Studies have demonstrated that the actions of chemokines are mediated by subfamilies of G-protein coupled receptors, among which there are the receptors designated CCR1, CCR2, CCR2A, CCR2B, CCR3, CCR4, CCR5, CCR6, CCR7, CCR8, CCR9, CCR10, CXCR1, CXCR2, CXCR3, CXCR4, CXCR5 and CX3CR1. These receptors represent good targets for drug development since agents which modulate these receptors would be useful in the treatment of disorders and diseases such as those mentioned above.

U.S. Pat. No. 5,712,270 describes a range of thiazole derivatives useful for the treatment of neurological diseases.

WO-03/072197 (Pfizer) discloses bipiperidine derivatives useful as acetyl coenzyme A carboxylase inhibitors for use in the treatment of cardiovascular disorders.

The applicants have found a class of compounds containing a cyclic moiety which has useful antagonism of C—C chemokine receptors and in particular of the CCR2b receptor.

The present invention now provides a compound of formula (I)

$$Q\text{-}L\text{-}W\text{—}C(=X)\text{—}Z\text{—}P \quad (I)$$

wherein

Q is an amine of the formula —N(R$^1$)(R$^2$) wherein R$^1$ and R$^2$ are independently selected from hydrogen (with the proviso that R$^1$ and R$^2$ are not both hydrogen), C$_{1-6}$ alkyl, C$_{3-7}$ cycloalkyl, C$_{2-6}$ alkenyl, C$_{2-6}$ alkynyl, cycloalkyl-alkyl of up to 14 ring and chain atoms, heterocyclyl of up to 7 ring atoms, heterocyclyl-alkyl of up to 14 ring and chain atoms, heterocyclyl-cycloalkyl of up to 14 ring atoms, heterocyclyl-heterocyclyl-alkyl of up to 20 ring and chain atoms, heterocyclyl-aryl-alkyl of up to 20 ring and chain atoms, heterocyclyl-aryl of up to 20 ring atoms; aryl-alkyl of up to 14 ring and chain atoms, aryl-heterocyclyl-alkyl of up to 20 ring and chain atoms, aryl-oxy-alkyl of up to 14 ring and chain atoms, aryl-cycloalkyl of up to 14 ring atoms, aryl-aryl-alkyl of up to 20 ring and chain atoms;

and wherein each chain or ring is independently optionally substituted by up to 3 substituents each independently selected from halogen, hydroxy, C$_{1-6}$ alkyl, C$_{1-4}$ alkoxy optionally substituted by C$_{1-4}$ alkoxy, cyano, C$_{1-4}$alkylsulfonyl, trifluoromethyl, carboxy, C$_{1-4}$ alkoxycarbonyl, C$_{1-2}$ alkyloxycarbonylphenyl, phenyl, NH$_2$, NO$_2$, =O, C$_{1-4}$ alkylcarbonyl, C$_{3-7}$ cycloalkyl-heteroaryl of up to 10 ring atoms, and a nitrogen atom of a heteroaromatic ring may be substituted by an oxide group.

or R$^1$ and R$^2$ taken together with the nitrogen atom of Q represent a 4-7 membered saturated ring comprising an optional further heteroatom selected from O, N, or S and optionally substituted by up to 3 substituents each each independently selected from the substituents listed above;

L is a linker comprising C$_{1-6}$ alkyl, C$_{1-6}$ alkyl —C$_{4-10}$ cycloalkyl, or C$_{4-10}$ cycloalkyl-C$_{1-6}$ alkyl wherein in each case the alkyl and/or cycloalkyl group may further comprise 1, 2, or 3 heteroatoms selected independently from N, O, S, and/or an =O group, or taken together with the nitrogen atom of the amine Q and R$^2$, L represents a heterocyclyl or heterocyclyl —C$_{1-6}$ alkyl group wherein the heterocyclyl group is of up to 10 ring atoms and wherein, in addition to the nitrogen atom of amine Q the heterocyclyl and/or alkyl group may optionally comprise 1 or 2 further heteroatoms selected independently from N, O, S and/or an =O group; and wherein each chain or ring is independently optionally substituted by hydroxy, halogen or C$_{1-4}$ alkyl;

with the proviso that (i) where L is a C$_{5-7}$ cycloalkyl-C$_1$ alkyl group as defined above, then Q is not a saturated heterocyclic ring having two nitrogen heteroatoms and being either unsubstituted or substituted on a ring nitrogen heteroatom by a protecting group, and (ii) where L represents a heterocyclyl —C$_{1-6}$ alkyl group as defined above and the heterocyclyl group does not comprise further heteroatoms, then R$^1$ does not represent a saturated heteroring having a single nitrogen heteroatom and such ring being either unsubstituted or having a protecting group on the nitrogen heteroatom;

W is a 6- or 7-membered aliphatic ring comprising ring atoms Y$^1$ and Y$^2$ and linked by Y$^1$ and Y$^2$ to groups L and C(=X) respectively, Y$^1$ and Y$^2$ are independently selected from N and C, and where Y$^1$ and Y$^2$ are both N or both C then W is optionally substituted on any ring atom by 1, 2 or 3 R$^1$ groups each independently selected or by a C$_2$ bridge between two ring carbon atoms; and where Y$^1$ is C and Y$^2$ is N then Y$^1$ is optionally substituted by hydroxy or halogen;

X is O, N, N—CN or S

Z is $NR^3$ wherein $R^3$ is hydrogen or $C_{1-4}$ alkyl, or when $Y^2$ is N then Z can also be O;

P is a monocyclic or bicyclic $C_{5-10}$ aryl or heteroaryl group of up to 20 ring atoms, each of which is optionally substituted by 1, 2 or 3 substituents independently selected from halogen, $C_{1-4}$ alkyl, $C_{2-4}$ alkenyl, $C_{2-4}$ alkynyl, cyano, trifluoromethyl, trifluoromethoxy, $C_{1-4}$ alkoxy, $C_{1-4}$ thioalkyl, trifluoromethylthio, carboxy $C_{1-4}$ alkyl and $NO_2$;

or P is optionally substituted by phenyl, phenoxy or aralkyloxy of up to 10 carbon atoms each optionally substituted by 1 or 2 of any other substituent listed for P above;

or a pharmaceutically acceptable salt or solvate thereof.

Compounds of formula (I) can be used in the treatment of diseases in which the chemokine receptor belongs to the C—C receptor subfamily, more preferably the target chemokine receptor is the CCR2 receptor.

CCR2 is a receptor for the Monocyte chemoattractant protein-1 (MCP-1). MCP-1 is a member of the chemokine family of pro-inflammatory proteins which mediate leukocyte chemotaxis and activation. MCP-1 is a C—C chemokine which is potent T-cell and monocyte chemoattractant. MCP-1 has been implicated in the pathophysiology of a large number of inflammatory diseases including rheumatoid arthritis, chronic obstructive pulmonary disease, atherosclerosis and inflammatory bowel disease.

MCP-1 acts through the CCR2 receptor. MCP-2, MCP-3 and MCP-4 may also act, at least in part, through this receptor. Therefore in this specification, when reference is made to "inhibition or antagonism of MCP-1" or "MCP-1 mediated effects" this includes inhibition or antagonism of MCP-2 and/or MCP-3 and/or MCP-4 mediated effects when MCP-2 and/or MCP-3 and/or MCP-4 are acting through the CCR2 receptor.

In addition we have found that certain compounds of formula (I) modulate the function of the CCR5 receptor. The CCR5 receptor is expressed on T-lymphocytes, monocytes, macrophages, dendritic cells, microglia and other cell types. These detect and respond to several chemokines, principally "regulated on activation normal T-cell expressed and secreted" (RANTES, CCL5), macrophage inflammatory proteins (MIP) MIP-1α (CCL3) and MIP-1β (CCL4) and monocyte chemoattractant protein-2 (MCP-2, CCL8).

This results in the recruitment of cells of the immune system to sites of disease. In many diseases it is the cells expressing CCR5 which contribute, directly or indirectly, to tissue damage. Consequently, inhibiting the recruitment of these cells is beneficial in a wide range of diseases.

CCR5 is also a co-receptor for HIV-1 and other viruses, allowing these viruses to enter cells. Blocking the receptor with a CCR5 antagonist or inducing receptor internalisation with a CCR5 agonist protects cells from viral infection.

Conveniently in the compounds of formula I each of the substituents is selected independently from the values set out below, or any combination thereof:

Q is an amine of the formula $-N(R^1)(R^2)$ wherein $R^1$ and $R^2$ are independently selected from hydrogen (with the proviso that $R^1$ and $R^2$ are not both hydrogen), $C_{1-4}$ alkyl, $C_{3-6}$ cycloalkyl, $C_{2-4}$ alkenyl or $C_{2-4}$ alkynyl, cycloalkyl-alkyl of up to 10 ring and chain atoms, heterocyclyl of up to 6 ring atoms, heterocyclyl-alkyl of up to 10 ring and chain atoms, heterocyclyl-cycloalkyl of up to 12 ring atoms, heterocyclyl-heterocyclyl-alkyl of up to 14 ring and chain atoms, hetero-cyclyl-aryl-alkyl of up to 14 ring and chain atoms, heterocyclyl-aryl of up to 12 ring atoms; aryl-alkyl of up to 10 ring and chain atoms, aryl-heterocyclyl-alkyl of up to 14 ring and chain atoms, aryl-oxy-alkyl of up to 12 ring and chain atoms, aryl-cycloalkyl of up to 12 ring atoms, aryl-aryl-alkyl of up to 14 ring and chain atoms;

and wherein each chain or ring is independently optionally substituted by up to 3 substituents each independently selected from halogen, hydroxy, $C_{1-4}$ alkyl, $C_{1-4}$ alkoxy (optionally substituted by $C_{1-2}$ alkoxy) cyano, $C_{1-2}$ alkylsulfonyl, trifluoromethyl, carboxy, carboxy-$C_{1-2}$ alkyl, carboxy-benzyl, phenyl, $NH_2$, $NO_2$, carbonyl-$C_{1-2}$ alkyl, $C_{3-6}$ cycloalkyl, heteroaryl of up to 6 ring atoms, and a nitrogen atom of a heteroaromatic ring may be substituted by an oxide group.

or $R^1$ and $R^2$ taken together with Q represent a 5-6 membered saturated ring comprising an optional further heteroatom selected from O, N, or S and optionally substituted by $C_{1-2}$ alkyl, halogen or hydroxy;

L is a linker comprising straight chain $C_{1-4}$ alkyl or $C_{4-8}$ cycloalkylalkyl wherein in each case the alkyl or cycloalkyl group may further comprise a heteroatom selected from N, O or S, and/or a carbonyl group, or taken together with the nitrogen atom of the amine Q and $R^2$, L represents a heterocyclylalkyl group such as a saturated heterocyclyl group of up to 8 ring and chain atoms wherein in addition to the nitrogen atom of amine Q the heterocycle and/or alkyl group may comprise 1 or 2 further heteroatoms selected independently from N, O or S, and/or a carbonyl group; and wherein each chain or ring is independently optionally substituted by hydroxy, halogen or $C_{1-4}$ alkyl;

W is a 6- or 7-membered aliphatic ring comprising ring atoms $Y^1$ and $Y^2$ and linked by $Y^1$ and $Y^2$ to groups L and C(=X) respectively and where W is optionally substituted on any ring atom by 1, 2 or 3 groups independently selected from $C_{1-4}$ alkyl, hydroxy, =O or halogen;

$Y^1$ and $Y^2$ are independently selected from N and C;

X is N, O or S;

Z is $NR^3$ wherein $R^3$ is hydrogen or $C_{1-2}$ alkyl, or when $Y^2$ is N then Z can also be O, P is a monocyclic or bicyclic $C_{5-10}$ aryl or heteroaryl group of up to 10 ring atoms, each of which is optionally substituted by 1, 2 or 3 substituents independently selected from halogen, $C_{1-3}$ alkyl, $C_{2-4}$ alkenyl, $C_{2-4}$ alkynyl, cyano, trifluoromethyl, trifluoromethoxy, phenyl, phenoxy, $C_{1-3}$ alkoxy, $C_{1-3}$ alkylthio, trifluoromethylthio, $C_{1-3}$ alkoxycarbonyl, and $NO_2$;

or P is optionally substituted by phenyl, phenoxy or aralkyloxy of up to 10 carbon atoms each optionally substituted by 1 or 2 of halogen, $C_{1-3}$ alkyl or hydroxy, each independently selected;

or a pharmaceutically acceptable salt or solvate thereof.

More conveniently in the compounds of formula I

Q is a secondary or tertiary amine of the formula $-N(R^1)(R^2)$ wherein $R^1$ and $R^2$ are independently selected from any one of, or combination of, hydrogen, methyl, ethyl, propyl, propenyl, propynyl, isopropyl, cyclopropylmethyl, cyclopropylethyl, butyl, t-butyl, cyclopentylmethyl, cyclopentylethyl, cyclohexyl, cyclohexylmethyl, cyclohexylethyl, benzyl, phenethyl, phenylpropyl, thienylethyl, thienylmethyl, furanylethyl, furanylmethyl, pyrrolidinyl, pyrrolidinylmethyl, pyrrolidinylethyl, pyrrolylethyl, pyrrolylmethyl, pyridylethyl, pyridylmethyl, thiazolylethyl, thiazolylmethyl, benzimidazole, isoxazole, isoxazolylethyl, imidazolylethyl, imidazolylmethyl, pyrazolylethyl, pyrazolylmethyl, indolylmethyl, indolylethyl, indolinylmethyl, piperidinylmethyl, piperazinylmethyl, morpholinyl, morpholinylmethyl, pyridazinyl, pyridazinylmethyl, pyrimidinyl, pyrimidinylmethyl; and wherein each chain or ring is independently optionally substituted by one or two of fluorine, hydroxy, hydroxymethyl, methyl, methoxy, ethyl, ethoxy, propenyl, carboxy, methoxycarbonyl, ethoxycarbonyl, cyano, or methylsulfonyl each selected independently, or $R^1$ and $R^2$ taken together with Q represent piperidine, morpholine or pyrroline;

L is methylene, ethylene or propylene for example methylene, or taken together with the nitrogen atom of the amine Q and with $R^2$, represents a saturated heterocyclylalkyl group of up to 8 ring and chain atoms wherein in addition to the nitrogen atom of amine Q the heterocycle may comprise 1 or 2 further heteroatoms selected independently from N, O or S, such as N or O, for example N, and the alkyl group may comprise a =O group; such as for example 3-piperidinylmethylene, 3-morpholinylmethylene, 3-piperazinylcarbonyl or 3-piperazinylmethylene, in particular 3-piperazinylcarbonyl; and wherein each chain or ring is independently optionally substituted by hydroxy, halogen or $C_{1-4}$ alkyl;

W is piperidine, piperazine or 1,4-diazepane, such as piperazine, optionally substituted on any ring atom by 1, 2 or 3 groups independently selected from $C_{1-4}$ alkyl, hydroxy, =O or halogen, such as unsubstituted or monosubstituted by hydroxy, =O or halogen;

X is O

Z is $NR^3$ wherein $R^3$ is hydrogen or methyl, or when $Y^2$ is N then Z can also be O;

P is phenyl or naphthyl, or an up to 10 ring membered heteroaryl group comprising 1 or 2 heteroatoms independently selected from N, O or S such as thiophene, isoxazole, benzisoxazole, thiazole, isothiazole, thiadiazole, pyridine, pyrazole, benzthiazole; all of which are optionally substituted by 1, 2 or 3 substituents each independently selected from chlorine, fluorine, bromine, methyl, ethyl, cyano, trifluoromethyl, methoxy, trifluoromethoxy, phenyl, phenoxy, benzoxy, thiomethyl, thioethyl, trifluoromethylthio, methoxycarbonyl, ethoxycarbonyl, and $NO_2$.

Compounds of the invention having 2R stereochemistry are a particular aspect of this invention.

As used herein, the term "heteroatom" refers to non-carbon atoms such as oxygen, nitrogen or sulphur atoms.

The term 'alkyl' when used either alone or as a suffix includes straight chain and branched structures. These groups may contain up to 10, conveniently up to 6 and more conveniently up to 4 carbon atoms. Similarly the terms "alkenyl" and "alkynyl" refer to unsaturated straight or branched structures containing for example from 2 to 10, preferably from 2 to 6, such as 2-4 carbon atoms. Cyclic moieties such as cycloalkyl, cycloalkenyl and cycloalkynyl are similar in nature but have at least 3 carbon atoms. They may be bridged. Terms such as "alkoxy" and "alkanoyl" comprise alkyl moieties as defined above, attached to the appropriate functionality.

The term "halo" includes fluoro, chloro, bromo and iodo. References to aryl groups include aromatic carbocylic groups such as phenyl and naphthyl.

The term "heterocyclyl" includes aromatic or non-aromatic rings, or partially unsaturated ring systems, for example containing from 4-20 atoms, such as up to 16, up to 14, up to 12 or up to 10 ring atoms, or containing 5-10 ring atoms such as 5-7 ring atoms, at least one of which is a heteroatom such as oxygen, sulphur or nitrogen. Rings may be mono-, bi- or tricyclic. They may also contain bridges, in particular alkyl bridges of up to 4, up to 3 or up to 2 carbon atoms. Examples of such groups include furyl, thienyl, pyrrolyl, pyrrolidinyl, imidazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzthiazolyl, benzoxazolyl, benzothienyl, benzofuranyl, tetrahydrofuryl, chromanyl, piperidinyl, 1,2,3,4-tetrahydroquinolinyl, 1,2,3,4-tetrahydroisoquinolinyl, piperazinyl, quinoxalinyl, quinazolinyl, cinnolinyl, indolyl, indolinyl, benzimidazolyl, indazolyl, oxazolyl, benzoxazolyl, isoxazolyl, morpholinyl, dioxolane, benzodioxolane, 4H-1,4-benzoxazinyl, 4H-1,4-benzothiazinyl, 1,2,3-triazolyl, 1,2,4-triazolyl, oxadiazolyl, furazanyl, thiadiazolyl, dibenzofuranyl, dibenzothienyl oxiranyl, oxetanyl, azetidinyl, oxepanyl, oxazepanyl, tetrahydro-1,4-thiazinyl, 1,1-dioxotetrahydro-1,4-thiazinyl, homopiperidinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, aralkyl, cycloalkyl, cycloalkenyl or cycloalkynyl.

The compounds of Formula I may be prepared as follows: Route a by Reaction of a Compound of Formula II with a Compound of Formula III:

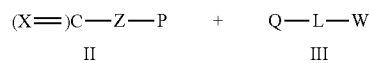

Route A1

Compounds of Formula I wherein X is O and Z is $NR^4$, can be suitably prepared by reacting an isocyanate compound of Formula II, wherein X is O and Z is $NR^4$ and a compound of formula III where Q, L and W are defined in relation to Formula I. The reaction is suitably effected in an organic solvent such as chloroform at ambient temperature.

Route A2

Compounds of Formula I wherein X is S and Z is $NR^4$, can be suitably prepared by reacting an isothiocyanate compound of Formula II, wherein X is S and Z is $NR^4$ and a compound of formula III where Q, L and W are defined in relation to Formula I. The reaction is suitably effected in an organic solvent such as chloroform in the presence of a base such as sodium(trimethylsilyl)amide at ambient temperature.

Route A3

Compounds of Formula I wherein X is N—CN and Z is $NR^4$, can be suitably prepared by reacting an isothiocyanate compound of Formula II, wherein X is S and Z is $NR^4$ and a compound of Formula III where Q, L and W are defined in relation to formula I in the presence of sodium hydrogen cyanamide. The reaction is suitably effected in an organic solvent such as N,N-dimethylformamide in the presence of 1-(3-dimethylaminopropyl)-3-ethylcarbodiimide hydrochloride at ambient temperature.

Route A4

Compounds of Formula I wherein X is O and Z is O, can be suitably prepared by reacting a compound of Formula II, wherein X is O and a leaving group such as halogen is attached to the carbon atom of C(=X), and a compound of Formula III where Q, L and W are defined in relation to formula I. The reaction is suitably effected in an organic solvent such as dichloromethane in the presence of a base such as N,N-diisopropylethylamine at ambient temperature.

A compound of Formula II in this instance can be prepared from suitably chosen commercially available starting materials wherein X and Z are defined in relation to Formula I.

Route A5

Compounds of Formula I wherein X is O and Z is NR⁴, can be suitably prepared by reacting a compound of Formula II, wherein X is O and Z is NR⁴ and a compound of formula III where Q, L and W are defined in relation to Formula I and W comprises a carbonyl group. The reaction is suitably effected in an organic solvent system of dichloromethane and N,N-dimethlformamide in the presence of a base such as N,N-diisopropylethylamine at ambient temperature.

Route A6

Compounds of Formula I wherein Y² is C, X is O and Z is NR⁴, can be suitably prepared by reacting an isocyanate compound of Formula II, wherein X is O and Z is NR⁴ and a compound of Formula III where Q, L and W are defined in relation to formula I. The reaction is suitably effected in an organic solvent system of dichloromethane and N,N-dimethlformamide in the presence of a base such as N,N-diisopropylethylamine at ambient temperature.

Route A7

Compounds of Formula I wherein X is O, Z is NR⁴ and W is a 7-membered ring can be suitably prepared by reacting an isocyanate compound of Formula II, wherein X is O and Z is NR⁴ and a compound of Formula III where Q, L and W are defined in relation to formula I. The reaction is suitably effected in an organic solvent system of dichloromethane and N,N-dimethylformamide in the presence of a base such as N,N-diisopropylethylamine at ambient temperature.

Route A8

Compounds of Formula I wherein X is O, and Z is NR⁴, can be suitably prepared by reacting an isocyanate compound of Formula II, wherein X is O and Z is NR⁴ and a compound of formula III where Q, L and W are defined in relation to Formula I and W comprises a methyl substituent. The reaction is suitably effected in an organic solvent system of dichloromethane and N,N-dimethlformamide in the presence of a base such as N,N-diisopropylethylamine at ambient temperature.

Route A9

Compounds of Formula I wherein X is O, and Z is NR⁴, can be suitably prepared by reacting an isocyanate compound of Formula II, wherein X is O and Z is NR⁴ and a compound of formula III where Q and W are defined in relation to Formula I and taken together with the nitrogen atom of the amine Q and R², L represents a heterocyclyl or heterocyclyl —C₁₋₆ alkyl group wherein the heterocyclyl group is of up to 10 ring atoms and in addition to the nitrogen atom of amine Q comprises a further nitrogen heteroatom. The reaction is suitably effected in an organic solvent system of dichloromethane in the presence of an organic base such as triethylamine at ambient temperature. Deprotection was then effected using an appropriate mixture of trifluoroacetic acid and dichloromethane at ambient temperature.

Route B for Compounds of Formula I Wherein X is N, by Reaction of a Compound of Formula I Wherein X is S:

Route B1

Compounds of Formula I wherein X is NH, and Z is NR⁴, can be suitably prepared by reacting a compound of Formula I, wherein X is S and Z is NR⁴. The reaction is suitably effected in an organic solvent system of dichloromethane and tetrahydrofuran in the presence of ammonia and a promoter such as silver triflate at −30° C. to ambient temperature.

Route C by Reaction of a Compound of Formula IV with a Compound of Formula V

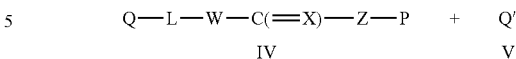

wherein L, W, C(=X), Z and P are as defined in relation to Formula I and Q is also as defined in relation to Formula I but comprises a free nitrogen group for reaction with Q' being a substituent part of Q. Q' conveniently comprises a leaving group such as halogen for reaction with the free nitrogen in Q to yield Q. Alternatively Q' comprises an electrophilic carbonyl group for reaction with the free nitrogen in Q to yield Q. Such reactions are detailed in Route C1 below.

Route C1

Compounds of Formula I wherein L is a 5- or 6-membered heterocycle, can be suitably prepared by reacting a compound of Formula IV, wherein L, W, C(=X), Z and P are defined in relation to Formula I with Q' as defined above. The reaction is suitably effected in an organic solvent such as acetone and an alkali metal carbonate base, such as potassium carbonate at elevated temperatures. As an alternative to this method, reactions can also be suitably effected in an organic solvent such as acetonitrile at ambient temperature. Reaction can also be suitably effected in an organic solvent such as dichloromethane in the presence of a base such as N,N-diisopropylethylamine and an appropriately selected reductant such as sodium triacetoxyborohydride. Additionally, compounds can be formed through reaction with a suitably chosen acid or derivative thereof, and subsequently reduced using an appropriate reductant such as borane in an organic solvent such as tetrahydrofuran.

Route C2

Compounds of Formula I wherein L is a 6-membered heteroring, can be suitably prepared by reacting a compound of Formula IV, wherein L, W, C(=X), Z and P are defined in relation to Formula I with Q' as defined above. The reaction is suitably effected in an organic solvent such as N,N-dimethylformamide and an alkali metal carbonate base, such as potassium carbonate at ambient temperature.

Route C3

Compounds of Formula I wherein L is a 5- or 6-membered heteroring, can be suitably prepared by reacting a compound of Formula IV, wherein L, W, C(=X), Z and P are defined in relation to Formula I with Q' as defined above. The reaction is suitably effected in an organic solvent such as N,N-dimethylformamide and an alkali metal carbonate base, such as potassium carbonate at ambient temperature.

Route D by Reaction of a Compound of Formula I with a Different Compound of Formula I Route D1

Compounds of Formula I wherein Y² is C, can be suitably prepared from a compound of Formula I wherein Y² is C. The reaction is suitably effected in an organic solvent such as ethanol in the presence of a suitable catalyst such as activated palladium on carbon under an atmosphere of hydrogen at ambient temperature.

Route E by Reaction of a Compound of Formula X with a Compound of Formula VI

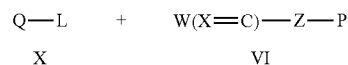

Route E1

Compounds of Formula I wherein X is O and Z is $NR^4$, can be suitably prepared by reacting a compound of Formula VI, wherein X is O and Z is $NR^4$ and W is defined in relation to formula I with a compound of Formula X where Q and L are also defined in relation to formula I. The reaction is suitably effected in an organic solvent such as tetrahydrofuran in the presence of a suitably chosen coupling reagent such as HATU, carboxylic acid and organic base, such as N,N-diisopropylethylamine at ambient temperature.

Intermediate II of Formula (X=)C—Z—P wherein Z is N and X is O or S, and a leaving group such as halogen is attached to the carbon atom of C(=X) and P is defined in relation to Formula I, are for example isocyanates or isothiocyanates and may be obtained from commercial sources. Or, wherein Z is O and X is O, and P is defined in relation to Formula I, compounds of formula (X=)C—Z—P can be suitably prepared through reaction of a commercially available phenol with diphosgene in the presence of a base such as N,N-diisopropylethylamine in an organic solvent such as dichloromethane at temperatures ranging from −30° C. to ambient.

Intermediate III of formula Q-L-W may be obtained by reaction of a compound of Formula X and a compound of Formula IX.

Compounds of Formula III wherein Q, L and W are defined in relation to Formula I are suitably prepared through reaction of a compound of Formula X with a compound of Formula IX, typically in the presence of an alkali metal carbonate base, such as potassium carbonate in an organic solvent such as acetone at elevated temperatures.

Compounds of Formula X are suitably prepared by deprotecting a compound of formula X which has been suitably protected with an amine protecting group such as tertiary butyloxycarbonyl (Boc) or benzyloxycarbonyl (Cbz). Suitable deprotection conditions would be apparent to a skilled person, but may include treatment with an acid such as trifluoroacetic acid to deprotect tertiary butyloxycarbonyl (Boc) or treatment with hydrogen in the presence of a catalyst, typically activated palladium on charcoal to deprotect benzyloxycarbonyl (Cbz).

Protected forms of compounds of Formula X are suitably prepared by reacting a compound of Formula V with a compound of Formula VII in the presence of a reducing agent, typically sodium triacetoxyborohydride in an organic solvent such as dichloromethane at ambient temperature.

Alternatively, Intermediate III may be obtained by reaction of a compound Formula XI and Formula V.

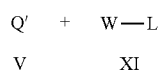

wherein Q' is a precursor of Q yielding Q upon reaction of XI with Q'. Q' conveniently comprises a leaving group such as halogen for reaction with the free nitrogen in L to yield Q.

Alternatively Q' comprises an electrophilic carbonyl group for reaction with the free nitrogen in L to yield Q. Such reactions are detailed in Route C1 above.

Compounds of Formula III wherein Q, L and W are defined in relation to formula I are prepared through reaction of a suitably protected compound of formula V wherein the amine protecting group used is typically tertiary butoxycarbonyl with a compound of formula XI, typically in the presence of an alkali metal hydride base, such as sodium hydride in an organic solvent such as N,N-dimethylformamide at ambient temperature. Suitable deprotection conditions would be apparent to a skilled person, but may include treatment with an acid such as trifluoroacetic acid.

Compounds of Formula XI are typically prepared through sulfonylation of an alcohol in the presence of a sulfonylating reagent, typically para-toluenesulfonylchloride in a suitable solvent such as dichloromethane at ambient temperature. The alcohols used in these procedures are typically formed through metal assisted, typically lithium aluminium hydride reduction of a commercially available ester, typically ethyl 1-benzylpiperidine-3-carboxylate in an organic solvent such as tetrahydrofuran at temperatures ranging from 5° C. to ambient.

As an alternative approach compounds of Formula III are prepared by reaction of a suitably protected, typically tertiary butoxycarbonyl, compound of Formula V with a compound of Formula XI in the presence of an alkali metal carbonate base, typically potassium carbonate in an organic solvent such as acetonitrile at elevated temperatures under microwave irradiation.

As an alternative approach compounds of Formula III are prepared by reaction of a suitably protected, typically tertiary butoxycarbonyl, compound of Formula V with a compound of formula XI in the presence of a strong metal base, typically tertiary butyl lithium in pentane in an organic solvent such as diethyl ether at temperatures ranging from −78° C. to ambient. Suitable deprotection conditions would be apparent to a skilled person, but may include treatment with an acid such as trifluoroacetic acid.

Intermediate IV may be obtained by reaction of a compound of Formula VI and a compound of Formula VII.

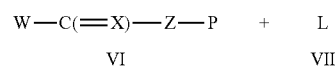

Compounds of Formula IV wherein L, W, C(X), Z and P are defined in relation to formula I are prepared through reaction of a suitably protected compound of Formula VI wherein the amine protecting group used is typically tertiary butoxycarbonyl with a compound of Formula VI, typically in the presence of a hydride source, such as sodium triacetoxyborohydride in an organic solvent such as dichloromethane at ambient temperature. Suitable deprotection conditions would be apparent to a skilled person, but may include treatment with an acid such as trifluoroacetic acid.

Intermediate VI may be obtained by reaction of a compound of Formula II and a compound of Formula IX

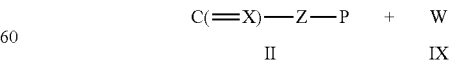

Compounds of Formula VI wherein W, C(X), Z and P are defined in relation to formula I are prepared through reaction of a suitably protected compound of Formula IX wherein the amine protecting group used is typically tertiary butoxycarbonyl with a compound of Formula II, in an organic solvent such as chloroform at ambient temperature. Suitable deprotection conditions would be apparent to a skilled person, but may include treatment with an acid such as trifluoroacetic acid.

A compound of Formula I, or a pharmaceutically acceptable salt thereof, may be used in the treatment of:

1. Respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. Bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. Pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. Skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. Eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. Gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. Abdominal: hepatitis, including autoimmune, alcoholic and viral; fibrosis and cirrhosis of the liver; cholecystitis; pancreatitis, both acute and chronic;

8. Genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. Allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. Other disorders with an inflammatory or immunological component; including HIV infection and acquired immune deficiency syndrome (AIDS), leprosy, Sezary syndrome, and paraneoplastic syndromes;

13. Cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. Oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. Gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

The invention further provides a compound of formula (I) as defined above for use in the treatment of C—C-chemokine mediated disease such as inflammatory disease. When used in this way, the compounds are suitably formulated into pharmaceutical compositions which further contain a pharmaceutically acceptable carrier and these form a further aspect of the invention. The compound is conveniently used for the treatment of a CCR2b mediated inflammatory disease and/or a CCR5 mediated inflammatory disease.

Furthermore, the invention provides the use of a compound of formula (I) as defined above in the preparation of a medicament for treating C—C chemokine mediated disease, and in particular for the treatment of CCR2B mediated inflammatory disease.

Furthermore, the invention provides the use of a compound of formula (I) as defined above in the preparation of a medicament for treating a CCR5 mediated disease state.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention,
or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739, 010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1 s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, gabapentin, pregabalin, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a yinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Some compounds of formula (I) may possess chiral centres. It is to be understood that the invention encompasses the use of all such optical isomers and diastereoisomers as well as compounds of formula (I) in any of these forms, and pharmaceutical compositions containing compounds of formula (I).

The invention further relates to all tautomeric forms of the compounds of formula (IA) and pharmaceutical compositions containing these.

It is also to be understood that certain compounds of the formula I can exist in solvated as well as unsolvated forms such as, for example, hydrated forms. It is to be understood that the invention encompasses all such solvated forms and pharmaceutical compositions containing these.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intermuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, and esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30µ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

In a further aspect, the invention provides a method of treating inflammatory disease by administering a compound of formula (I) as described above, or a pharmaceutical composition as described above.

The invention is further illustrated, but not limited by the following Biological Assay and Examples in which the following general procedures were used unless stated otherwise:

Anhydrous N,N-Dimethylformamide (DMF) and tetrahydrofuran (THF) were obtained from Aldrich SURESEAL™ bottles. Other commercially available reagents and solvents were used without further purification unless otherwise stated. Organic solvent extracts were dried over anhydrous $MgSO_4$. $^1H$, $^{13}C$ and $^{19}F$ NMR were recorded on Bruker WM200, WM250, WM300 or WM400 instruments using $Me_2SO-d_6$ with $Me_4Si$ or $CCl_3F$ as internal standard as appropriate, unless otherwise stated. Chemical shifts are in d (ppm) and peak multiplicities are designated as follows: s, singlet; d, doublet; dd, doublet of doublets; t, triplet; dt, doublet of triplets; q, quartet; m, multiplet; br, broad. Mass spectra were recorded on VG 12-12 quadrupole, VG 70-250 SE, VG ZAB 2-SE or a VG modified AEI/Kratos MS9 spectrometers. For TLC analysis, Merck precoated TLC plates (silica gel 60 F254, d=0.25 mm) were used. Flash chromatography was performed on silica (Merck Kieselgel: Art.9385). Melting point determinations were performed on a Kofler block or with a Büchi melting point apparatus and are uncorrected. All temperatures are in degrees Centigrade.

Biological Assay

Biological Assays for hMCP-1 Antagonists
a) hMCP-1 Receptor-Binding Assay
i) Cloning and Expression of hMCP-1 Receptor The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA*, 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pcDNA3 (InVitrogen) to generate pcDNA3/CC-CKR2A and pcDNA3/CCR2B respectively.

Linearised pcDNA3/CCR2B DNA was transfected into CHO-K1 cells by calcium phosphate precipitation (Wigler et al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6, 134). CHO-K1 clone 7 (CHO-CCR2B) was identified as the highest MCP-1 receptor B expressor.

ii) Preparation of Membrane Fragments

CHO-CCR2B cells were grown in DMEM supplemented with 10% foetal calf serum, 2 mM glutamine, 1× Non-Essential Amino Acids, 1× Hypoxanthine and Thymidine Supplement and Penicillin-Streptomycin (at 50 μg streptomycin/ml, Gibco BRL). Membrane fragments were prepared using cell lysis/differential centrifugation methods as described previously (Siciliano et al., 1990, *J. Biol. Chem.*, 265, 19658). Protein concentration was estimated by BCA protein assay (Pierce, Rockford, Ill.) according to the manufacturer's instructions.

iii) Assay $^{125}$I-labeled MCP-1 was prepared using Bolton and Hunter conjugation (Bolton et al., 1973, *Biochem. J.*, 133, 529; Amersham International plc].

Test compounds were dissolved in DMSO and further diluted in assay buffer (50 mM HEPES, 1 mM $CaCl_2$, 5 nM $MgCl_2$, 0.03% BSA, pH 7.2) to give a range of concentrations starting with a top final concentration of 10 uM. All incubations had a 100 ul final volume and a DMSO concentration of 1%. Incubations contained 200 pM $^{125}$I-labeled MCP-1 (Amersham Pharmacia), 2.5 mg/ml Scintillation proximity assay beads (Amersham Pharmacia RPNQ) and approx 5 ug CHO-CCR2B cell membranes. Non-specific binding was determined by the inclusion of a 1 uM unlabelled MCP-1 in the place of test compound. Total binding was determined in the presence of 1% DMSO without compound. Incubations were performed in sealed optiplates and kept at room temperature for 16 hours after which the plates were counted on a Packard TopCount (Packard TopCount™). Dose-response curves were generated from duplicate date points and $IC_{50}$ values were calculated using GraphPad Prizm® software. Percent inhibitions were calculated for single concentrations of compound by using the following formula 100–((compound binding minus non-specific binding)/(total binding minus non-specific binding)×100).

Alternative Assay for hMCP-1 Antagonists
a) hMCP-1 THP1 Receptor-Binding Assay
i) Preparation of Membrane Fragments THP1 cells were grown in RPMI (Sigma) supplemented with 10% foetal calf serum, 2 mM glutamine (Gibco), 100 units/mL Penicillin and 100 μg/mL Streptomycin (Invitrogen). Membrane fragments were prepared using cell lysis/differential centrifugation methods as described previously (Siciliano et al., 1990, *J. Biol. Chem.*, 265, 19658). Protein concentration was estimated by BCA protein assay (Pierce, Rockford, Ill.) according to the manufacturer's instructions.

ii) Assay $^{125}$I-labeled MCP-1 was prepared using Bolton and Hunter conjugation (Bolton et al., 1973, *Biochem. J.*, 133, 529; Amersham International plc].

Test compounds were dissolved in DMSO and further diluted in assay buffer (50 mM HEPES, 1 mM $CaCl_2$, 5 mM $MgCl_2$, 0.03% BSA, pH 7.2) to give a range of concentrations starting with a top final concentration of 10 uM. All incubations had a 100 ul final volume and a DMSO concentration of 1%. Incubations contained 250 pM $^{125}$I-labeled MCP-1 (Amersham Pharmacia), 2.5 mg/ml Scintillation proximity assay beads (Amersham Pharmacia RPNQ) and cell membranes containing $0.5 \times 10^5$ cells/ml equivalent. Non-specific binding was determined by the inclusion of 250 nM of a known CCR2B antagonist in the place of test compound. Total binding was determined in the presence of 1% DMSO without compound. Incubations were performed in sealed optiplates and kept at room temperature for 16 hours after which the plates were counted on a Packard TopCount (Packard TopCount™). Dose-response curves were generated and $IC_{50}$ values were calculated using GraphPad Prizm® software. Percent inhibitions were calculated for single concentrations of compound by using the following formula 100–((compound binding minus non-specific binding)/(total binding minus non-specific binding)×100).

Each compound set out in the Examples below was tested in one of the above assays and shown to have an $IC_{50}$ value of better than 20 μmol.

Biological Assay for the Ability of Compounds to Inhibit the Binding of MIP-1α

This ability is assessed using an in vitro radioligand binding assay. Membranes are prepared from Chinese hamster ovary cells which express the recombinant human CCR5 receptor. These membranes are incubated with 0.1 nM iodinated MIP-1α, scintillation proximity beads and various concentrations of the compounds of the invention in 96-well plates. The amount of iodinated MIP-1α bound to the receptor is then determined by scintillation counting. Competition curves are obtained for compounds and the concentration of compound which displaces 50% of bound iodinated MIP-1α is calculated ($IC_{50}$).

In the above assay the compounds as set out in Examples 1, 18, 19, 26, 34, 41, 42, 44, 47, 79, 84, 89, 90, 91, 106, 107, 108, 109, 110, 111, 112, 113, 115, 118, 119, 120, 121, 122, 131, 132, 133, 134, 135, 138, 139, 145, 146, 147, 148, 149, 150, 152, 153, 154, 161, 170, 171, 172, 175, 176, 180, 181, 183, 185, 186, 187, 188, 192, 197, 199, 200, 203, 205, 209, 210, 211, 212, 213, 214, 215, 216, 218, 219, 220, 221, 222, 223, 228, 229, 231, 232, 233, 234, 235, 236, 237, 245, 246, 247, 248, 249, 250, 251, 252, 253, 254, 255, 256, 257, 258, 259, 260, 261, 262, 263, 264, 265, 266, 267, 268, 269, 270, 271, 273, 275, 276, 277, 279, 280, 281, 287, 288, 290, 292, 303, 304, 311, 322, 324, 325, 326, 327, and 328 showed an $IC_{50}$ value of better than 10 μmol.

Each of the following Examples and any combination thereof represents a separate and independent aspect of the invention. Further comprised in the invention are pharmaceutically acceptable salts or solvates of each exemplified compound and any combination thereof

Examples

| Example No. | Structure | Characterisation Data | Chemistry Route |
|---|---|---|---|
| 1 | 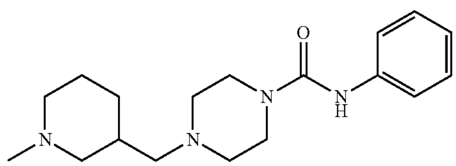 [SMILES: CN1CCCC(CN2CCN(C(=O)Nc3ccccc3)CC2)C1] | 4-[(1-methylpiperidin-3-yl)methyl]-N-phenylpiperazine-1-carboxamide LCMS M/z(+) 317.43 (M + H⁺) $^1$H-NMR (DMSO-$d_6$) 0.85 (1H, m), 1.40 to 1.67 (4H, m), 1.73 to 1.87 (2H, m), 2.10 to 2.19 (5H, m), 2.27 to 2.39 (4H, m), 2.64 (1H, m), 2.78 (1H, d), 3.43 (4H, t), 6.92 (1H, t), 7.22 (2H, t), 7.45 (2H, d), 8.45 (1H, s) | A1 |
| 2 | 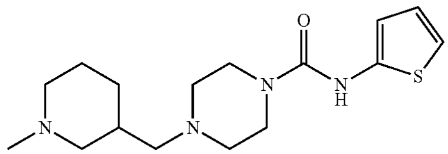 [SMILES: CN1CCCC(CN2CCN(C(=O)Nc3cccs3)CC2)C1] | 4-[(1-methylpiperidin-3-yl)methyl]-N-2-thienylpiperazine-1-carboxamide LCMS M/z(+) 323.14 (M + H⁺) $^1$H-NMR (DMSO-$d_6$) 0.84 (1H, m), 1.41 to 1.65 (4H, m), 1.75 to 1.87 (2H, m), 2.10 to 2.18 (5H, m), 2.27 to 2.39 (4H, m), 2.65 (1H, d), 2.77 (1H, d), 3.43 (4H, t), 6.59 (1H, dd), 6.75 to 6.79 (2H, m), 9.61 (1H, s) | A1 |
| 3 | 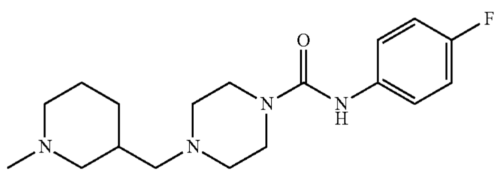 [SMILES: CN1CCCC(CN2CCN(C(=O)Nc3ccc(F)cc3)CC2)C1] | N-(4-fluorophenyl)-4-[(1-methylpiperidin-3-yl)methyl]piperazine-1-carboxamide LCMS M/z(+) 335 (M + H⁺) | A1 |
| 4 | 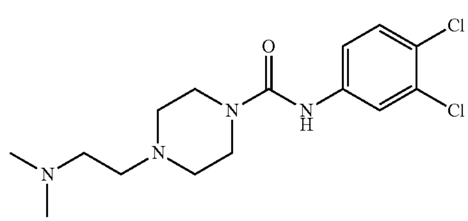 [SMILES: CN(C)CCN1CCN(C(=O)Nc2ccc(Cl)c(Cl)c2)CC1] | N-(3,4-dichlorophenyl)-4-[2-(dimethyl-amino)ethyl]piperazine-1-carboxamide LCMS M/z(+) 345 (M + H⁺) | A1 |
| 5 | 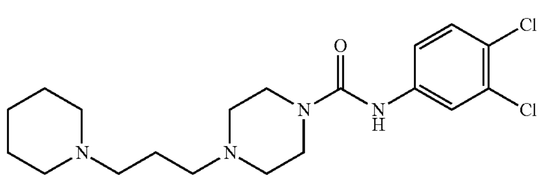 [SMILES: O=C(Nc1ccc(Cl)c(Cl)c1)N1CCN(CCCN2CCCCC2)CC1] | N-(3,4-dichlorophenyl)-4-(3-piperidin-1-ylpropyl)piperazine-1-carboxamide LCMS M/z(+) 399 (M + H⁺) | A1 |
| 6 | 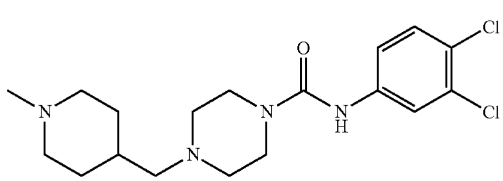 [SMILES: CN1CCC(CN2CCN(C(=O)Nc3ccc(Cl)c(Cl)c3)CC2)CC1] | N-(3,4-dichlorophenyl)-4[(1-methylpiperidin-4-yl)methyl]piperazine-1-carboxamide LCMS M/z(+) 386 (M + H⁺) | A1 |

-continued

Examples

| Example No. | Structure | Characterisation Data | Chemistry Route |
|---|---|---|---|
| 7 | 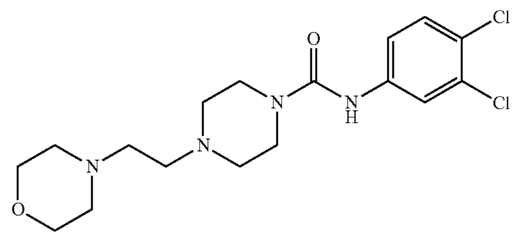 [SMILES: O=C(Nc1ccc(Cl)c(Cl)c1)N1CCN(CCN2CCOCC2)CC1] | N-(3,4-dichlorophenyl)-4-(2-morpholin-4-ylethyl)piperazine-1-carboxamide<br>LCMS M/z(+) 388 (M + H$^+$) | A1 |
| 8 | 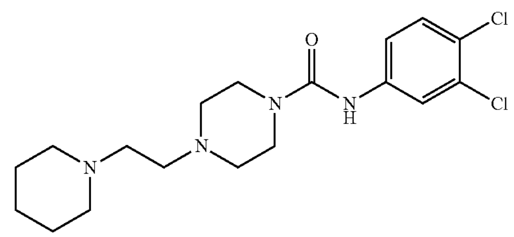 [SMILES: O=C(Nc1ccc(Cl)c(Cl)c1)N1CCN(CCN2CCCCC2)CC1] | N-(3,4-dichlorophenyl)-4-(2-piperidin-1-ylethyl)piperazine-1-carboxamide<br>LCMS M/z(+) 385 (M + H$^+$) | A1 |
| 9 | 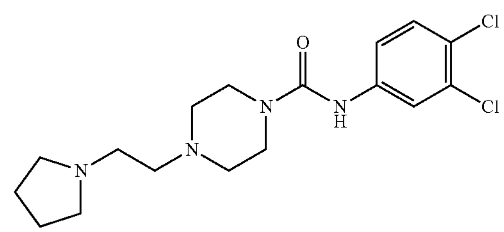 [SMILES: O=C(Nc1ccc(Cl)c(Cl)c1)N1CCN(CCN2CCCC2)CC1] | N-(3,4-dichlorophenyl)-4-(2-pyrrolidin-1-ylethyl)piperazine-1-carboxamide<br>LCMS M/z(+) 372 (M + H$^+$) | A1 |
| 10 | 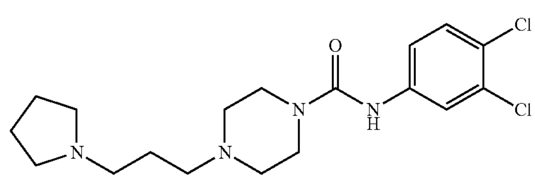 [SMILES: O=C(Nc1ccc(Cl)c(Cl)c1)N1CCN(CCCN2CCCC2)CC1] | N-(3,4-dichlorophenyl)-4-(3-pyrrolidin-1-ylpropyl)piperazine-1-carboxamide<br>LCMS M/z(+) 385 (M + H$^+$) | A1 |
| 11 | 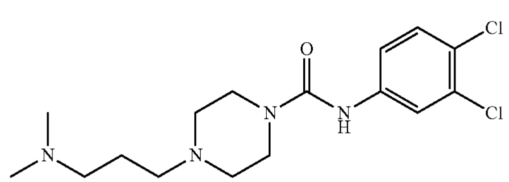 [SMILES: CN(C)CCCN1CCN(C(=O)Nc2ccc(Cl)c(Cl)c2)CC1] | N-(3,4-dichlorophenyl)-4-[3-(dimethylamino)propyl]piperazine-1-carboxamide<br>LCMS M/z(+) 359 (M + H$^+$) | A1 |
| 12 | 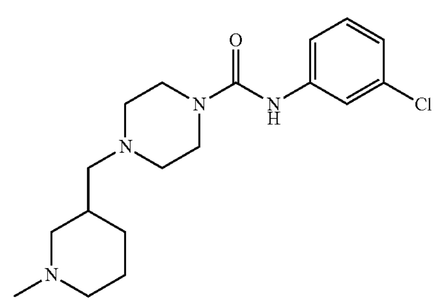 [SMILES: CN1CCCC(CN2CCN(C(=O)Nc3cccc(Cl)c3)CC2)C1] | N-(3-chlorophenyl)-4-[(1-methylpiperidin-3-yl)methyl]piperazine-1-carboxamide<br>LCMS M/z(+) 351 (M + H$^+$) | A1 |

-continued

Examples

| Example No. | Structure | Characterisation Data | Chemistry Route |
|---|---|---|---|
| 13 | 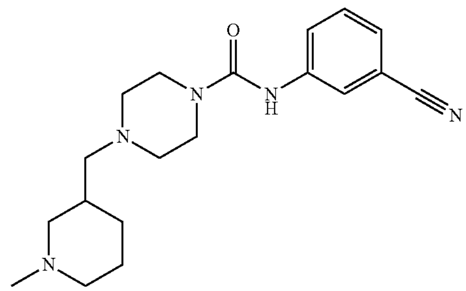 [SMILES: CN1CCCC(CN2CCN(C(=O)Nc3cccc(C#N)c3)CC2)C1] | N-(3-cyanophenyl)-4-[(1-methylpiperidin-3-yl)methyl]piperazine-1-carboxamide<br>LCMS M/z(+) 342 (M + H$^+$) | A1 |
| 14 | 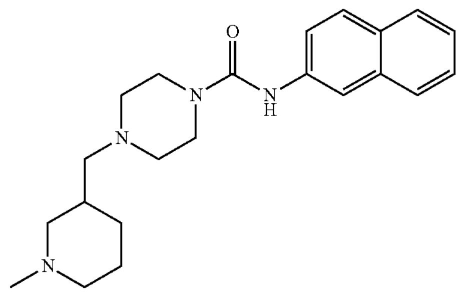 [SMILES: CN1CCCC(CN2CCN(C(=O)Nc3ccc4ccccc4c3)CC2)C1] | 4-[(1-methylpiperidin-3-yl)methyl]-N-2-naphthylpiperazine-1-carboxamide<br>LCMS M/z(+) 367 (M + H$^+$) | A1 |
| 15 | 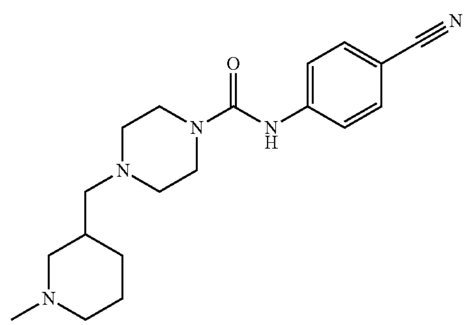 [SMILES: CN1CCCC(CN2CCN(C(=O)Nc3ccc(C#N)cc3)CC2)C1] | N-(4-cyanophenyl)-4-[(1-methylpiperidin-3-yl)methyl]piperazine-1-carboxamide<br>LCMS M/z(+) 342 (M + H$^+$) | A1 |
| 16 | 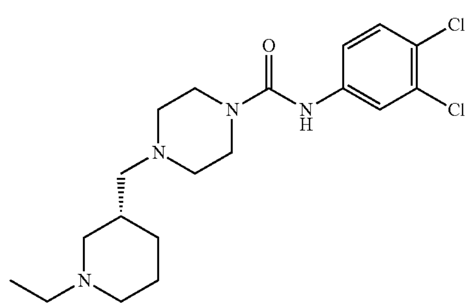 | N-(3,4-dichlorophenyl)-4-{[(3R)-1-ethylpiperidin-3-yl]methyl}-piperazine-1-carboxamide<br>LCMS M/z(+) 399.31, 401.29 (M + H$^+$)<br>LCMS M/z(−) 397.33, 399.33 (M − H$^−$)<br>$^1$H-NMR (DMSO-d$_6$) 0.85 (1H, m), 1.00 (3H, t), 1.60 to 2.10 (6H, m), 2.32 (6H, m), 3.25 (4H, t), 3.41 (4H, t), 7.45 (2H, d), 7.80 (1H, s), 8.74 (1H, s) | C1 |
| 17 | 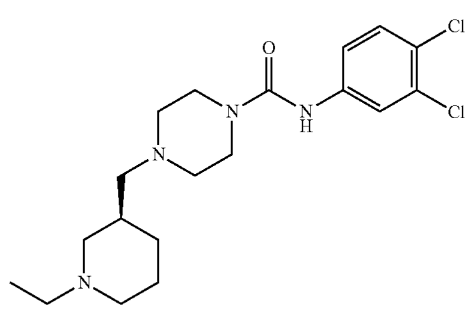 [SMILES: CCN1CCC[C@H](CN2CCN(C(=O)Nc3ccc(Cl)c(Cl)c3)CC2)C1] | N-(3,4-dichlorophenyl)-4-{[(3S)-1-ethylpiperidin-3-yl]methyl}-piperazine-1-carboxamide<br>LCMS M/z(+) 399.31, 401.29 (M + H$^+$)<br>LCMS M/z(−) 397.33, 399.33 (M − H$^−$)<br>$^1$H-NMR (DMSO-d$_6$): 0.85 (1H, m), 1.00 (3H, t), 1.60 to 2.10 (6H, m), 2.32 (6H, m), 3.25 (4H, t), 3.41 (4H, t), 7.45 (2H, d), 7.80 (1H, s), 8.74 (1H, s) | C1 |

-continued

Examples

| Example No. | Structure | Characterisation Data | Chemistry Route |
|---|---|---|---|
| 18 | 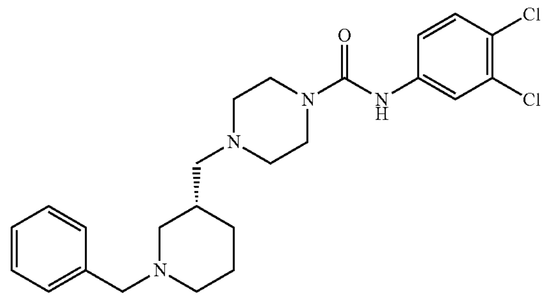 | 4-{[(3R)-1-benzylpiperidin-3-yl]methyl}-N-(3,4-dichlorophenyl)piperazine-1-carboxamide<br>LCMS M/z(+) 461 (M + H$^+$)<br>$^1$H-NMR (CDCl$_3$) 0.86-1.01 (1H, m), 1.58-1.88 (4H, m), 1.91-2.11 (2H, m), 2.12-2.24 (2H, m), 2.33 (2H, quintet), 2.42 (2H, quintet), 2.85 (1H, d), 3.01 (1H, d), 3.37-3.48 (4H, m), 3.52 (1H, d), 3.70 (1H, d), 6.82 (1H, s), 7.23-7.38 (7H, m), 7.63 (1H, d) | C1 |
| 19 | 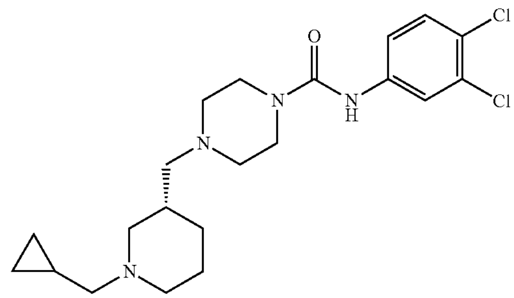 [SMILES: O=C(Nc1ccc(Cl)c(Cl)c1)N1CCN(C[C@@H]2CCCN(CC3CC3)C2)CC1] | 4-{[(3R)-1-(cyclopropylmethyl)-piperidin-3-yl]methyl}-N-(3,4-dichlorophenyl)-piperazine-1-carboxamide<br>LCMS M/z(+) 425.28, 427.23 (M + H$^+$)<br>LCMS M/z(−) 423.28, 425.28 (M − H$^-$)<br>$^1$H-NMR (DMSO-d$_6$) 0.02 (2H, s), 0.33 (2H, s), 0.70 (2H, s), 1.35 (1H, m), 1.51 (2H, m), 1.75 (2H, m), 2.00 (3H, m), 2.20 (4H, m), 2.80 to 3.25 (8H, m), 7.31 (2H, d), 7.68 (1H, s), 8.60 (1H, s) | C1 |
| 20 | 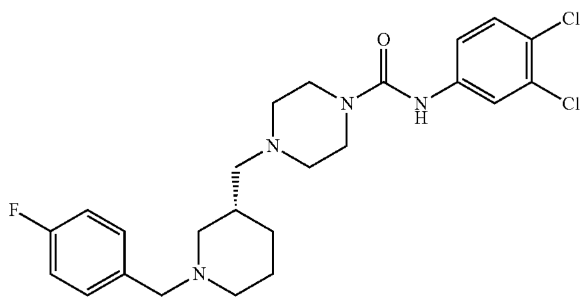 [SMILES: O=C(Nc1ccc(Cl)c(Cl)c1)N1CCN(C[C@@H]2CCCN(Cc3ccc(F)cc3)C2)CC1] | N-(3,4-dichlorophenyl)-4-{[(3R)-1-(4-fluorobenzyl)piperidin-3-yl]methyl}piperazine-1-carboxamide LCMS M/z(+) 479 (M + H$^+$)<br>$^1$H-NMR (CDCl$_3$) 0.87-1.01 (1H, m), 1.50-2.04 (6H, m), 2.15-2.25 (2H, m), 2.37 (2H, quintet), 2.44 (2H, quintet), 2.78 (1H, d), 2.93 (1H, d), 3.37-3.49 (1H, m), 3.44 (4H, t), 3.58 (1H, d), 6.35 (1H, s), 7.00 (2H, t), 7.20 (1H, dd), 7.24-7.35 (3H, m), 7.59 (1H, d) | C1 |
| 21 | 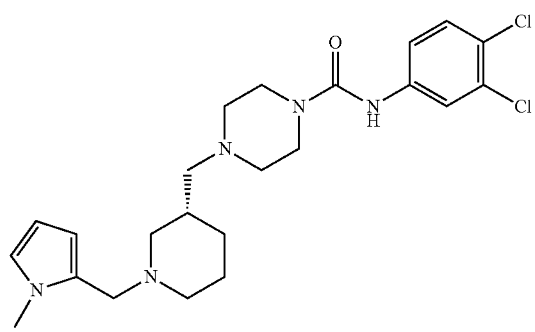 [SMILES: Cn1cccc1CN1CCC[C@@H](CN2CCN(C(=O)Nc3ccc(Cl)c(Cl)c3)CC2)C1] | N-(3,4-dichlorophenyl)-4-({(3S)-1-[(1-methyl-1H-pyrrol-2-yl)methyl]piperidin-3-yl}methyl)piperazine-1-carboxamide LCMS M/z(+) 464 (M + H$^+$)<br>$^1$H-NMR (CDCl$_3$): 0.89-1.03 (1H, m), 1.40-2.11 (6H, m), 2.14-2.27 (2H, m), 2.40 (4H, d.quintet), 2.70-2.99 (2H, m), 3.38-3.59 (6H, m), 3.66 (3H, s), 6.00-6.07 (2H, m), 6.51 (1H, s), 6.60 (1H, s), 7.22 (1H, dd), 7.31 (1H, d), 7.6 | C1 |
| 22 | 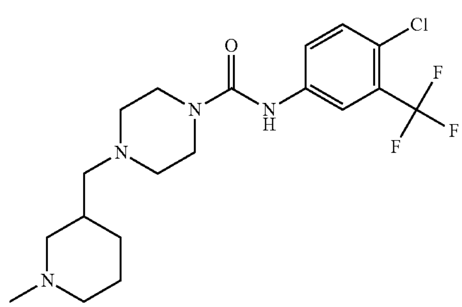 | N-[3-chloro-4-(trifluoromethyl)phenyl]-4-[(1-methylpiperidin-3-yl)methyl]-piperazine-1-carboxamide<br>LCMS M/z(+) 369.37, 371.36 (M + H$^+$)<br>LCMS M/z(−) 367.39, 369.37 (M − H$^-$)<br>$^1$H-NMR (DMSO-d$_6$) 0.93 (1H, m), 1.55 (1H, m), 1.38 (2H, d), 1.92 (1H, m), 2.17 to 2.38 (11H, m), 2.94 to 3.03 (2H, d), 3.45 (4H, t), 7.29 to 7.32 (1H, dd), 7.41 (1H, t), 7.63 to 7.67 (1H, dd), 8.83 (1H, s) | A1 |

-continued

Examples

| Example No. | Structure | Characterisation Data | Chemistry Route |
|---|---|---|---|
| 23 | 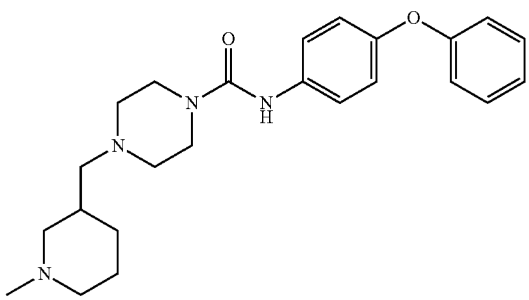 [SMILES: CN1CCCC(CN2CCN(C(=O)Nc3ccc(Oc4ccccc4)cc3)CC2)C1] | 4-[(1-methylpiperidin-3-yl)methyl]-N-(4-phenoxyphenyl)piperazine-1-carboxamide<br>LCMS M/z(+) 409.36 (M + H$^+$)<br>$^1$H-NMR (DMSO-d$_6$) 0.87 (1H, m), 1.44 to 1.67 (4H, m), 1.76 to 1.97 (2H, m), 2.13 to 2.19 (5H, m), 2.28 to 2.40 (4H, m), 2.69 (1H, m), 2.83 (1H, d), 3.43 (4H, t), 6.94 (4H, m), 7.08 (1H, t), 7.35 (2H, dd), 7.47 (2H, m), 8.49 (1H, s) | A1 |
| 24 | 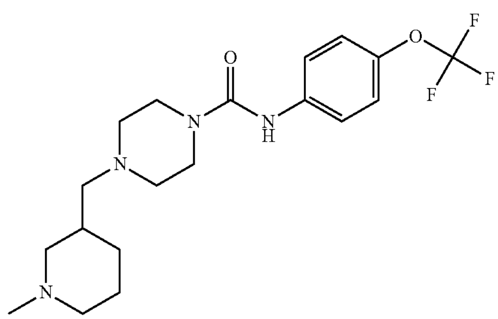 [SMILES: CN1CCCC(CN2CCN(C(=O)Nc3ccc(OC(F)(F)F)cc3)CC2)C1] | 4-[(1-methylpiperidin-3-yl)methyl]-N-[4-(trifluoromethoxy)phenyl]piperazine-1-carboxamide<br>LCMS M/z(+) 401.33 (M + H$^+$)<br>$^1$H-NMR (DMSO-d$_6$) 0.84 (1H, m), 1.40 to 1.66 (4H, m), 1.72 to 1.86 (2H, m), 2.10 to 2.18 (5H, m), 2.28 to 2.40 (4H, m), 2.64 (1H, d), 2.77 (1H, d), 3.44 (4H, t), 7.22 (2H, d), 7.56 (2H, d), 8.66 (1H, s) | A1 |
| 25 | 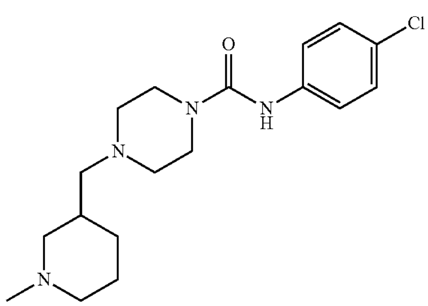 [SMILES: CN1CCCC(CN2CCN(C(=O)Nc3ccc(Cl)cc3)CC2)C1] | N-(4-chlorophenyl)-4[(1-methylpiperidin-3-yl)methyl]piperazine-1-carboxamide<br>LCMS M/z(+) 351.38, 353.44 (M + H$^+$)<br>$^1$H-NMR (DMSO-d$_6$) 0.85 (1H, m), 1.42 to 1.51 (1H, m), 1.57 to 1.67 (3H, m), 1.78 (1H, m), 1.87 (1H, t), 2.10 to 2.18 (5H, m), 2.27 to 2.39 (4H, m), 2.67 (1H, m), 2.80 (1H, d), 3.43 (4H, t), 7.27 (2H, d), 7.51 (2H, d), 8.60 (1H, s) | A1 |
| 26 | 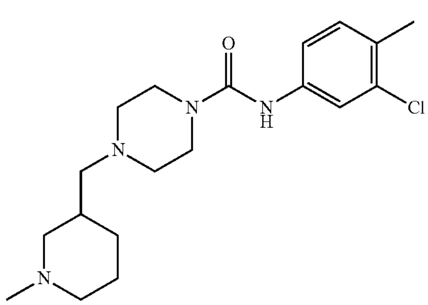 [SMILES: Cc1ccc(NC(=O)N2CCN(CC3CCCN(C)C3)CC2)cc1Cl] | N-(3-chloro-4-methylphenyl)-4-[(1-methylpiperidin-3-yl)methyl]piperazine-1-carboxamide<br>LCMS M/z(+) 365.41, 367.41 (M + H$^+$)<br>$^1$H-NMR (DMSO-d$_6$) 0.86 (1H, m), 1.41 to 1.53 (2H, m), 1.57 to 1.67 (2H, m), 1.79 (1H, m), 1.89 (1H, t), 2.14 (2H, m), 2.18 (3H, s), 2.24 (3H, s), 2.77 to 2.39 (4H, m), 2.69 (1H, m), 2.82 (1H, d), 3.42 (4H, t), 7.18 (1H, d), 7.31 (1H, dd), 7.63 (1H, d), 8.55 (1H, s) | A1 |

-continued

Examples

| Example No. | Structure | Characterisation Data | Chemistry Route |
|---|---|---|---|
| 27 | 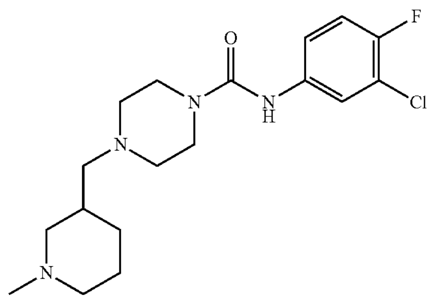 | N-(3-chloro-4-fluorophenyl)-4-[(1-methylpiperidin-3-yl)methyl]piperazine-1-carboxamide<br>LCMS M/z(+) 369.37, 371.35 (M + H$^+$)<br>$^1$H-NMR (DMSO-d$_6$) 0.85 (1H, m), 1.40 to 1.66 (4H, m), 1.72 to 1.86 (2H, m), 2.10 to 2.18 (5H, m), 2.27 to 2.39 (4H, m), 2.64 (1H, d), 2.78 (1H, d), 3.43 (4H, t), 7.22 (1H, m), 7.29 (1H, t), 7.61 (1H, m), 8.67 (1H, s) | A1 |
| 28 | 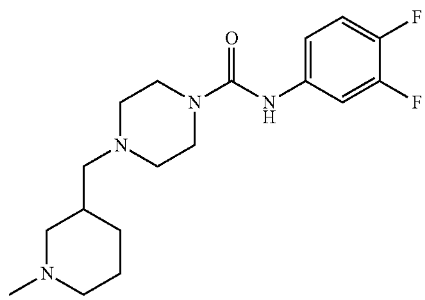 [SMILES: CN1CCCC(CN2CCN(C(=O)Nc3ccc(F)c(F)c3)CC2)C1] | N-(3,4-difluorophenyl)-4-[(1-methylpiperidin-3-yl)methyl]piperazine-1-carboxamide<br>LCMS M/z(+) 353.43 (M + H$^+$)<br>$^1$H-NMR (DMSO-d$_6$) 0.85 (1H, m), 1.40 to 1.66 (4H, m), 1.73 to 1.88 (2H, m), 2.10 to 2.18 (5H, m), 2.27 to 2.39 (4H, m), 2.65 (1H, d), 2.78 (1H, d), 3.43 (4H, t), 7.27 (1H, t), 7.41 (1H, m), 7.74 (1H, dd), 8.66 (1H, s) | A1 |
| 29 | 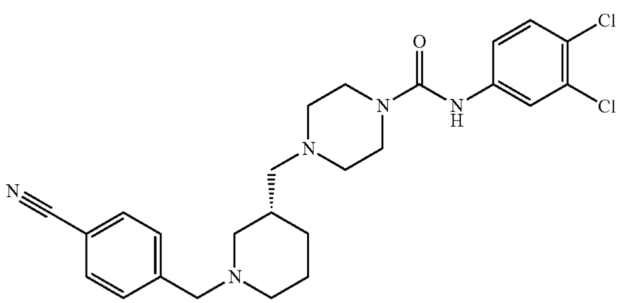 [SMILES: N#Cc1ccc(CN2CCC[C@@H](CN3CCN(C(=O)Nc4ccc(Cl)c(Cl)c4)CC3)C2)cc1] | 4-{[(3R)-1-(4-cyanobenzyl)piperidin-3-yl]methyl}-N-(3,4-dichlorophenyl)-piperazine-1-carboxamide<br>LCMS M/z(+) 485, 487 (M + H$^+$) | C1 |
| 30 | 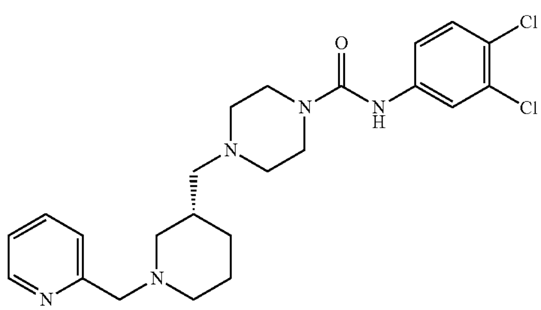 [SMILES: O=C(Nc1ccc(Cl)c(Cl)c1)N1CCN(C[C@@H]2CCCN(Cc3ccccn3)C2)CC1] | N-(3,4-dichlorophenyl)-4-{[(3S)-1-(pyridin-2-ylmethyl)piperidin-3-yl]methyl}piperazine-1-carboxamide<br>LCMS M/z(+) 461, 463 (M + H$^+$) | C1 |
| 31 | 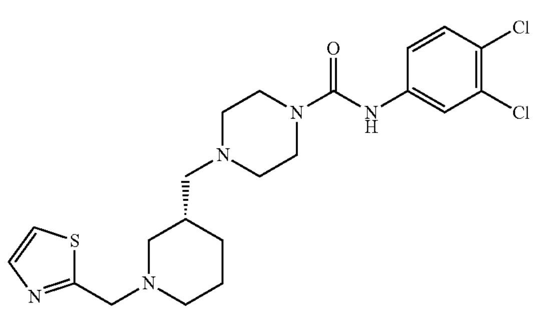 [SMILES: O=C(Nc1ccc(Cl)c(Cl)c1)N1CCN(C[C@@H]2CCCN(Cc3nccs3)C2)CC1] | N-(3,4-dichlorophenyl)-4-{[(3S)-1-(1,3-thiazol-2-ylmethyl)piperidin-3-yl]methyl}piperazine-1-carboxamide<br>LCMS M/z(+) 467, 469 (M + H$^+$) | C1 |

| Example No. | Structure | Characterisation Data | Chemistry Route |
|---|---|---|---|
| 32 | 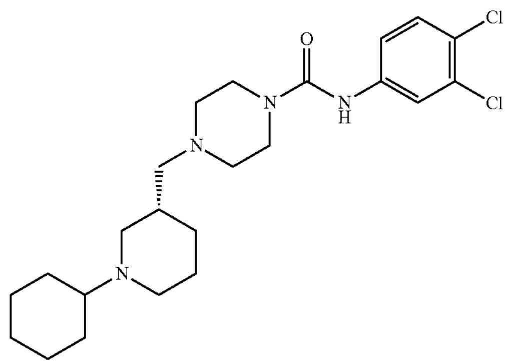 [SMILES: O=C(Nc1ccc(Cl)c(Cl)c1)N1CCN(C[C@@H]2CCCN(C3CCCCC3)C2)CC1] | 4-{[(3S)-1-cyclohexylpiperidin-3-yl]methyl}-N-(3,4-dichloro-phenyl)piperazine-1-carboxamide<br>LCMS M/z(+) 453.22, 455.30 (M + H$^+$)<br>LCMS M/z(−) 451.32, 453.31 (M − H$^-$)<br>$^1$H-NMR (DMSO-d$_6$) 1.10 to 1.47 (10H, m), 1.70 (6H, m), 2.00 (3H, m), 2.08 (2H, s), 2.83 (1H, m), 3.25 (4H, m), 3.50 (4H, m), 7.47 (2H, d), 7.81 (1H, s), 8.80 (1H, s) | C1 |
| 33 | 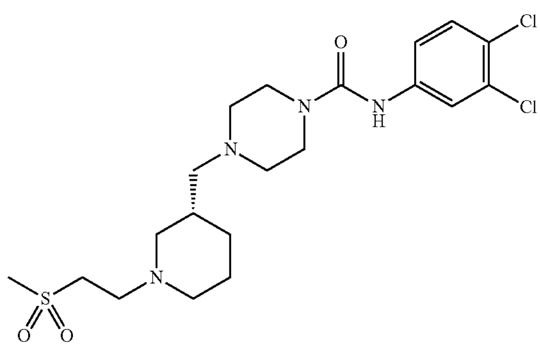 [SMILES: CS(=O)(=O)CCN1CCC[C@@H](CN2CCN(C(=O)Nc3ccc(Cl)c(Cl)c3)CC2)C1] | N-(3,4-dichlorophenyl)-4-({(3S)-1-[2-(methylsulfonyl)ethyl]piperidin-3-yl}methyl)piperazine-1-carboxamide<br>LCMS M/z(+) 476, 478 (M + H$^+$) | C1 |
| 34 | 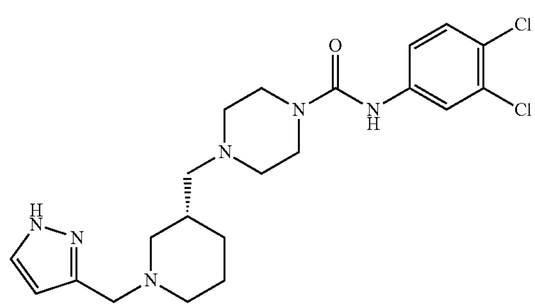 [SMILES: O=C(Nc1ccc(Cl)c(Cl)c1)N1CCN(C[C@@H]2CCCN(Cc3cc[nH]n3)C2)CC1] | N-(3,4-dichlorophenyl)-4-{[(3S)-1-(1H-pyrazol-3-ylmethyl)-piperidin-3-yl]methyl}piperazine-1-carboxamide<br>LCMS M/z(+) 452.27 (M + H$^+$)<br>LCMS M/z(−) 449.24, 451.23 (M − H$^-$)<br>$^1$H-NMR (DMSO-d$_6$) 0.90 (1H, m), 1.20 to 1.60 (6H, m), 2.08 (2H, s), 2.11 to 2.37 (4H, m), 3.20 to 3.35 (8H, m), 4.02 (1H, m), 6.14 (1H, s), 7.43 (2H, d), 7.82 (1H, s), 8.76 (1H, d), 12.6 (1H, s) | C1 |
| 35 | 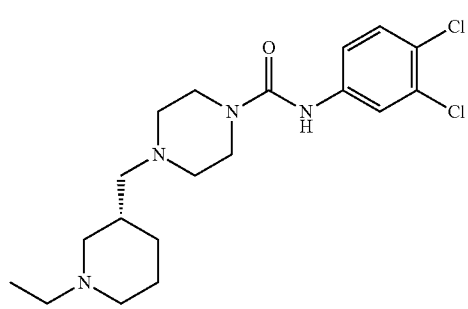 | N-(3,4-dichlorophenyl)-1-{[(3R)-1-ethylpiperidin-3-yl]methyl}piperidine-4-carboxamide<br>LCMS M/z(+) 398 (M + H$^+$)<br>$^1$H-NMR (CDCl$_3$) 0.78-0.94 (1H, m), 1.08 (3H, t), 1.49-2.03 (12H, m), 2.14 (2H, d), 2.12-2.27 (1H, m), 2.30-2.50 (2H, m), 2.89 (2H, d), 2.99 (2H, d), 7.16 (1H, s), 7.29-7.38 (2H, m), 7.77 (1H, d) | C2 |

-continued

Examples

| Example No. | Structure | Characterisation Data | Chemistry Route |
|---|---|---|---|
| 36 | 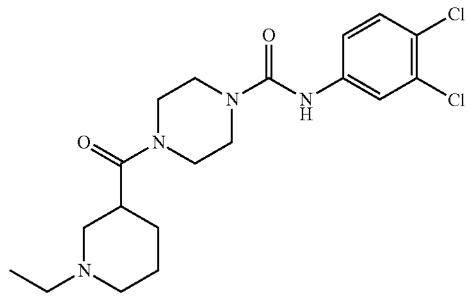 | N-(3,4-dichlorophenyl)-4-[(1-ethylpiperidin-3-yl)carbonyl]piperazine-1-carboxamide<br>LCMS M/z(+) 413 (M + H$^+$)<br>$^1$H-NMR (CDCl$_3$) 1.08 (3H, t), 1.45-1.70 (2H, m), 1.73-1.96 (3H, m), 2.14 (1H, t), 2.44 (2H, q), 2.75-2.85 (1H, m), 2.87-3.00 (2H, m), 3.40-3.75 (8H, m), 6.72 (1H, s), 7.22 (1H, dd), 7.33 (1H, d), 7.56 (1H, d). | C3 |
| 37 | 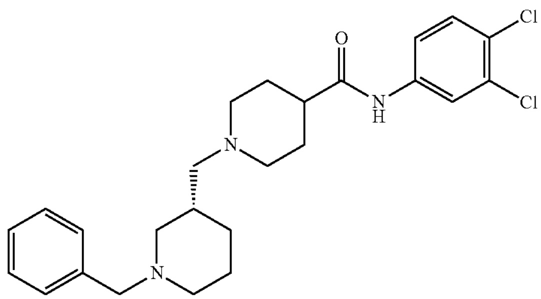 [SMILES: O=C(Nc1ccc(Cl)c(Cl)c1)C1CCN(C[C@@H]2CCCN(Cc3ccccc3)C2)CC1] | 1-{[(3S)-1-benzylpiperidin-3-yl]methyl}-N-(3,4-dichlorophenyl)piperidine-4-carboxamide<br>LCMS M/z(+) 460 (M + H$^+$)<br>$^1$H-NMR (CDCl$_3$) 0.77-2.30 (14H, m), 2.80-3.09 (4H, m), 3.35-3.80 (3H, m), 7.20-7.41 (7H, m), 7.78 (1H, s) | C2 |
| 38 | 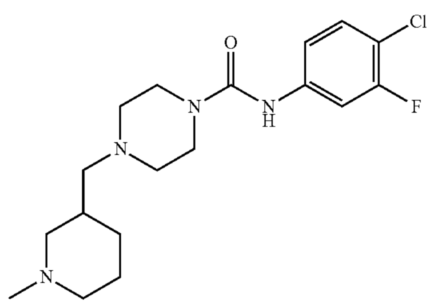 | N-(4-chloro-3-fluorophenyl)-4-[(1-methylpiperidin-3-yl)methyl]piperazine-1-carboxamide<br>LCMS M/z(+) 369 (M + H$^+$) | A1 |
| 39 | 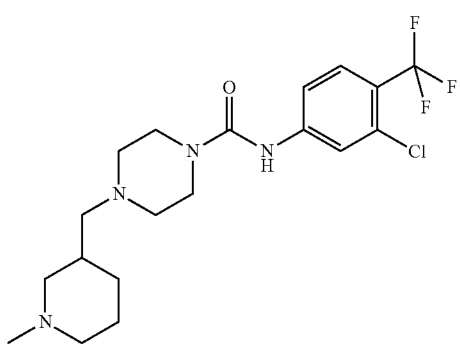 [SMILES: CN1CCCC(CN2CCN(C(=O)Nc3ccc(C(F)(F)F)c(Cl)c3)CC2)C1] | N-[3-chloro-4-(trifluoromethyl)phenyl]-4-[(1-methylpiperidin-3-yl)methyl]piperazine-1-carboxamide<br>LCMS M/z(+) 419 (M + H$^+$) | A1 |

-continued

| Example No. | Structure | Characterisation Data | Chemistry Route |
|---|---|---|---|
| 40 | 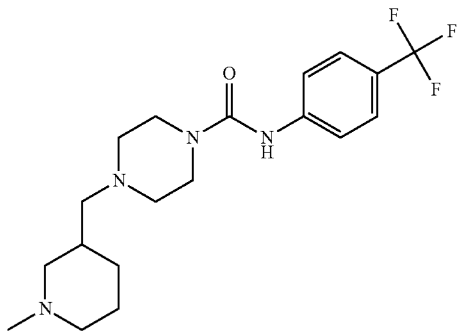 [SMILES: CN1CCCC(CN2CCN(C(=O)Nc3ccc(C(F)(F)F)cc3)CC2)C1] | 4-[(1-methylpiperidin-3-yl)methyl]-N-[4-(trifluoromethyl)phenyl]piperazine-1-carboxamide<br>LCMS M/z(+) 385.40 (M + H$^+$)<br>LCMS M/z(−) 383.44 (M − H$^−$)<br>$^1$H-NMR (DMSO-d$_6$) 0.86 (1H, m), 1.48 (1H, m), 1.58 to 1.67 (3H, m), 1.78 (1H, m), 1.87 (1H, t), 2.15 (2H, d), 2.18 (3H, s), 2.28 to 2.41 (4H, m), 2.67 (1H, m), 2.80 (1H, d), 3.46 (4H, t), 7.56 to 7.70 (4H, dd), 8.87 (1H, s) | A1 |
| 41 | 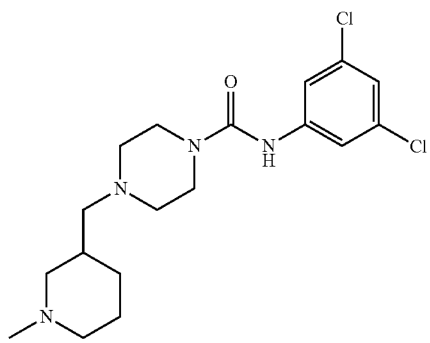 [SMILES: CN1CCCC(CN2CCN(C(=O)Nc3cc(Cl)cc(Cl)c3)CC2)C1] | N-(3,5-dichlorophenyl)-4-[(1-methylpiperidin-3-yl)methyl]piperazine-1-carboxamide<br>LCMS M/z(+) 385.34, 387.34 (M + H$^+$)<br>LCMS M/z(−) 383.39, 385.38 (M − H$^−$)<br>$^1$H-NMR (DMSO-d$_6$) 0.83 (1H, m), 1.40 to 1.66 (4H, m), 1.72 to 1.87 (2H, m), 2.10 to 2.18 (5H, m), 2.27 to 2.40 (4H, m), 2.64 (1H, d), 2.77 (1H, d), 3.44 (4H, t), 7.10 (1H, t), 7.59 (2H, d), 8.81 (1H, s) | A1 |
| 42 | 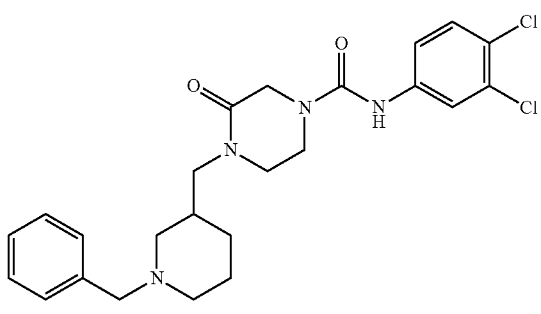 [SMILES: O=C1CN(C(=O)Nc2ccc(Cl)c(Cl)c2)CCN1CC1CCCN(Cc2ccccc2)C1] | 4-[(1-benzylpiperidin-3-yl)methyl]-N-(3,4-dichlorophenyl)-3-oxopiperazine-1-carboxamide<br>LCMS M/z(+) 475 (M + H$^+$)<br>$^1$H-NMR (CDCl$_3$) 1.00-1.16 (1H, m), 1.45-1.74 (3H, m), 1.80-1.91 (1H, m), 1.96-2.12 (2H, m), 2.58-2.75 (2H, m), 3.25-3.54 (6H, m), 3.58-3.72 (2H, m), 4.15 (2H, s), 7.01 (1H, s), 7.19-7.37 (7H, m), 7.70 (1H, t) | A5 |
| 43 | 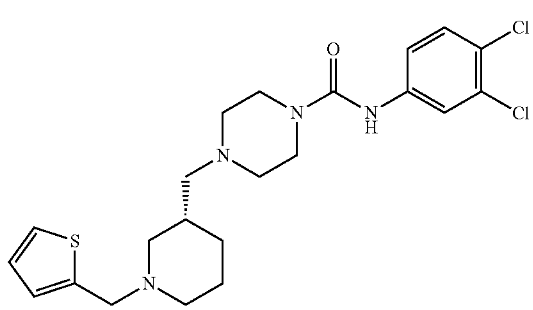 [SMILES: O=C(Nc1ccc(Cl)c(Cl)c1)N1CCN(C[C@@H]2CCCN(Cc3cccs3)C2)CC1] | N-(3,4-dichlorophenyl)-4-{[(3S)-1-(2-thienylmethyl)piperidin-3-yl]methyl}-piperazine-1-carboxamide<br>LCMS M/z(+) 467 (M + H$^+$) | C1 |

-continued

Examples

| Example No. | Structure | Characterisation Data | Chemistry Route |
|---|---|---|---|
| 44 | 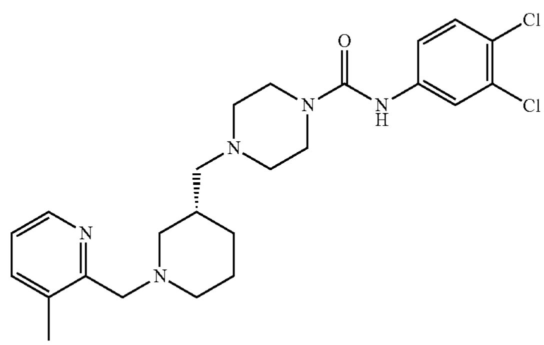 [SMILES: Cc1cccnc1CN1CCC[C@@H](CN2CCN(C(=O)Nc3ccc(Cl)c(Cl)c3)CC2)C1] | N-(3,4-dichlorophenyl)-4-({(3S)-1-[(3-methylpyridin-2-yl)methyl]piperidin-3-yl}methyl)piperazine-1-carboxamide<br>LCMS M/z(+) 476 (M + H$^+$) | C1 |
| 45 | 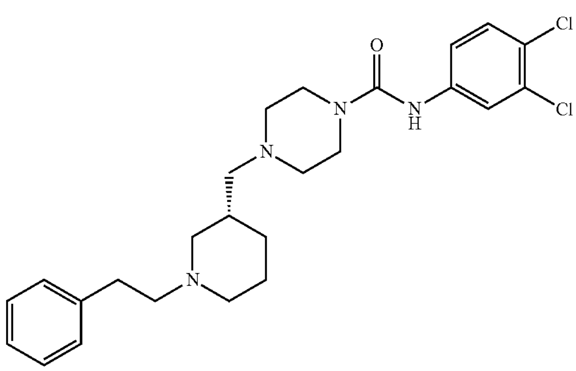 [SMILES: O=C(Nc1ccc(Cl)c(Cl)c1)N1CCN(C[C@@H]2CCCN(CCc3ccccc3)C2)CC1] | N-(3,4-dichlorophenyl)-4-{[(3R)-1-(2-phenylethyl)piperidin-3-yl]methyl}piperazine-1-carboxamide<br>LCMS M/z(+) 475.27, 477.23 (M + H$^+$)<br>LCMS M/z(−) 473.26, 475.26 (M − H$^−$)<br>$^1$H-NMR (DMSO-d$_6$) 0.92 (1H, m), 1.49 (1H, m), 1.66 (2H, t), 1.79 (1H, s), 2.03 (1H, s), 2.16 (2H, m), 2.28 to 2.39 (4H, m), 2.75 (2H, t), 2.89 (1H, m), 3.17 (4H, d), 3.44 (4H, t), 7.16 to 7.30 (5H, m), 7.46 (2H, t), 7.84 (1H, s), 8.77 (1H, s) | C1 |
| 46 | 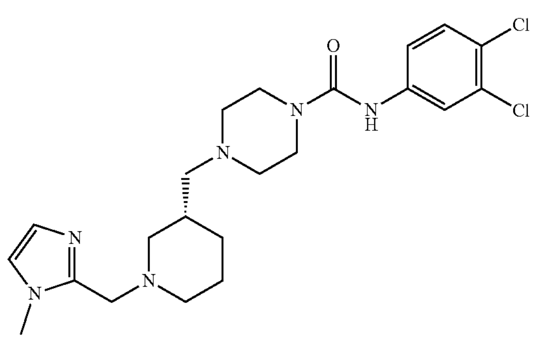 [SMILES: Cn1ccnc1CN1CCC[C@@H](CN2CCN(C(=O)Nc3ccc(Cl)c(Cl)c3)CC2)C1] | N-(3,4-dichlorophenyl)-4-({(3S)-1-[(1-methyl-1H-imidazol-2-yl)methyl]piperidin-3-yl}methyl)piperazine-1-carboxamide<br>LCMS M/z(+) 465 (M + H$^+$) | C1 |
| 47 | 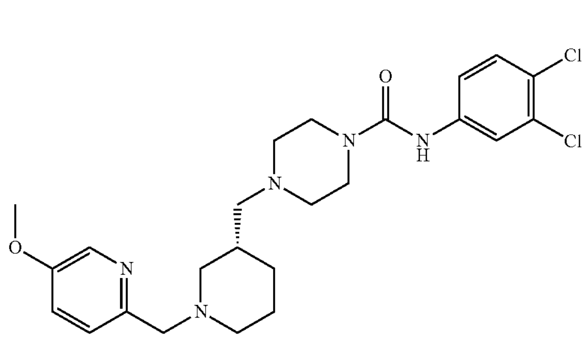 [SMILES: COc1ccc(CN2CCC[C@@H](CN3CCN(C(=O)Nc4ccc(Cl)c(Cl)c4)CC3)C2)nc1] | N-(3,4-dichlorophenyl)-4-{[(3R)-1-(4-methoxybenzyl)piperidin-3-yl]methyl}piperazine-1-carboxamide<br>LCMS M/z(+) 491 (M + H$^+$) | C1 |

-continued

Examples

| Example No. | Structure | Characterisation Data | Chemistry Route |
|---|---|---|---|
| 48 | 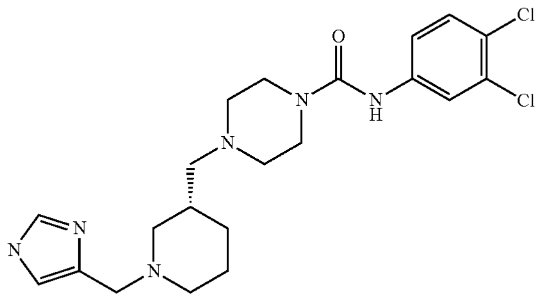 [SMILES: O=C(Nc1ccc(Cl)c(Cl)c1)N1CCN(C[C@@H]2CCCN(Cc3c[nH]cn3)C2)CC1] | N-(3,4-dichlorophenyl)-4-{[(3S)-1-(1H-imidazol-4-ylmethyl)piperidin-3-yl]methyl}piperazine-1-carboxamide<br>LCMS M/z(+) 451 (M + H⁺) | C1 |
| 49 | 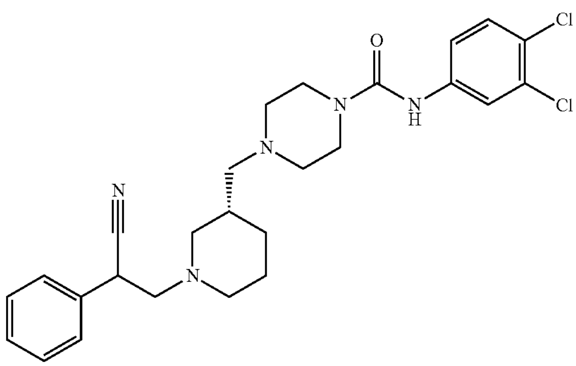 [SMILES: N#CC(CN1CCC[C@@H](CN2CCN(C(=O)Nc3ccc(Cl)c(Cl)c3)CC2)C1)c1ccccc1] | 4-{[(3R)-1-(2-cyano-2-phenylethyl)piperidin-3-yl]methyl}-N-(3,4-dichlorophenyl)piperazine-1-carboxamide<br>LCMS M/z(+) 501 (M + H⁺) | C1 |
| 50 | 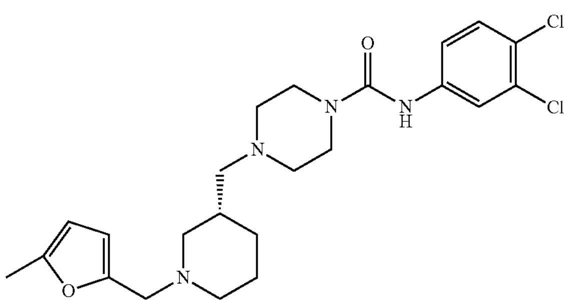 [SMILES: Cc1ccc(CN2CCC[C@@H](CN3CCN(C(=O)Nc4ccc(Cl)c(Cl)c4)CC3)C2)o1] | N-(3,4-dichlorophenyl)-4-({(3S)-1-[(5-methyl-2-furyl)methyl]piperidin-3-yl}methyl)piperazine-1-carboxamide<br>LCMS M/z(+) 465 (M + H⁺) | C1 |
| 51 | 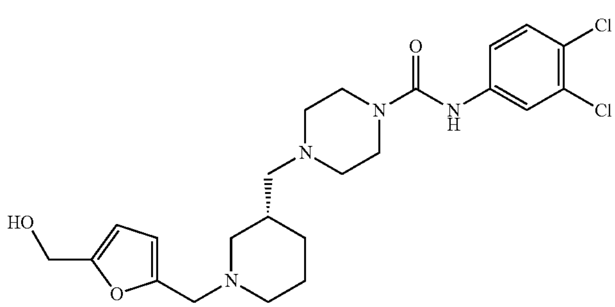 [SMILES: O=C(Nc1ccc(Cl)c(Cl)c1)N1CCN(C[C@@H]2CCCN(Cc3ccc(CO)o3)C2)CC1] | N-(3,4-dichlorophenyl)-4-[(3S)-1-{[5-(hydroxymethyl)-2-furyl]methyl}piperidin-3-yl)methyl]piperazine-1-carboxamide<br>LCMS M/z(+) 481 (M + H⁺) | C1 |

-continued

Examples

| Example No. | Structure | Characterisation Data | Chemistry Route |
|---|---|---|---|
| 52 | 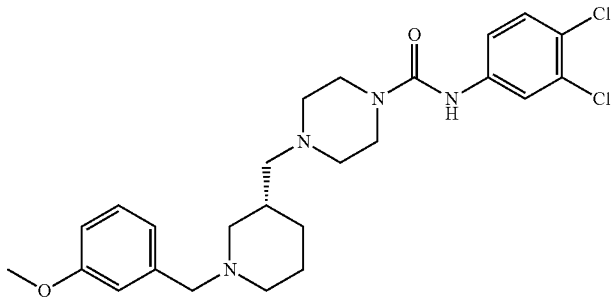 [SMILES: COc1cccc(CN2CCC[C@@H](CN3CCN(C(=O)Nc4ccc(Cl)c(Cl)c4)CC3)C2)c1] | N-(3,4-dichlorophenyl)-4-{[((3R)-1-(3-methoxybenzyl)piperidin-3-yl]methyl}piperazine-1-carboxamide<br>LCMS M/z(+) 491 (M + H$^+$) | C1 |
| 53 | 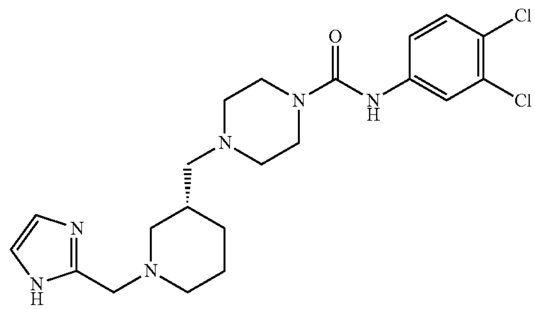 [SMILES: O=C(Nc1ccc(Cl)c(Cl)c1)N1CCN(C[C@@H]2CCCN(Cc3ncc[nH]3)C2)CC1] | N-(3,4-dichlorophenyl)-4-{[(3S)-1-(1H-imidazol-2-ylmethyl)piperidin-3-yl]methyl}piperazine-1-carboxamide<br>LCMS M/z(+) 451 (M + H$^+$) | C1 |
| 54 | 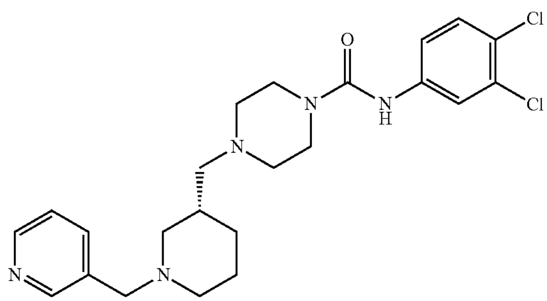 [SMILES: O=C(Nc1ccc(Cl)c(Cl)c1)N1CCN(C[C@@H]2CCCN(Cc3cccnc3)C2)CC1] | N-(3,4-dichlorophenyl)-4-{[(3R)-1-(pyridin-3-ylmethyl)piperidin-3-yl]methyl}piperazine-1-carboxamide<br>LCMS M/z(+) 462 (M + H$^+$) | C1 |
| 55 | 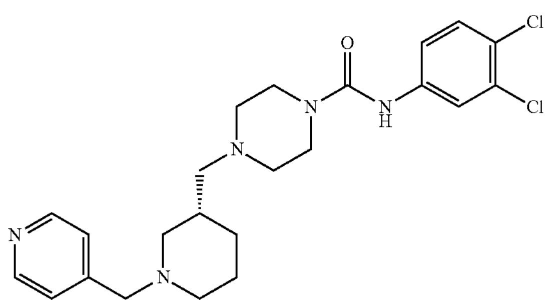 | N-(3,4-dichlorophenyl)-4-{[(3R)-1-(pyridin-4-ylmethyl)piperidin-3-yl]methyl}piperazine-1-carboxamide<br>LCMS M/z(+) 462 (M + H$^+$) | C1 |
| 56 | 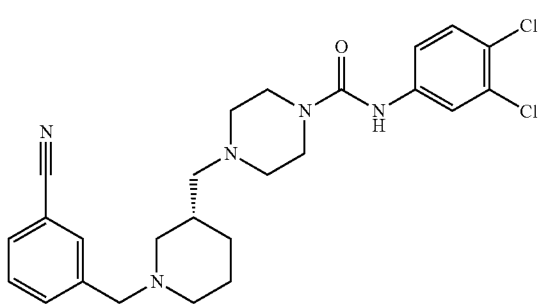 [SMILES: N#Cc1cccc(CN2CCC[C@@H](CN3CCN(C(=O)Nc4ccc(Cl)c(Cl)c4)CC3)C2)c1] | 4-{[(3R)-1-(3-cyanobenzyl)piperidin-3-yl]methyl}-N-(3,4-dichlorophenyl)piperazine-1-carboxamide<br>LCMS M/z(+) 486 (M + H$^+$) | C1 |

-continued

Examples

| Example No. | Structure | Characterisation Data | Chemistry Route |
|---|---|---|---|
| 57 | 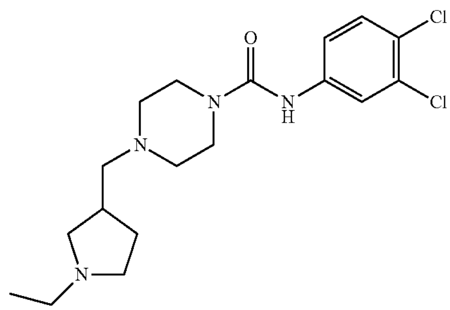 [SMILES: CCN1CCC(CN2CCN(C(=O)Nc3ccc(Cl)c(Cl)c3)CC2)C1] | N-(3,4-dichlorophenyl)-4-[(1-ethylpyrrolidin-3-yl)methyl]piperazine-1-carboxamide<br>LCMS M/z(+) 385.29, 387.27 (M + H$^+$)<br>LCMS M/z(−) 383.36, 385.31 (M − H$^-$)<br>$^1$H-NMR (DMSO-d$_6$) 1.13 (3H, t), 1.52 (1H, m), 1.97 (1H, m), 2.27 to 2.45 (7H, m), 2.82 (2H, s), 2.90 (1H, s), 3.03 (1H, s), 3.44 (4H, t), 7.47 (2H, m), 7.85 (1H, s), 8.79 (1H, s) | C1 |
| 58 | 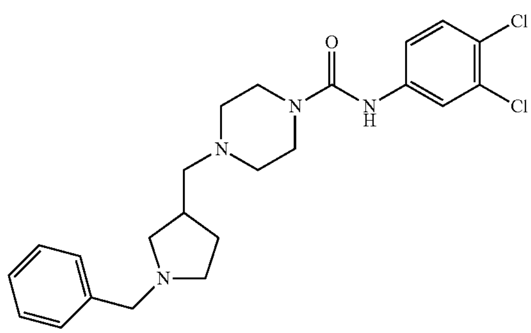 [SMILES: O=C(Nc1ccc(Cl)c(Cl)c1)N1CCN(CC2CCN(Cc3ccccc3)C2)CC1] | 4-[(1-benzylpyrrolidin-3-yl)methyl]-N-(3,4-dichlorophenyl)piperazine-1-carboxamide LCMS M/z(+) 447.26, 449.24 (M + H$^+$)<br>LCMS M/z(−) 445.26, 447.27 (M − H$^-$)<br>$^1$H-NMR (DMSO-d$_6$) 1.25 (6H, s), 1.49 (1H, s), 1.95 (1H, s), 2.26 to 2.43 (7H, m), 3.15 (1H, s), 3.42 (4H, t), 3.61 (1H, s), 3.81 (1H, s), 7.30 to 7.38 (5H, m), 7.46 (2H, m), 7.83 (1H, d), 8.77 (1H, s) | C1 |
| 59 | 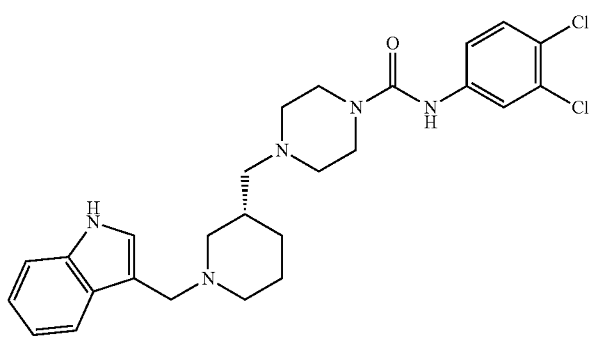 [SMILES: O=C(Nc1ccc(Cl)c(Cl)c1)N1CCN(C[C@@H]2CCCN(Cc3c[nH]c4ccccc34)C2)CC1] | N-(3,4-dichlorophenyl)-4-{[(3R)-1-(1H-indol-3-ylmethyl)-piperidin-3-yl]methyl}-piperazine-1-carboxamide<br>LCMS M/z(−) 498.25, 500.24 (M − H$^-$)<br>$^1$H-NMR (DMSO-d$_6$) 0.96 (1H, s), 1.40 to 1.70 (6H, m), 2.15 (2H, s), 2.30 (4H, m), 3.24 to 3.36 (8H, m), 6.98 (1H, t), 7.08 (1H, t), 7.22 (1H, d), 7.32 (1H, d), 7.43 (2H, d), 7.62 (1H, d), 7.80 (1H, s), 8.70 (1H, s), 10.90 (1H, s) | C1 |
| 60 | 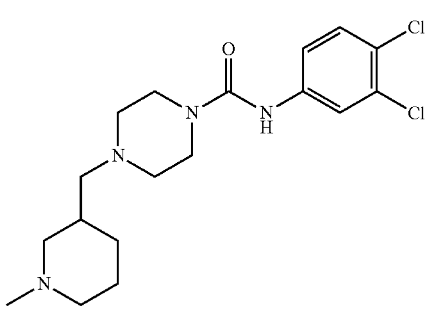 [SMILES: CN1CCCC(CN2CCN(C(=O)Nc3ccc(Cl)c(Cl)c3)CC2)C1] | 3,4-dichlorophenyl 4-[(1-methylpiperidin-3-yl)methyl]piperazine-1-carboxylate<br>LCMS M/z(+) 386.30, 388.28 (M + H$^+$)<br>LCMS M/z(−) 386.28, 388.26 (M − H$^-$)<br>$^1$H-NMR (DMSO-d$_6$) 1.04 (1H, m), 1.72 (3H, q), 2.07 (1H, s), 2.33 (2H, m), 2.36 (2H, m), 2.46 (2H, m), 2.60 (3H, s), 3.18 (2H, t), 3.44 (2H, s), 3.57 (2H, s), 7.20 (1H, dd), 7.54 (1H, d), 7.66 (1H, d) | A4 |

Examples

| Example No. | Structure | Characterisation Data | Chemistry Route |
|---|---|---|---|
| 61 | 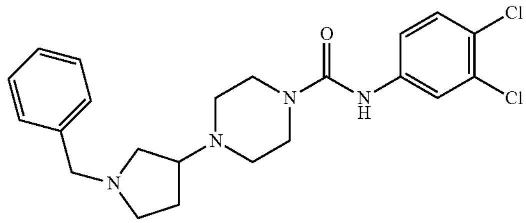 [SMILES: O=C(Nc1ccc(Cl)c(Cl)c1)N1CCN(C2CCN(Cc3ccccc3)C2)CC1] | 4-(1-benzylpyrrolidin-3-yl)-N-(3,4-dichlorophenyl)piperazine-1-carboxamide LCMS M/z(+) 433.32, 435.30 (M + H$^+$) LCMS M/z(−) 431.31, 433.32 (M − H$^-$) $^1$H-NMR (DMSO-d$_6$) 1.71 (1H, s), 1.92 (1H, s), 2.34 to 2.47 (5H, m), 3.30 (4H, s), 3.42 (4H, t), 3.63 (2H, s) 7.28 (1H, m), 7.33 (4H, m), 7.46 (2H, m), 7.83 (1H, d), 8.76 (1H, s) | C1 |
| 62 | 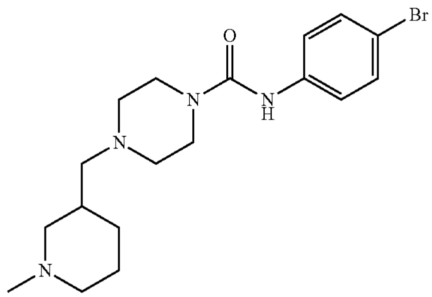 [SMILES: CN1CCCC(CN2CCN(C(=O)Nc3ccc(Br)cc3)CC2)C1] | N-(4-bromophenyl)-4-[(1-methylpiperidin-3-yl)methyl]piperazine-1-carboxamide LCMS M/z(+) 395.44, 397.44 (M + H$^+$) $^1$H-NMR (DMSO-d$_6$) 0.83 (1H, m), 1.41 to 1.66 (4H, m), 1.72 to 1.86 (2H, m), 2.10 to 2.18 (5H, m), 2.27 to 2.39 (4H, m), 2.63 (1H, d), 2.77 (1H, d), 3.43 (4H, t), 7.38 to 7.46 (4H, dd), 8.59 (1H, s) | A1 |
| 63 | 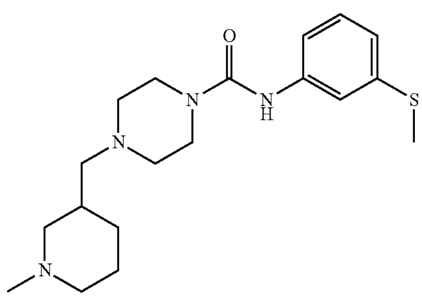 | 4-[(1-methylpiperidin-3-yl)methyl]-N-[3-(methylthio)phenyl]piperazine-1-carboxamide LCMS M/z(+) 363.55 (M + H$^+$) LCMS M/z(−) 361.67 (M − H$^-$) $^1$H-NMR (DMSO-d$_6$) 0.84 (1H, m), 1.41 to 1.66 (4H, m), 1.75 to 1.85 (2H, m), 2.10 to 2.18 (5H, m), 2.26 to 2.39 (4H, m), 2.44 (3H, s), 2.64 (1H, d), 2.77 (1H, d), 3.43 (4H, t), 6.82 (1H, m), 7.16 (1H, t), 7.27 (1H, m), 7.43 (1H, t), 8.48 (1H, s) | A1 |
| 64 | 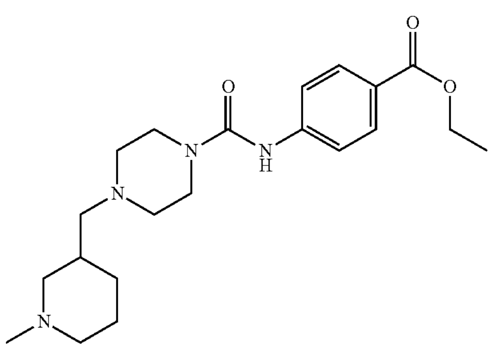 [SMILES: CCOC(=O)c1ccc(NC(=O)N2CCN(CC3CCCN(C)C3)CC2)cc1] | Ethyl 4-[({4-[(1-methylpiperidin-3-yl)methyl]piperazin-1-yl}carbonyl)amino]benzoate LCMS M/z(+) 389.57 (M + H$^+$) $^1$H-NMR (DMSO-d$_6$) 0.84 (1H, m), 1.31 (3H, t), 1.40 to 1.66 (4H, m), 1.73 to 1.85 (2H, m), 2.08 to 2.19 (5H, m), 2.28 to 2.40 (4H, m), 2.63 (1H, d), 2.76 (1H, d), 3.46 (4H, t), 4.27 (2H, q), 7.61 (2H, d), 7.83 (2H, d), 8.86 (1H, s) | A1 |
| 65 | 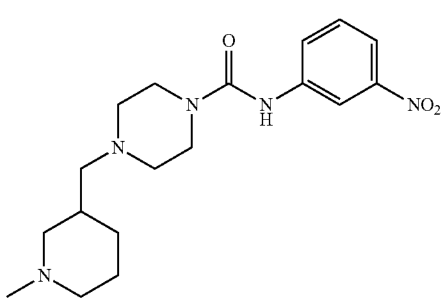 [SMILES: CN1CCCC(CN2CCN(C(=O)Nc3cccc([N+](=O)[O-])c3)CC2)C1] | 4-[(1-methylpiperidin-3-yl)methyl]-N-(3-nitrophenyl)piperazine-1-carboxamide LCMS M/z(+) 362.55 (M + H$^+$) $^1$H-NMR (DMSO-d$_6$) 0.84 (1H, m), 1.41 to 1.67 (4H, m), 1.75 to 1.85 (2H, m), 2.11 to 2.19 (5H, m), 2.29 to 2.41 (4H, m), 2.63 (1H, d), 2.77 (1H, d), 3.47 (4H, t), 7.52 (1H, t), 7.78 (1H, m), 7.90 (1H, m), 8.48 (1H, t), 8.99 (1H, s) | A1 |

-continued

Examples

| Example No. | Structure | Characterisation Data | Chemistry Route |
|---|---|---|---|
| 66 | 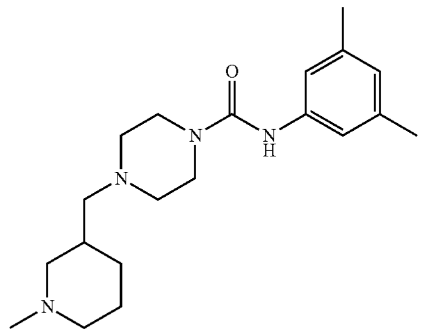 | N-(3,5-dimethylphenyl)-4-[(1-methylpiperidin-3-yl)methyl]piperazine-1-carboxamide<br>LCMS M/z(+) 345.59 (M + H$^+$)<br>$^1$H-NMR (DMSO-d$_6$) 0.83 (1H, m), 1.41 to 1.66 (4H, m), 1.72 to 1.85 (2H, m), 2.09 to 2.16 (5H, m), 2.20 (6H, s), 2.26 to 2.38 (4H, m), 2.63 (1H, m), 2.76 (1H, d), 3.41 (4H, t), 6.57 (1H, s), 7.08 (2H, s), 8.30 (1H, s) | A1 |
| 67 | 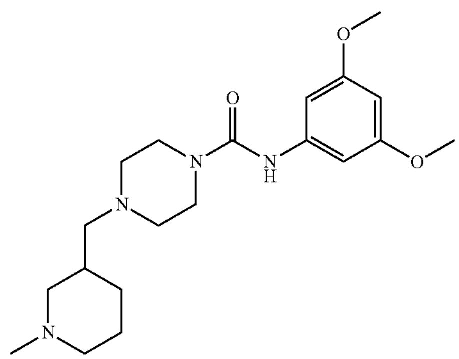 | N-(3,5-dimethoxyphenyl)-4-[(1-methylpiperidin-3-yl)methyl]piperazine-1-carboxamide<br>LCMS M/z(+) 377.42 (M + H$^+$)<br>$^1$H-NMR (DMSO-d$_6$) 0.92 (1H, m), 1.48 to 1.75 (4H, m), 1.81 to 1.95 (2H, m), 2.18 to 2.26 (5H, m), 2.35 to 2.47 (4H, m), 2.74 (1H, d), 2.86 (1H, d), 3.50 (4H, t), 3.77 (6H, s), 6.17 (1H, t), 6.85 (2H, d), 8.48 (1H, s) | A1 |
| 68 | 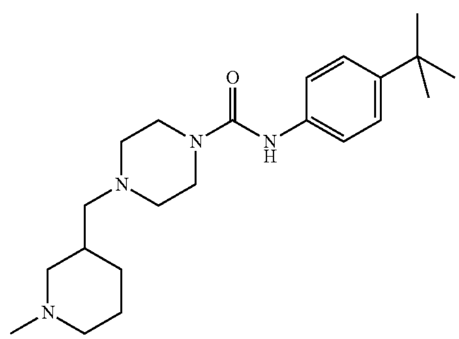 [SMILES: CN1CCCC(CN2CCN(C(=O)Nc3ccc(C(C)(C)C)cc3)CC2)C1] | N-(4-tert-butylphenyl)-4[(1-methylpiperidin-3-yl)methyl]piperazine-1-carboxamide<br>LCMS M/z(+) 373.46 (M + H$^+$)<br>$^1$H-NMR (DMSO-d$_6$) 0.88 (1H, m), 1.29 (9H, s), 1.44 to 1.70 (4H, m), 1.77 to 1.98 (2H, m), 2.13 to 2.24 (5H, m), 2.30 to 2.42 (4H, m), 2.69 (1H, m), 2.82 (1H, d), 3.45 (4H, t), 7.26 to 7.40 (4H, dd), 8.41 (1H, s) | A1 |
| 69 | 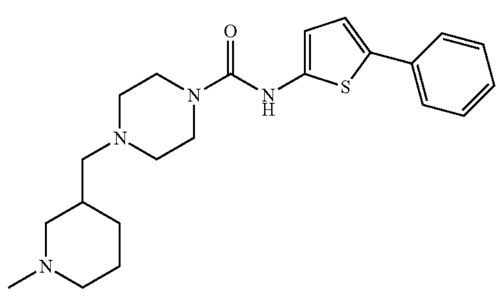 [SMILES: CN1CCCC(CN2CCN(C(=O)Nc3ccc(-c4ccccc4)s3)CC2)C1] | 4-[(1-methylpiperidin-3-yl)methyl]-N-(5-phenyl-2-thienyl)piperazine-1-carboxamide<br>LCMS M/z(+) 399.37 (M + H$^+$)<br>LCMS M/z(−) 397.40 (M − H$^−$)<br>$^1$H-NMR (DMSO-d$_6$) 0.85 (1H, m), 1.41 to 1.67 (4H, m), 1.74 to 1.86 (2H, m), 2.11 to 2.19 (5H, m), 2.29 to 2.41 (4H, m), 2.65 (1H, m), 2.77 (1H, d), 3.45 (4H, t), 6.59 (1H, d), 7.17 (1H, d), 7.19 (1H, t), 7.35 (2H, t), 7.52 (2H, dd), 9.74 (1H, s) | A1 |

-continued

Examples

| Example No. | Structure | Characterisation Data | Chemistry Route |
|---|---|---|---|
| 70 | 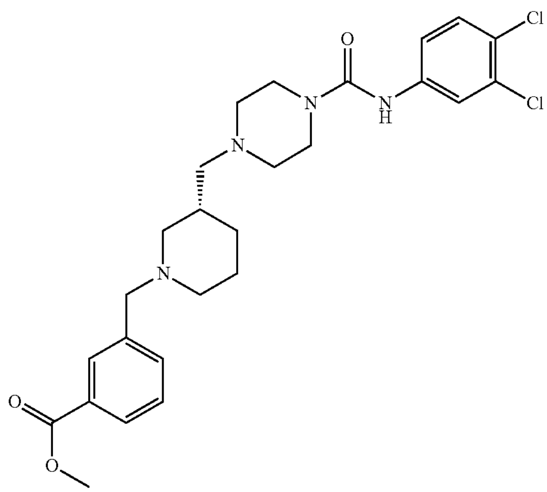 [SMILES: COC(=O)c1cccc(CN2CCC[C@@H](CN3CCN(C(=O)Nc4ccc(Cl)c(Cl)c4)CC3)C2)c1] | Methyl 3-({(3R)-3-[(4-{[(3,4-dichlorophenyl)amino]carbonyl}piperazin-1-yl)methyl]piperidin-1-yl}methyl)benzoate<br>LCMS M/z(+) 519.23, 521.32 (M + H$^+$).<br>$^1$H-NMR (DMSO-d$_6$) 0.70 (2H, m), 1.42 to 1.70 (6H, m), 2.31 (4H, m), 3.38 (4H, m), 3.47 to 3.58 (4H, t), 3.86 (3H, s), 7.50 (1H, s), 7.48 (2H, d), 7.57 (2H, d), 7.90 (1H, s), 8.71 (1H, s). | C1 |
| 71 | 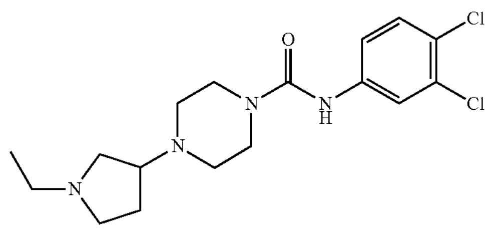 [SMILES: CCN1CCC(N2CCN(C(=O)Nc3ccc(Cl)c(Cl)c3)CC2)C1] | N-(3,4-dichlorophenyl)-4-(1-ethylpyrrolidin-3-yl)piperazine-1-carboxamide<br>LCMS M/z(+) 371.30, 373.28 (M + H$^+$)<br>LCMS M/z(−) 369.31, 371.30 (M − H$^−$)<br>$^1$H-NMR (DMSO-d$_6$) 1.01 (3H, t), 1.63 (1H, m), 1.85 (1H, m), 2.29 to 2.46 (8H, m), 2.56 (1H, q), 2.69 (1H, t), 2.81 (1H, m), 3.43 (4H, t), 7.46 (2H, m), 7.84 (1H, s), 8.75 (1H, s) | C1 |
| 72 | 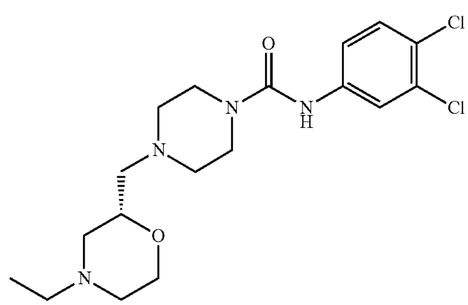 | N-(3,4-dichlorophenyl)-4-{[(2S)-4-ethylmorpholin-2-yl]methyl}piperazine-1-carboxamide<br>LCMS M/z(+) 401.24, 403.19 (M + H$^+$)<br>LCMS M/z(−) 399.24, 401.25 (M − H$^−$)<br>$^1$H-NMR (DMSO-d$_6$) 1.00 (3H, t), 1.70 (1H, m), 1.94 (1H, m), 2.27 to 2.48 (8H, m), 2.67 (1H, m), 2.79 (1H, m), 3.37 to 3.51 (5H, m), 3.59 (1H, m), 3.75 (1H, m), 7.43 to 7.48 (2H, m), 7.84 (1H, m), 8.75 (1H, s) | C1 |
| 73 | 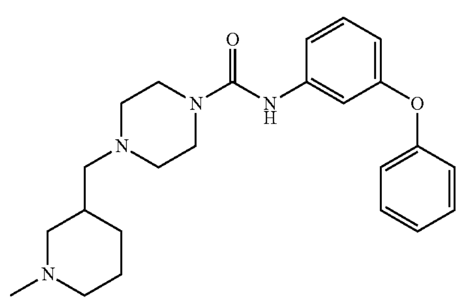 [SMILES: CN1CCCC(CN2CCN(C(=O)Nc3cccc(Oc4ccccc4)c3)CC2)C1] | 4-[(1-methylpiperidin-3-yl)methyl]-N-(3-phenoxyphenyl)piperazine-1-carboxamide<br>LCMS M/z(+) 409.38 (M + H$^+$)<br>$^1$H-NMR (DMSO-d$_6$) 0.91 (1H, m), 1.55 (1H, m), 1.64 to 1.74 (3H, m), 1.86 (1H, m), 1.95 (1H, m), 2.17 to 2.27 (5H, m), 2.33 to 2.46 (4H, m), 2.75 (1H, d), 2.87 (1H, d), 3.49 (4H, t), 6.67 (1H, m), 7.09 (2H, d), 7.21 (1H, t), 7.28 to 7.35 (3H, m), 7.47 (2H, m), 8.63 (1H, s) | A1 |

| Example No. | Structure | Characterisation Data | Chemistry Route |
|---|---|---|---|
| 74 | 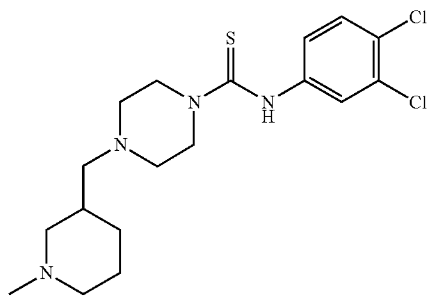 | N-(3,4-dichlorophenyl)-4-[(1-methylpiperidin-3-yl)methyl]piperazine-1-carbothioamide<br>LCMS M/z(+) 401.20, 403.17 (M + H⁺)<br>LCMS M/z(−) 399.23, 401.22 (M − H⁻)<br>¹H-NMR (DMSO-d₆) 0.85 (1H, m), 1.41 to 1.67 (4H, m), 1.73 to 1.87 (2H, m), 2.12 to 2.21 (5H, m), 2.34 to 2.46 (4H, m), 2.65 (1H, d), 2.78 (1H, d), 3.89 (4H, t), 7.33 (1H, dd), 7.53 (1H, d), 7.62 (1H, d), 9.43 (1H, s) | A2 |
| 75 | 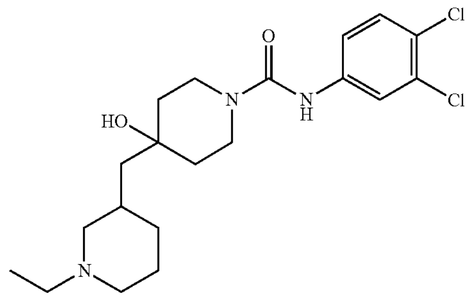 [SMILES: CCN1CCCC(CC2(O)CCN(C(=O)Nc3ccc(Cl)c(Cl)c3)CC2)C1] | N-(3,4-dichlorophenyl)-4-[(1-ethylpiperidin-3-yl)methyl]-4-hydroxypiperidine-1-carboxamide<br>LCMS M/z(+) 414 (M + H⁺)<br>¹H-NMR (CDCl₃) 0.80-0.90 (1H, m), 0.96-1.98 (13H, m), 1.07 (3H, t), 2.30-2.45 (2H, m), 2.74-2.87 (2H, m), 3.27-3.37 (2H, m), 3.73-3.82 (2H, m), 6.38 (1H, s), 7.19 (1H, dd), 7.32 (1H, d), 7.59 (1H, d) | A6 |
| 76 | 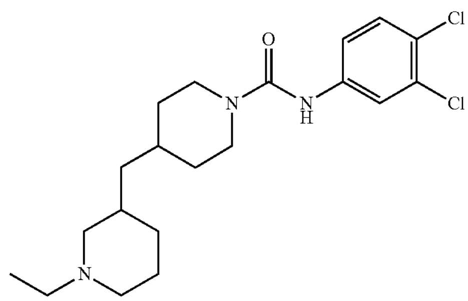 | N-(3,4-dichlorophenyl)-4-[(1-ethylpiperidin-3-yl)methyl]piperidine-1-carboxamide<br>LCMS M/z(+) 398 (M + H⁺)<br>¹H-NMR (CDCl₃) 0.85 (1H, dq), 1.08 (3H, t), 1.11-1.23 (1H, m), 1.14 (2H, t), 1.50-1.85 (10H, m), 3.30-2.46 (2H, m), 2.80-2.94 (4H, m), 4.01 (2H, d), 6.36 (1H, s), 7.19 (1H, dd), 7.31 (1H, d), 7.59 (1H, d) | D1 |
| 77 | 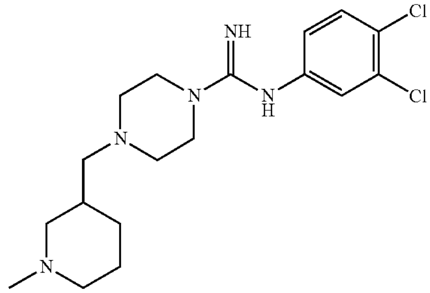 [SMILES: CN1CCCC(CN2CCN(C(=N)Nc3ccc(Cl)c(Cl)c3)CC2)C1] | N-(3,4-dichlorophenyl)-4-[(1-methylpiperidin-3-yl)methyl]piperazine-1-carboximidamide<br>LCMS M/z(+) 385.30, 387.27 (M + H⁺)<br>LCMS M/z(−) 383.31, 385.29 (M − H⁻)<br>¹H-NMR (DMSO-d₆) 0.83 (1H, m), 1.40 to 1.66 (4H, m), 1.72 to 1.86 (2H, m), 2.10 to 2.18 (5H, m), 2.27 to 2.39 (4H, m), 2.63 (1H, d), 2.76 (1H, d), 3.44 (4H, t), 7.46 (2H, t), 7.84 (1H, s), 8.76 (1H, s) | B1 |

-continued

Examples

| Example No. | Structure | Characterisation Data | Chemistry Route |
|---|---|---|---|
| 78 | 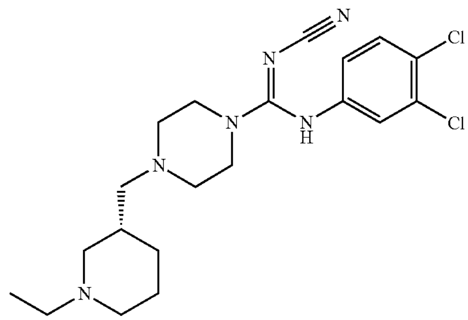 [SMILES: CCN1CCC[C@@H](CN2CCN(/C(=N/C#N)Nc3ccc(Cl)c(Cl)c3)CC2)C1] | N'-cyano-N-(3,4-dichlorophenyl)-4-{[(3R)-1-ethylpiperidin-3-yl]methyl}piperazine-1-carboximidamide<br>LCMS M/z(+) 423.29, 425.23 (M + H$^+$)<br>LCMS M/z(−) 421.29, 423.27 (M − H$^-$)<br>$^1$H-NMR (DMSO-d$_6$) 0.83 (1H, m), 0.99 (3H, t), 1.43 (1H, q), 1.59 to 1.80 (4H, m), 1.88 (1H, t), 2.12 to 2.20 (2H, m), 2.25 to 2.45 (6H, m), 2.74 to 2.90 (2H, m), 3.50 (4H, t), 7.05 (1H, dd), 7.29 (1H, d), 7.55 (1H, d), 9.49 (1H, s) | A3 |
| 79 | 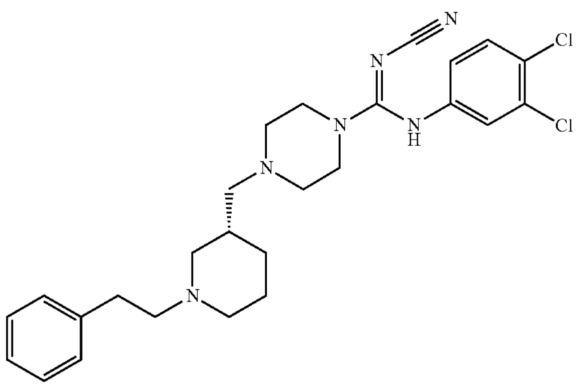 [SMILES: N#C/N=C(\Nc1ccc(Cl)c(Cl)c1)N1CCN(C[C@@H]2CCCN(CCc3ccccc3)C2)CC1] | N-cyano-N-(3,4-dichlorophenyl)-4-{[(3R)-1-(2-phenylethyl)piperidin-3-yl]methyl}piperazine-1-carboximidamide LCMS M/z(+) 499.28, 501.30 (M + H$^+$)<br>LCMS M/z(−) 497.26, 499.26 (M − H$^-$)<br>$^1$H-NMR (DMSO-d$_6$) 0.90 (1H, q), 1.44 (1H, q), 1.89 to 1.74 (4H, m), 1.99 (1H, t), 2.12 to 2.21 (2H, m), 2.34 to 2.43 (4H, m), 2.72 (2H, t), 2.80 (1H, d), 2.88 (1H, d), 3.30 (2H, m), 3.51 (4H, t), 7.05 (1H, dd), 7.17 (1H, t), 7.21 to 7.24 (2H, m), 7.25 to 7.30 (3H, m), 7.55 (1H, d), 9.51 (1H, s) | A3 |
| 80 | 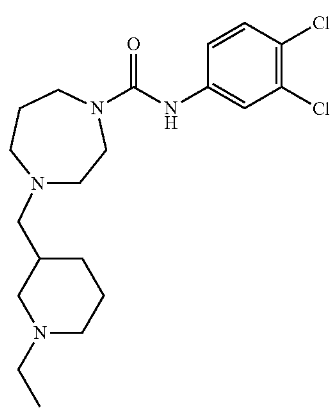 [SMILES: CCN1CCCC(CN2CCCN(C(=O)Nc3ccc(Cl)c(Cl)c3)CC2)C1] | N-(3,4-dichlorophenyl)-4[(1-ethylpiperidin-3-yl)methyl]-1,4-diazepane-1-carboxamide<br>LCMS M/z(+) 413 (M + H$^+$)<br>$^1$H-NMR (400.132 MHz, CDCl$_3$) 0.78-0.93 (1H, m), 1.07 (3H, t), 1.50-1.94 (8H, m), 2.23-2.47 (4H, m), 2.55-2.79 (4H, m), 2.89 (1H, d), 2.99 (1H, d), 3.48-3.64 (4H, m), 6.30 (1H, s), 7.22 (1H, dd), 7.31 (1H, d), 7.64 (1H, d) | A7 |
| 81 | 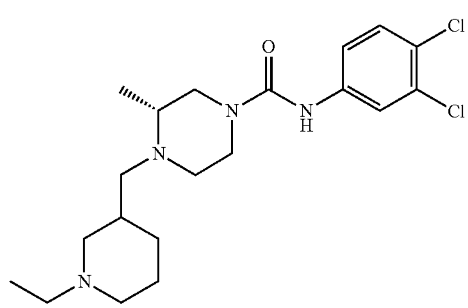 [SMILES: CCN1CCCC(CN2CCN(C(=O)Nc3ccc(Cl)c(Cl)c3)C[C@H]2C)C1] | (3R)-N-(3,4-dichlorophenyl)-4-[(1-ethylpiperidin-3-yl)methyl]-3-methylpiperazine-1-carboxamide<br>LCMS M/z(+) 413 (M + H$^+$)<br>$^1$H-NMR (400.132 MHz, CDCl$_3$) 0.80-0.95 (1H, m), 1.04 (1.5H, d), 1.06 (1.5H, d), 0.61-0.68 (3H, m), 1.43-1.76 (4H, m), 1.77-1.95 (2H, m), 1.97-2.05 (1H, m), 2.12-2.21 (0.5H, m), 2.23-2.32 (0.5H, m), 2.33-2.57 (4H, m), 2.78-3.04 (3.5H, m), 3.08-3.16 (0.5H, m), 3.19-3.34 (1H, m), 3.57-3.73 (2H, m), 6.33 (1H, s), 7.21 (1H, d), 7.33 (1H, d), 7.60 (1H, s) | A8 |

| Example No. | Structure | Characterisation Data | Chemistry Route |
|---|---|---|---|
| 82 | 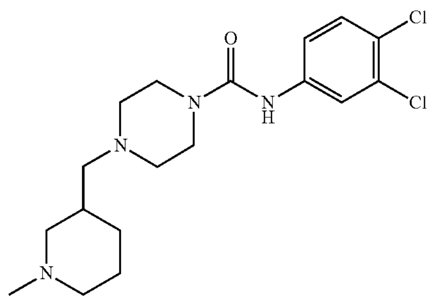 | N-(3,4-dichlorophenyl)-4-[(1-methylpiperidin-3-yl)methyl]piperazine-1-carboxamide<br>LCMS M/z(+) 385, 387 (M + H+)<br>1H-NMR (400.132 MHz, DMSO-d6) 0.80 (1H, q), 1.40 to 1.60 (6H, m), 1.80 (2H, m), 2.20 (5H, m), 2.40 (2H, m), 2.50 (1H, d), 2.80 (1H, d), 2.88 (1H, d), 3.50 (4H, t), 7.50 (2H, s), 7.80 (1H, s), 8.80 (1H, s) | A1 |
| 83 | 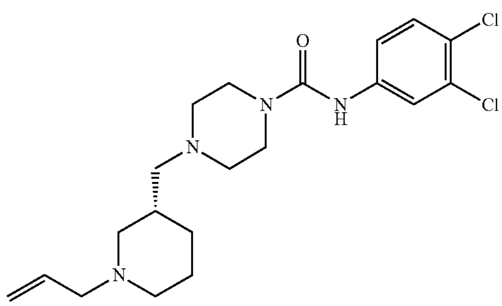 [SMILES: C=CCN1CCC[C@@H](CN2CCN(C(=O)Nc3ccc(Cl)c(Cl)c3)CC2)C1] | 4-{[(3R)-1-allylpiperidin-3-yl]methyl}-N-(3,4-dichlorophenyl)piperazine-1-carboxamide<br>LCMS M/z(+) 410.87 (M + H+)<br>1H NMR (400.132 MHz, DMSO-d6) 0.81-0.94 (m, 1H), 1.37-1.51 (m, 1H), 1.53-1.71 (m, 3H), 1.71-1.82 (m, 1H), 1.82-1.93 (m, 1H), 2.08-2.19 (m, 2H), 2.26-2.40 (m, 4H), 2.66-2.76 (m, 1H), 2.78-2.99 (m, 3H), 3.42 (t, 4H), 5.07-5.20 (m, 2H), 5.75-5.87 (m, 1H), 7.42-7.49 (m, 2H), 7.84 (s, 1H), 8.75 (s, 1H) | C1 |
| 84 | 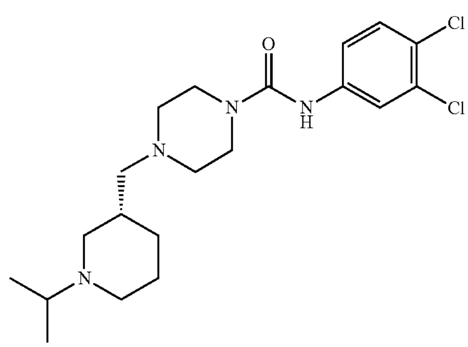 [SMILES: CC(C)N1CCC[C@@H](CN2CCN(C(=O)Nc3ccc(Cl)c(Cl)c3)CC2)C1] | N-(3,4-dichlorophenyl)-4-{[(3S)-1-isopropylpiperidin-3-yl]methyl}piperazine-1-carboxamide<br>LCMS M/z(+) 412.83 (M + H+)<br>1H NMR (400.132 MHz, DMSO-d6) 0.80-0.92 (m, 1H), 0.96 (t, 6H), 1.34-1.47 (m, 1H), 1.55-1.77 (m, 3H), 1.80 (t, 1H), 2.02-2.21 (m, 3H), 2.27-2.40 (m, 4H), 2.62-2.71 (m, 2H), 2.76 (d, 1H), 3.43 (t, 4H), 7.43-7.49 (m, 2H), 7.83-7.85 (m, 1H), 8.75 (s, 1H) | C1 |
| 85 | 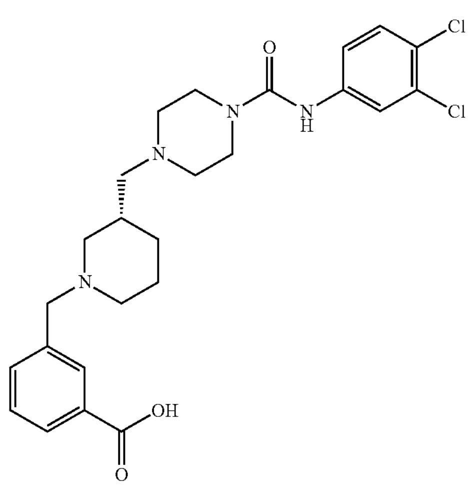 [SMILES: O=C(O)c1cccc(CN2CCC[C@@H](CN3CCN(C(=O)Nc4ccc(Cl)c(Cl)c4)CC3)C2)c1] | 3-({(3R)-3-[(4-{[(3,4-dichlorophenyl)amino]carbonyl}piperazin-1-yl)methyl]piperidin-1-yl}methyl)benzoic acid<br>LCMS M/z(+) 504.82 (M + H+)<br>1H NMR (400.132 MHz, DMSO-d6) 0.85-1.00 (m, 1H), 1.40-1.54 (m, 1H), 1.55-1.87 (m, 4H), 1.94-2.04 (m, 1H), 2.08-2.22 (m, 2H), 2.24-2.38 (m, 4H), 2.62-2.71 (m, 1H), 2.80 (d, 1H), 3.09-3.61 (m, 7H), 7.40-7.48 (m, 3H), 7.53 (d, 1H), 7.80-7.84 (m, 2H), 7.89 (s, 1H), 8.75 (s, 1H) | C1 |

-continued

Examples

| Example No. | Structure | Characterisation Data | Chemistry Route |
|---|---|---|---|
| 86 | 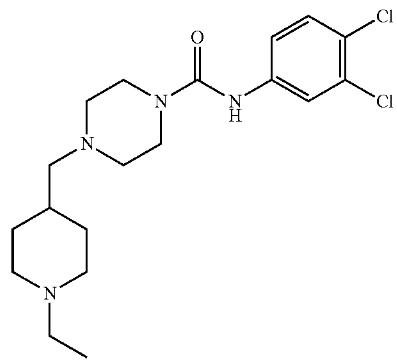 [SMILES: CCN1CCC(CN2CCN(C(=O)Nc3ccc(Cl)c(Cl)c3)CC2)CC1] | N-(3,4-dichlorophenyl)-4-[(1-ethylpiperidin-4-yl)methyl]piperazine-1-carboxamide<br>LCMS M/z(+) 398.88 (M + H$^+$)<br>$^1$H NMR (400.132 MHz, CDCl$_3$) 1.09 (t, 3H), 1.19-1.31 (m, 2H), 1.44-1.55 (m, 1H), 1.75 (d, 2H), 1.83-1.93 (m, 2H), 2.21 (d, 2H), 2.35-2.47 (m, 6H), 2.95 (d, 2H), 3.47 (t, 4H), 6.33 (s, 1H), 7.20 (dd, 1H), 7.32 (d, 1H), 7.59 (d, 1H) | C1 |
| 87 | 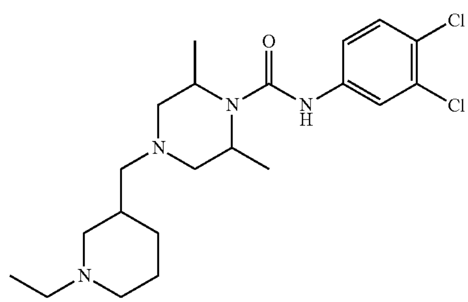 [SMILES: CCN1CCCC(CN2CC(C)N(C(=O)Nc3ccc(Cl)c(Cl)c3)C(C)C2)C1] | N-(3,4-dichlorophenyl)-4-[(1-ethylpiperidin-3-yl)methyl]-2,6-dimethylpiperazine-1-carboxamide<br>LCMS M/z(+) 426.88 (M + H$^+$)<br>$^1$H NMR (400.132 MHz, CDCl$_3$) 0.78-0.92 (m, 1H), 1.42-1.52 (m, 6H), 1.55 (t, 3H), 1.61-2.81 (m, 10H), 2.91-3.12 (m, 4H), 3.09 (q, 2H), 4.07-4.15 (m, 1H), 4.18-4.27 (m, 1H), 6.53 (s, 1H), 7.23-7.28 (m, 1H), 7.29-7.37 (m, 1H), 7.71 (d, 1H) | A8 |
| 88 | 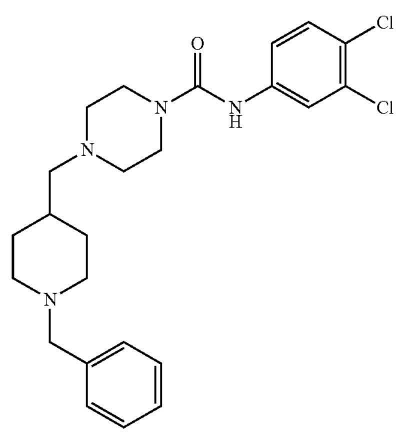 [SMILES: O=C(Nc1ccc(Cl)c(Cl)c1)N1CCN(CC2CCN(Cc3ccccc3)CC2)CC1] | 4-[(1-benzylpiperidin-4-yl)methyl]-N-(3,4-dichlorophenyl)piperazine-1-carboxamide<br>LCMS M/z(+) 460.85 (M + H$^+$)<br>$^1$H NMR (400.132 MHz, CDCl$_3$) 1.30-1.42 (m, 2H), 1.45-1.58 (m, 1H), 1.75 (d, 2H), 2.21 (d, 2H), 2.42 (t, 4H), 2.63-2.89 (m, 2H), 3.01 (d, 2H), 3.46 (t, 4H), 3.64 (s, 2H), 6.37 (s, 1H), 7.19 (dd, 1H), 7.27-7.35 (m, 6H), 7.58 (d, 1H) | C1 |
| 89 | 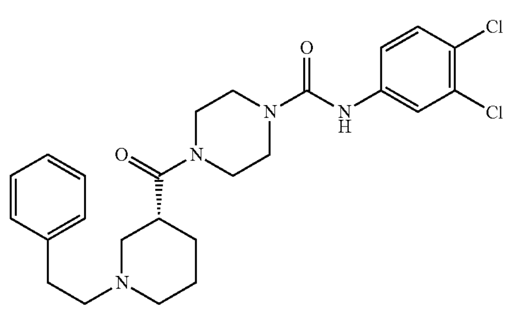 [SMILES: O=C(Nc1ccc(Cl)c(Cl)c1)N1CCN(C(=O)[C@@H]2CCCN(CCc3ccccc3)C2)CC1] | N-(3,4-dichlorophenyl)-4-{[(3R)-1-(2-phenylethyl)piperidin-3-yl]carbonyl}piperazine-1-carboxamide<br>LCMS M/z(+) 488.81 (M + H$^+$)<br>$^1$H NMR (400.132 MHz, CDCl$_3$) 1.48-1.87 (m, 4H), 2.02-2.12 (m, 1H), 2.30 (t, 1H), 2.61-2.70 (m, 2H), 2.77-2.89 (m, 3H), 3.02 (t, 2H), 3.42-3.76 (m, 8H), 6.40 (s, 1H), 7.16-7.36 (m, 7H), 7.59 (d, 1H) | C3 |

Examples

| Example No. | Structure | Characterisation Data | Chemistry Route |
|---|---|---|---|
| 90 | 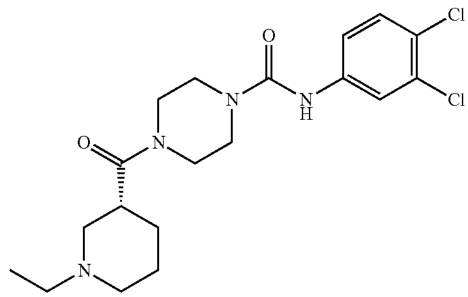 [SMILES: CCN1CCC[C@@H](C(=O)N2CCN(C(=O)Nc3ccc(Cl)c(Cl)c3)CC2)C1] | N-(3,4-dichlorophenyl)-4-{[(3R)-1-ethylpiperidin-3-yl]carbonyl}piperazine-1-carboxamide<br>LCMS M/z(+) 412.83 (M + H$^+$)<br>$^1$H NMR (400.132 MHz, CDCl$_3$) 1.10 (t, 3H), 1.46-1.59 (m, 1H), 1.59-1.73 (m, 1H), 1.74-1.85 (m, 2H), 1.88-1.99 (m, 1H), 2.18 (t, 1H), 2.47 (q, 2H), 2.78-2.89 (m, 1H), 2.96 (t, 2H), 3.40-3.77 (m, 8H), 6.52 (s, 1H), 7.22 (dd, 1H), 7.34 (d, 1H), 7.59 (d, 1H) | C3 |
| 91 | 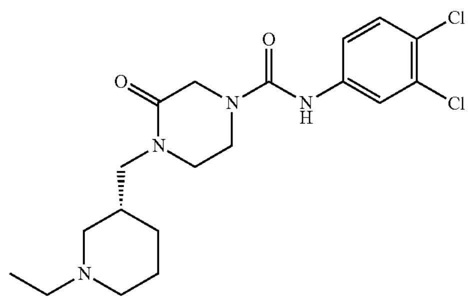 [SMILES: CCN1CCC[C@@H](CN2CCN(C(=O)Nc3ccc(Cl)c(Cl)c3)CC2=O)C1] | N-(3,4-dichlorophenyl)-4-{[(3R)-1-ethylpiperidin-3-yl]methyl}-3-oxopiperazine-1-carboxamide<br>LCMS M/z(+) 412.83 (M + H$^+$)<br>$^1$H NMR (400.132 MHz, CDCl$_3$) 0.93-1.09 (m, 1H), 1.05 (t, 3H), 1.47-1.61 (m, 1H), 1.61-1.77 (m, 3H), 1.81-1.91 (m, 1H), 1.94-2.06 (m, 1H), 2.29-2.45 (m, 2H), 2.74 (d, 1H), 2.84 (d, 1H), 3.36 (d, 2H), 3.44 (t, 2H), 3.70-3.89 (m, 2H), 4.21-4.33 (m, 2H), 7.33 (d, 1H), 7.39-7.45 (m, 2H), 7.73 (d, 1H) | A5 |
| 92 | 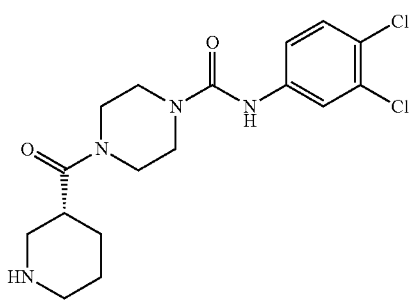 [SMILES: O=C(Nc1ccc(Cl)c(Cl)c1)N1CCN(C(=O)[C@@H]2CCCNC2)CC1] | N-(3,4-dichlorophenyl)-4-[(3R)-piperidin-3-ylcarbonyl]piperazine-1-carboxamide hydrochloride<br>LCMS M/z(+) 384.84 (M + H$^+$) (Free base)<br>$^1$H NMR (400.132 MHz, DMSO-d$_6$) 1.51-1.65 (m, 1H), 1.69-1.91 (m, 3H), 2.83-3.04 (m, 1H), 3.09-3.25 (m, 2H), 3.39-3.63 (m, 8H), 3.91 (s, 2H), 7.44-7.55 (m, 2H), 7.89 (d, 1H), 8.80-9.20 (m, 3H) | A5 |
| 93 | 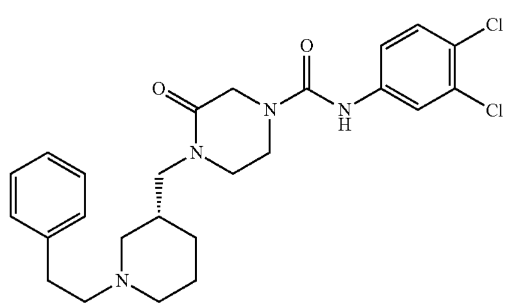 [SMILES: O=C1CN(C(=O)Nc2ccc(Cl)c(Cl)c2)CCN1C[C@@H]1CCCN(CCc2ccccc2)C1] | N-(3,4-dichlorophenyl)-3-oxo-4-{[(3R)-1-(2-phenylethyl)piperidin-3-yl]methyl}piperazine-1-carboxamide<br>LCMS M/z(+) 488.78 (M + H$^+$)<br>$^1$H NMR (400.132 MHz, CDCl$_3$) 0.96-1.10 (m, 1H), 1.48-1.78 (m, 3H), 1.79-1.92 (m, 1H), 1.95-2.12 (m, 2H), 2.48-2.65 (m, 2H), 2.69-2.93 (m, 4H), 3.28-3.45 (m, 4H), 3.67-3.84 (m, 2H), 4.23 (s, 2H), 7.13-7.43 (m, 8H), 7.72 (d, 1H) | A5 |

-continued

Examples

| Example No. | Structure | Characterisation Data | Chemistry Route |
|---|---|---|---|
| 94 | 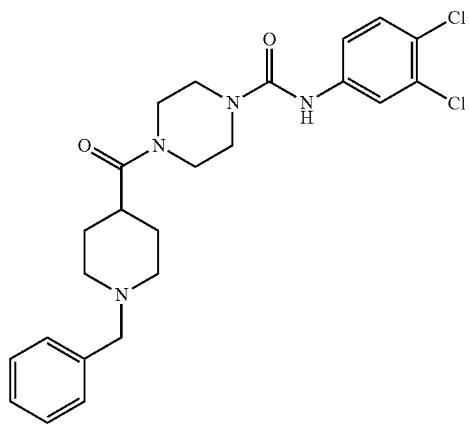 [SMILES: O=C(Nc1ccc(Cl)c(Cl)c1)N1CCN(C(=O)C2CCN(Cc3ccccc3)CC2)CC1] | 4-[(1-benzylpiperidin-4-yl)carbonyl]-N-(3,4-dichlorophenyl)piperazine-1-carboxamide<br>LCMS M/z(+) 474.76 (M + H$^+$)<br>$^1$H NMR (400.132 MHz, CDCl$_3$) 1.70-1.82 (m, 2H), 1.86-1.99 (m, 2H), 2.25 (t, 2H), 2.48-2.60 (m, 1H), 2.98-3.09 (m, 2H), 3.44-3.72 (m, 10H), 7.23-7.39 (m, 8H), 7.67 (d, 1H) | C3 |
| 95 | 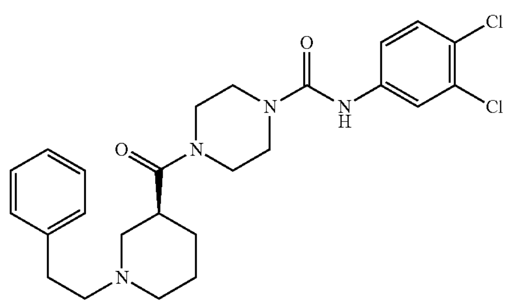 [SMILES: O=C(Nc1ccc(Cl)c(Cl)c1)N1CCN(C(=O)[C@H]2CCCN(CCc3ccccc3)C2)CC1] | N-(3,4-dichlorophenyl)-4-{[(3S)-1-(2-phenylethyl)piperidin-3-yl]carbonyl}piperazine-1-carboxamide<br>LCMS M/z(+) 488.76 (M + H$^+$)<br>$^1$H NMR (400.132 MHz, CDCl$_3$) 1.48-1.86 (m, 4H), 2.01-2.12 (m, 1H), 2.29 (t, 1H), 2.61-2.69 (m, 2H), 2.77-2.88 (m, 3H), 3.01 (t, 2H), 3.40-3.77 (m, 8H), 6.44 (s, 1H), 7.16-7.36 (m, 7H), 7.59 (d, 1H) | C3 |
| 96 | 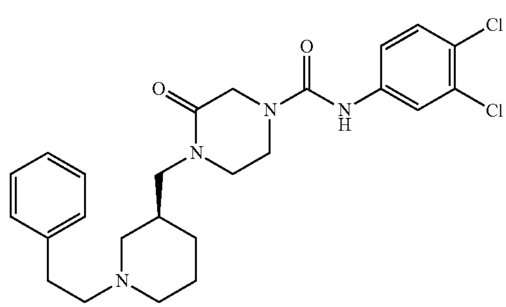 [SMILES: O=C1CN(C(=O)Nc2ccc(Cl)c(Cl)c2)CCN1C[C@H]1CCCN(CCc2ccccc2)C1] | N-(3,4-dichlorophenyl)-3-oxo-4-{[(3S)-1-(2-phenylethyl)piperidin-3-yl]methyl}piperazine-1-carboxamide<br>LCMS M/z(+) 488.77 (M + H$^+$)<br>$^1$H NMR (400.132 MHz, CDCl$_3$) 0.96-1.09 (m, 1H), 1.49-1.77 (m, 3H), 1.84 (t, 1H), 1.95-2.09 (m, 2H), 2.48-2.63 (m, 2H), 2.69-2.91 (m, 4H), 3.32-3.41 (m, 4H), 3.68-3.83 (m, 2H), 4.19-4.30 (m, 2H), 7.14-7.43 (m, 8H), 7.73 (d, 1H) | A5 |
| 97 | 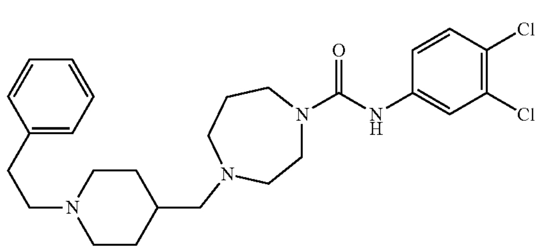 [SMILES: O=C(Nc1ccc(Cl)c(Cl)c1)N1CCCN(CC2CCN(CCc3ccccc3)CC2)CC1] | N-(3,4-dichlorophenyl)-4-{[1-(2-phenylethyl)piperidin-4-yl]methyl}-1,4-diazepane-1-carboxamide<br>LCMS M/z(+) 488.77 (M + H$^+$)<br>$^1$H NMR (400.132 MHz, CDCl$_3$) 1.18-1.31 (m, 2H), 1.38-1.51 (m, 1H), 1.56-1.82 (m, 2H), 1.86-2.04 (m, 4H), 2.33 (d, 2H), 2.54-2.67 (m, 4H), 2.69-2.74 (m, 2H), 2.77-2.85 (m, 2H), 3.00 (d, 2H), 3.50-3.63 (m, 4H), 6.29 (s, 1H), 7.16-7.33 (m, 7H), 7.63 (d, 1H) | A7 |

-continued

Examples

| Example No. | Structure | Characterisation Data | Chemistry Route |
|---|---|---|---|
| 98 | 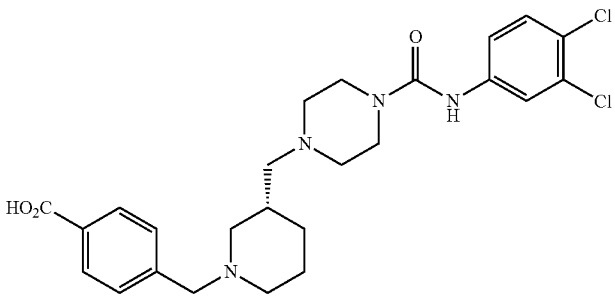 [SMILES: O=C(O)c1ccc(CN2CCC[C@@H](CN3CCN(C(=O)Nc4ccc(Cl)c(Cl)c4)CC3)C2)cc1] | 4-({(3R)-3-[(4-{[(3,4-dichlorophenyl)amino]carbonyl}piperazin-1-yl)methyl]piperidin-1-yl}methyl)benzoic acid<br>LCMS M/z(+) 504.83 (M + H$^+$)<br>$^1$H NMR (400.132 MHz, DMSO-d$_6$) 0.85-0.99 (m, 1H), 1.40-1.54 (m, 1H), 1.55-1.87 (m, 4H), 1.98 (t, 1H), 2.09-2.22 (m, 2H), 2.25-2.38 (m, 4H), 2.66 (d, 1H), 2.78 (d, 1H), 3.33-3.44 (m, 5H), 3.46 (d, 1H), 3.56 (d, 1H), 7.39-7.47 (m, 4H), 7.82-7.85 (m, 1H), 7.89 (d, 2H), 8.75 (s, 1H) | C1 |
| 99 | 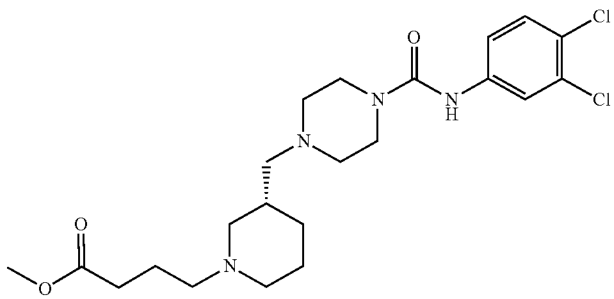 [SMILES: COC(=O)CCCN1CCC[C@@H](CN2CCN(C(=O)Nc3ccc(Cl)c(Cl)c3)CC2)C1] | Methyl 4-{(3R)-3-[(4-{[(3,4-dichlorophenyl)amino]carbonyl}piperazin-1-yl)methyl]piperidin-1-yl}butanoate<br>LCMS M/z(+) 470.86 (M + H$^+$)<br>$^1$H NMR (400.132 MHz, DMSO-d$_6$) 0.80-0.96 (m, 1H), 1.34-1.50 (m, 1H), 1.54-1.81 (m, 6H), 1.89 (t, 1H), 2.08-2.42 (m, 10H), 2.62-2.72 (m, 1H), 2.77 (d, 1H), 3.44 (t, 4H), 3.59 (s, 3H), 7.43-7.49 (m, 2H), 7.83-7.85 (m, 1H), 8.75 (s, 1H) | C1 |
| 100 | 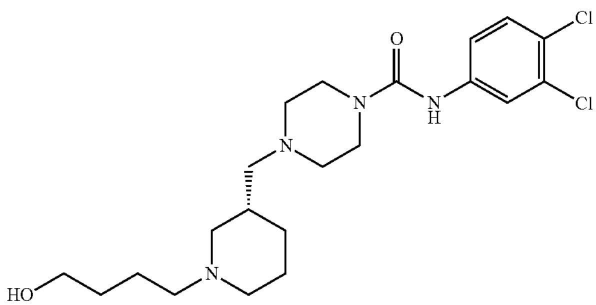 | N-(3,4-dichlorophenyl)-4-{[(3R)-1-(4-hydroxybutyl)piperidin-3-yl]methyl}piperazine-1-carboxamide<br>LCMS M/z(+) 442.89 (M + H$^+$)<br>$^1$H NMR (400.132 MHz, DMSO-d$_6$) 0.80-0.95 (m, 1H), 1.35-1.50 (m, 4H), 1.52-1.94 (m, 6H), 2.09-2.40 (m, 8H), 2.66-2.87 (m, 2H), 3.19-3.49 (m, 7H), 7.43-7.49 (m, 2H), 7.83-7.85 (m, 1H), 8.76 (s, 1H) | C1 |
| 101 | 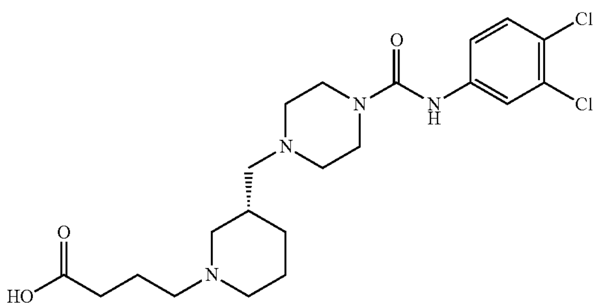 | 4-{(3R)-3-[(4-{[(3,4-dichlorophenyl)amino]carbonyl}piperazin-1-yl)methyl]piperidin-1-yl}butanoic acid LCMS M/z(+) 456.83 (M + H$^+$)<br>$^1$H NMR (400.132 MHz, DMSO-d$_6$) 0.83-1.00 (m, 1H), 1.40-1.53 (m, 1H), 1.58-1.72 (m, 4H), 1.74-1.83 (m, 2H), 2.01 (t, 1H), 2.10-2.23 (m, 2H), 2.26 (t, 2H), 2.28-2.41 (m, 6H), 2.80 (d, 1H), 2.87 (d, 1H), 3.38 (s, 1H), 3.44 (t, 4H), 7.43-7.49 (m, 2H), 7.83-7.85 (m, 1H), 8.76 (s, 1H) | C1 |

-continued

Examples

| Example No. | Structure | Characterisation Data | Chemistry Route |
|---|---|---|---|
| 102 | 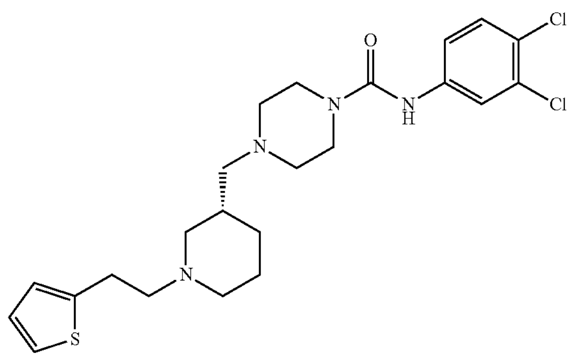 [SMILES: O=C(Nc1ccc(Cl)c(Cl)c1)N1CCN(C[C@@H]2CCCN(CCc3cccs3)C2)CC1] | N-(3,4-dichlorophenyl)-4-({(3R)-1-[2-(2-thienyl)ethyl]piperidin-3-yl}methyl)piperazine-1-carboxamide<br>LCMS M/z(+) 481.06 (M + H$^+$)<br>$^1$H NMR (400.132 MHz, CDCl$_3$) 0.84-1.01 (m, 1H), 1.36-2.15 (m, 7H), 2.16-2.27 (m, 2H), 2.33-2.43 (m, 2H), 2.45-2.54 (m, 2H), 2.61-2.80 (m, 2H), 2.85-3.21 (m, 3H), 3.42-3.53 (m, 4H), 6.37 (s, 1H), 6.83 (d, 1H), 6.89-6.94 (m, 1H), 7.10-7.14 (m, 1H), 7.20 (dd, 1H), 7.32 (d, 1H), 7.60 (d, 1H) | C1 |
| 103 | 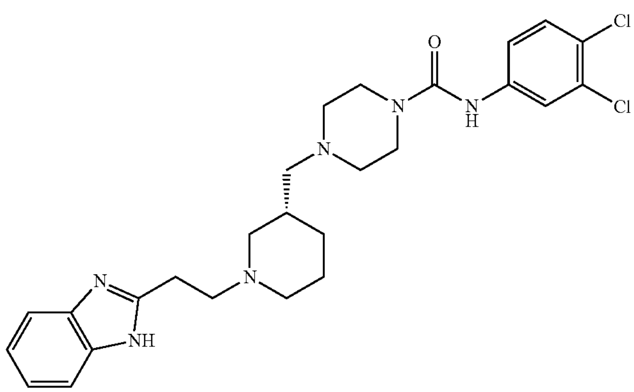 [SMILES: O=C(Nc1ccc(Cl)c(Cl)c1)N1CCN(C[C@@H]2CCCN(CCc3nc4ccccc4[nH]3)C2)CC1] | 4-({(3R)-1-[2-(1H-benzimidazol-2-yl)ethyl]piperidin-3-yl}methyl)-N-(3,4-dichlorophenyl)piperazine-1-carboxamide<br>LCMS M/z(+) 514.87 (M + H$^+$)<br>$^1$H NMR (400.132 MHz, DMSO-d$_6$) 0.82-0.96 (m, 1H), 1.39-1.53 (m, 1H), 1.57-1.83 (m, 4H), 1.95-2.05 (m, 1H), 2.08-2.21 (m, 2H), 2.25-2.40 (m, 4H), 2.70-2.86 (m, 3H), 2.91 (d, 1H), 2.97 (t, 2H), 3.43 (t, 4H), 7.08-7.13 (m, 2H), 7.41-7.50 (m, 4H), 7.83-7.86 (m, 1H), 8.76 (s, 1H), 12.09 (s, 1H) | C1 |
| 104 | 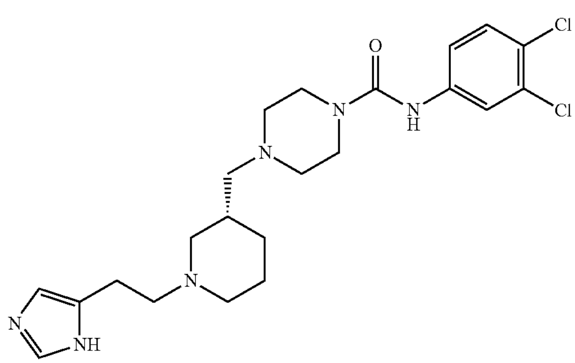 [SMILES: O=C(Nc1ccc(Cl)c(Cl)c1)N1CCN(C[C@@H]2CCCN(CCc3cnc[nH]3)C2)CC1] | N-(3,4-dichlorophenyl)-4-({(3R)-1-[2-(1H-imidazol-5-yl)ethyl]piperidin-3-yl}methyl)piperazine-1-carboxamide<br>LCMS M/z(+) 466.61 (M + H$^+$)<br>$^1$H NMR (400.132 MHz, DMSO-d$_6$) 0.82-0.97 (m, 1H), 1.39-1.54 (m, 1H), 1.55-1.86 (m, 5H), 1.91-2.04 (m, 1H), 2.08-2.22 (m, 2H), 2.25-2.44 (m, 4H), 2.45-2.59 (m, 2H), 2.64 (t, 2H), 2.80 (d, 1H), 2.89 (d, 1H), 3.44 (t, 4H), 6.74 (s, 1H), 7.46 (s, 2H), 7.48 (d, 1H), 7.84 (s, 1H), 8.76 (s, 1H) | C1 |
| 105 | 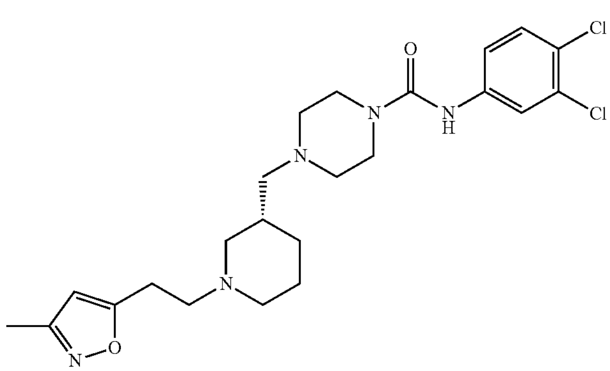 [SMILES: Cc1cc(CCN2CCC[C@@H](CN3CCN(C(=O)Nc4ccc(Cl)c(Cl)c4)CC3)C2)on1] | N-(3,4-dichlorophenyl)-4-({(3R)-1-[2-(3-methylisoxazol-5-yl)ethyl]piperidin-3-yl}methyl)piperazine-1-carboxamide<br>LCMS M/z(+) 479.78 (M + H$^+$)<br>$^1$H NMR (400.132 MHz, DMSO-d$_6$) 0.81-0.96 (m, 1H), 1.37-1.51 (m, 1H), 1.53-1.82 (m, 4H), 1.89-2.03 (m, 1H), 2.08-2.23 (m, 2H), 2.18 (s, 3H), 2.26-2.39 (m, 4H), 2.54-2.64 (m, 2H), 2.72-2.80 (m, 2H), 2.85 (t, 2H), 3.44 (t, 4H), 6.13 (s, 1H), 7.43-7.49 (m, 2H), 7.84 (d, 1H), 8.79 (s, 1H) | C1 |

-continued

Examples

| Example No. | Structure | Characterisation Data | Chemistry Route |
|---|---|---|---|
| 106 | 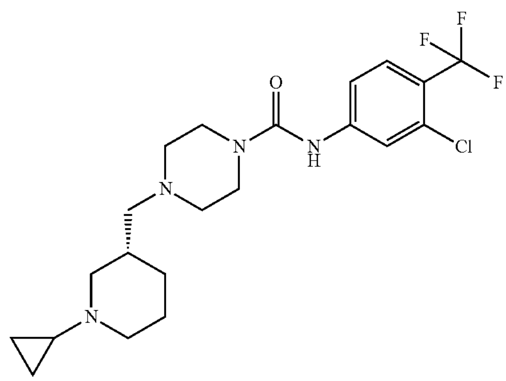 [SMILES: O=C(Nc1ccc(C(F)(F)F)c(Cl)c1)N1CCN(C[C@@H]2CCCN(C3CC3)C2)CC1] | N-[3-chloro-4-(trifluoromethyl)phenyl]-4-{[(3S)-1-cyclopropylpiperidin-3-yl]methyl}piperazine-1-carboxamide<br>LCMS M/z(+) 444.92 (M + H$^+$)<br>$^1$H NMR (400.132 MHz, DMSO-$d_6$) 0.22-0.32 (m, 2H), 0.36-0.44 (m, 2H), 0.83-0.95 (m, 1H), 1.31-1.44 (m, 1H), 1.51-1.62 (m, 2H), 1.62-1.75 (m, 2H), 1.83 (t, 1H), 2.07-2.20 (m, 3H), 2.28-2.40 (m, 4H), 2.82 (d, 1H), 2.94 (d, 1H), 3.46 (t, 4H), 7.58-7.63 (m, 1H), 7.70 (d, 1H), 7.90 (d, 1H), 9.03 (s, 1H) | A1 |
| 107 | 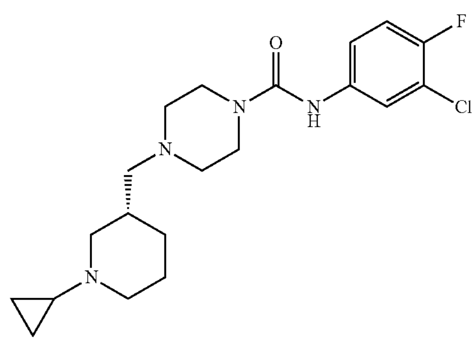 [SMILES: O=C(Nc1ccc(F)c(Cl)c1)N1CCN(C[C@@H]2CCCN(C3CC3)C2)CC1] | N-(3-chloro-4-fluorophenyl)-4-{[(3S)-1-cyclopropylpiperidin-3-yl]methyl}piperazine-1-carboxamide<br>LCMS M/z(+) 394.92 (M + H$^+$)<br>$^1$H NMR (400.132 MHz, DMSO-$d_6$) 0.21-0.32 (m, 2H), 0.36-0.45 (m, 2H), 0.83-0.96 (m, 1H), 1.31-1.44 (m, 1H), 1.50-1.75 (m, 4H), 1.78-1.90 (m, 1H), 2.06-2.20 (m, 3H), 2.26-2.40 (m, 4H), 2.77-2.87 (m, 1H), 2.94 (d, 1H), 3.42 (t, 4H), 7.26 (t, 1H), 7.38-7.43 (m, 1H), 7.75 (dd, 1H), 8.65 (s, 1H) | A1 |
| 108 | 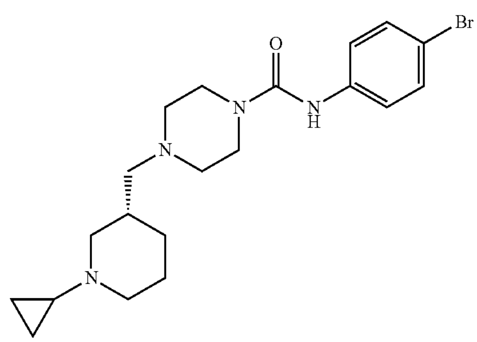 [SMILES: O=C(Nc1ccc(Br)cc1)N1CCN(C[C@@H]2CCCN(C3CC3)C2)CC1] | N-(4-bromophenyl)-4-{[(3S)-1-cyclopropylpiperidin-3-yl]methyl}piperazine-1-carboxamide<br>LCMS M/z(+) 420.93 (M + H$^+$)<br>$^1$H NMR (400.132 MHz, DMSO-$d_6$) 0.22-0.31 (m, 2H), 0.36-0.44 (m, 2H), 0.82-0.95 (m, 1H), 1.30-1.43 (m, 1H), 1.50-1.61 (m, 2H), 1.62-1.74 (m, 2H), 1.81 (t, 1H), 2.06-2.19 (m, 3H), 2.26-2.39 (m, 4H), 2.81 (d, 1H), 2.94 (d, 1H), 3.42 (t, 4H), 7.36-7.48 (m, 4H), 8.59 (s, 1H) | A1 |
| 109 | 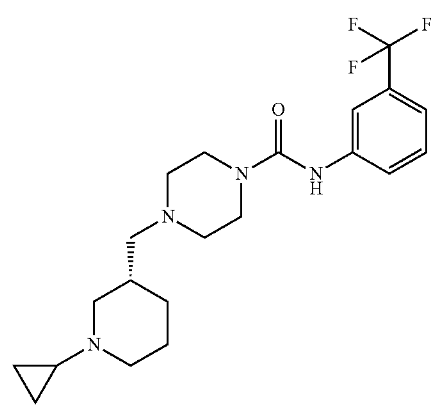 [SMILES: O=C(Nc1cccc(C(F)(F)F)c1)N1CCN(C[C@@H]2CCCN(C3CC3)C2)CC1] | 4-{[(3S)-1-cyclopropylpiperidin-3-yl]methyl}-N-[3-(trifluoromethyl)phenyl]piperazine-1-carboxamide<br>LCMS M/z(+) 411.01 (M + H$^+$)<br>$^1$H NMR (400.132 MHz, DMSO-$d_6$) 0.27 (s, 2H), 0.36-0.46 (m, 2H), 0.83-0.96 (m, 1H), 1.31-1.45 (m, 1H), 1.49-1.76 (m, 4H), 1.78-1.90 (m, 1H), 2.06-2.21 (m, 3H), 2.27-2.42 (m, 4H), 2.78-2.87 (m, 1H), 2.90-2.99 (m, 1H), 3.45 (t, 4H), 7.26 (d, 1H), 7.45 (t, 1H), 7.74 (d, 1H), 7.92 (s, 1H), 8.80 (s, 1H) | A1 |

-continued

Examples

| Example No. | Structure | Characterisation Data | Chemistry Route |
|---|---|---|---|
| 110 | 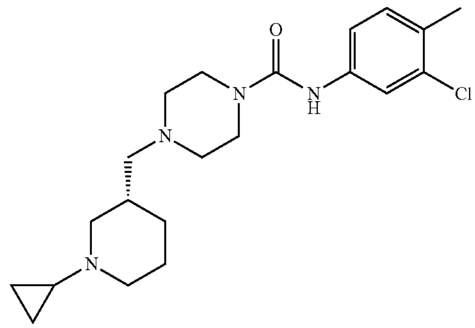 [SMILES: Cc1ccc(NC(=O)N2CCN(C[C@@H]3CCCN(C4CC4)C3)CC2)cc1Cl] | N-(3-chloro-4-methylphenyl)-4-{[(3S)-1-cyclopropylpiperidin-3-yl]methyl}piperazine-1-carboxamide<br>LCMS M/z(+) 391.02 (M + H$^+$)<br>$^1$H NMR (400.132 MHz, CDCl$_3$) 0.36-0.51 (m, 4H), 0.83-0.98 (m, 1H), 1.44-1.90 (m, 6H), 2.07-2.23 (m, 3H), 2.30 (s, 3H), 2.34-2.49 (m, 4H), 2.99 (d, 1H), 3.10 (d, 1H), 3.47 (t, 4H), 6.30 (s, 1H), 7.08-7.16 (m, 2H), 7.43 (d, 1H) | A1 |
| 111 | 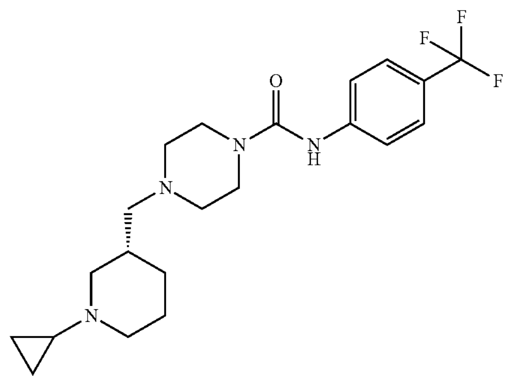 [SMILES: O=C(Nc1ccc(C(F)(F)F)cc1)N1CCN(C[C@@H]2CCCN(C3CC3)C2)CC1] | 4-{[(3S)-1-cyclopropylpiperidin-3-yl]methyl}-N-[4-(trifluoromethyl)phenyl]piperazine-1-carboxamide<br>LCMS M/z(+) 411.01 (M + H$^+$)<br>$^1$H NMR (400.132 MHz, CDCl$_3$) 0.39-0.68 (m, 4H), 0.86-1.00 (m, 1H), 1.43-2.04 (m, 6H), 2.13-2.28 (m, 3H), 2.34-2.44 (m, 2H), 2.44-2.54 (m, 2H), 3.02-3.28 (m, 2H), 3.42-3.57 (m, 4H), 6.57 (s, 1H), 7.51 (q, 4H) | A1 |
| 112 | 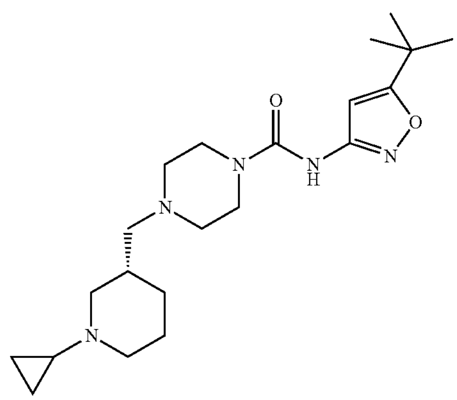 [SMILES: CC(C)(C)c1cc(NC(=O)N2CCN(C[C@@H]3CCCN(C4CC4)C3)CC2)no1] | N-(5-tert-butylisoxazol-3-yl)-4-{[(3S)-1-cyclopropylpiperidin-3-yl]methyl}piperazine-1-carboxamide<br>LCMS M/z(+) 390.06 (M + H$^+$)<br>$^1$H NMR (400.132 MHz, DMSO-d$_6$) 0.20-0.32 (m, 2H), 0.35-0.45 (m, 2H), 0.81-0.94 (m, 1H), 1.28 (s, 9H), 1.30-1.45 (m, 1H), 1.49-1.60 (m, 2H), 1.61-1.73 (m, 2H), 1.81 (t, 1H), 2.06-2.18 (m, 3H), 2.23-2.36 (m, 4H), 2.76-2.86 (m, 1H), 2.88-2.97 (m, 1H), 3.42 (t, 4H), 6.43 (s, 1H), 9.57 (s, 1H) | A1 |
| 113 | 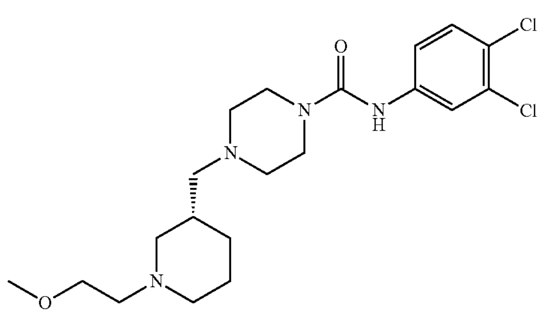 [SMILES: COCCN1CCC[C@@H](CN2CCN(C(=O)Nc3ccc(Cl)c(Cl)c3)CC2)C1] | N-(3,4-dichlorophenyl)-4-{[(3S)-1-(2-methoxyethyl)piperidin-3-yl]methyl}piperazine-1-carboxamide<br>LCMS M/z(+) 428.94 (M + H$^+$)<br>$^1$H NMR (400.132 MHz, DMSO-d$_6$) 0.79-0.94 (m, 1H), 1.37-1.51 (m, 1H), 1.53-1.83 (m, 4H), 1.88-2.04 (m, 1H), 2.07-2.21 (m, 2H), 2.26-2.40 (m, 4H), 2.40-2.57 (m, 2H), 2.71-2.92 (m, 2H), 3.23 (s, 3H), 3.40-3.46 (m, 6H), 7.43-7.49 (m, 2H), 7.82-7.85 (m, 1H), 8.76 (s, 1H) | C1 |

-continued

Examples

| Example No. | Structure | Characterisation Data | Chemistry Route |
|---|---|---|---|
| 114 | 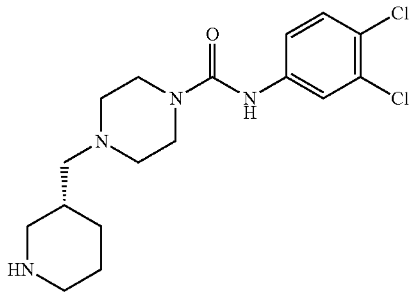 [SMILES: O=C(Nc1ccc(Cl)c(Cl)c1)N1CCN(C[C@@H]2CCCNC2)CC1] | N-(3,4-dichlorophenyl)-4-[(3R)-piperidin-3-ylmethyl]piperazine-1-carboxamide<br>LCMS M/z(+) (M + H$^+$)<br>$^1$H NMR (400.132 MHz, CDCl$_3$) 1.03 (dq, 1H), 1.46 (qt, 1H), 1.61-1.74 (m, 2H), 1.76-1.89 (m, 2H), 2.06-2.29 (m, 3H), 2.40 (dquintet, 4H), 2.55 (td, 1H), 3.00 (d, 1H), 3.15 (d, 1H), 3.46 (t, 4H), 6.66 (s, 1H), 7.20 (dd, 1H), 7.30 (d, 1H), 7.56 (d, 1H) | C1 |
| 115 | 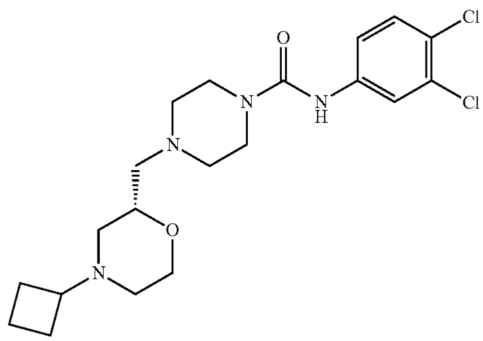 [SMILES: O=C(Nc1ccc(Cl)c(Cl)c1)N1CCN(C[C@H]2CN(C3CCC3)CCO2)CC1] | 4-{[(2S)-4-cyclobutylmorpholin-2-yl]methyl}-N-(3,4-dichlorophenyl)piperazine-1-carboxamide<br>LCMS M/z(+) 427, 429 (M + H$^+$)<br>$^1$H-NMR (400.132 MHz, CDCl$_3$) 1.50-2.15 (9H, m), 2.32 (1H, dd), 2.55 (5H, m), 2.80 (2H, m), 3.50 (4H, m), 3.75 (2H, m), 3.93 (1H, m), 6.32 (1H, s), 7.21 (1H, d), 7.30 (1H, d), 7.62 (1H, d) | C1 |
| 116 | 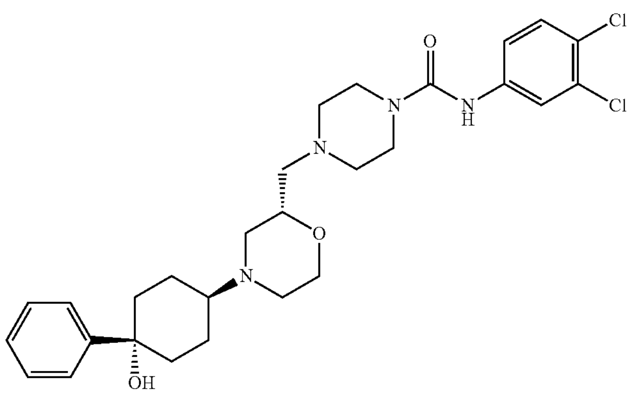 [SMILES: O=C(Nc1ccc(Cl)c(Cl)c1)N1CCN(C[C@H]2CN([C@H]3CC[C@@](O)(c4ccccc4)CC3)CCO2)CC1] | N-(3,4-dichlorophenyl)-4-{[(2S)-4-(trans-4-hydroxy-4-phenylcyclohexyl) morpholin-2-yl]methyl}piperazine-1-carboxamide<br>LCMS M/z(+) 547, 549 (M + H$^+$)<br>$^1$H-NMR (400.132 MHz, CDCl$_3$) 1.60-2.60 (17H, m), 2.90 (2H, m), 3.50 (4H, m), 3.65 (2H, m), 3.78 (1H, m), 3.92 (1H, d), 6.48 (1H, s), 7.20 (1H, d), 7.30 (2H, m), 7.37 (2H, t), 7.55 (2H, d), 7.59 (1H, s) | C1 |
| 117 | 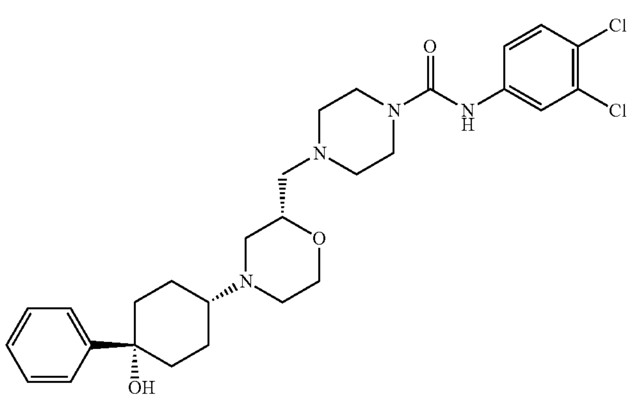 [SMILES: O=C(Nc1ccc(Cl)c(Cl)c1)N1CCN(C[C@H]2CN([C@H]3CC[C@](O)(c4ccccc4)CC3)CCO2)CC1] | N-(3,4-dichlorophenyl)-4-{[(2S)-4-(cis-4-hydroxy-4-phenylcyclohexyl)morpholin-2-yl]methyl}piperazine-1-carboxamide<br>LCMS M/z(+) 547, 549 (M + H$^+$)<br>$^1$H-NMR (400.132 MHz, CDCl$_3$) 1.55-2.62 (17H, m), 2.90 (2H, m), 3.50 (5H, m), 3.72 (2H, m), 3.95 (1H, d), 6.35 (1H, s), 7.20 (1H, dd), 7.28 (1H, m), 7.30 (3H, m), 7.46 (2H, d), 7.60 (1H, s) | C1 |

-continued

Examples

| Example No. | Structure | Characterisation Data | Chemistry Route |
|---|---|---|---|
| 118 | 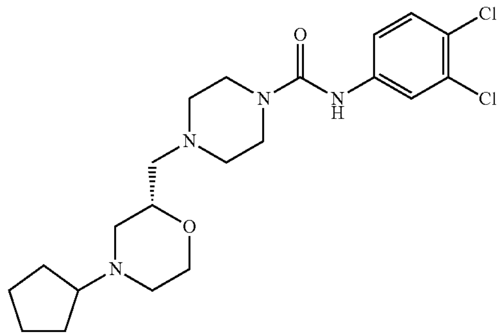 [SMILES: O=C(Nc1ccc(Cl)c(Cl)c1)N1CCN(C[C@H]2CN(C3CCCC3)CCO2)CC1] | 4-{[(2S)-4-cyclopentylmorpholin-2-yl]methyl}-N-(3,4-dichlorophenyl)piperazine-1-carboxamide LCMS M/z(+) 441, 443 (M + H⁺) ¹H-NMR (400.132 MHz, CDCl₃) 1.40-1.95 (10H, m), 2.19 (1H, m), 2.32 (1H, m), 2.55 (5H, m), 2.88 (2H, m), 3.50 (4H, m), 3.74 (2H, m), 3.90 (1H, d), 6.32 (1H, s), 7.19 (1H, dd), 7.31 (1H, d), 7.60 (1H, s) | C1 |
| 119 | 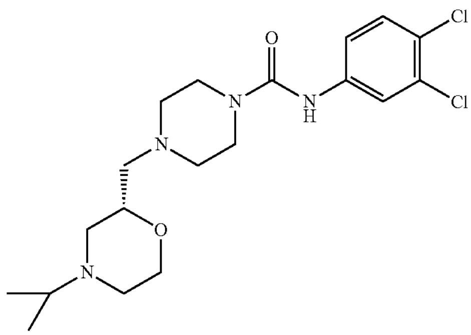 [SMILES: CC(C)N1CCO[C@@H](CN2CCN(C(=O)Nc3ccc(Cl)c(Cl)c3)CC2)C1] | N-(3,4-dichlorophenyl)-4-{[(2S)-4-isopropylmorpholin-2-yl]methyl}piperazine-1-carboxamide LCMS M/z(+) 415, 417 (M + H⁺) ¹H-NMR (400.132 MHz, CDCl₃) 1.10 (6H, br. s), 2.05 (1H, m), 2.32 (2H, m), 2.51-2.90 (8H, m), 3.50 (4H, m), 3.72 (2H, m), 3.93 (1H, m), 6.30 (1H, s), 7.20 (1H, dd), 7.32 (1H, m), 7.61 (1H, s) | C1 |
| 120 | 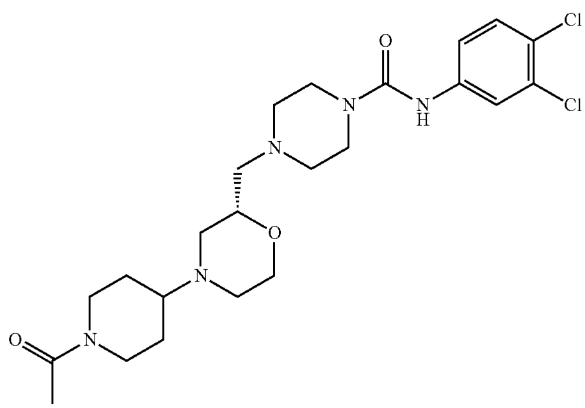 [SMILES: CC(=O)N1CCC(N2CCO[C@@H](CN3CCN(C(=O)Nc4ccc(Cl)c(Cl)c4)CC3)C2)CC1] | 4-{[(2S)-4-(1-acetylpiperidin-4-yl)morpholin-2-yl]methyl}-N-(3,4-dichlorophenyl)piperazine-1-carboxamide LCMS M/z(+) 498, 500 (M + H⁺) ¹H-NMR (400.132 MHz, CDCl₃) 1.85 (2H, m), 2.05 (1H, m), 2.09 (3H, s), 2.30 (2H, m), 2.42 (1H, m), 2.53 (7H, m), 2.69 (1H, d), 2.78 (1H, d), 3.05 (1H, t), 3.50 (5H, m), 3.65 (2H, m), 3.89 (2H, m), 4.62 (1H, d), 6.30 (1H, s), 7.21 (1H, d), 7.31 (1H, d), 7.59 (1H, s) | C1 |
| 121 | 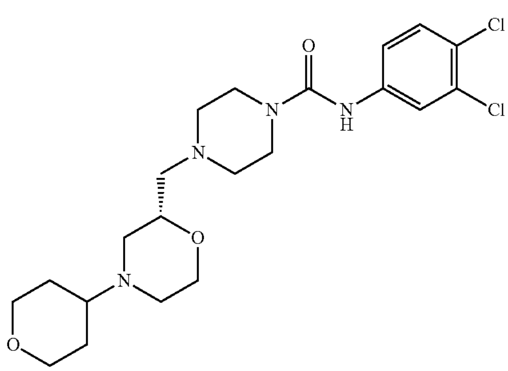 [SMILES: O=C(Nc1ccc(Cl)c(Cl)c1)N1CCN(C[C@H]2CN(C3CCOCC3)CCO2)CC1] | N-(3,4-dichlorophenyl)-4-{[(2S)-4-(tetrahydro-2H-pyran-4-yl)morpholin-2-yl]methyl}piperazine-1-carboxamide LCMS M/z(+) 457, 459 (M + H⁺) ¹H-NMR (400.132 MHz, CDCl₃) 1.50-4.10 (26H, m), 6.32 (1H, s), 7.20 (1H, d), 7.32 (1H, d), 7.58 (1H, s) | C1 |

-continued

Examples

| Example No. | Structure | Characterisation Data | Chemistry Route |
|---|---|---|---|
| 122 | 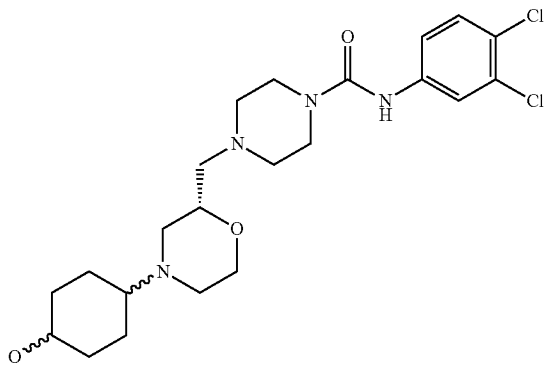 [SMILES: O=C(Nc1ccc(Cl)c(Cl)c1)N1CCN(C[C@H]2CN(C3CCC(O)CC3)CCO2)CC1] | N-(3,4-dichlorophenyl)-4-{[(2S)-4-(4-hydroxycyclohexyl)morpholin-2-yl]methyl}piperazine-1-carboxamide (1:1 mix of cis:trans diastereomers)<br>LCMS M/z(+) 471, 473 (M + H$^+$)<br>$^1$H-NMR (400.132 MHz, CDCl$_3$) 1.30-2.82 (20H, m), 3.50-4.00 (8H, m), 6.30 (1H, s), 7.20 (1H, m), 7.30 (1H, d), 7.60 (1H, s) | C1 |
| 123 | 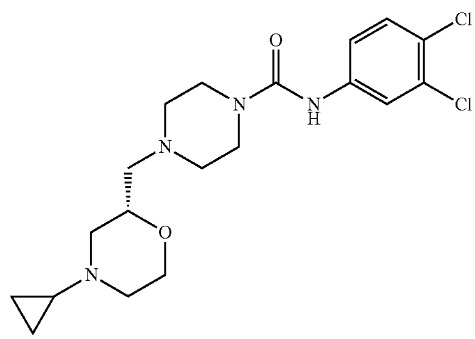 [SMILES: O=C(Nc1ccc(Cl)c(Cl)c1)N1CCN(C[C@H]2CN(C3CC3)CCO2)CC1] | 4-{[(2S)-4-cyclopropylmorpholin-2-yl]methyl}-N-(3,4-dichlorophenyl)piperazine-1-carboxamide LCMS M/z(+) 413, 415 (M + H$^+$)<br>$^1$H-NMR (400.132 MHz, CDCl$_3$) 0.45 (4H, m), 1.62 (1H, m), 2.08 (1H, t), 2.35 (2H, t), 2.55 (5H, m), 2.80 (1H, d), 2.88 (1H, d), 3.60 (6H, m), 3.88 (1H, m), 6.31 (1H, s), 7.18 (1H, dd), 7.32 (1H, d), 7.56 (1H, d) | C1 |
| 124 | 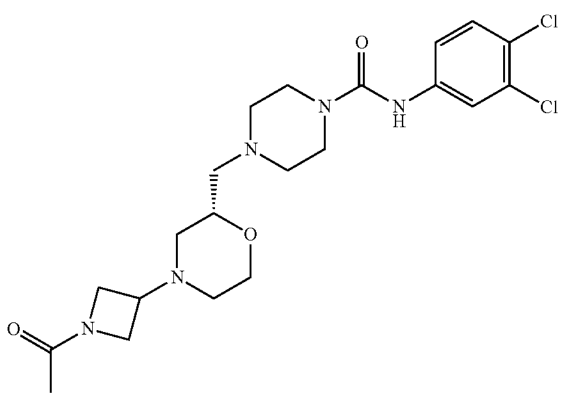 [SMILES: CC(=O)N1CC(N2CCO[C@@H](CN3CCN(C(=O)Nc4ccc(Cl)c(Cl)c4)CC3)C2)C1] | 4-{[(2S)-4-(1-acetylazetidin-3-yl)morpholin-2-yl]methyl}-N-(3,4-dichlorophenyl)piperazine-1-carboxamide LCMS M/z(+) 468, 470 (M + H$^+$)<br>$^1$H-NMR (400.132 MHz, CDCl$_3$) 1.51-1.82 (6H, m), 1.86 (3H, s), 2.22 (2H, m), 2.40 (2H, m), 2.50 (2H, m), 2.73 (1H, m), 2.88 (1H, m), 3.12 (2H, m), 3.50 (4H, m), 3.86 (1H, m), 4.02 (2H, m), 4.13 (1H, m), 6.47 (1H, s), 7.22 (1H, m), 7.31 (1H, d), 7.61 (1H, s) | C1 |
| 125 | 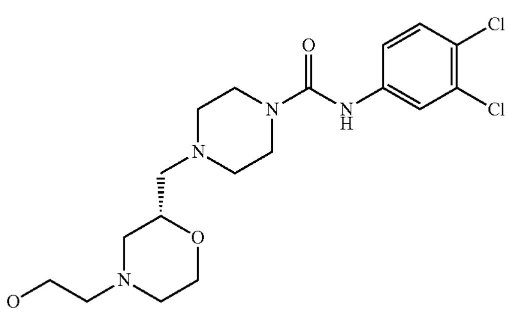 [SMILES: O=C(Nc1ccc(Cl)c(Cl)c1)N1CCN(C[C@H]2CN(CCO)CCO2)CC1] | N-(3,4-dichlorophenyl)-4-{[(2S)-4-(2-hydroxyethyl)morpholin-2-yl]methyl}piperazine-1-carboxamide LCMS M/z(+) 417, 419 (M + H$^+$)<br>$^1$H-NMR (400.132 MHz, CDCl$_3$) 2.32 (2H, m), 2.56 (5H, m), 2.64 (2H, m), 2.85 (1H, d), 2.93 (1H, d), 3.51 (5H, m), 3.69 (3H, m), 3.80 (1H, m), 3.92 (1H, dd), 4.10 (1H, br. s), 6.48 (1H, s), 7.20 (1H, dd), 7.31 (1H, d), 7.59 (1H, d) | C1 |

-continued

| Example No. | Structure | Characterisation Data | Chemistry Route |
|---|---|---|---|
| 126 | 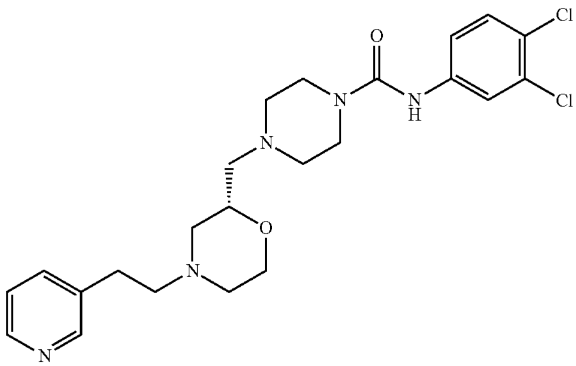 [SMILES: O=C(Nc1ccc(Cl)c(Cl)c1)N1CCN(C[C@H]2CN(CCc3cccnc3)CCO2)CC1] | N-(3,4-dichlorophenyl)-4-{[(2S)-4-(2-pyridin-3-ylethyl)morpholin-2-yl]methyl}piperazine-1-carboxamide<br>LCMS M/z(+) 478, 480 (M + H⁺)<br>¹H-NMR (400.132 MHz, CDCl₃) 1.92 (1H, t), 2.20 (1H, m), 2.32 (1H, dd), 2.55 (7H, m), 2.80 (4H, m), 3.50 (4H, m), 3.65 (1H, m), 3.72 (1H, m), 3.90 (1H, d), 6.51 (1H, s), 7.20 (2H, m), 7.31 (1H, d), 7.53 (1H, d), 7.59 (1H, s), 8.47 (2H, m) | C1 |
| 127 | 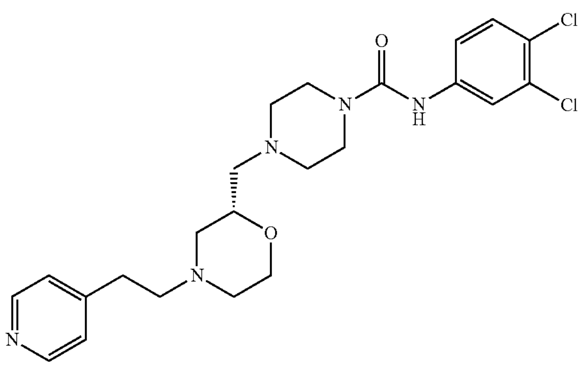 [SMILES: O=C(Nc1ccc(Cl)c(Cl)c1)N1CCN(C[C@H]2CN(CCc3ccncc3)CCO2)CC1] | N-(3,4-dichlorophenyl)-4-{[(2S)-4-(2-pyridin-4-ylethyl)morpholin-2-yl]methyl}piperazine-1-carboxamide<br>LCMS M/z(+) 478, 480 (M + H⁺)<br>¹H-NMR (400.132 MHz, CDCl₃) 1.92 (1H, t), 2.20 (1H, m), 2.30 (1H, dd), 2.57 (7H, m), 2.78 (4H, m), 3.50 (4H, m), 3.70 (2H, m), 3.92 (1H, m), 6.38 (1H, s), 7.15 (2H, m), 7.19 (1H, d), 7.31 (1H, d), 7.50 (1H, s), 8.51 (2H, d) | C1 |
| 128 | 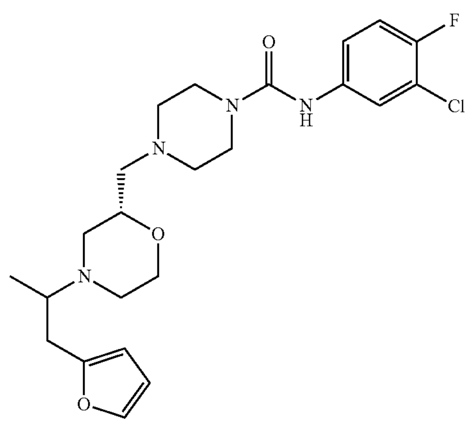 [SMILES: CC(Cc1ccco1)N1CCO[C@@H](CN2CCN(C(=O)Nc3ccc(F)c(Cl)c3)CC2)C1] | N-(3-chloro-4-fluorophenyl)-4-({(2S)-4-[(1R)-2-(2-furyl)-1-methylethyl]morpholin-2-yl}methyl)piperazine-1-carboxamide<br>LCMS M/z(+) 465.48 (M + H⁺)<br>¹H-NMR (400.132 MHz, DMSO-d₆) 0.88-0.94 (m, 3H), 1.13-1.49 (m, 4H), 2.25-2.87 (m, 9H), 3.28-3.62 (m, 6H + water), 3.76 (m, 1H), 6.13 (d, 1H), 6.34 (d, 1H), 7.26 (d, 1H), 7.28 (t, 1H), 7.39 (m, 1H) and 7.74 (m, 1H) | C1 |
| 129 | 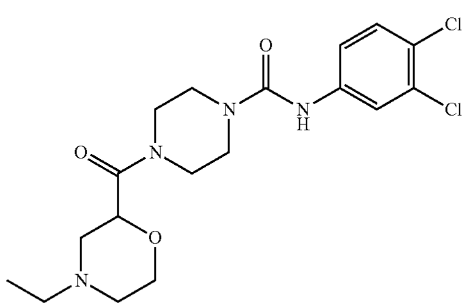 [SMILES: CCN1CCOC(C(=O)N2CCN(C(=O)Nc3ccc(Cl)c(Cl)c3)CC2)C1] | N-(3,4-dichlorophenyl)-4-[(4-ethylmorpholin-2-yl)carbonyl]piperazine-1-carboxamide<br>LCMS M/z(+) 415, 417 (M + H⁺)<br>¹H-NMR (400.132 MHz, CDCl₃) 1.12 (3H, t), 2.22 (1H, td), 2.40 (1H, t), 2.53 (2H, m), 2.78 (1H, d), 3.00 (1H, d), 3.65 (9H, m), 3.95 (1H, d), 4.28 (1H, d), 6.49 (1H, s), 7.20 (1H, dd), 7.32 (1H, d), 7.59 (1H, d) | C3 |

-continued

Examples

| Example No. | Structure | Characterisation Data | Chemistry Route |
|---|---|---|---|
| 130 | 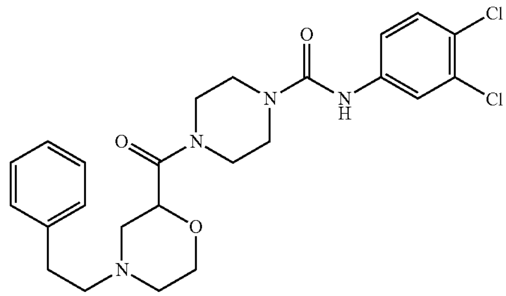 | N-(3,4-dichlorophenyl)-4-{[4-(2-phenylethyl)morpholin-2-yl]carbonyl}piperazine-1-carboxamide<br>LCMS M/z(+) 491, 493 (M + H$^+$)<br>$^1$H-NMR (400.132 MHz, CDCl$_3$) 2.30 (1H, m), 2.46 (1H, t), 2.68 (2H, m), 2.80 (3H, m), 3.02 (1H, d), 3.70 (10H, m), 4.25 (1H, dd), 6.36 (1H, s), 7.30 (7H, m), 7.60 (1H, s) | C3 |
| 131 | 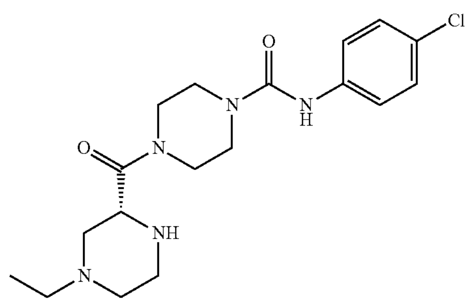 [SMILES: CCN1CCN[C@@H](C(=O)N2CCN(C(=O)Nc3ccc(Cl)cc3)CC2)C1] | N-(4-Chlorophenyl)-4-{[(2R)-4-ethylpiperazin-2-yl]carbonyl}piperazine-1-carboxamide<br>LCMS M/z(+) 380, 382 (M + H$^+$)<br>$^1$H-NMR (400.132 MHz, CDCl$_3$) 1.18 (3H, t), 2.12 (1H, t), 2.22 (1H, t), 2.62 (2H, m), 3.10 (3.57 (6H, m), 3.78 (2H, m), 4.01 (1H, d), 6.42 (1H, s), 7.30 (4H, m) | A9 |
| 132 | 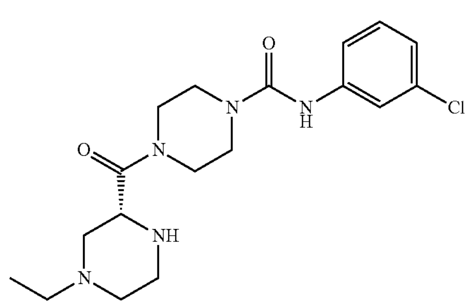 [SMILES: CCN1CCN[C@@H](C(=O)N2CCN(C(=O)Nc3cccc(Cl)c3)CC2)C1] | N-(3-Chlorophenyl)-4-{[(2R)-4-ethylpiperazin-2-yl]carbonyl}piperazine-1-carboxamide<br>LCMS M/z(+) 380, 382 (M + H$^+$)<br>$^1$H-NMR (400.132 MHz, CDCl$_3$) 1.12 (3H, t), 1.75 (1H, br. s), 1.92 (1H, m), 2.02 (1H, t), 2.48 (2H, m), 2.90 (3H, m), 3.10 (1H, d), 3.60 (6H, m), 3.80 (3H, m), 6.40 (1H, s), 7.03 (1H, m), 7.21 (2H, m), 7.46 (1H, s) | A9 |
| 133 | 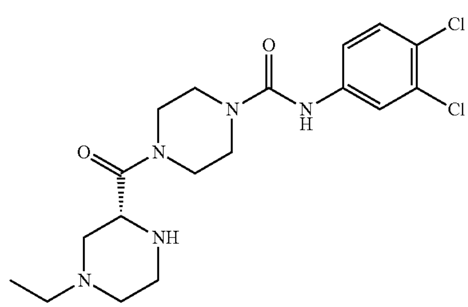 [SMILES: CCN1CCN[C@@H](C(=O)N2CCN(C(=O)Nc3ccc(Cl)c(Cl)c3)CC2)C1] | N-(3,4-Dichlorophenyl)-4-{[(2R)-4-ethylpiperazin-2-yl]carbonyl}piperazine-1-carboxamide<br>LCMS M/z(+) 414.21 (M + H$^+$)<br>$^1$H-NMR (400.132 MHz, DMSO-d$_6$) 1.02 (3H, t), 1.99 (2H, m), 2.40 (2H, m), 2.74 (2H, m), 2.90 (3H, m), 3.50 (4H, m), 3.57 (4H, m), 3.77 (1H, m), 7.44 (2H, m), 7.81 (1H, m), 8.57 (1H, m) | C3 |

| Example No. | Structure | Characterisation Data | Chemistry Route |
|---|---|---|---|
| 134 | 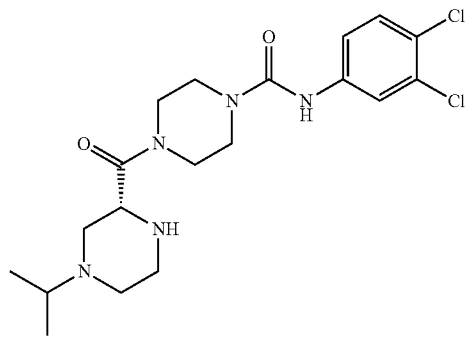 [SMILES: CC(C)N1CCN[C@@H](C(=O)N2CCN(C(=O)Nc3ccc(Cl)c(Cl)c3)CC2)C1] | N-(3,4-dichlorophenyl)-4-{[(2R)-4-isopropylpiperazin-2-yl]carbonyl}piperazine-1-carboxamide LCMS M/z(+) 428, 430 (M + H$^+$) $^1$H-NMR (400.132 MHz, CDCl$_3$) 1.30 (6H, m), 2.60 (1H, m), 2.75 (1H, m), 2.98 (1H, m), 3.20-3.83 (12H, m), 4.39 (1H, m), 6.55 (1H, s), 7.22 (1H, dd), 7.33 (1H, d), 7.63 (1H, d) | E |
| 135 | 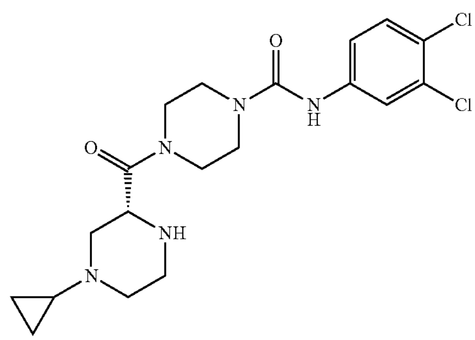 [SMILES: O=C(Nc1ccc(Cl)c(Cl)c1)N1CCN(C(=O)[C@H]2CN(C3CC3)CCN2)CC1] | 4-[(2R)(4-Cyclopropylpiperazin-2-yl)carbonyl]-N-(3,4-dichlorophenyl)piperazine-1-carboxamide LCMS M/z(−) 424.23 (M − H$^-$), M/z(+) 426.23 (M + H$^+$) $^1$H-NMR (400.132 MHz, DMSO-d$_6$) 0.50 (4H, m), 1.80 (1H, m), 2.40 (1H, m), 2.60 (1H, m), 3.00 (2H, m), 3.10 (1H, m) 3.50 (1H, m), 3.70 (4H, m), 4.50 (1H, m), 7.50 (2H, m), 7.80 (1H, m), 8.90 (1H, m), 9.20 (1H, m) (4H obscured) | C3 |
| 136 | 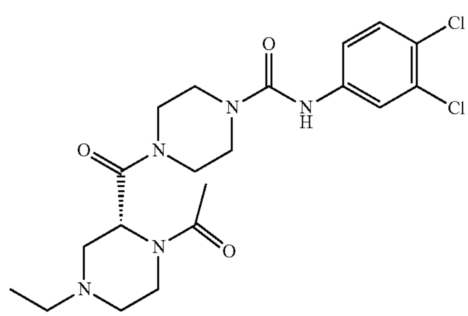 [SMILES: CCN1CCN(C(C)=O)[C@@H](C(=O)N2CCN(C(=O)Nc3ccc(Cl)c(Cl)c3)CC2)C1] | 4-{[(2R)-1-Acetyl-4-ethylpiperazin-2-yl]carbonyl}-N-(3,4-dichlorophenyl)piperazine-1-carboxamide LCMS M/z(−) 454.22 (M − H$^-$), M/z(+) 456.23 (M + H$^+$) $^1$H-NMR (400.132 MHz, CDCl$_3$) 1.07 (3H, m), 1.64 (3H, m), 2.13 (3H, m), 2.25 (1H, m), 2.37 (1H, m), 2.49 (1H, m), 2.89 (1H, m), 3.05 (1H, m), 3.56 (4H, m), 3.99 (1H, m), 5.30 (1H, m), 6.69 (1H, s), 7.20 (1H, m), 7.22 (2H, m), 7.33 (1H, s), 7.35 (1H, s), 7.59 (1H, m) | E |
| 137 | 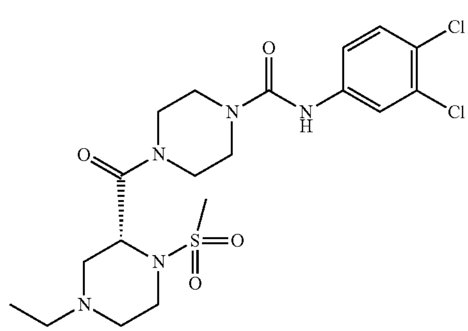 [SMILES: CCN1CCN(S(C)(=O)=O)[C@@H](C(=O)N2CCN(C(=O)Nc3ccc(Cl)c(Cl)c3)CC2)C1] | N-(3,4-Dichlorophenyl)-4-{[(2R)-4-ethyl-1-(methylsulfonyl)piperazin-2-yl]carbonyl}piperazine-1-carboxamide LCMS M/z(−) 490.06 (M − H$^-$), M/z(+) 492.12 (M + H$^+$) $^1$H-NMR (400.132 MHz, CDCl$_3$) 0.86 (1H, m), 1.05 (3H, m), 2.25 (1H, m), 2.44 (3H, m), 2.84 (1H, m), 2.95 (4H, s), 2.99 (2H, m), 3.59 (6H, m), 3.91 (1H, m), 4.79 (1H, m), 6.42 (1H, m), 7.20 (1H, m), 7.34 (1H, d), 7.58 (1H, s) | E |

-continued

Examples

| Example No. | Structure | Characterisation Data | Chemistry Route |
|---|---|---|---|
| 138 | 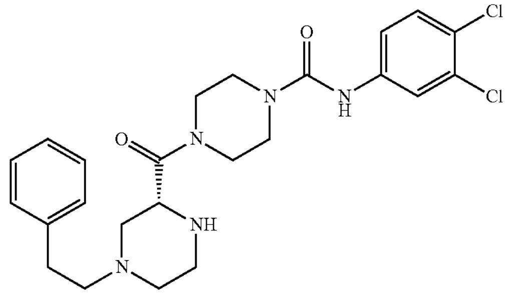 [SMILES: O=C(Nc1ccc(Cl)c(Cl)c1)N1CCN(C(=O)[C@H]2CN(CCc3ccccc3)CCN2)CC1] | N-(3,4-Dichlorophenyl)-4-{[(2R)-4-(2-phenylethyl)piperazin-2-yl]carbonyl}piperazine-1-carboxamide<br>LCMS M/z(−) 488.11 (M − H⁻), M/z(+) 490.14 (M + H⁺)<br>¹H-NMR (400.132 MHz, DMSO-d₆) 1.89 (2H, m), 2.70 (4H, m), 2.88 (2H, m), 3.52 (8H, m), 7.16 (1H, m), 7.21 (2H, m), 7.26 (2H, m), 7.46 (2H, m), 7.83 (1H, s), 8.85 (1H, s) (4 protons obscured) | C3 |
| 139 | 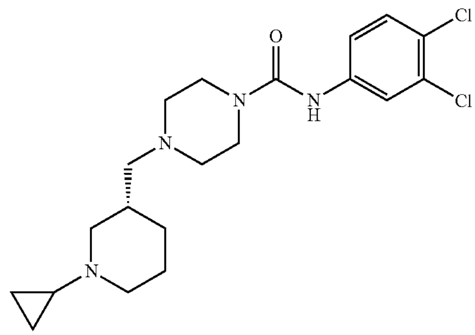 | 1-{[(3R)-1-Cyclopropylpiperidin-3-yl]methyl}-N-(3,4-dichlorophenyl)piperazine-4-carboxamide<br>LCMS M/z(+) 411.21 (M + H⁺)<br>¹H-NMR (400.132 MHz, CDCl₃) 0.41 (4H, m), 0.8-0.95 (2H, m), 1.27 (1H, m), 1.5 (1H obscured, m), 1.63 (1H obscured, m), 1.74 (1H, m), 1.81 (1H, t), 2.11 (1H, dt), 2.18 (2H, dd), 2.35-2.48 (4H, two quintets), 2.96 (1H, d), 3.08 (1H, d), 3.47 (4H, t), 6.30 (1H, s), 7.18 (1H, dd), 7.31 (1H, d), 7.58 (1H, d) | C1 |
| 140 | 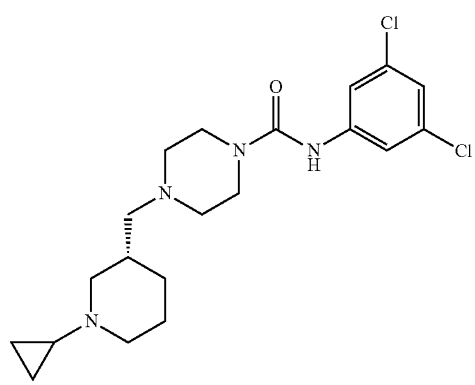 [SMILES: O=C(Nc1cc(Cl)cc(Cl)c1)N1CCN(C[C@@H]2CCCN(C3CC3)C2)CC1] | 1-{[(3R)-1-Cyclopropylpiperidin-3-yl]methyl}-N-(3,5-dichlorophenyl)piperazine-4-carboxamide<br>LCMS M/z(+) 411 (M + H⁺)<br>¹H-NMR (400.132 MHz, CDCl₃) 0.47 (4H, m), 0.8-1.8 (8H, m), 2.19 (2H, d), 2.35-2.5 (4H, two quintets), 3.02 (1H, m), 3.14 (1H, m), 3.47 (4H, t), 6.37 (1H, brs), 6.99 (1H, t), 7.34 (2H, d) | A1 |
| 141 | 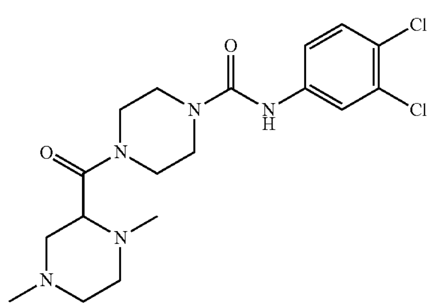 [SMILES: CN1CCN(C)C(C(=O)N2CCN(C(=O)Nc3ccc(Cl)c(Cl)c3)CC2)C1] | 1-{[1,4-Dimethylpiperazin-3-yl]carbonyl}-N-(3,4-dichlorophenyl)piperazine-4-carboxamide<br>LCMS M/z(+) 414.22 (M + H⁺)<br>¹H-NMR (400.132 MHz, DMSO-d₆) 2.05-2.25 (3H, m, obscured), 2.13 (3H, s), 2.18 (3H, s), 2.56-2.68 (2H, m), 2.78 (1H, brd), 3.10-3.17 (<1H, m), 3.40-3.55 (6H, m), 3.8 (1H, brm), 3.86-3.98 (<1H, brm), 7.44 (1H, dd), 7.48 (1H, d), 7.83 (1H, d), 8.83 (1H, s) | E |

-continued

Examples

| Example No. | Structure | Characterisation Data | Chemistry Route |
|---|---|---|---|
| 142 | 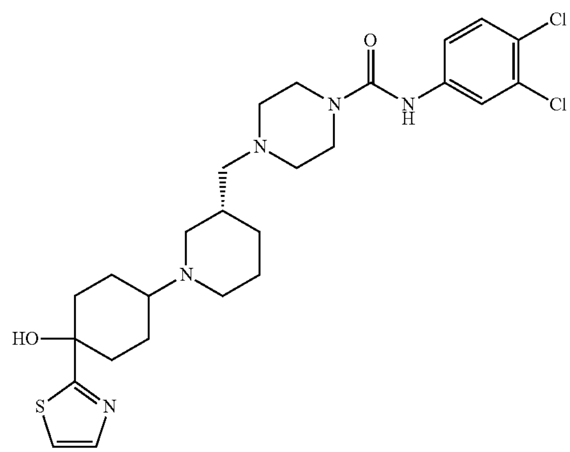 [SMILES: O=C(Nc1ccc(Cl)c(Cl)c1)N1CCN(C[C@@H]2CCCN(C3CCC(O)(c4nccs4)CC3)C2)CC1] | N-(3,4-dichlorophenyl)-4-({(3S)-1-[4-hydroxy-4-(1,3-thiazol-2-yl)cyclohexyl]piperidin-3-yl}methyl)piperazine-1-carboxamide<br>LCMS M/z(−) 549.76 (M − H$^+$)<br>$^1$H-NMR (400.132 MHz, CDCl$_3$) 0.85-0.98 (m, 1H), 1.40-1.96 (m, 12H), 2.11-2.28 (m, 3H), 2.36-2.52 (m, 6H), 2.79-3.05 (m, 2H), 3.44 (t, 4H), 6.30 (s, 1H), 7.18 (d, 1H), 7.32 (d, 2H), 7.59 (s, 1H) and 7.72 (dd, 1H) | C1 |
| 143 | 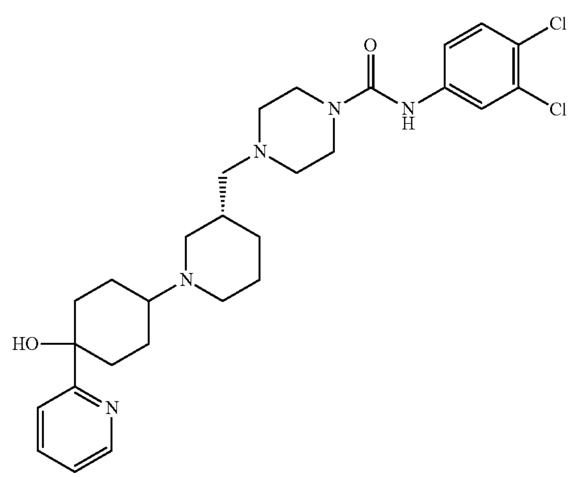 [SMILES: O=C(Nc1ccc(Cl)c(Cl)c1)N1CCN(C[C@@H]2CCCN(C3CCC(O)(c4ccccn4)CC3)C2)CC1] | N-(3,4-dichlorophenyl)-4-{[(3S)-1-(4-hydroxy-4-pyridin-2-ylcyclohexyl)piperidin-3-yl]methyl}piperazine-1-carboxamide<br>LCMS M/z(+) 548.12 (M + H$^+$)<br>$^1$H-NMR (400.132 MHz, CDCl$_3$) 0.85-0.98 (m, 1H), 1.52-1.96 (m, 12H), 2.16-2.29 (m, 3H), 2.37-2.51 (m, 6H), 2.89-3.17 (m, 2H), 3.48 (t, 4H), 6.38 (s, 1H), 7.18 (d, 1H), 7.25 (t, 1H), 7.32-7.34 (m, 2H), 7.59 (s, 1H), 7.73 (t, 1H) and 8.54 (d, 1H). | C1 |
| 144 | 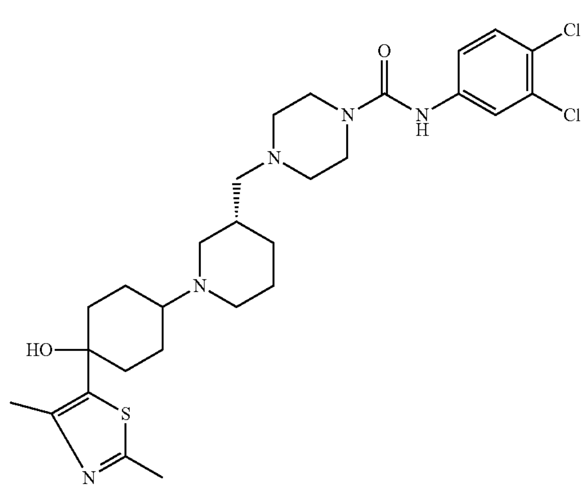 [SMILES: Cc1nc(C)c(C2(O)CCC(N3CCC[C@@H](CN4CCN(C(=O)Nc5ccc(Cl)c(Cl)c5)CC4)C3)CC2)s1] | N-(3,4-dichlorophenyl)-4-({(3S)-1-[4-(2,4-dimethyl-1,3-thiazol-5-yl)-4-hydroxycyclohexyl]piperidin-3-yl}methyl)piperazine-1-carboxamide<br>LCMS M/z(−) 578.33 (M − H$^+$)<br>$^1$H-NMR (400.132 MHz, CDCl$_3$) 0.85-0.96 (m, 1H), 1.49-1.89 (m, 12H), 2.16-2.25 (m, 3H), 2.35-2.51 (m, 9H), 2.59 (s, 3H), 2.84-3.00 (m, 2H), 3.44 (t, 4H), 6.34 (s, 1H), 7.18 (d, 1H), 7.32 (d, 1H) and 7.59 (s, 1H) | C1 |

-continued

Examples

| Example No. | Structure | Characterisation Data | Chemistry Route |
|---|---|---|---|
| 145 | 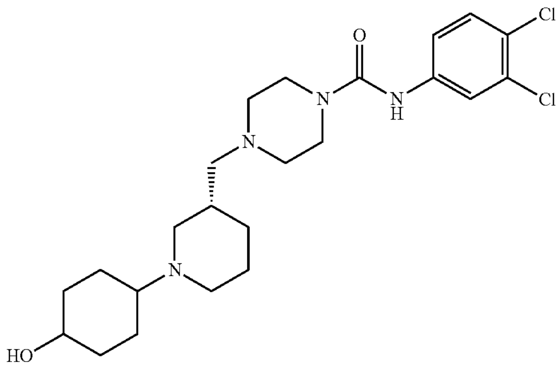 [SMILES: O=C(Nc1ccc(Cl)c(Cl)c1)N1CCN(C[C@@H]2CCCN(C3CCC(O)CC3)C2)CC1] | N-(3,4-dichlorophenyl)-4-{[(3S)-1-(4-hydroxycyclohexyl)piperidin-3-yl]methyl}piperazine-1-carboxamide<br>LCMS M/z(+) 468.98 (M + H$^+$)<br>$^1$H-NMR (400.132 MHz, CDCl$_3$) 0.89 (m, 1H), 1.29 (m, 2H), 1.49-1.89 (m, 14H), 2.18 (m, 2H), 2.38 (m, 2H), 2.46 (m, 2H), 2.85 (t, 1H), 2.96 (t, 1H), 3.47 (t, 4H), 6.33 (s, 1H), 7.19 (d, 1H), 7.31 (d, 1H), and 7.59 (s, 1H) | C1 |
| 146 | 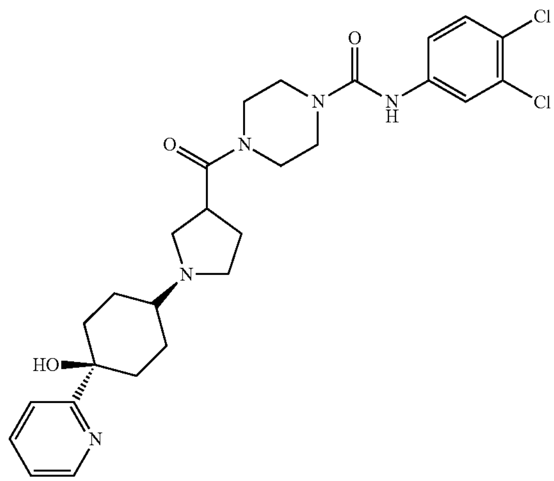 | N-(3,4-dichlorophenyl)-4-{[1-(4-hydroxy-4-pyridin-2-ylcyclohexyl)pyrrolidin-3-yl]carbonyl}piperazine-1-carboxamide<br>LCMS M/z(+) 546.81 (M + H$^+$)<br>$^1$H-NMR (400.132 MHz, CDCl$_3$) 1.51-1.80 (m, 4H), 1.91-2.00 (m, 2H), 2.05-2.16 (m, 2H), 2.23-2.40 (m, 3H), 2.06-2.13 (m, 1H), 2.75-2.85 (m, 2H), 2.84 (t, 1H), 3.22 (t, 1H), 3.49 (bs, 2H), 3.61 (bs, 4H), 3.75 (bs, 2H), 6.52 (s, 1H), 7.17-7.30 (m, 3H), 7.35 (d, 1H), 7.50 (s, 1H), 7.72 (t, 1H) and 8.52 (s, 1H) | C3 |
| 147 | 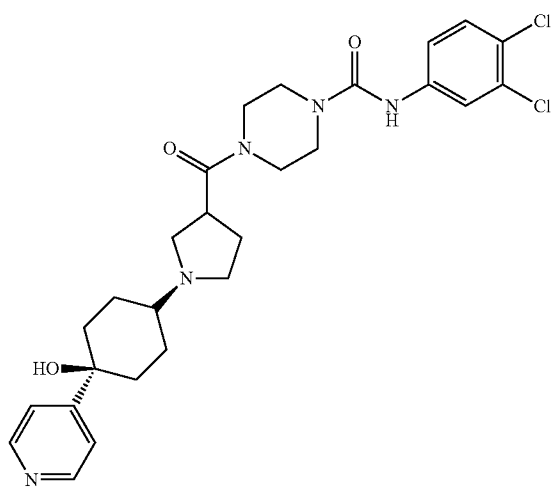 | N-(3,4-dichlorophenyl)-4-{[1-(cis-4-hydroxy-4-pyridin-4-ylcyclohexyl)pyrrolidin-3-yl]carbonyl}piperazine-1-carboxamide<br>LCMS M/z(+) 546.81 (M + H$^+$)<br>$^1$H-NMR (400.132 MHz, CDCl$_3$) 1.51-1.80 (m, 4H), 1.91-2.00 (m, 2H), 2.05-2.16 (m, 2H), 2.23-2.40 (m, 3H), 2.56-2.63 (m, 1H), 2.75-2.85 (m, 2H), 2.84 (t, 1H), 3.22 (t, 1H), 3.49 (bs, 2H), 3.61 (bs, 4H), 3.75 (bs, 2H), 6.52 (s, 1H), 7.22 (d, 1H), 7.38 (d, 1H), 7.47 (d, 2H), 7.62 (d, 1H) and 8.60 (d, 2H) | C3 |

-continued

Examples

| Example No. | Structure | Characterisation Data | Chemistry Route |
|---|---|---|---|
| 148 | 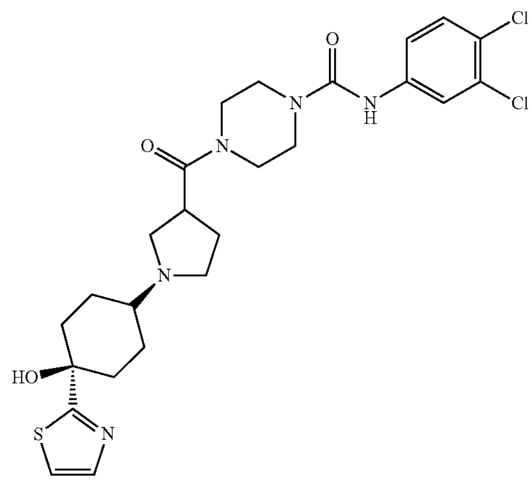 | N-(3,4-dichlorophenyl)-4-({1-[cis-4-hydroxy-4-(1,3-thiazol-2-yl)cyclohexyl]pyrrolidin-3-yl}carbonyl)piperazine-1-carboxamide<br>LCMS M/z(+) 552.82 (M + H$^+$)<br>$^1$H-NMR (400.132 MHz, CDCl$_3$) 1.60-1.72 (m, 4H), 1.85-1.95 (m, 2H), 1.95-2.06 (m, 2H), 2.30-2.44 (m, 3H), 2.54-2.63 (m, 2H), 2.80-2.88 (m, 1H), 2.99 (t, 1H), 3.17 (t, 1H), 3.40 (bs, 2H), 3.50 (m, 4H), 3.62 (bs, 2H), 6.49 (s, 1H), 7.18 (d, 1H), 7.20 (d, 1H), 7.28 (d, 1H), 7.52 (d, 1H) and 7.63 (d, 1H) | C3 |
| 149 | 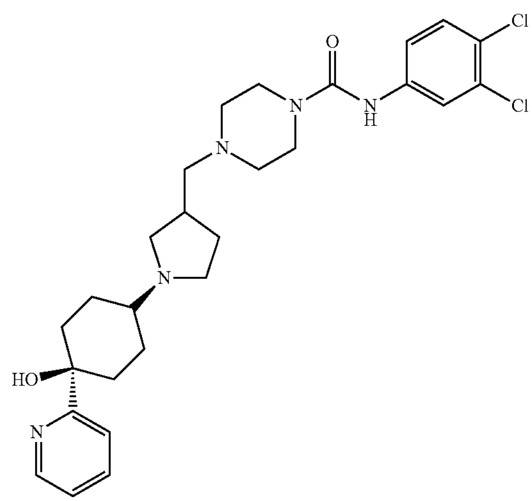 | N-(3,4-dichlorophenyl)-4-{[1-(4-hydroxy-2-pyridin-2-ylcyclohexyl)pyrrolidin-3-yl]methyl}piperazine-1-carboxamide<br>LCMS M/z(+) 532.91 (M + H$^+$)<br>$^1$H-NMR (400.132 MHz, CDCl$_3$) 1.34-1.49 (m, 3H), 1.86-2.02 (m, 4H), 2.11-2.60 (m, 14H), 2.68-2.75 (m, 1H), 3.40 (t, 4H), 6.30 (s, 1H), 7.11-7.14 (m, 2H), 7.28 (d, 1H), 7.53 (d, 1H), 7.63 (t, 1H) and 8.46 (d, 1H) | C1 |
| 150 | 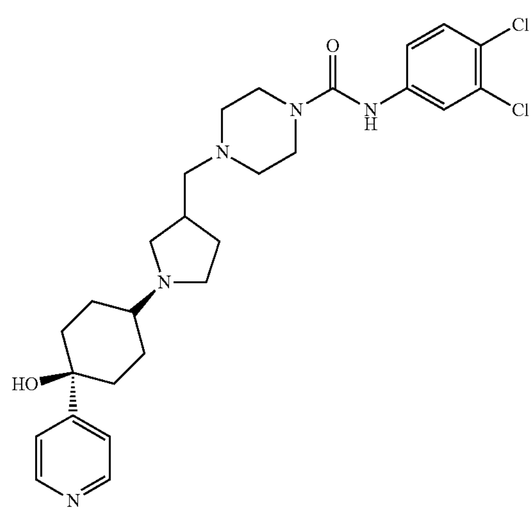 | N-(3,4-dichlorophenyl)-4-{[1-(4-hydroxy-4-pyridin-4-ylcyclohexyl)pyrrolidin-3-yl]methyl}piperazine-1-carboxamide<br>LCMS M/z(+) 532.35 (M + H$^+$)<br>$^1$H-NMR (400.132 MHz, CDCl$_3$) 1.48-1.70 (m, 3H), 1.80-1.95 (m, 4H), 2.15-2.56 (m, 14H), 2.60-2.79 (m, 1H), 3.40 (t, 4H), 6.27 (s, 1H), 7.12 (d, 1H), 7.26 (d, 1H), 7.34 (d, 2H), 7.52 (d, 1H) and 8.50 (d, 2H) | C1 |

-continued

Examples

| Example No. | Structure | Characterisation Data | Chemistry Route |
|---|---|---|---|
| 151 | 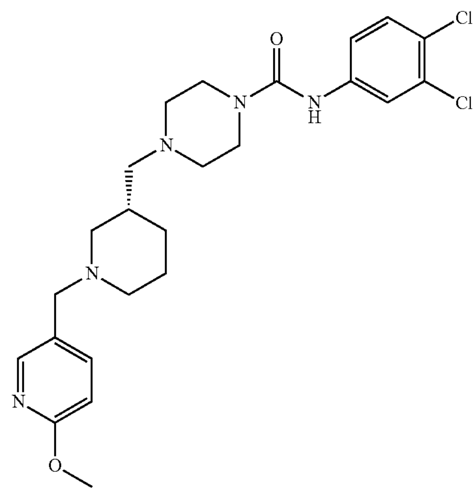 [SMILES: COc1ccc(CN2CCC[C@@H](CN3CCN(C(=O)Nc4ccc(Cl)c(Cl)c4)CC3)C2)cn1] | N-(3,4-Dichlorophenyl)-4-({(3R)-1-[(6-methoxypyridin-3-yl)methyl]piperidin-3-yl}methyl)piperazine-1-carboxamide<br>LCMS M/z(+) 492.29, 493.95 (M + H$^+$)<br>LCMS M/z(−) 490.29, 492.29 (M − H$^-$)<br>$^1$H-NMR (400.132 MHz, DMSO-d$_6$) 1.40 (1H, m), 1.50 to 1.60 (3H, m), 1.80 (1H, m), 2.10 (2H, m), 2.30 (4H, m), 2.60 (1H, d), 2.74 (1H, d), 3.24 to 3.50 (8H, m), 3.80 (3H, s), 6.73 (1H, d), 7.42 (2H, s), 7.60 (1H, d), 7.80 (1H, s), 8.00 (1H, s), 8.75 (1H, s) | C1 |
| 152 | 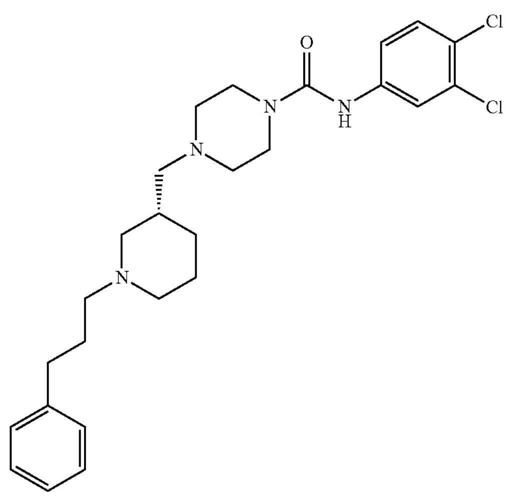 [SMILES: O=C(Nc1ccc(Cl)c(Cl)c1)N1CCN(C[C@@H]2CCCN(CCCc3ccccc3)C2)CC1] | N-(3,4-Dichlorophenyl)-4-{[(3R)-1-(2-phenylpropyl)piperidin-3-yl]methyl}piperazine-1-carboxamide<br>LCMS M/z(+) 489.33, 491.23 (M + H$^+$)<br>LCMS M/z(−) 487.29, 489.33 (M − H$^-$)<br>$^1$H-NMR (400.132 MHz, DMSO-d$_6$) 1.45 (1H, m), 1.60 to 1.90 (8H, m), 2.26 to 2.35 (6H, m), 2.55 (2H, m), 3.25 (4H, m), 3.40 (4H, m), 7.15 to 7.30 (5H, m), 7.47 (2H, d), 7.85 (1H, s), 8.75 (1H, s) | C1 |
| 153 | 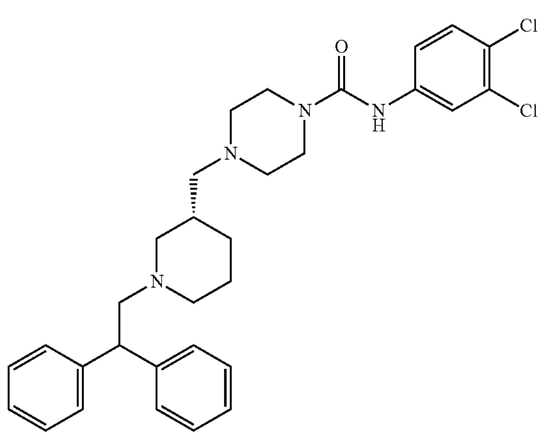 [SMILES: O=C(Nc1ccc(Cl)c(Cl)c1)N1CCN(C[C@@H]2CCCN(CC(c3ccccc3)c3ccccc3)C2)CC1] | N-(3,4-Dichlorophenyl)-4-{[(3R)-1-(2,2-diphenylethyl)piperidin-3-yl]methyl}piperazine-1-carboxamide<br>LCMS M/z(+) 551.22, 553.40 (M + H$^+$)<br>LCMS M/z(−) 549.20, 551.19 (M − H$^-$)<br>$^1$H-NMR (400.132 MHz, DMSO-d$_6$) 0.97 (1H, m), 1.58 (4H, m), 2.10 (4H, m), 2.28 (4H, m), 2.65 (1H, d), 2.75 (1H, d), 3.41 (7H, m), 7.23 (10H, m), 7.80 (1H, d), 8.48 (1H, s) | C1 |

-continued

| Example No. | Structure | Characterisation Data | Chemistry Route |
|---|---|---|---|
| 154 | 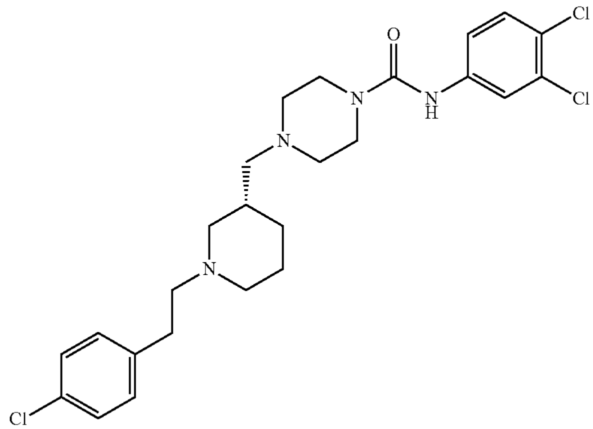 [SMILES: O=C(Nc1ccc(Cl)c(Cl)c1)N1CCN(C[C@@H]2CCCN(CCc3ccc(Cl)cc3)C2)CC1] | 4-({(3R)-1-[2-(4-Chlorophenyl)ethyl]piperidin-3-yl}methyl)-N-(3,4-dichlorophenyl)piperazine-1-carboxamide<br>LCMS M/z(+) 509.11, 511.56 (M + H$^+$)<br>$^1$H-NMR (400.132 MHz, DMSO-d$_6$) 0.97 (1H, m), 1.55 (1H, m), 2.13 (2H, s), 2.32 (4H, q), 3.18 (1H, d), 3.30 (9H, m), 3.41 (4H, m), 7.28 (2H, m), 7.32 (2H, m), 7.48 (2H, m), 7.81 (1H, s), 8.72 (1H, s) | C1 |
| 155 | 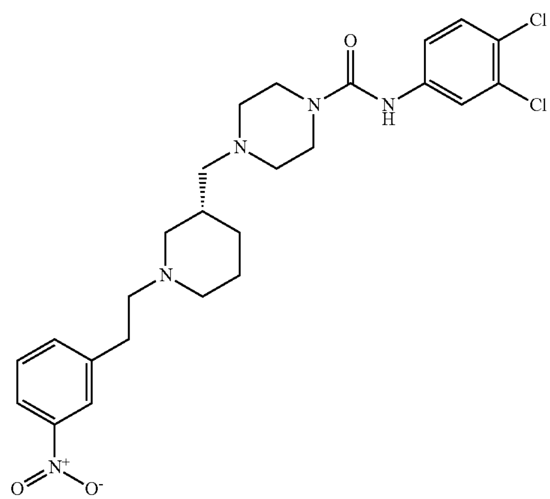 [SMILES: O=C(Nc1ccc(Cl)c(Cl)c1)N1CCN(C[C@@H]2CCCN(CCc3cccc([N+](=O)[O-])c3)C2)CC1] | N-(3,4-Dichlorophenyl)-4-({(3R)-1-[2-(3-nitrophenyl)ethyl]piperidin-3-yl}methyl)piperazine-1-carboxamide<br>LCMS M/z(+) 520.18, 522.20 (M + H$^+$)<br>$^1$H-NMR (400.132 MHz, DMSO-d$_6$) 0.93 (1H, m), 1.45 (1H, q), 1.63 (2H, t), 1.79 (2H, s), 2.01 (1H, m), 2.15 (2H, m), 2.31 (4H, q), 2.80 (1H, m), 2.90 (3H, m), 3.30 (2H, m), 3.42 (4H, q), 7.41 (1H, s), 7.58 (1H, m), 7.71 (1H, d), 7.80 (1H, s), 8.05 (1H, d), 8.10 (1H, s), 8.71 (1H, s) | C1 |
| 156 | 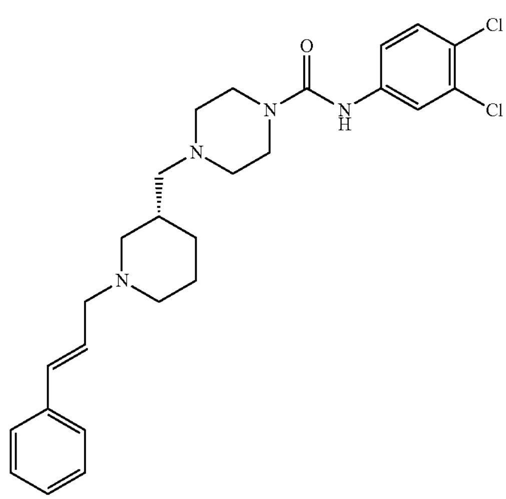 [SMILES: O=C(Nc1ccc(Cl)c(Cl)c1)N1CCN(C[C@@H]2CCCN(C/C=C/c3ccccc3)C2)CC1] | N-(3,4-Dichlorophenyl)-4-({(3R)-1-[(2E)-3-phenylprop-2-en-1-yl]piperidin-3-yl}methyl)piperazine-1-carboxamide<br>LCMS M/z(+) 487.20, 489.19 (M + H$^+$)<br>$^1$H-NMR (400.132 MHz, DMSO-d$_6$) 0.98 (1H, m), 1.50 (1H, m), 1.68 (2H, m), 1.85 (1H, m), 2.15 (3H, m), 2.31 (5H, m), 3.00 (4H, m), 3.41 (4H, m), 6.31 (1H, m), 6.51 (1H, m), 7.26 (1H, m), 7.41 (2H, m), 7.48 (4H, m), 7.82 (1H, s) 8.78 (1H, s) | C1 |

-continued

Examples

| Example No. | Structure | Characterisation Data | Chemistry Route |
|---|---|---|---|
| 157 | 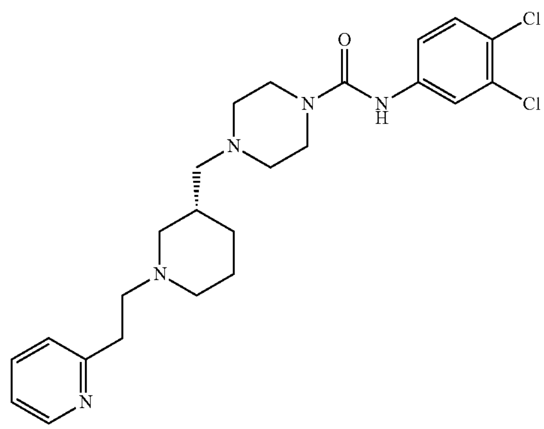 [SMILES: O=C(Nc1ccc(Cl)c(Cl)c1)N1CCN(C[C@@H]2CCCN(CCc3ccccn3)C2)CC1] | N-(3,4-Dichlorophenyl)-4-{[(3R)-1-(2-pyridin-2-ylethyl)piperidin-3-yl]methyl}piperazine-1-carboxamide<br>LCMS M/z(+) 476.20, 478.01 (M + H$^+$)<br>$^1$H-NMR (400.132 MHz, DMSO-d$_6$) 0.91 (1H, m), 1.43 (1H, m), 1.65 (2H, m), 1.71 (1H, m), 2.12 (3H, m), 2.31 (4H, m), 2.62 (1H, m), 2.89 (3H, m), 3.25 (2H, m), 3.40 (4H, s), 7.21 (2H, dt), 7.41 (2H, s), 7.70 (1H, m), 7.85 (1H, s), 8.49 (1H, d), 8.78 (1H, s) | C1 |
| 158 | 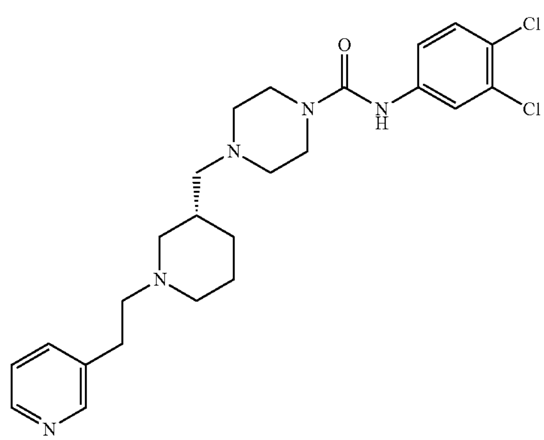 [SMILES: O=C(Nc1ccc(Cl)c(Cl)c1)N1CCN(C[C@@H]2CCCN(CCc3cccnc3)C2)CC1] | N-(3,4-Dichlorophenyl)-4-{[(3R)-1-(pyridin-3-ylethyl)piperidin-3-yl]methyl}piperazine-1-carboxamide<br>LCMS M/z(+) 476.20, 478.20 (M + H$^+$)<br>LCMS M/z(−) 474.26, 476.26 (M − H$^-$)<br>$^1$H-NMR (400.132 MHz, DMSO-d$_6$) 0.92 (1H, m), 1.45 (1H, m), 1.62 (2H, m), 1.71 (2H, m), 2.00 (1H, m), 2.16 (2H, m), 2.31 (4H, m), 2.71 (4H, m), 3.35 (2H, m), 3.45 (4H, m), 7.30 (1H, m), 7.42 (2H, m), 7.65 (1H, m), 7.82 (1H, s), 8.47 (2H, d), 8.73 (1H, s) | C1 |
| 159 | 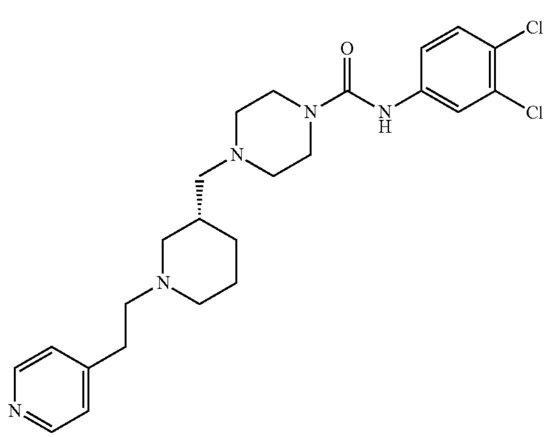 [SMILES: O=C(Nc1ccc(Cl)c(Cl)c1)N1CCN(C[C@@H]2CCCN(CCc3ccncc3)C2)CC1] | N-(3,4-Dichlorophenyl)-4-{[(3R)-1-(2-pyridin-4-ylethyl)piperidin-3-yl]methyl}piperazine-1-carboxamide<br>LCMS M/z(+) 476.21, 478.23 (M + H$^+$)<br>LCMS M/z(−) 474.19, 476.11 (M − H$^-$)<br>$^1$H-NMR (400.132 MHz, DMSO-d$_6$) 1.50 (1H, m), 1.61 (2H, m), 1.83 (2H, m), 2.17 (2H, m), 2.31 (4H, m), 2.70 (2H, m), 2.80 (2H, m), 2.92 (2H, m), 3.30 (2H, m), 3.42 (4H, m), 7.10 (1H, m), 7.49 (2H, m), 8.13 (1H, d), 8.28 (1H, d), 8.44 (2H, m), 8.75 (1H, s) | C1 |

-continued

Examples

| Example No. | Structure | Characterisation Data | Chemistry Route |
|---|---|---|---|
| 160 | 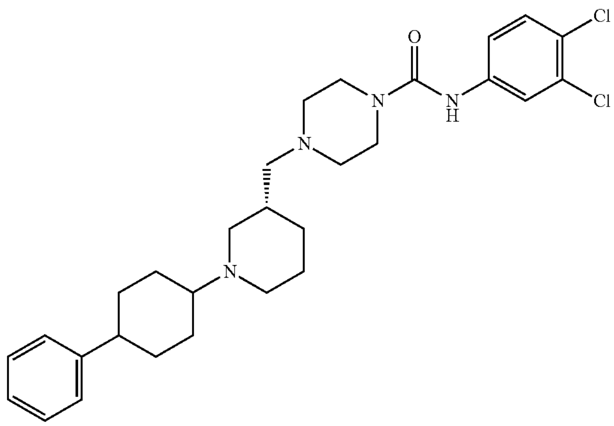 [SMILES: O=C(Nc1ccc(Cl)c(Cl)c1)N1CCN(C[C@@H]2CCCN(C3CCC(c4ccccc4)CC3)C2)CC1] | N-(3,4-Dichlorophenyl)-4-{[(3S)-1-(4-phenylcyclohexyl)piperidin-3-yl]methyl}piperazine-1-carboxamide<br>LCMS M/z(+) 529.19, 531.02 (M + H$^+$)<br>LCMS M/z(−) 527.15, 529.14 (M − H$^-$)<br>$^1$H-NMR (400.132 MHz, DMSO-d$_6$) 1.00 (1H, m), 1.42 (5H, m), 1.65 (2H, d), 1.90 (5H, m), 2.13 (2H, m), 2.30 (6H, m), 3.30 (3H, m), 3.40 (5H, m), 7.12 to 7.30 (5H, m), 7.46 (2H, m), 7.81 (1H, m), 8.72 (1H, s) | C1 |
| 161 | 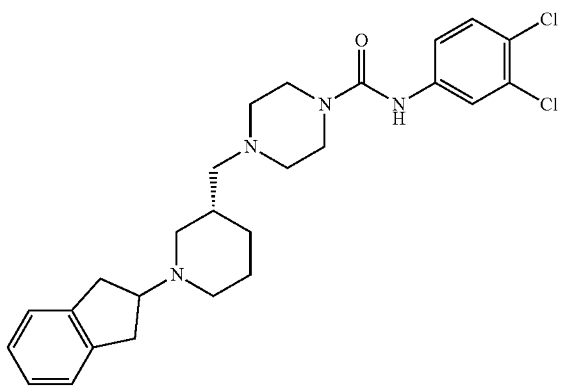 [SMILES: O=C(Nc1ccc(Cl)c(Cl)c1)N1CCN(C[C@@H]2CCCN(C3Cc4ccccc4C3)C2)CC1] | N-(3,4-dichlorophenyl)-4-{[(3S)-1-(2,3-dihydro-1H-inden-2-yl)piperidin-3-yl]methyl}piperazine-1-carboxamide<br>LCMS M/z(+) 487.23, 489.21, (M + H$^+$)<br>$^1$H-NMR (400.132 MHz, DMSO-d$_6$) 0.93 (1H, m), 1.48 (1H, m), 1.56-1.89 (4H, m), 1.99 (1H, s), 2.13-2.22 (2H, m), 2.30-2.41 (4H, m), 2.70-2.85 (3H, m), 2.87-2.95 (1H, m), 2.95-3.07 (2H, m), 3.80-3.21 (1H, s), 3.45 (4H, t), 7.11 (2H, m), 7.18 (2H, m), 7.47 (2H, m), 7.85 (1H, t), 8.76 (1H, s) | C1 |
| 162 | 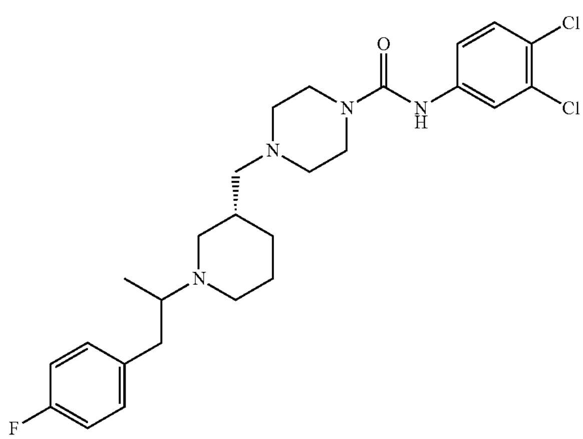 [SMILES: CC(Cc1ccc(F)cc1)N1CCC[C@@H](CN2CCN(C(=O)Nc3ccc(Cl)c(Cl)c3)CC2)C1] | N-(3,4-dichlorophenyl)-4-({(3S)-1-[2-(4-fluorophenyl)-1-methylethyl]piperidin-3-methyl)piperazine-1-carboxamide<br>LCMS M/z(+) 507.23, 509.25, (M + H$^+$)<br>LCMS M/z(−) 505.21, 507.14 (M − H$^-$)<br>$^1$H-NMR (400.132 MHz, DMSO-d$_6$) 0.96 (3H, s), 1.04 (1H, m), 1.48 (1H, s), 1.69 (2H, m), 1.78 (1H, s), 2.22 (2H, m), 2.38 (4H, m), 2.75-3.00 (6H, m), 3.47 (4H, m), 3.69 (1H, m), 7.06 (2H, t), 7.25 (2H, m), 7.42 (1H, d), 7.47 (1H, m), 7.83 (1H, t), 8.52 (1H, s) | C1 |

-continued

Examples

| Example No. | Structure | Characterisation Data | Chemistry Route |
|---|---|---|---|
| 163 | 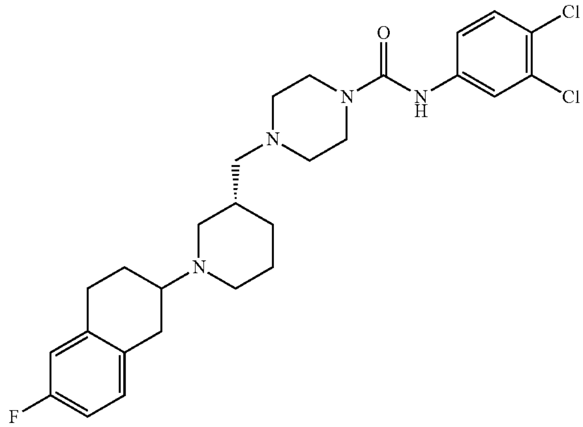 [SMILES: O=C(Nc1ccc(Cl)c(Cl)c1)N1CCN(C[C@@H]2CCCN(C3CCc4cc(F)ccc4C3)C2)CC1] | N-(3,4-dichlorophenyl)-4-{[(3S)-1-(6-fluoro-1,2,3,4-tetrahydronaphthalen-2-yl)piperidin-3-yl]methyl}piperazine-1-carboxamide<br>LCMS M/z(+) 519.25, 521.26 (M + H$^+$)<br>LCMS M/z(−) 517.22, 519.15 (M − H$^-$)<br>$^1$H-NMR (400.132 MHz, DMSO-d$_6$) 0.93 (1H, m), 1.32-1.84 (5H, m), 1.86-2.06 (2H, s), 2.10-2.18 (23H, m), 2.27-2.42 (4H, m), 2.62-2.90 (7H, m), 3.44 (4H, t), 6.90 (2H, t), 7.11 (1H, s), 7.46 (2H, m), 7.84 (1H, s), 8.76 (1H, s) | C1 |
| 164 | 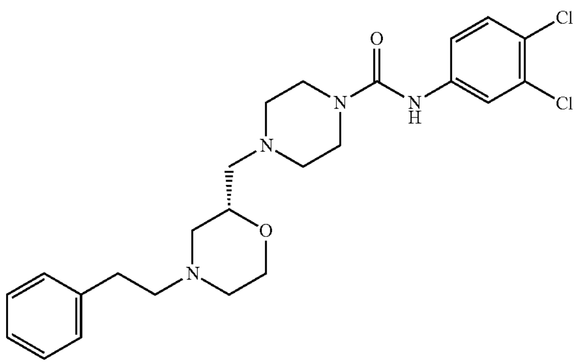 [SMILES: O=C(Nc1ccc(Cl)c(Cl)c1)N1CCN(C[C@H]2CN(CCc3ccccc3)CCO2)CC1] | N-(3,4-dichlorophenyl)-4-{[(2S)-4-(2-phenylethyl)morpholin-2-yl]methyl}piperazine-1-carboxamide<br>LCMS M/z(+) 477.28, 479.35 (M + H$^+$)<br>LCMS M/z(−) 475.23, 477.24 (M − H$^-$)<br>$^1$H-NMR (400.132 MHz, DMSO-d$_6$) 1.81 (1H, t), 2.04 (1H, m), 2.32-2.47 (6H, m), 2.74 (3H, t), 2.85 (1H, d), 3.43 (4H, t), 3.49 (1H, m), 3.60 (1H, m), 3.76 (1H, m), 7.16-7.30 (5H, m), 7.43-7.48 (2H, m), 7.84 (1H, d), 8.75 (1H, s) | C1 |
| 165 | 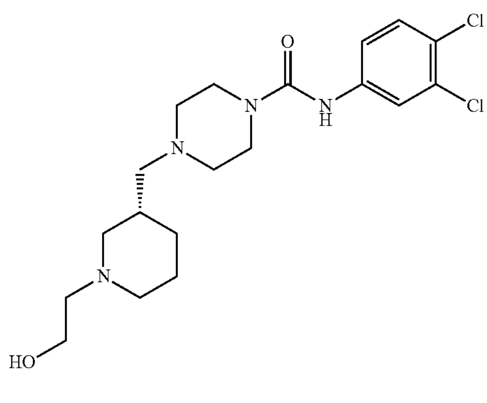 [SMILES: O=C(Nc1ccc(Cl)c(Cl)c1)N1CCN(C[C@@H]2CCCN(CCO)C2)CC1] | N-(3,4-Dichlorophenyl)-4-{[(3S)-1-(2-hydroxyethyl)piperidin-3-yl]methyl}piperazine-1-carboxamide<br>LCMS M/z(+) 415.23, 417.13 (M + H$^+$)<br>LCMS M/z(−) 415.20, 413.30 (M − H$^-$)<br>$^1$H-NMR (400.132 MHz, DMSO-d$_6$) 0.90 (1H, m), 1.45 (1H, m), 1.58 (1H, m), 1.67 (1H, m), 1.78 (1H, m), 1.91 (1H, m), 2.13 (2H, m), 2.39 (5H, m), 3.30 (5H, m), 3.46 (5H, m), 4.28 (1H, s), 7.43 (2H, dd), 7.82 (1H, s), 8.80 (1H, s) | C1 |

-continued

Examples

| Example No. | Structure | Characterisation Data | Chemistry Route |
|---|---|---|---|
| 166 | 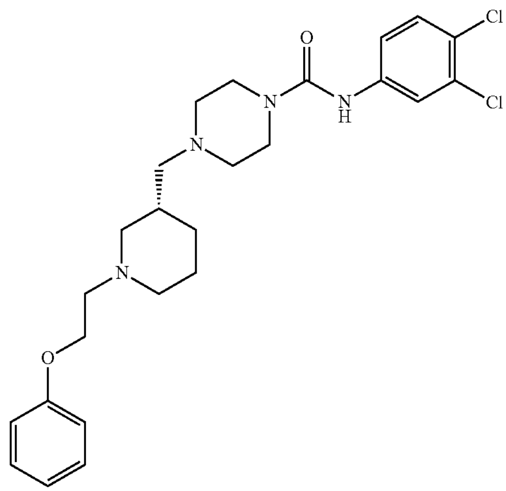 [SMILES: O=C(Nc1ccc(Cl)c(Cl)c1)N1CCN(C[C@@H]2CCCN(CCOc3ccccc3)C2)CC1] | N-(3,4-Dichlorophenyl)-4-{[(3S)-1-(2-phenoxyethyl)piperidin-3-yl]methyl}piperazine-1-carboxamide<br>LCMS M/z(+) 491.21, 493.14 (M + H$^+$)<br>LCMS M/z(−) 489.22, 491.21 (M − H$^-$)<br>$^1$H-NMR (400.132 MHz, DMSO-d$_6$) 0.90 (1H, m), 1.45 (1H, q), 1.59 (2H, m), 1.75 (2H, s), 2.00 (1H, m), 2.11 (2H, m), 2.31 (4H, m), 2.66 (2H, m), 2.87 (2H, m), 3.40 (4H, m), 4.04 (2H, m), 6.92 (3H, m), 7.28 (2H, m), 7.42 (2H, dd), 7.80 (1H, s), 8.72 (1H, s) | C1 |
| 167 | 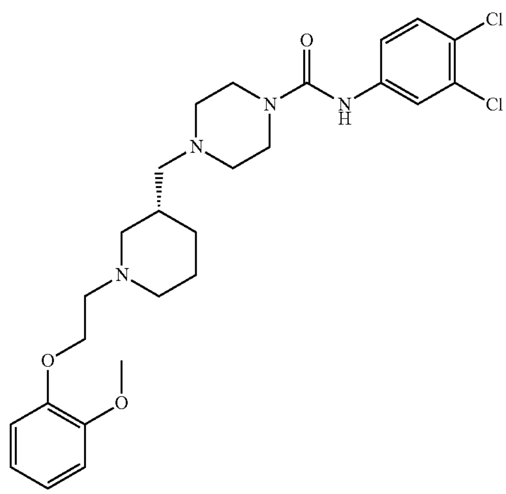 [SMILES: COc1ccccc1OCCN1CCC[C@@H](CN2CCN(C(=O)Nc3ccc(Cl)c(Cl)c3)CC2)C1] | N-(3,4-Dichlorophenyl)-4-({(3S)-1-[2-(2-methoxyphenoxy)ethyl]piperidin-3-yl}methyl)piperazine-1-carboxamide<br>LCMS M/z(+) 521.21, 523.15 (M + H$^+$)<br>LCMS M/z(−) 519.24, 521.21 (M − H$^-$)<br>$^1$H-NMR (400.132 MHz, DMSO-d$_6$) 0.90 (1H, m), 1.42 (5H, m), 1.50 (3H, m), 1.60 (2H, m), 2.01 (1H, s), 2.11 (2H, s), 2.32 (4H, m), 2.58 (2H, s), 2.82 (1H, d), 3.72 (3H, s), 4.01 (2H, s), 6.80 (2H, m), 6.92 (2H, m), 7.45 (2H, dd) 7.82 (1H, s), 8.75 (1H, s) | C1 |
| 168 | 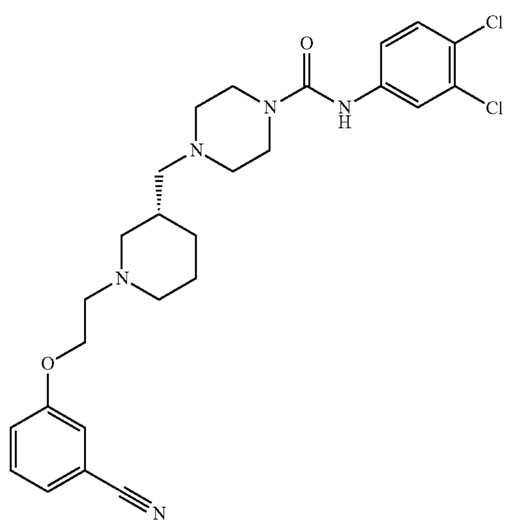 [SMILES: N#Cc1cccc(OCCN2CCC[C@@H](CN3CCN(C(=O)Nc4ccc(Cl)c(Cl)c4)CC3)C2)c1] | 4-({(3S)-1-[2-(3-Cyanophenoxy)ethyl]piperidin-3-yl}methyl)-N-(3,4-dichlorophenyl)piperazine-1-carboxamide<br>LCMS M/z(+) 516.21, 518.20 (M + H$^+$)<br>LCMS M/z(−) 514.21, 516.21 (M − H$^-$)<br>$^1$H-NMR (400.132 MHz, DMSO-d$_6$) 0.89 (2H, m), 1.40 (2H, q), 1.69 (3H, m), 2.00 (2H, m), 2.10 (3H, m), 2.31 (5H, m), 2.65 (2H, m), 2.88 (2H, m), 4.13 (2H, m), 7.29 (1H, m), 7.39 (1H, m), 7.45 (4H, m), 7.81 (1H, s), 8.74 (1H, s) | C1 |

-continued

Examples

| Example No. | Structure | Characterisation Data | Chemistry Route |
|---|---|---|---|
| 169 | 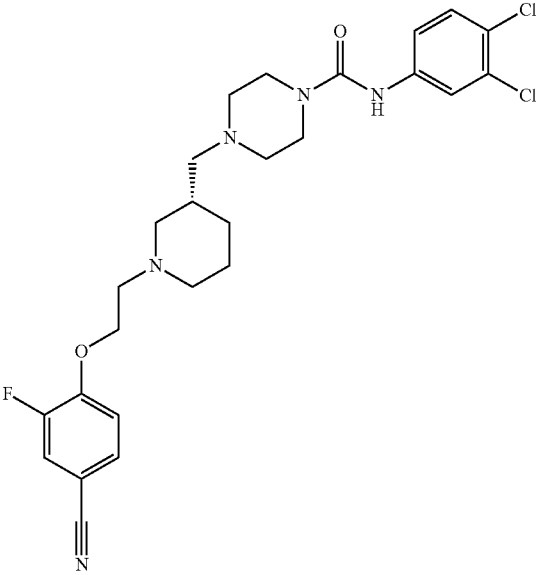 [SMILES: N#Cc1ccc(OCCN2CCC[C@@H](CN3CCN(C(=O)Nc4ccc(Cl)c(Cl)c4)CC3)C2)c(F)c1] | 4-({(3S)-1-[2-(4-Cyano-2-fluorophenoxy)ethyl]piperidin-3-yl}methyl)-N-(3,4-dichlorophenyl)piperazine-1-carboxamide<br>LCMS M/z(+) 534.16, 536.24 (M + H$^+$)<br>$^1$H-NMR (400.132 MHz, DMSO-d$_6$) 0.90 (2H, t), 1.35 (2H, m), 1.60 (3H, m), 1.74 (2H, m), 2.06 (1H, m), 2.12 (2H, m), 2.31 (3H, m), 2.71 (2H, m), 2.80 (1H, d), 2.90 (1H, d), 3.40 (2H, m), 4.27 (2H, t), 7.38 (1H, t), 7.45 (2H, dd), (7.67 (1H, d), 7.81 (2H, m), 8.72 (1H, s) | C1 |
| 170 | 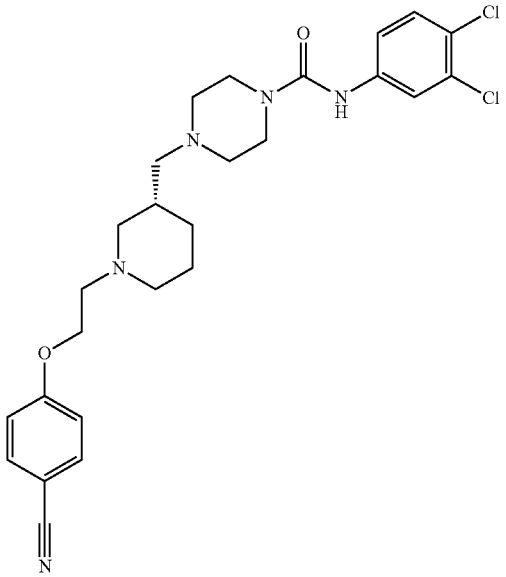 [SMILES: N#Cc1ccc(OCCN2CCC[C@@H](CN3CCN(C(=O)Nc4ccc(Cl)c(Cl)c4)CC3)C2)cc1] | 4-({(3S)-1-[2-(4-Cyanophenoxy)ethyl]piperidin-3-yl}methyl)-N-(3,4-dichlorophenyl)piperazine-1-carboxamide<br>LCMS M/z(+) 516.08, 517.98 (M + H$^+$)<br>LCMS M/z(−) 514.17, 516.08 (M − H$^-$)<br>$^1$H-NMR (400.132 MHz, DMSO-d$_6$) 0.90 (1H, q), 1.40 (1H, m), 1.60 (2H, d), 1.67 (2H, d), 2.00 (1H, t), 2.11 (2H, m), 2.18 (2H, m), 2.30 (1H, d), 2.31 (4H, m), 2.40 (1H, d), 3.40 (4H, t), 4.16 (2H, t), 7.12 (2H, d), 7.45 (2H, d), 7.77 (2H, dd), 7.82 (1H, s), 8.72 (1H, s) | C1 |

-continued

Examples

| Example No. | Structure | Characterisation Data | Chemistry Route |
|---|---|---|---|
| 171 | 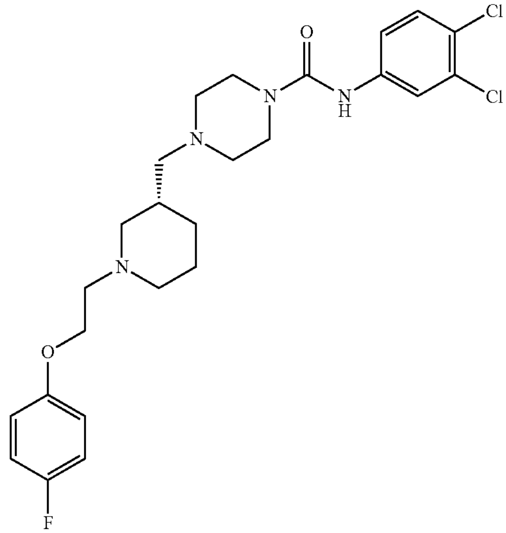 [SMILES: O=C(Nc1ccc(Cl)c(Cl)c1)N1CCN(C[C@@H]2CCCN(CCOc3ccc(F)cc3)C2)CC1] | N-(3,4-Dichlorophenyl)-4-({(3S)-1-[2-(4-fluorophenoxy)ethyl]piperidin-3-yl}methyl)piperazine-1-carboxamide<br>LCMS M/z(+) 509.18, 511.08 (M + H$^+$)<br>LCMS M/z(−) 507.19, 509.19 (M − H$^-$)<br>$^1$H-NMR (400.132 MHz, DMSO-d$_6$) 0.90 (1H, q), 1.45 (1H, q), 1.67 (2H, d), 1.78 (2H, s), 2.02 (1H, t), 2.15 (2H, m), 2.32 (4H, m), 2.68 (2H, m), 2.82 (1H, d), 2.90 (1H, d), 3.41 (4H, m), 4.10 (2H, m), 6.95 (2H, m), 7.11 (2H, m), 7.44 (2H, dd), 7.82 (1H, s), 8.72 (1H, s) | C1 |
| 172 | 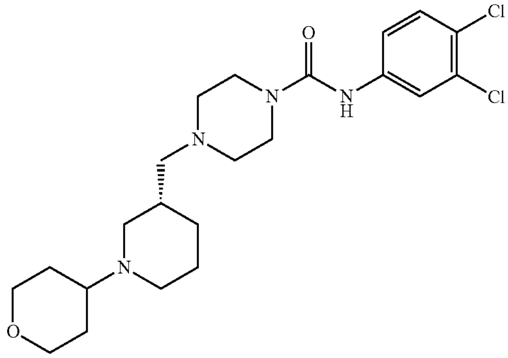 | N-(3,4-Dichlorophenyl)-4-{[(3S)-1-(tetrahydro-2H-pyran-4-yl)piperidin-3-yl]methyl}piperazine-1-carboxamide<br>LCMS M/z(+) 455.18, 457.09 (M + H$^+$)<br>LCMS M/z(−) 453.16, 455.08 (M − H$^-$)<br>$^1$H-NMR (400.132 MHz, DMSO-d$_6$) 0.92 (1H, d), 1.46 (3H, m), 1.65 (4H, m), 1.82 (2H, m), 2.12 (3H, m), 2.33 (5H, m), 2.71 to 2.91 (2H, d), 3.30 (2H, m), 3.40 (4H, m), 3.88 (2H, d), 7.45 (2H, dd), 7.82 (1H, s), 8.76 (1H, s) | C1 |
| 173 | 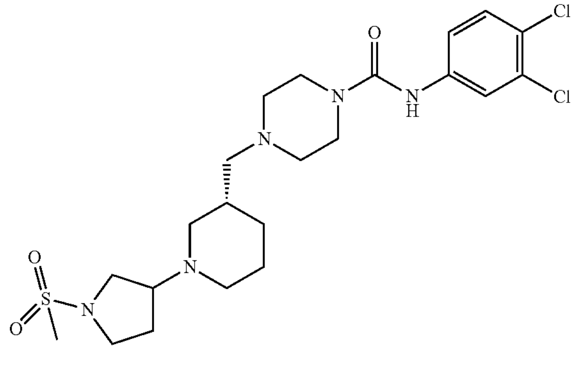 [SMILES: CS(=O)(=O)N1CCC(N2CCC[C@@H](CN3CCN(C(=O)Nc4ccc(Cl)c(Cl)c4)CC3)C2)C1] | N-(3,4-Dichlorophenyl)-4-({(3S)-1-[1-(methylsulfonyl)pyrrolidin-3-yl]piperidin-3-yl}methyl)piperazine-1-carboxamide<br>LCMS M/z(+) 518.13, 520.00 (M + H$^+$)<br>LCMS M/z(−) 517.97 (M − H$^-$)<br>$^1$H-NMR (400.132 MHz, DMSO-d$_6$) 0.90 (1H, m), 1.47 (1H, m), 1.71 (5H, m), 2.02 (2H, m), 2.12 (2H, m), 2.32 (4H, m), 2.87 (3H, s), 2.96 (1H, s), 3.20 (1H, q), 3.41 (5H, s), 7.47 (2H, t), 7.82 (1H, s), 8.72 (1H, s) | C1 |

-continued

Examples

| Example No. | Structure | Characterisation Data | Chemistry Route |
|---|---|---|---|
| 174 | 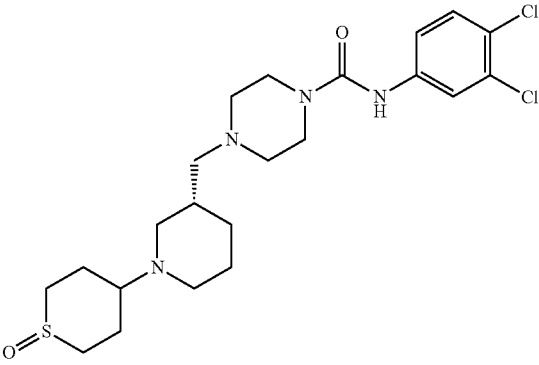 [SMILES: O=C(Nc1ccc(Cl)c(Cl)c1)N1CCN(C[C@@H]2CCCN(C3CCS(=O)CC3)C2)CC1] | N-(3,4-Dichlorophenyl)-4-{[(3S)-1-(1-oxidotetrahydro-2H-thiopyran-4-yl)piperidin-3-yl]methyl}piperazine-1-carboxamide<br>LCMS M/z(+) 488.91, (M + H$^+$)<br>LCMS M/z(−) 485.11, 487.14 (M − H$^−$)<br>$^1$H-NMR (400.132 MHz, DMSO-d$_6$) 1.43 (1H, m), 1.66 (5H, m), 2.00 (1H, m), 2.06 (5H, m), 2.20 (5H, m), 2.60 (2H, t), 2.90 (2H, m), 3.12 (1H, m), 3.40 (5H, m), 7.45 (2H, dd), 7.81 (1H, s), 8.74 (1H, s) | C1 |
| 175 | 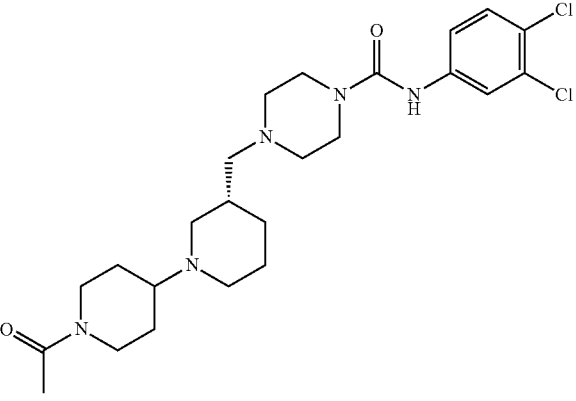 [SMILES: CC(=O)N1CCC(N2CCC[C@@H](CN3CCN(C(=O)Nc4ccc(Cl)c(Cl)c4)CC3)C2)CC1] | 4-{[(3S)-1'-Acetyl-1,4'-bipiperidin-3-yl]methyl}-N-(3,4-dichlorophenyl)piperazine-1-carboxamide<br>LCMS M/z(+) 496.24, 498.22 (M + H$^+$)<br>LCMS M/z(−) 494.21, 496.24 (M − H$^−$)<br>$^1$H-NMR (400.132 MHz, DMSO-d$_6$) 0.90 (1H, m), 1.22 (1H, m), 1.43 (1H, m), 1.68 (5H, m), 2.00 (3H, s), 2.17 (2H, m), 2.35 (4H, m), 2.51 (2H, m), 2.95 (1H, t), 3.30 (5H, m), 3.31 (1H, d), 3.41 (4H, t), 4.40 (1H, d), 7.45 (2H, dd), 7.82 (1H, s), 8.75 (1H, s) | C1 |
| 176 | 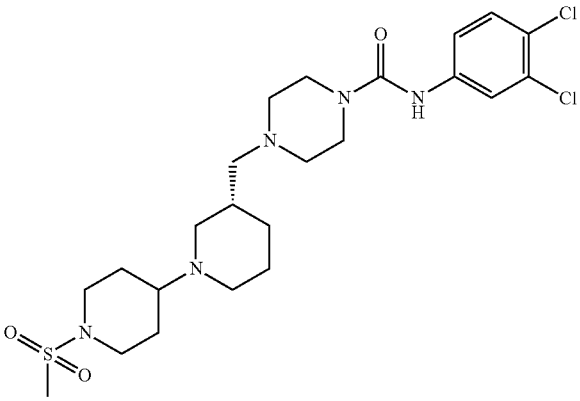 [SMILES: CS(=O)(=O)N1CCC(N2CCC[C@@H](CN3CCN(C(=O)Nc4ccc(Cl)c(Cl)c4)CC3)C2)CC1] | N-(3,4-Dichlorophenyl)-4-{[(3S)-1'-(methylsulfonyl)-1,4'-bipiperidin-3-yl]methyl}piperazine-1-carboxamide<br>LCMS M/z(+) 533.73, (M + H$^+$)<br>LCMS M/z(−) 531.89 (M − H$^−$)<br>$^1$H-NMR (400.132 MHz, DMSO-d$_6$) 1.09 (1H, m), 1.71 (4H, m), 1.90 (1H, m), 2.07 to 2..38 (8H, dd), 2.74 (3H, m), 2.90 (3H, s), 3.28 (3H, m), 3.42 (6H, s), 3.70 (2H, s), 7.47 (2H, dd), 7.82 (1H, s), 8.79 (1H, s) | C1 |

-continued

Examples

| Example No. | Structure | Characterisation Data | Chemistry Route |
|---|---|---|---|
| 177 | 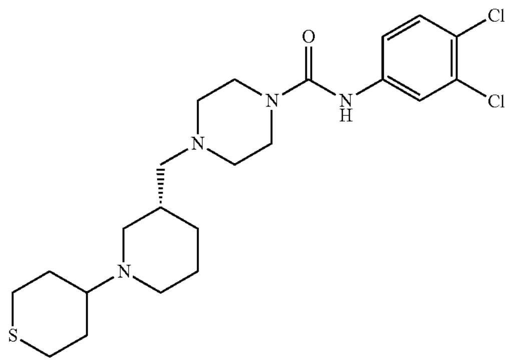 [SMILES: O=C(Nc1ccc(Cl)c(Cl)c1)N1CCN(C[C@@H]2CCCN(C3CCSCC3)C2)CC1] | N-(3,4-Dichlorophenyl)-4-{[(3S)-1'-(tetrahydro-2H-thiopyran-4-yl)-1,4'-bipiperidin-3-yl]methyl}piperazine-1-carboxamide<br>LCMS M/z(+) 471.06, 473.07 (M + H$^+$)<br>LCMS M/z(−) 469.15, 471.08 (M − H$^-$)<br>$^1$H-NMR (400.132 MHz, DMSO-d$_6$) 0.90 (1H, m), 1.41 (1H, m), 1.60 (5H, m), 1.97 (3H, m), 2.12 (3H, m), 2.31 (5H, m), 2.62 (5H, m), 2.80 (1H, d), 3.40 (4H, s), 7.46 (2H, t), 7.85 (1H, s), 8.75 (1H, s) | C1 |
| 178 | 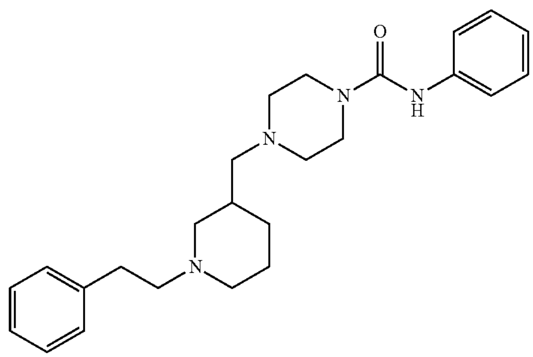 [SMILES: O=C(Nc1ccccc1)N1CCN(CC2CCCN(CCc3ccccc3)C2)CC1] | 4-[(1-phenylethylpiperidin-3-yl)methyl]-N-phenylpiperazine-1-carboxamide<br>LCMS M/z(+) 407.37 (M + H$^+$)<br>$^1$H-NMR (400.132 MHz, DMSO-d$_6$) 1.0 (1H, m), 1.8 (4H, m), 2.2 (2H, m), 2.3 (4H, m), 2.9 (4H, m), 3.1 (4H, m), 3.5 (4H, m), 6.9 (1H, t), 7.2 (7H, m), 7.45 (2H, d), 8.45 (1H, s) | A1 |
| 179 | 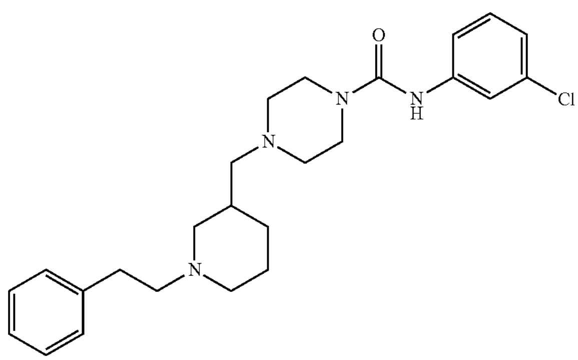 [SMILES: O=C(Nc1cccc(Cl)c1)N1CCN(CC2CCCN(CCc3ccccc3)C2)CC1] | N-(3-chlorophenyl)-4-[(1-phenylethyl piperidin-3-yl)methyl]piperazine-1-carboxamide<br>LCMS M/z(+) 441.28 (M + H$^+$)<br>$^1$H-NMR (400.132 MHz, DMSO-d$_6$) 1.0 (2H, m), 1.4 (1H, m), 1.6 (2H, m), 1.75 (2H, m), 1.95 (1H, m), 2.1 (2H, m), 2.3 (4H, m), 2.8 (4H, m), 3.5 (5H, m), 6.9 (1H, d), 7.2 (6H, m), 7.4 (1H, d), 7.6 (1H, s), 8.6 (1H, s) | A1 |
| 180 | 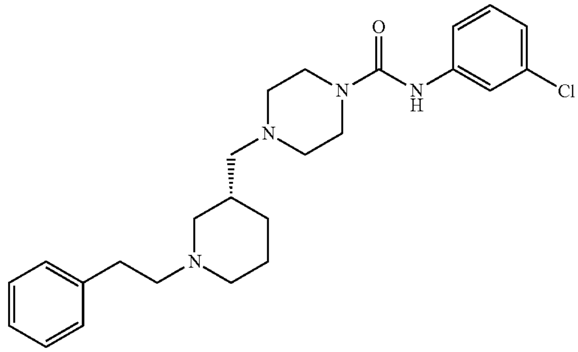 [SMILES: O=C(Nc1cccc(Cl)c1)N1CCN(C[C@@H]2CCCN(CCc3ccccc3)C2)CC1] | N-(3-chlorophenyl)-4-{[(3R)-1-(2-phenylethyl)piperidin-3-yl]methyl}piperazine-1-carboxamide<br>LCMS M/z(+) 440.90 (M + H$^+$)<br>$^1$H-NMR (400.132 MHz, DMSO-d$_6$) 0.9 (1H, m), 1.7 (4H, m), 2.3 (6H, m), 2.7-3.6 (12H, m), 6.95 (1H, d), 7.2 (6H, m), 7.4 (1H, d), 7.65 (1H, s), 8.65 (1H, s) | A1 |

-continued

Examples

| Example No. | Structure | Characterisation Data | Chemistry Route |
|---|---|---|---|
| 181 | 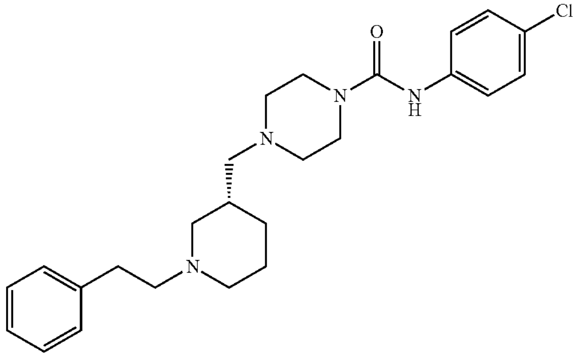 [SMILES: O=C(Nc1ccc(Cl)cc1)N1CCN(C[C@@H]2CCCN(CCc3ccccc3)C2)CC1] | N-(4-chlorophenyl)-4-{[(3R)-1-(2-phenylethyl)piperidin-3-yl]methyl}piperazine-1-carboxamide<br>LCMS M/z(+) 440.88 (M + H$^+$)<br>$^1$H-NMR (400.132 MHz, DMSO-d$_6$) 0.9-1.8 (5H, m), 2.3 (6H, m), 2.6-3.5 (12H, m), 7.2 (7H, m), 7.5 (2H, m), 8.6 (1H, s) | A1 |
| 182 | 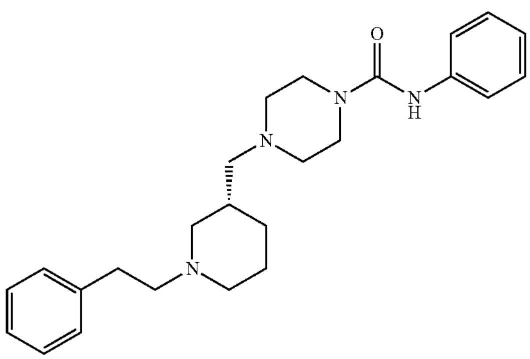 [SMILES: O=C(Nc1ccccc1)N1CCN(C[C@@H]2CCCN(CCc3ccccc3)C2)CC1] | N-Phenyl-4-{[(3R)-1-(2-phenylethyl)piperidin-3-yl]methyl}piperazine-1-carboxamide<br>LCMS M/z(+) 406.97 (M + H$^+$)<br>$^1$H-NMR (400.132 MHz, DMSO-d$_6$) 1.4 (3H, m), 2.1 (2H, m), 2.3-3.5 (18H, m), 6.9 (1H, t), 7.25 (7H, m), 7.45 (2H, d), 8.45 (1H, s) | A1 |
| 183 | 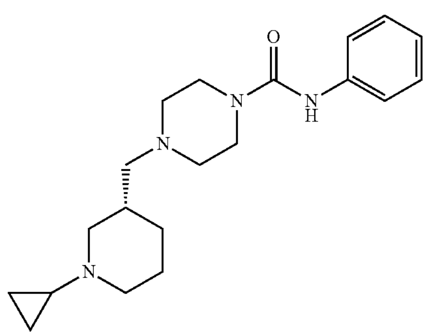 [SMILES: O=C(Nc1ccccc1)N1CCN(C[C@@H]2CCCN(C3CC3)C2)CC1] | N-Phenyl-4-{[(3R)-1-(2-cyclopropyl)piperidin-3-yl]methyl}piperazine-1-carboxamide<br>LCMS M/z(+) 343.01 (M + H$^+$)<br>$^1$H-NMR (400.132 MHz, DMSO-d$_6$) 0.7 (4H, m), 1.4 (3H, m), 1.85 (2H, m), 2.1 (2H, m), 2.5-3.1 (5H, m), 3.2 (8H, m), 6.7 (1H, t), 6.95 (2H, t), 7.2 (2H, d), 8.2 (1H, s) | A1 |
| 184 | 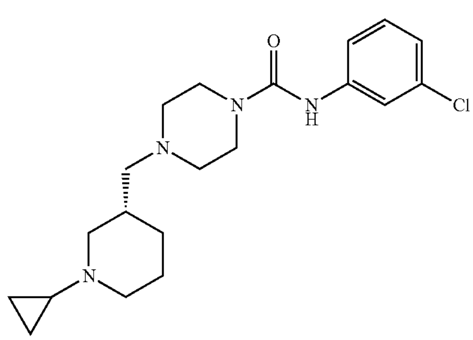 [SMILES: O=C(Nc1cccc(Cl)c1)N1CCN(C[C@@H]2CCCN(C3CC3)C2)CC1] | N-(3-chlorophenyl)-4-{[(3R)-1-(2-cyclopropyl)piperidin-3-yl]methyl}piperazine-1-carboxamide<br>LCMS M/z(+) 377.51 (M + H$^+$)<br>$^1$H-NMR (400.132 MHz, DMSO-d$_6$) 1.1 (9H, m), 2.2 (4H, m), 2.5-3.5 (11H, m), 7.0 (1H, d), 7.25 (1H, t), 7.4 (1H, d), 7.65 (1H, s), 8.7 (1H, s) | A1 |

| Example No. | Structure | Characterisation Data | Chemistry Route |
|---|---|---|---|
| 185 | 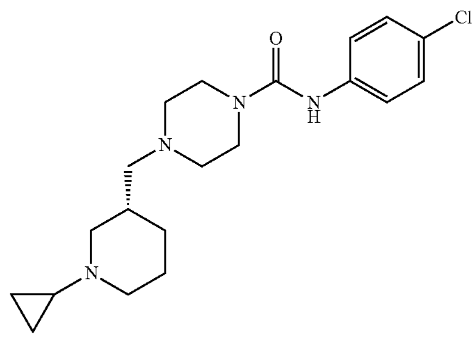 [SMILES: O=C(Nc1ccc(Cl)cc1)N1CCN(C[C@@H]2CCCN(C3CC3)C2)CC1] | N-(4-chlorophenyl)-4-{[(3R)-1-(2-cyclopropyl)piperidin-3-yl]methyl}piperazine-1-carboxamide<br>LCMS M/z(+) 377.45 (M + H$^+$)<br>$^1$H-NMR (400.132 MHz, DMSO-d$_6$) 0.2 (4H, m), 1.2 (5H, m), 1.9 (6H, m), 2.6 (2H, m), 3.2 (7H, m), 6.9 (2H, d), 7.1 (2H, d), 8.25 (1H, s) | A1 |
| 186 | 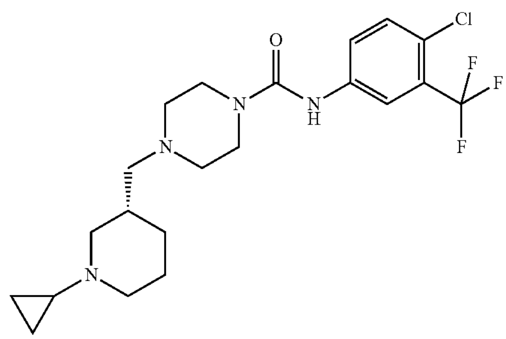 [SMILES: O=C(Nc1ccc(Cl)c(C(F)(F)F)c1)N1CCN(C[C@@H]2CCCN(C3CC3)C2)CC1] | N-[4-chloro-3-(trifluoromethyl)phenyl]-4-{[(3S)-1-cyclopropylpiperidin-3-yl]methyl}piperazine-1-carboxamide<br>LCMS M/z(+) 444.93 (M + H$^+$)<br>$^1$H NMR (400.132 MHz, CDCl$_3$) 0.36-0.68 (m, 4H), 0.85-1.03 (m, 1H), 1.40-2.06 (m, 6H), 2.15-2.26 (m, 3H), 2.34-2.43 (m, 2H), 2.44-2.53 (m, 2H), 2.99-3.30 (m, 2H), 3.42-3.57 (m, 4H), 6.58 (s, 1H), 7.39 (d, 1H), 7.72 (s, 1H) | A1 |
| 187 | 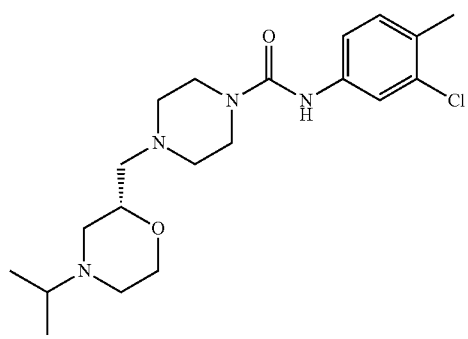 [SMILES: Cc1ccc(NC(=O)N2CCN(C[C@H]3CN(C(C)C)CCO3)CC2)cc1Cl] | N-(3-chloro-4-methylphenyl)-4-{[(2S)-4-isopropylmorpholin-2-yl]methyl}piperazine-1-carboxamide<br>LCMS M/z(+) 394.92 (M + H$^+$)<br>$^1$H NMR (400.132 MHz, CDCl$_3$) 1.04 (d, 3H), 1.06 (d, 3H), 1.99 (t, 1H), 2.23-2.34 (m, 2H), 2.30 (s, 3H), 2.49-2.71 (m, 7H), 2.73-2.79 (m, 1H), 3.44-3.56 (m, 4H), 3.64 (td, 1H), 3.68-3.75 (m, 1H), 3.88-3.94 (m, 1H), 6.23 (s, 1H), 7.09-7.15 (m, 2H), 7.43 (d, 1H) | A1 |
| 188 | 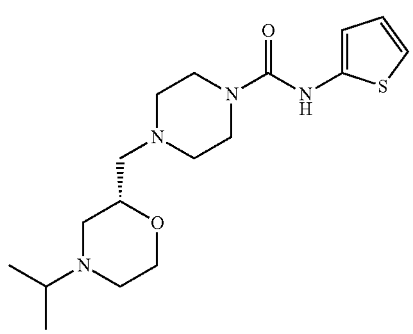 [SMILES: CC(C)N1CCO[C@@H](CN2CCN(C(=O)Nc3cccs3)CC2)C1] | 4-{[(2S)-4-isopropylmorpholin-2-yl]methyl}-N-2-thienylpiperazine-1-carboxamide<br>LCMS M/z(+) 352.94 (M + H$^+$)<br>$^1$H NMR (400.132 MHz, CDCl$_3$) 1.04 (d, 3H), 1.06 (d, 3H), 1.98 (t, 1H), 2.23-2.34 (m, 2H), 2.48-2.70 (m, 7H), 2.72-2.78 (m, 1H), 3.45-3.57 (m, 4H), 3.64 (dt, 1H), 3.68-3.75 (m, 1H), 3.88-3.94 (m, 1H), 6.52 (dd, 1H), 6.78-6.83 (m, 2H), 6.94 (s, 1H) | A1 |

-continued

Examples

| Example No. | Structure | Characterisation Data | Chemistry Route |
|---|---|---|---|
| 189 | 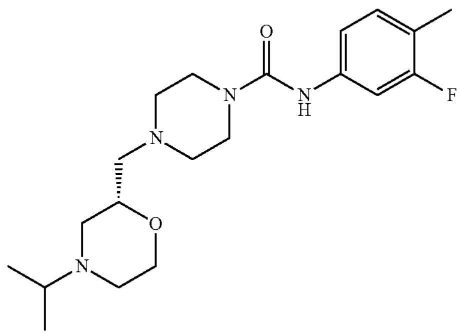 [SMILES: Cc1ccc(NC(=O)N2CCN(C[C@H]3CN(C(C)C)CCO3)CC2)cc1F] | N-(3-fluoro-4-methylphenyl)-4-{[(2S)-4-isopropylmorpholin-2-yl]methyl}piperazine-1-carboxamide<br>LCMS M/z(+) 378.98 (M + H$^+$)<br>$^1$H NMR (400.132 MHz, MeOD) 0.98 (d, 3H), 1.00 (d, 3H), 1.91 (t, 1H), 2.09 (d, 3H), 2.20 (td, 1H), 2.30 (dd, 1H), 2.37-2.49 (m, 5H), 2.54 (quintet, 1H), 2.65 (d, 1H), 2.74 (d, 1H), 3.43 (t, 4H), 3.53 (td, 1H), 3.60-3.67 (m, 1H), 3.75-3.81 (m, 1H), 6.90 (dd, 1H), 6.98 (t, 1H), 7.08 (dd, 1H) | A1 |
| 190 | 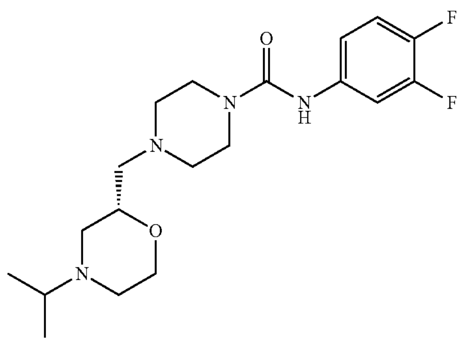 [SMILES: CC(C)N1CCO[C@@H](CN2CCN(C(=O)Nc3ccc(F)c(F)c3)CC2)C1] | N-(3,4-difluorophenyl)-4-{[(2S)-4-isopropylmorpholin-2-yl]methyl}piperazine-1-carboxamide<br>LCMS M/z(+) 382.95 (M + H$^+$)<br>$^1$H NMR (400.132 MHz, MeOD) 0.98 (d, 3H), 0.99 (d, 3H), 1.91 (t, 1H), 2.19 (td, 1H), 2.30 (dd, 1H), 2.37-2.49 (m, 5H), 2.53 (quintet, 1H), 2.65 (d, 1H), 2.74 (d, 1H), 3.43 (t, 4H), 3.53 (td, 1H), 3.59-3.67 (m, 1H), 3.75-3.81 (m, 1H), 6.95-7.07 (m, 2H), 7.27-7.34 (m, 1H) | A1 |
| 191 | 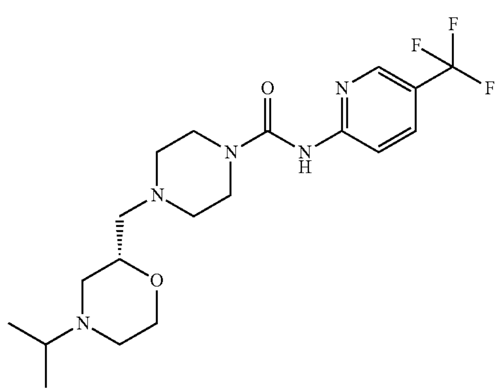 [SMILES: CC(C)N1CCO[C@@H](CN2CCN(C(=O)Nc3ccc(C(F)(F)F)cn3)CC2)C1] | 4-{[(2S)-4-isopropylmorpholin-2-yl]methyl}-N-[5-(trifluoromethyl)pyridin-2-yl]piperazine-1-carboxamide<br>LCMS M/z(+) 415.94 (M + H$^+$)<br>$^1$H NMR (400.132 MHz, CDCl$_3$) 1.07 (t, 6H), 2.02 (t, 1H), 2.25-2.36 (m, 2H), 2.48-2.83 (m, 8H), 3.51-3.81 (m, 6H), 3.90-3.96 (m, 1H), 7.36 (s, 1H), 7.85 (dd, 1H), 8.16 (d, 1H), 8.45 (s, 1H) | A1 |
| 192 | 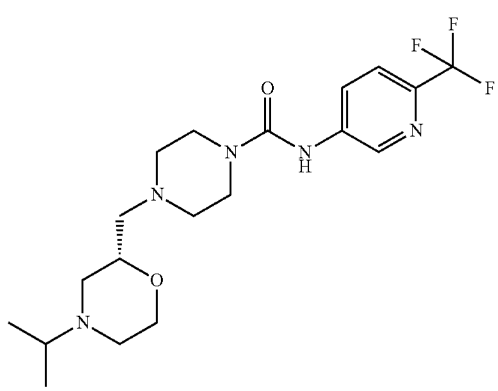 [SMILES: CC(C)N1CCO[C@@H](CN2CCN(C(=O)Nc3ccc(C(F)(F)F)nc3)CC2)C1] | 4-{[(2S)-4-isopropylmorpholin-2-yl]methyl}-N-[6-(trifluoromethyl)pyridin-3-yl]piperazine-1-carboxamide<br>LCMS M/z(+) 415.92 (M + H$^+$)<br>$^1$H NMR (400.132 MHz, CDCl$_3$) 1.05 (d, 3H), 1.06 (d, 3H), 2.00 (t, 1H), 2.30 (ddd, 2H), 2.51-2.79 (m, 8H), 3.50-3.61 (m, 4H), 3.65 (td, 1H), 3.69-3.76 (m, 1H), 3.89-3.95 (m, 1H), 6.59 (s, 1H), 7.61 (d, 1H), 8.23 (dd, 1H), 8.48 (d, 1H) | A1 |

-continued

Examples

| Example No. | Structure | Characterisation Data | Chemistry Route |
|---|---|---|---|
| 193 | 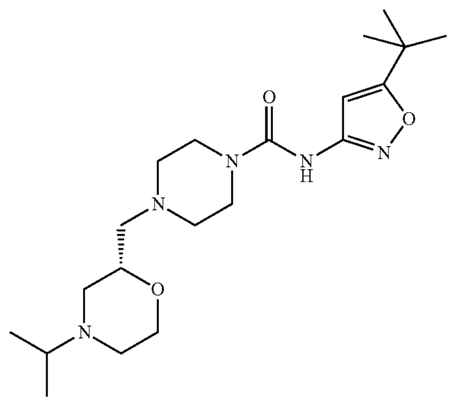 [SMILES: CC(C)N1CCO[C@@H](CN2CCN(C(=O)Nc3cc(C(C)(C)C)on3)CC2)C1] | N-(5-tert-butylisoxazol-3-yl)-4-{[(2S)-4-isopropylmorpholin-2-yl]methyl}piperazine-1-carboxamide<br>LCMS M/z(+) 394.00 (M + H$^+$)<br>$^1$H NMR (400.132 MHz, CDCl$_3$) 1.06 (d, 3H), 1.05 (d, 3H), 1.32 (s, 9H), 1.99 (t, 1H), 2.24-2.33 (m, 2H), 2.48-2.79 (m, 8H), 3.53-3.77 (m, 6H), 3.89-3.95 (m, 1H), 6.63 (s, 1H), 8.70 (s, 1H) | A1 |
| 194 | 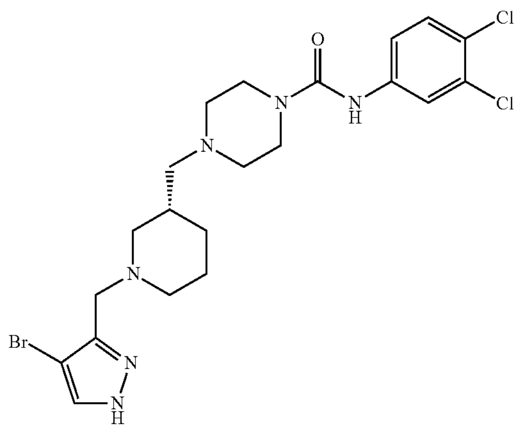 [SMILES: O=C(Nc1ccc(Cl)c(Cl)c1)N1CCN(C[C@@H]2CCCN(Cc3n[nH]cc3Br)C2)CC1] | 4-({(3S)-1-[(4-Bromo-1H-pyrazol-3-yl)methyl]piperidin-3-yl}methyl)-N-(3,4-dichlorophenyl)piperazine-1-carboxamide LCMS M/z(+) 531.08 (M + H$^+$)<br>$^1$H-NMR (400.132 MHz, DMSO-d$_6$) 0.88 (1H, m), 1.43 (1H, m), 1.61 (2H, m), 1.77 (2H, s), 2.02 (1H, m), 2.15 (2H, m), 2.33 (4H, m), 2.66 (1H, m), 2.80 (1H, m), 3.43 (6H, m), 7.49 (2H, s), 7.86 (1H, s), 8.14 (1H, s), 8.76 (1H, s), 9.90 (1H, s) | C1 |
| 195 | 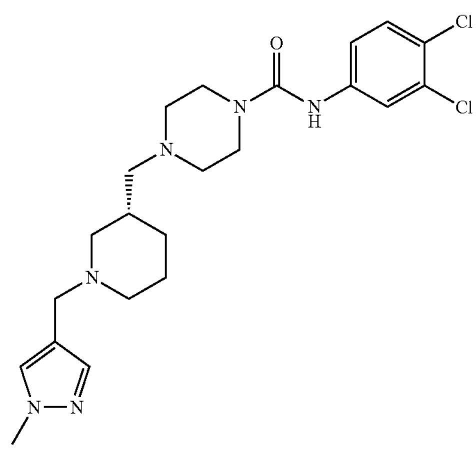 [SMILES: Cn1cc(CN2CCC[C@@H](CN3CCN(C(=O)Nc4ccc(Cl)c(Cl)c4)CC3)C2)cn1] | N-(3,4-Dichlorophenyl)-4-({(3R)-1-[(1-methyl-1H-pyrazol-4-yl)methyl]piperidin-3-yl}methyl)piperazine-1-carboxamide<br>LCMS M/z(−) 463.20 (M − H$^−$)<br>$^1$H-NMR (400.132 MHz, DMSO-d$_6$) 0.85 (1H, m), 0.98 (1H, m), 1.55 (1H, m), 1.72 (2H, m), 1.96 (2H, m), 2.19 (3H, m), 2.34 (5H, m), 3.42 (4H, m), 3.84 (3H, s), 7.47 (3H, s), 7.78 (1H, s), 7.84 (1H, m), 8.78 (1H, m) (2H obscured) | C1 |

-continued

Examples

| Example No. | Structure | Characterisation Data | Chemistry Route |
|---|---|---|---|
| 196 | 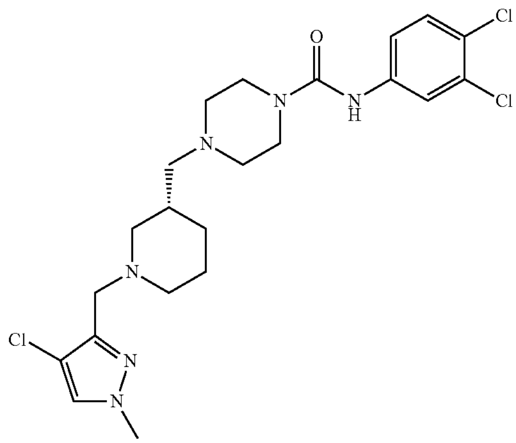 [SMILES: Cn1cc(Cl)c(CN2CCC[C@@H](CN3CCN(C(=O)Nc4ccc(Cl)c(Cl)c4)CC3)C2)n1] | 4-({(3S)-1-[(4-Chloro-1-methyl-1H-pyrazol-3-yl)methyl]piperidin-3-yl}methyl)-N-(3,4-dichlorophenyl)piperazine-1-carboxamide<br>LCMS M/z(−) 497.17 (M − H⁻), M/z(+) 499.21 (M + H⁺)<br>¹H-NMR (400.132 MHz, DMSO-d₆) 0.88 (1H, m), 1.44 (1H, m), 1.62 (2H, m), 1.79 (2H, m), 2.01 (1H, m), 2.15 (2H, m), 2.34 (4H, m), 2.81 (2H, m), 3.45 (6H, m), 3.80 (3H, s), 7.46 (2H, s), 7.87 (2H, m), 8.77 (1H, s) | C1 |
| 197 | 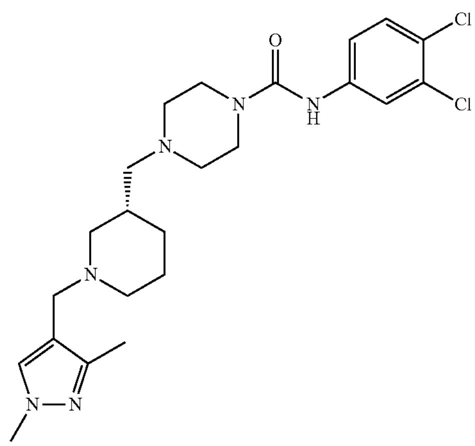 [SMILES: Cc1nn(C)cc1CN1CCC[C@@H](CN2CCN(C(=O)Nc3ccc(Cl)c(Cl)c3)CC2)C1] | N-(3,4-Dichlorophenyl)-4-({(3R)-1-[(1,3-dimethyl-1H-pyrazol-4-yl)methyl]piperidin-3-yl}methyl)piperazine-1-carboxamide<br>LCMS M/z(−) 477.24 (M − H⁻), M/z(+) 479.23 (M + H⁺)<br>¹H-NMR (400.132 MHz, DMSO-d₆) 0.90 (3H, m), 1.14 (1H, m), 1.27 (1H, m), 1.49 (1H, m), 1.67 (1H, m), 1.85 (1H, m), 2.14 (4H, m), 2.33 (4H, m), 2.88 (2H, m), 3.42 (6H, m), 3.73 (3H, s), 7.48 (3H, m), 7.84 (1H, m), 8.78 (1H, s) | C1 |
| 198 | 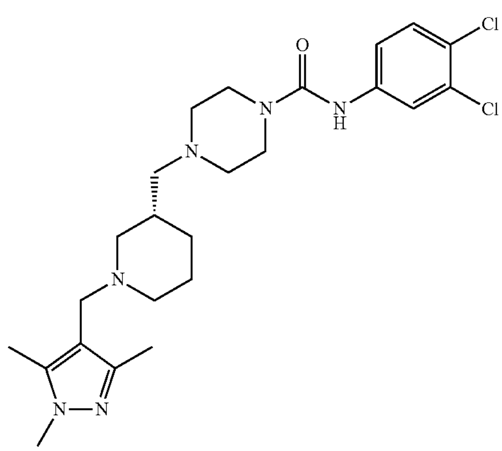 [SMILES: Cc1nn(C)c(C)c1CN1CCC[C@@H](CN2CCN(C(=O)Nc3ccc(Cl)c(Cl)c3)CC2)C1] | N-(3,4-Dichlorophenyl)-4-({(3R)-1-[(1,3,5-trimethyl-1H-pyrazol-4-yl)methyl]piperidin-3-yl}methyl)piperazine-1-carboxamide<br>LCMS M/z(−) 491.28 (M − H⁻), M/z(+) 493.29 (M + H⁺)<br>¹H-NMR (400.132 MHz, DMSO-d₆) 0.88 (1H, m), 1.39 (1H, m), 1.57 (1H, m), 1.71 (3H, m), 1.91 (1H, m), 2.05 (3H, m), 2.14 (5H, m), 2.32 (4H, m), 2.61 (1H, m), 2.75 (1H, m), 3.16 (2H, m), 3.42 (4H, m), 3.61 (3H, s), 7.46 (2H, m), 7.84 (1H, s), 8.75 (1H, s) | C1 |

-continued

Examples

| Example No. | Structure | Characterisation Data | Chemistry Route |
|---|---|---|---|
| 199 | 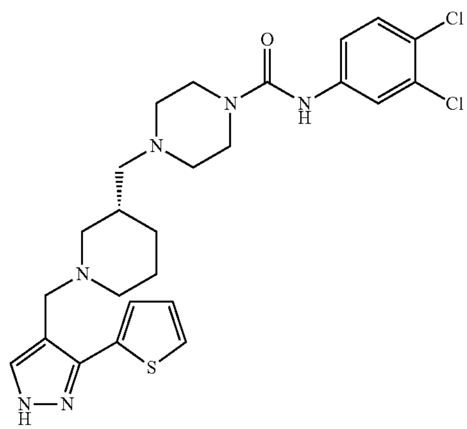 [SMILES: O=C(Nc1ccc(Cl)c(Cl)c1)N1CCN(C[C@@H]2CCCN(Cc3c[nH]nc3-c3cccs3)C2)CC1] | N-(3,4-Dichlorophenyl)-4-[((3R)-1-{[3-(2-thienyl)-1H-pyrazol-4-yl]methyl}piperidin-3-yl)methyl]piperazine-1-carboxamide<br>LCMS M/z(−) 531.18 (M − H$^-$), M/z(+) 533.18 (M + H$^+$)<br>$^1$H-NMR (400.132 MHz, DMSO-d$_6$) 0.84 (2H, m), 0.99 (1H, m), 1.46 (1H, m), 1.72 (4H, m), 2.24 (4H, m), 2.74 (1H, m), 3.39 (8H, m), 7.12 (1H, m), 7.47 (4H, m), 7.66 (1H, m), 7.84 (1H, m), 8.76 (1H, m), 12.74 (1H, m) | C1 |
| 200 | 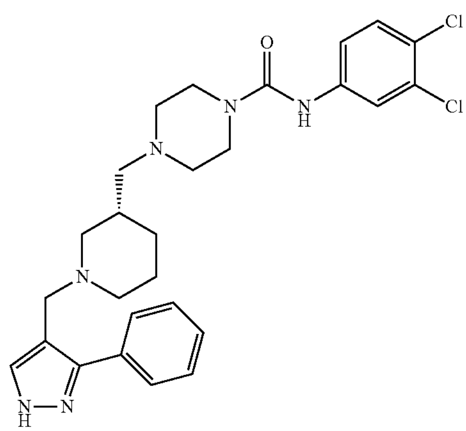 [SMILES: O=C(Nc1ccc(Cl)c(Cl)c1)N1CCN(C[C@@H]2CCCN(Cc3c[nH]nc3-c3ccccc3)C2)CC1] | N-(3,4-Dichlorophenyl)-4-({(3R)-1-[(3-phenyl-1H-pyrazol-4-yl)methyl]piperidin-3-yl}methyl)piperazine-1-carboxamide<br>LCMS M/z(−) 525.22 (M − H$^-$), M/z(+) 527.19 (M + H$^+$)<br>$^1$H-NMR (400.132 MHz, DMSO-d$_6$) 0.84 (1H, m), 0.98 (2H, m), 1.59 (4H, m), 1.92 (1H, m), 2.23 (6H, m), 2.96 (3H, m), 3.43 (6H, m), 7.43 (4H, m), 7.70 (3H, m), 7.85 (1H, m), 8.80 (1H, m) | C1 |
| 201 | 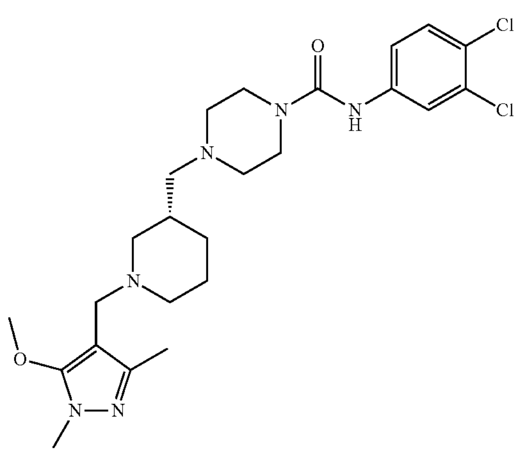 [SMILES: COc1c(CN2CCC[C@@H](CN3CCN(C(=O)Nc4ccc(Cl)c(Cl)c4)CC3)C2)c(C)nn1C] | N-(3,4-Dichlorophenyl)-4-({(3R)-1-[(5-methoxy-1,3-dimethyl-1H-pyrazol-4-yl)methyl]piperidin-3-yl}methyl)piperazine-1-carboxamide<br>LCMS M/z(−) 507 (M − H$^-$), M/z(+) 509 (M + H$^+$)<br>$^1$H-NMR (400.132 MHz, DMSO-d$_6$) 1.03 (1H, m), 1.48 (1H, m), 1.66 (2H, m), 1.80 (1H, m), 1.94 (1H, m), 2.04 (3H, m), 2.19 (3H, m), 2.36 (4H, m), 2.72 (1H, m), 2.83 (1H, m), 3.32 (2H, m), 3.41 (3H, m), 3.51 (3H, m), 3.93 (3H, m), 7.42 (2H, m), 7.80 (1H, s) 2 protons obscured under DMSO peak | C1 |

-continued

Examples

| Example No. | Structure | Characterisation Data | Chemistry Route |
|---|---|---|---|
| 202 | 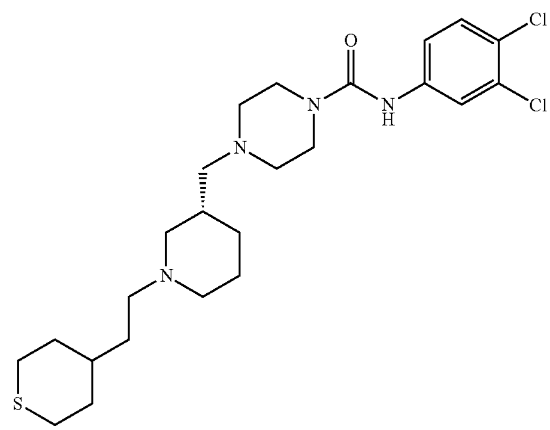 [SMILES: O=C(Nc1ccc(Cl)c(Cl)c1)N1CCN(C[C@@H]2CCCN(CCC3CCSCC3)C2)CC1] | N-(3,4-Dichlorophenyl)-4-({(3R)-1-[2-(tetrahydro-2H-thiopyran-4-yl)ethyl]piperidin-3-yl}methyl)piperazine-1-carboxamide<br>LCMS M/z(−) 497.15 (M − H⁻), M/z(+) 499.15 (M + H⁺)<br>¹H-NMR (400.132 MHz, DMSO-d₆) 0.89 (1H, m), 1.34 (6H, m), 1.66 (4H, m), 1.86 (1H, m), 1.96 (2H, m), 2.23 (8H, m), 2.57 (4H, m), 2.68 (1H, m), 2.76 (1H, m), 3.43 (4H, m), 7.46 (2H, s), 7.84 (1H, s), 8.76 (1H, s) | C1 |
| 203 | 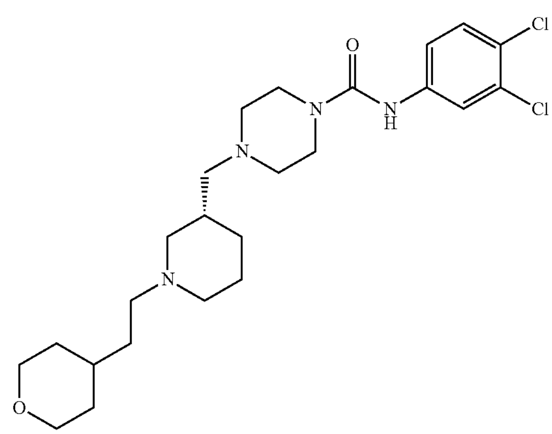 [SMILES: O=C(Nc1ccc(Cl)c(Cl)c1)N1CCN(C[C@@H]2CCCN(CCC3CCOCC3)C2)CC1] | N-(3,4-Dichlorophenyl)-4-({(3R)-1-[2-(tetrahydro-2H-pyran-4-yl)ethyl]piperidin-3-yl}methyl)piperazine-1-carboxamide<br>LCMS M/z(−) 481.20 (M − H⁻), M/z(+) 483.21 (M + H⁺)<br>¹H-NMR (400.132 MHz, DMSO-d₆) 0.88 (2H, m), 1.15 (2H, m), 1.35 (2H, m), 1.55 (4H, m), 1.83 (3H, s), 2.15 (4H, m), 2.30 (4H, m), 2.69 (1H, m), 2.78 (1H, m), 3.26 (2H, m), 3.43 (4H, m), 3.81 (2H, m), 7.46 (2H, m), 7.84 (1H, m), 8.79 (1H, s) (1H obscured) | C1 |
| 204 | 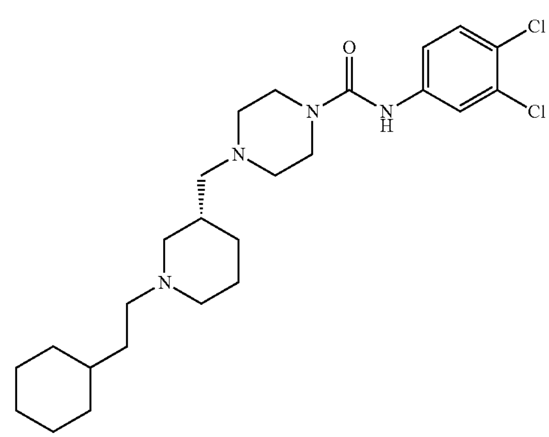 [SMILES: O=C(Nc1ccc(Cl)c(Cl)c1)N1CCN(C[C@@H]2CCCN(CCC3CCCCC3)C2)CC1] | 4-{[(3R)-1-(2-Cyclohexylethyl)piperidin-3-yl]methyl}-N-(3,4-dichlorophenyl)piperazine-1-carboxamide<br>LCMS M/z(−) 479.24 (M − H⁻), M/z(+) 481.27 (M + H⁺)<br>¹H-NMR (400.132 MHz, DMSO-d₆) 0.88 (3H, m), 1.22 (6H, m), 1.43 (1H, m), 1.67 (9H, m), 1.88 (1H, m), 2.14 (2H, m), 2.30 (6H, m), 2.70 (1H, m), 2.79 (1H, m), 3.43 (4H, m), 7.46 (2H, s), 7.84 (1H, s), 8.76 (1H, s) | C1 |

| Example No. | Structure | Characterisation Data | Chemistry Route |
|---|---|---|---|
| 205 | 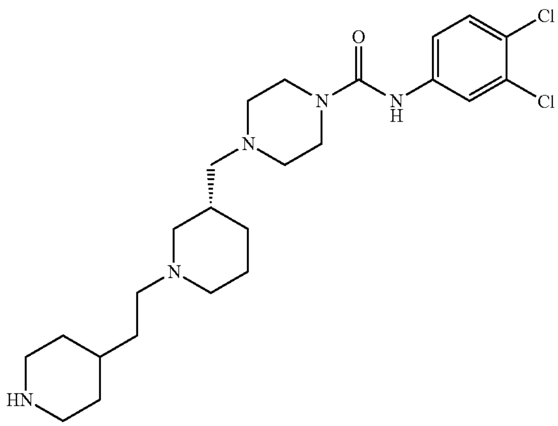 [SMILES: O=C(Nc1ccc(Cl)c(Cl)c1)N1CCN(C[C@@H]2CCCN(CCC3CCNCC3)C2)CC1] | N-(3,4-Dichlorophenyl)-4-{[(3R)-1-(2-piperidin-4-ylethyl)piperidin-3-yl]methyl}piperazine-1-carboxamide<br>$^1$H-NMR (400.132 MHz, DMSO-$d_6$) 0.88 (1H, m), 1.02 (3H, m), 1.33 (2H, m), 1.45 (1H, m), 1.61 (4H, m), 1.75 (1H, m), 1.85 (1H, m), 2.28 (8H, m), 2.68 (1H, m), 2.77 (1H, m), 2.91 (2H, m), 3.45 (8H, m), 7.45 (2H, m), 7.84 (1H, m), 8.76 (1H, m) | C1 |
| 206 | 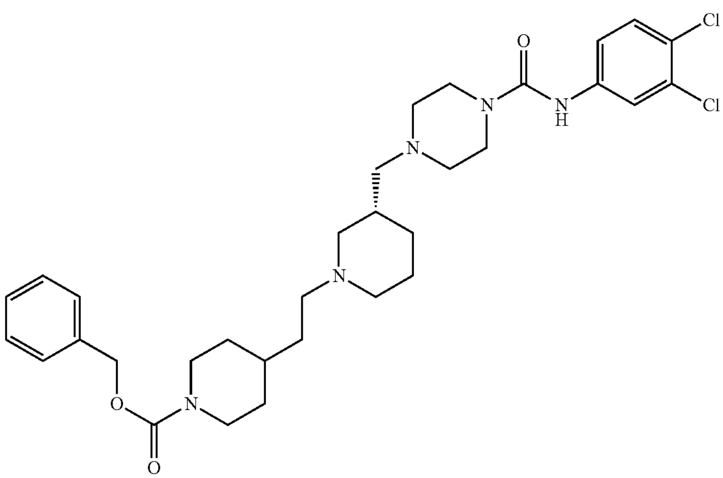 [SMILES: O=C(Nc1ccc(Cl)c(Cl)c1)N1CCN(C[C@@H]2CCCN(CCC3CCN(C(=O)OCc4ccccc4)CC3)C2)CC1] | Benzyl 4-(2-{(3R)-3-[(4-{[(3,4-dichlorophenyl)amino]carbonyl}pipezin-1-yl)methyl]piperidin-1-yl}ethyl)piperidine-1-carboxylate<br>LCMS M/z(−) 613.92 (M − H$^-$), M/z(+) 616.20 (M + H$^+$)<br>$^1$H-NMR (400.132 MHz, DMSO-$d_6$) 0.87 (2H, m), 1.02 (2H, m), 1.35 (2H, m), 1.45 (2H, m), 1.66 (4H, m), 1.85 (2H, m), 2.14 (2H, m), 2.30 (6H, m), 2.75 (4H, m), 3.43 (4H, m), 3.97 (2H, m), 5.06 (2H, s), 7.35 (5H, m), 7.46 (2H, m), 7.84 (1H, m), 8.77 (1H, s) | C1 |
| 207 | 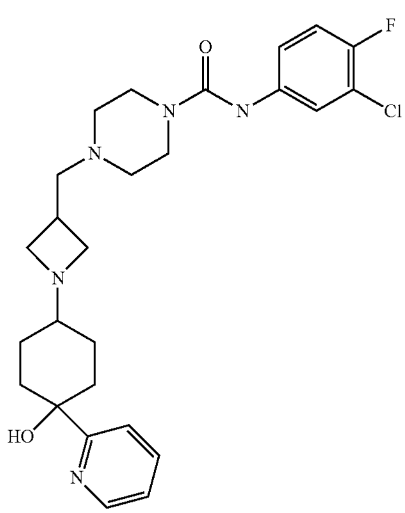 [SMILES: O=C(Nc1ccc(F)c(Cl)c1)N1CCN(CC2CN(C3CCC(O)(c4ccccn4)CC3)C2)CC1] | N-(3-Chloro-4-fluorophenyl)-4-{[1-(4-hydroxy-4-pyridin-2-ylcyclohexyl)azetidin-3-yl]methyl}piperazine-1-carboxamide<br>LCMS M/z(+) 501.86 (M + H$^+$)<br>$^1$H-NMR (400.132 MHz, DMSO-$d_6$) 1.1-1.8 (5H, m), 2.0-3.6 (19H, m), 4.85 (1H, s), 7.2 (2H, m), 7.4 (1H, m), 7.6 (1H, d), 7.7 (2H, m), 8.6 (2H, m) | C1 |

-continued

Examples

| Example No. | Structure | Characterisation Data | Chemistry Route |
|---|---|---|---|
| 208 | 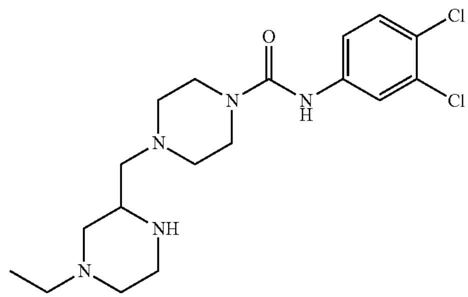 [SMILES: CCN1CCNC(CN2CCN(C(=O)Nc3ccc(Cl)c(Cl)c3)CC2)C1] | N-(3,4-Dichlorophenyl)-4-[(4-ethyl piperazin-2-yl)methyl]piperazine-1-carboxamide<br>LCMS M/z(+) 399 (M + H$^+$), 422.2 (M + Na$^+$)<br>$^1$H NMR (400.132 MHz, DMSO-d$_6$) 0.84 (3H, m), 0.99 (1H, m), 1.21 (2H, m), 2.34 (8H, m), 3.45 (8H, m), 7.46 (2H, m), 7.84 (1H, m), 8.00 (1H, m), 8.75 (1H, m) | C1 |
| 209 | 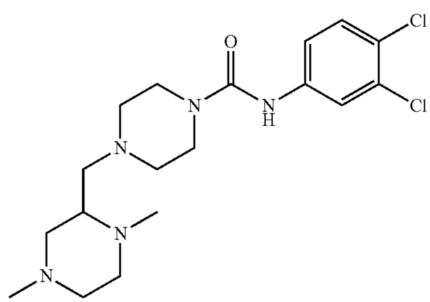 [SMILES: CN1CCN(C)C(CN2CCN(C(=O)Nc3ccc(Cl)c(Cl)c3)CC2)C1] | 1-{[1,4-Dimethylpiperazin-3-yl]methyl}-N-(3,4-dichlorophenyl)piperazine-4-carboxamide<br>LCMS M/z(+) 400.36 (M + H$^+$)<br>$^1$H-NMR (400.132 MHz, DMSO-d$_6$)(373K) 1.85 (1H, dd), 2.08 (1H, dt), 2.17 (3H, s), 2.20-2.25 (1H?, m, obscured), 2.26 (3H, s), 2.45 (3H, m), 2.52 (?H, obscured), 2.62-2.78 (2H, m), 3.42-3.48 (4H, m), 7.40 (1H, d), 7.45 (1H, dd), 7.81 (1H, d), 8.49 (1H, s) | C1 |
| 210 | 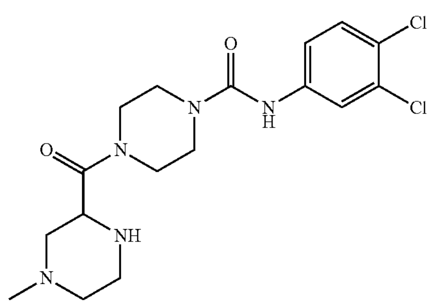 [SMILES: CN1CCNC(C(=O)N2CCN(C(=O)Nc3ccc(Cl)c(Cl)c3)CC2)C1] | N-(3,4-Dichlorophenyl)-4-{[(2R)-4-methylpiperazin-2-yl]carbonyl}piperazine-1-carboxamide<br>LCMS M/z(+) 400.35 (M + H$^+$)<br>$^1$H-NMR (400.132 MHz, DMSO-d$_6$)(373K): 1.84 (2H, m), 2.18 (3H, s), 2.175 (1H, s), 2.59 (1H, dquintet), 2.65-2.77 (3H, m), 2.89 (3H, m, partially obscured), 3.47-3.52 (3H, m), 3.54-3.59 (3H, m), 3.69 (1H, dd), 7.44 (2H, m), 7.82 (1H, d), 8.58 (1H, s) | C3 |
| 211 | 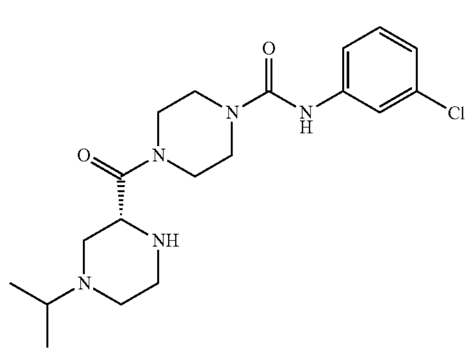 [SMILES: CC(C)N1CCN[C@@H](C(=O)N2CCN(C(=O)Nc3cccc(Cl)c3)CC2)C1] | N-(3-chlorophenyl)-4-{[(2R)-4-isopropylpiperazin-2-yl]carbonyl}piperazine-1-carboxamide<br>LCMS M/z(+) 394.94 (M + H$^+$)<br>$^1$H-NMR (400.132 MHz, CDCl$_3$) 1.06-1.18 (6H, m), 2.21-2.39 (2H, m), 2.69-2.97 (3H, m), 3.00-3.18 (2H, m), 3.38-3.69 (6H, m), 3.70-3.77 (2H, m), 4.12 (1H, d), 6.98 (1H, s), 7.01 (1H, s), 7.20 (1H, t), 7.29 (1H, d) and 7.51 (1H, d) | A1 |

-continued

| Example No. | Structure | Characterisation Data | Chemistry Route |
|---|---|---|---|
| 212 | 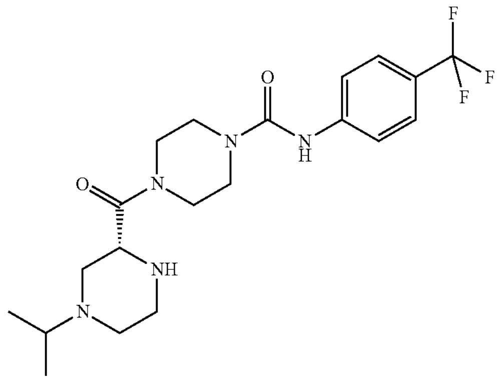 [SMILES: CC(C)N1CCN[C@@H](C(=O)N2CCN(C(=O)Nc3ccc(C(F)(F)F)cc3)CC2)C1] | 4-{[(2R)-4-isopropylpiperazin-2-yl]carbonyl}-N-[4-(trifluoromethyl)phenyl]piperazine-1-carboxamide<br>LCMS M/z(+) 428.56 (M + H$^+$)<br>$^1$H-NMR (400.132 MHz, CDCl$_3$) 1.04-1.20 (6H, m), 2.20-2.42 (2H, m), 2.80-3.00 (3H, m), 3.01-3.18 (2H, m), 3.39-3.69 (6H, m), 3.26-3.89 (2H, m), 3.96-4.0 (1H, d), 6.65 (1H, s), 7.49 (2H, d) and 7.57 (2H, d) | A1 |
| 213 | 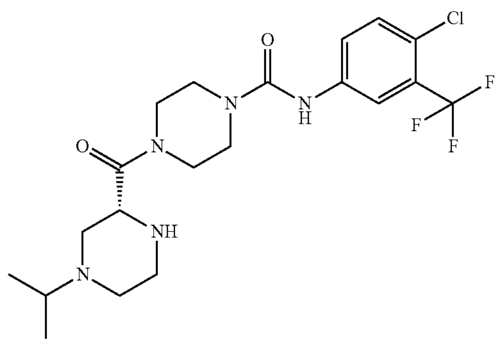 [SMILES: CC(C)N1CCN[C@@H](C(=O)N2CCN(C(=O)Nc3ccc(Cl)c(C(F)(F)F)c3)CC2)C1] | N-[4-chloro-3-(trifluoromethyl)phenyl]-4-{[(2R)-4-isopropylpiperazin-2-yl]carbonyl}piperazine-1-carboxamide<br>LCMS M/z(+) 462.83 (M + H$^+$)<br>$^1$H-NMR (400.132 MHz, CDCl$_3$) 1.10-1.23 (6H, m), 2.26-2.50 (2H, m), 2.89-3.06 (3H, m), 3.09-3.20 (2H, m), 3.39-3.72 (6H, m), 3.76-3.90 (2H, m), 4.07-4.10 (1H, d), 6.99 (1H, s), 7.49 (1H, d), 7.62 (1H, dd) and 7.77 (1H, d) | A1 |
| 214 | 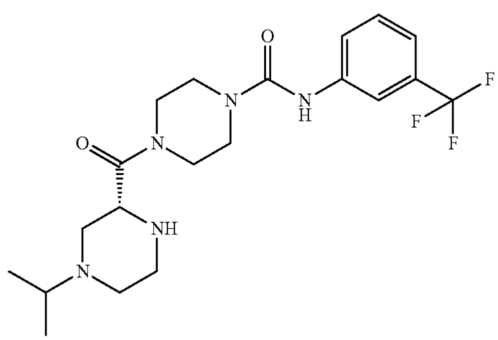 [SMILES: CC(C)N1CCN[C@@H](C(=O)N2CCN(C(=O)Nc3cccc(C(F)(F)F)c3)CC2)C1] | 4-{[(2R)-4-isopropylpiperazin-2-yl]carbonyl}-N-[3-(trifluoromethyl)phenyl]piperazine-1-carboxamide<br>LCMS M/z(+) 428.63 (M + H$^+$)<br>$^1$H-NMR (400.132 MHz, CDCl$_3$) 1.03-1.11 (6H, m), 2.14-2.29 (2H, m), 2.70-2.99 (4H, m), 3.10 (1H, d), 3.42-3.69 (6H, m), 3.70-3.90 (3H, m), 6.82 (1H, s), 7.30 (1H, d), 7.40 (1H, t), 7.49 (1H, d) and 7.68 (1H, s) | A1 |
| 215 | 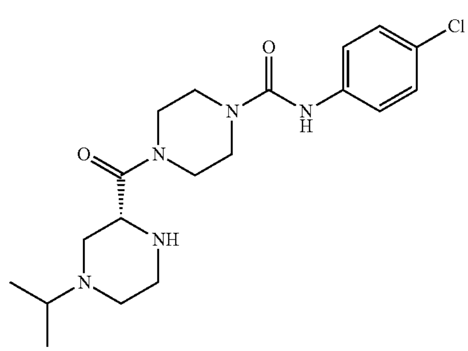 | N-(4-chlorophenyl)-4-{[(2R)-4-isopropylpiperazin-2-yl]carbonyl}piperazine-1-carboxamide<br>LCMS M/z(+) 394.98 (M + H$^+$)<br>$^1$H-NMR (400.132 MHz, CDCl$_3$) 1.02-1.12 (6H, m), 2.14-2.31 (2H, m), 2.74-2.86 (2H, m), 2.89-3.00 (2H, m), 3.11 (1H, d), 3.39-3.65 (6H, m), 3.70-3.91 (3H, m), 6.39 (1H, s) and 7.23-7.37 (4H, m) | A1 |

-continued

| Example No. | Structure | Characterisation Data | Chemistry Route |
|---|---|---|---|
| 216 | 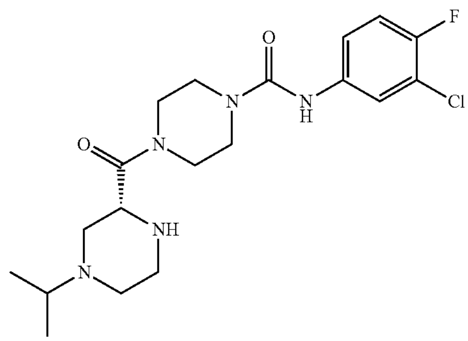 [SMILES: CC(C)N1CCN[C@@H](C(=O)N2CCN(C(=O)Nc3ccc(F)c(Cl)c3)CC2)C1] | N-(3-chloro-4-fluorophenyl)-4-{[(2R)-4-isopropylpiperazin-2-yl]carbonyl}piperazine-1-carboxamide<br>LCMS M/z(+) 412.95 (M + H$^+$)<br>$^1$H-NMR (400.132 MHz, CDCl$_3$) 1.04-1.18 (6H, m), 2.15-2.34 (2H, m), 2.53-3.06 (4H, m), 3.13 (1H, m), 3.39-3.65 (6H, m), 3.73-3.89 (2H, m), 3.95 (1H, d), 6.60 (1H, s), 7.07 (1H, t), 7.19-7.24 (1H, m) and 7.50-7.55 (1H, m) | A1 |
| 217 | 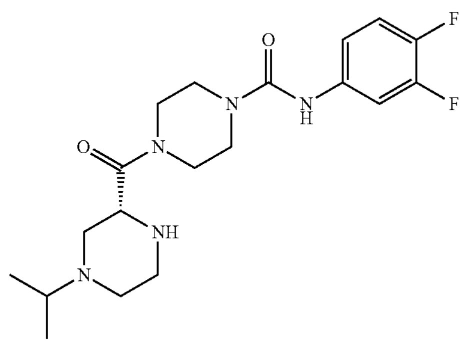 [SMILES: CC(C)N1CCN[C@@H](C(=O)N2CCN(C(=O)Nc3ccc(F)c(F)c3)CC2)C1] | N-(3,4-difluorophenyl)-4-{[(2R)-4-isopropylpiperazin-2-yl]carbonyl}piperazine-1-carboxamide<br>LCMS M/z(+) 396.73 (M + H$^+$)<br>$^1$H-NMR (400.132 MHz, CDCl$_3$) 1.03-1.19 (6H, m), 2.14-2.34 (2H, m), 2.73-3.12 (4H, m), 3.12 (dH, m), 3.39-3.68 (6H, m), 3.72-3.95 (3H, m), 6.45 (1H, s), 6.95 (1H, d), 7.07 (1H, m) and 7.41 (1H, m) | A1 |
| 218 | 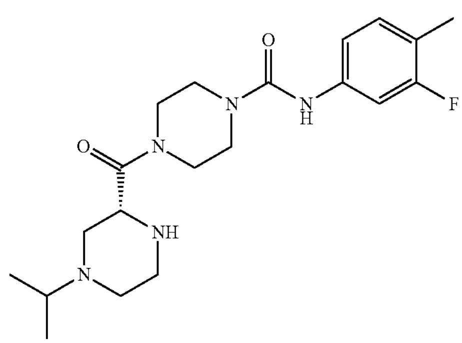 [SMILES: Cc1ccc(NC(=O)N2CCN(C(=O)[C@H]3CN(C(C)C)CCN3)CC2)cc1F] | N-(3-fluoro-4-methylphenyl)-4-{[(2R)-4-isopropylpiperazin-2-yl]carbonyl}piperazine-1-carboxamide<br>LCMS M/z(+) 392.45 (M + H$^+$)<br>$^1$H-NMR (400.132 MHz, CDCl$_3$) 1.09-1.20 (6H, m), 2.20 (3H, s), 2.35-2.45 (2H, m), 2.80-3.00 (3H, m), 3.05-3.40 (2H, m), 3.40-3.69 (6H, m), 3.73-3.86 (2H, m), 4.11 (1H, d), 6.53 (1H, s), 6.98 (1H, dd), 7.06 (1H, t) and 7.23 (1H, s) | A1 |
| 219 | 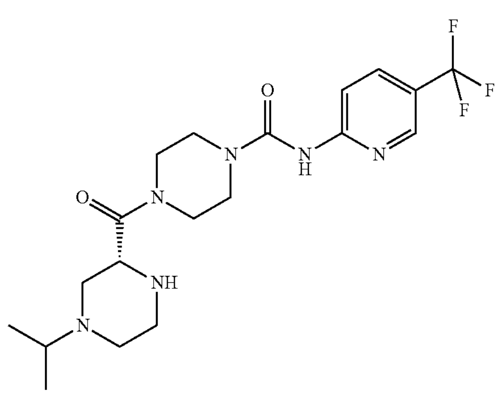 [SMILES: CC(C)N1CCN[C@@H](C(=O)N2CCN(C(=O)Nc3ccc(C(F)(F)F)cn3)CC2)C1] | 4-{[(2R)-4-isopropylpiperazin-2-yl]carbonyl}-N-[5-(trifluoromethyl)pyridin-2-yl]piperazine-1-carboxamide<br>LCMS M/z(+) 429.58 (M + H$^+$)<br>$^1$H-NMR (400.132 MHz, CDCl$_3$) 0.99-1.08 (6H, m), 2.02-2.24 (2H, m), 2.67-2.79 (2H, m), 2.81-2.97 (2H, m), 3.10 (1H, d), 3.45-.3.72 (6H, m), 3.78-3.92 (3H, m), 7.45 (1H, s), 7.88 (1H, dd), 8.15 (1H, d) and 8.48 (1H, s) | A1 |

Examples

| Example No. | Structure | Characterisation Data | Chemistry Route |
|---|---|---|---|
| 220 | 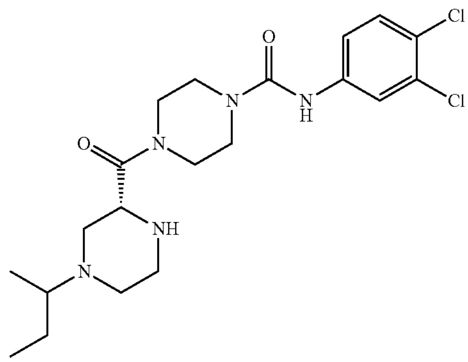 [SMILES: CCC(C)N1CCN[C@@H](C(=O)N2CCN(C(=O)Nc3ccc(Cl)c(Cl)c3)CC2)C1] | 4-{[(2R)-4-sec-butylpiperazin-2-yl]carbonyl}-N-(3,4-dichlorophenyl)piperazine-1-carboxamide<br>LCMS M/z(+) 441.91 (M + H$^+$)<br>1H NMR (300 MHz, DMSO-d$_6$) 0.85 (6H, m), 1.3 (1H, m), 1.5 (1H, m), 2.1-2.6 (4H, m), 2.75 (2H, d), 3.0 (1H, d), 3.2-3.7 (8H, m), 3.9 (1H, m), 7.5 (2H, m), 7.85 (1H, s), 8.9 (1H, s) | C3 |
| 221 | 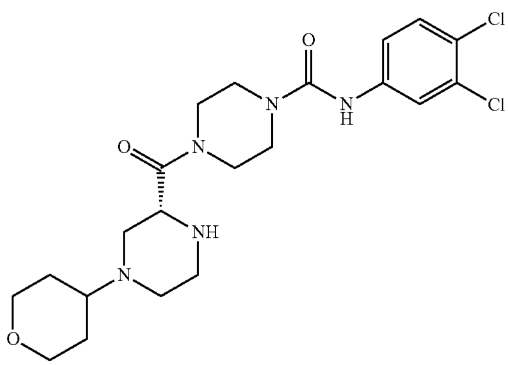 [SMILES: O=C(Nc1ccc(Cl)c(Cl)c1)N1CCN(C(=O)[C@H]2CN(C3CCOCC3)CCN2)CC1] | N-(3,4-dichlorophenyl)-4-{[(2R)-4-(tetrahydro-2H-pyran-4-yl)piperazin-2-yl]carbonyl}piperazine-1-carboxamide<br>LCMS M/z(+) 469.99 (M + H$^+$)<br>1H NMR (300 MHz, DMSO-d$_6$) δ 1.4 (2H, m), 1.7 (2H, d), 2.1 (2H, m), 2.4-3.6 (15H, m), 3.8 (1H, d), 3.9 (2H, d), 7.5 (2H, m), 7.85 (1H, s), 8.9 (1H, s) | C3 |
| 222 | 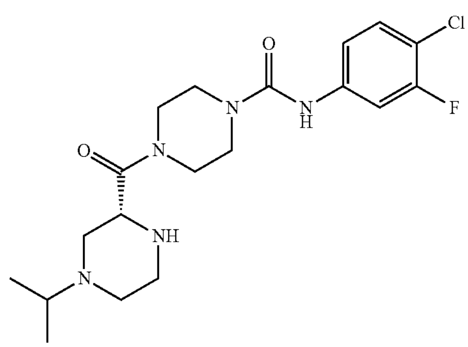 [SMILES: CC(C)N1CCN[C@@H](C(=O)N2CCN(C(=O)Nc3ccc(Cl)c(F)c3)CC2)C1] | N-(4-chloro-3-fluorophenyl)-4-{[(2R)-4-isopropylpiperazin-2-yl]carbonyl}piperazine-1-carboxamide<br>LCMS M/z(+) 412, 414 (M + H$^+$)<br>$^1$H NMR (400.132 MHz, CDCl$_3$) 1.3-1.36 (m, 6H), 2.70 (m, 1H), 2.80 (m, 1H), 3.20-3.45 (m, 5H), 3.48-3.80 (m, 8H), 4.45 (d, 1H), 7.03 (m, 2H), 7.27 (m, 1H), 7.45 (d, 1H) | A1 |
| 223 | 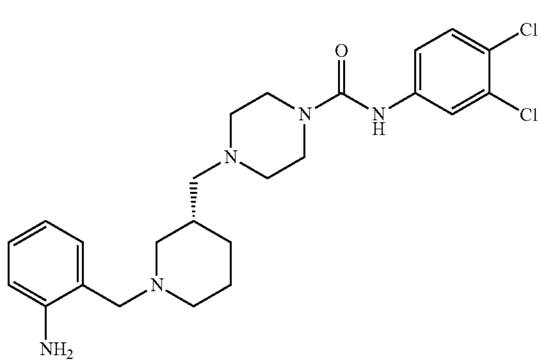 [SMILES: Nc1ccccc1CN1CCC[C@@H](CN2CCN(C(=O)Nc3ccc(Cl)c(Cl)c3)CC2)C1] | 4-{[(3R)-1-(2-aminobenzyl)piperidin-3-yl]methyl}-N-(3,4-dichlorophenyl)piperazine-1-carboxamide<br>LCMS M/z(+) 460.88 (M + H$^+$)<br>$^1$H NMR (300 MHz, DMSO-d$_6$) δ 1.0-1.9 (5H, m), 2.2-3.5 (16H, m), 6.5 (1H, m), 7.3 (2H, m), 7.7 (1H, m), 7.9 (1H, m), 8.65 (1H, s) | C1 |

| Example No. | Structure | Characterisation Data | Chemistry Route |
|---|---|---|---|
| 224 | 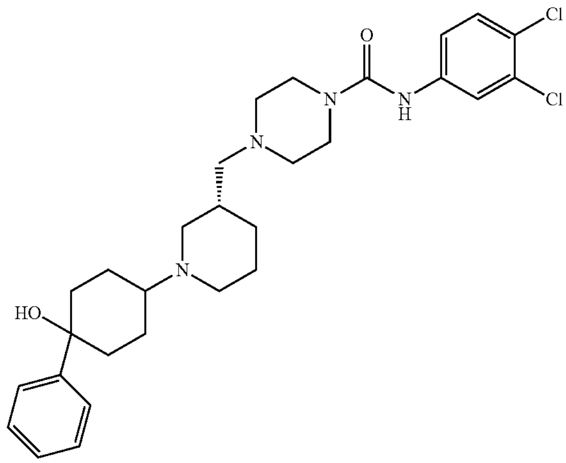 [SMILES: O=C(Nc1ccc(Cl)c(Cl)c1)N1CCN(C[C@@H]2CCCN(C3CCC(O)(c4ccccc4)CC3)C2)CC1] | N-(3,4-dichlorophenyl)-4-{[(3S)-1-(4-hydroxy-4-phenylcyclohexyl)piperidin-3-yl]methyl}piperazine-1-carboxamide<br>LCMS M/z(+) 543.14 (M − H⁺)<br>¹H-NMR (400.132 MHz, CDCl₃) 0.92 (m, 1H), 1.50 (m, 4H), 1.62-1.95 (m, 8H), 2.18 (m, 3H), 2.40 (m, 2H), 2.48 (m, 2H), 2.57 (m, 2H), 2.90 (m, 1H), 3.01 (m, 2H), 3.45 (m, 4H), 6.29 (s, 1H), 7.19 (, m1H), 7.27 (m, 3H), 7.37 (m, 2H) and 7.55 (m, 2H) | C1 |
| 225 | 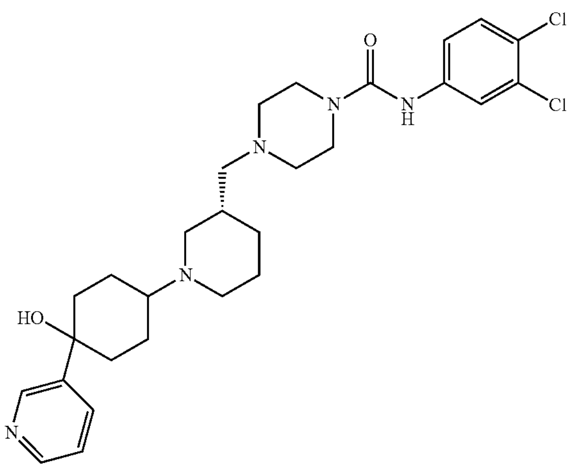 [SMILES: O=C(Nc1ccc(Cl)c(Cl)c1)N1CCN(C[C@@H]2CCCN(C3CCC(O)(c4cccnc4)CC3)C2)CC1] | N-(3,4-dichlorophenyl)-4-{[(3S)-1-(4-hydroxy-4-pyridin-3-ylcyclohexyl)piperidin-3-yl]methyl}piperazine-1-carboxamide<br>LCMS M/z(+) 546.32 (M + H⁺)<br>¹H-NMR (400.132 MHz, CDCl₃) 0.90 (m, 1H), 1.49-1.98 (m, 12H), 2.17-2.28 (m, 3H), 2.36-2.54 (m, 6H), 2.92 (m, 1H), 3.04 (m, 1H), 3.46 (m, 4H), 6.38 (s, 1H), 7.20 (dd, 1H), 7.25 (m, 1H), 7.32 (m, 1H), 7.58 (m, 1H), 7.82 (d, 1H), 8.49 (d, 1H) and 8.75 (s, 1H) | C1 |
| 226 | 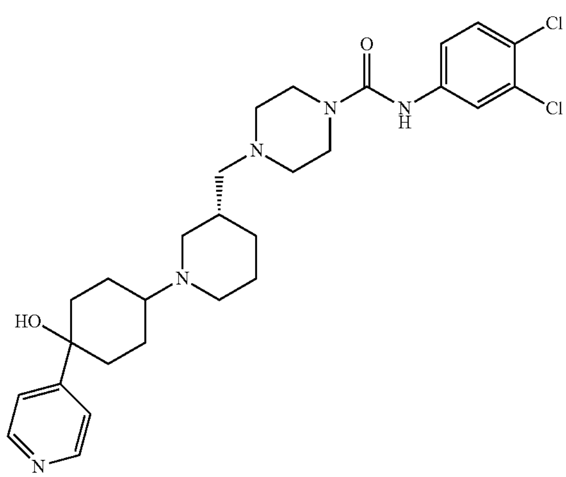 [SMILES: O=C(Nc1ccc(Cl)c(Cl)c1)N1CCN(C[C@@H]2CCCN(C3CCC(O)(c4ccncc4)CC3)C2)CC1] | N-(3,4-dichlorophenyl)-4-{[(3S)-1-(4-hydroxy-4-pyridin-4-ylcyclohexyl)piperidin-3-yl]methyl}piperazine-1-carboxamide<br>LCMS M/z(+) 544.31 (M − H⁺)<br>¹H-NMR (400.132 MHz, CDCl₃) 0.90 (m, 1H), 1.42-1.96 (m, 12H), 2.14-2.28 (m, 3H), 2.34-2.51 (m, 6H), 2.89 (m, 1H), 3.02 (m, 1H), 3.47 (m, 4H), 6.55 (s, 1H), 7.21 (dd, 1H), 7.27 (d, 2H), 7.39 (d, 1H), 7.57 (d, 1H) and 8.55 (d, 2H) | C1 |

Examples

| Example No. | Structure | Characterisation Data | Chemistry Route |
|---|---|---|---|
| 227 | 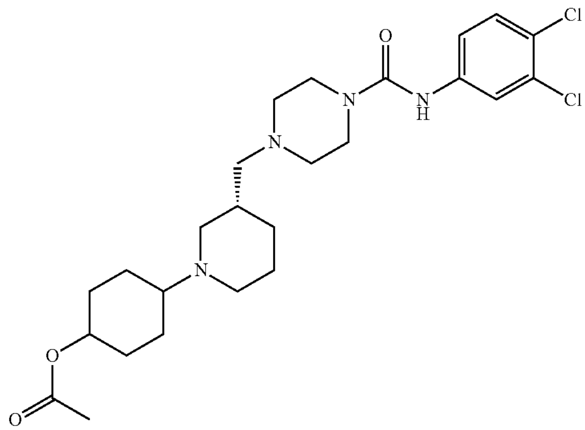 [SMILES: CC(=O)OC1CCC(N2CCC[C@@H](CN3CCN(C(=O)Nc4ccc(Cl)c(Cl)c4)CC3)C2)CC1] | 4-{(3S)-3-[(4-{[(3,4-dichlorophenyl)amino]carbonyl}piperazin-1-yl)methyl]piperidin-1-yl}cyclohexyl acetate<br>LCMS M/z(+) 511.35 (M + H$^+$)<br>$^1$H-NMR (400.132 MHz, CDCl$_3$) 0.89 (m, 1H), 1.33-1.98 (m, 12H), 2.06 (s, 1H), 2.15-2.25 (m, 3H), 2.35-2.52 (m, 6H), 2.89 (m, 1H), 2.99 (m, 1H), 3.48 (t, 4H), 6.29 (s, 1H), 7.19 (dd, 1H), 7.31 (d, 1H) and 7.58 (d, 1H) | C1 |
| 228 | 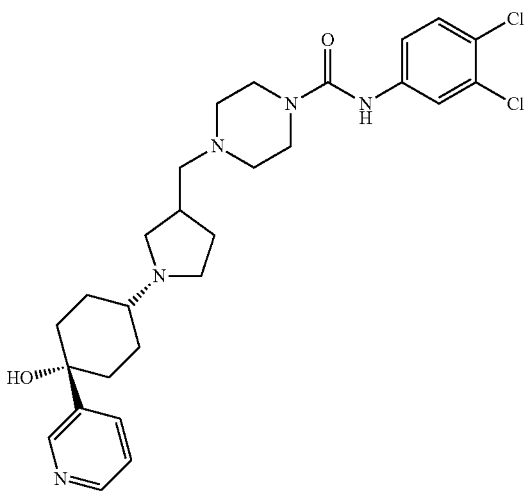 | N-(3,4-dichlorophenyl)-4-{[(3R)-1-(cis-4-hydroxy-4-pyridin-3-ylcyclohexyl)pyrrolidin-3-yl]methyl}piperazine-1-carboxamide<br>LCMS M/z(+) 532.4 (M + H$^+$)<br>$^1$H-NMR (400.132 MHz, CDCl$_3$) 1.38-1.70 (m, 12H), 1.80-1.95 (m, 3H), 2.14-2.63 (m, 11H), 3.40 (t, 4H), 6.48 (s, 1H), 7.15 (dd, 1H), 7.16-7.27 (m, 2H), 7.52 (s, 1H), 7.78 (d, 1H), 8.42 (m, 1H) and 8.69 (s, 1H) | C1 |
| 229 | 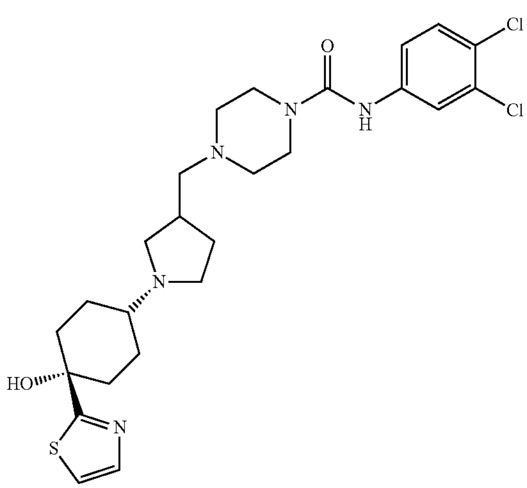 | N-(3,4-dichlorophenyl)-4-({(3S)-1-[cis-4-hydroxy-4-(1,3-thiazol-2-yl)cyclohexyl]pyrrolidin-3-yl}methyl)piperazine-1-carboxamide<br>LCMS M/z(+) 538.37 (M + H$^+$)<br>$^1$H-NMR (400.132 MHz, CDCl$_3$) 1.40 (m, 1H), 1.58-1.80 (m, 7H), 1.82-1.95 (m, 3H), 2.10-2.76 (m, 11H), 3.40 (t, 4H), 6.34 (s, 1H), 7.13 (dd, 1H), 7.17-7.28 (m, 2H), 7.53 (d, 1H) and 7.64 (d, 1H) | C1 |

-continued

Examples

| Example No. | Structure | Characterisation Data | Chemistry Route |
|---|---|---|---|
| 230 | 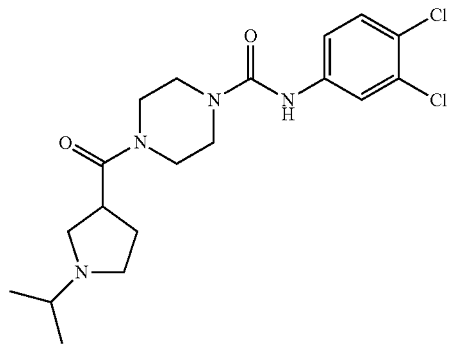 [SMILES: CC(C)N1CCC(C(=O)N2CCN(C(=O)Nc3ccc(Cl)c(Cl)c3)CC2)C1] | N-(3,4-dichlorophenyl)-4-{[(3R)-1-isopropylpyrrolidin-3-yl]carbonyl}piperazine-1-carboxamide<br>LCMS M/z(+) 413.94 (M + H$^+$)<br>$^1$H-NMR (400.132 MHz, CDCl$_3$)<br>1.04 (d, 6H), 2.01 (q, 2H), 2.31-2.54 (m, 2H), 2.56 (t, 1H), 2.86 (q, 1H), 2.99 (t, 1H), 3.14 (m, 1H), 3.40 (s, 2H), 3.48 (s, 4H), 3.63 (s, 2H), 6.42 (s, 1H), 7.14 (dd, 1H), 7.27 (d, 1H), and 7.52 (d, 1H) | C1 |
| 231 | 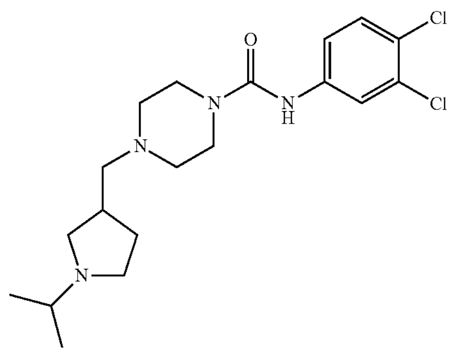 [SMILES: CC(C)N1CCC(CN2CCN(C(=O)Nc3ccc(Cl)c(Cl)c3)CC2)C1] | N-(3,4-dichlorophenyl)-4-{[(3S)-1-isopropylpyrrolidin-3-yl]methyl}piperazine-1-carboxamide<br>LCMS M/z(+) 401.23 (M + H$^+$)<br>$^1$H-NMR (400.132 MHz, CDCl$_3$)<br>1.04 (d, 6H), 1.40 (m, 1H), 1.88 (m, 1H), 2.10-2.46 (m, 10H), 2.63 (m, 1H), 2.78 (m, 1H), 3.40 (t, 4H), 6.29 (s, 1H), 7.12 (dd, 1H), 7.26 (d, 1H), and 7.51 (d, 1H) | C1 |
| 232 | 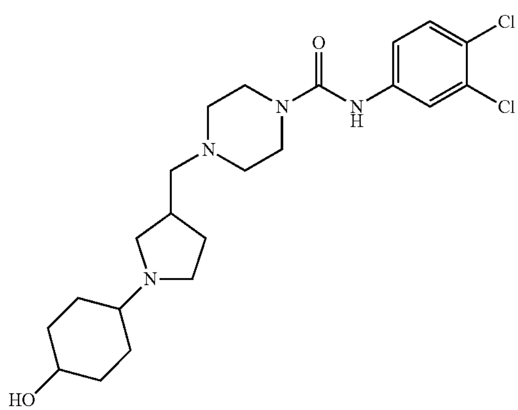 [SMILES: O=C(Nc1ccc(Cl)c(Cl)c1)N1CCN(CC2CCN(C3CCC(O)CC3)C2)CC1] | N-(3,4-dichlorophenyl)-4-{[(3R)-1-(trans-4-hydroxycyclohexyl)pyrrolidin-3-yl]methyl}piperazine-1-carboxamide<br>LCMS M/z(+) 457.64 (M + H$^+$) | C1 |
| 233 | 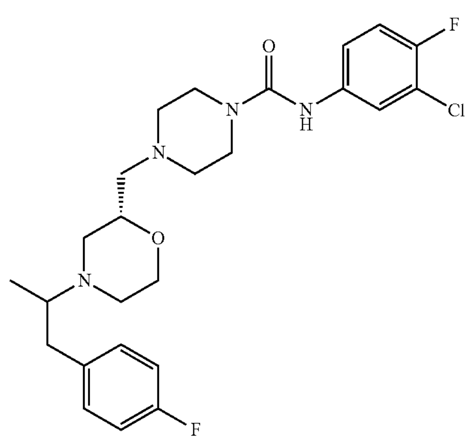 [SMILES: CC(Cc1ccc(F)cc1)N1CCO[C@@H](CN2CCN(C(=O)Nc3ccc(F)c(Cl)c3)CC2)C1] | N-(3-chloro-4-fluorophenyl)-4-({(2S)-4-[(1S)-2-(4-fluorophenyl)-1-methylethyl]morpholin-2-yl}methyl)piperazine-1-carboxamide<br>LCMS M/z(+) 493.69 (M + H$^+$)<br>$^1$H-NMR (400.132 MHz, CDCl$_3$)<br>0.86 (d, 3H), 2.13 (m, 1H), 2.19-2.72 (m, 11H), 2.85 (d, 1H), 3.42 (t, 4H), 3.52-3.69 (m, 2H), 3.85 (t, 1H), 6.22 (s, 1H), 6.90 (m, 2H), 6.98 (t, 1H), 7.04-7.13 (m, 3H) and 7.44 (m, 1H) | C1 |

| Example No. | Structure | Characterisation Data | Chemistry Route |
|---|---|---|---|
| 234 | 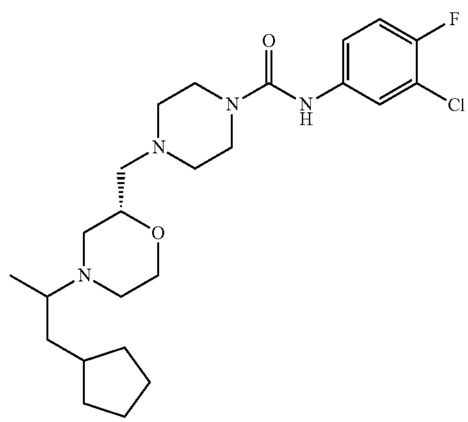 [SMILES: CC(CC1CCCC1)N1CCO[C@@H](CN2CCN(C(=O)Nc3ccc(F)c(Cl)c3)CC2)C1] | N-(3-chloro-4-fluorophenyl)-4-({(2S)-4-[(1R)-2-cyclopentyl-1-methylethyl]morpholin-2-yl}methyl)piperazine-1-carboxamide<br>LCMS M/z(+) 467.44 (M + H$^+$)<br>$^1$H-NMR (400.132 MHz, CDCl$_3$) 0.85-1.10 (m, 5H), 1.16-1.28 (m, 1H), 1.40-1.60 (m, 5H), 1.62-1.83 (m, 3H), 1.97-2.34 (m, 3H), 2.37-2.63 (m, 8H), 3.40 (t, 4H), 3.51-3.73 (m, 2H), 3.80 (m, 1H), 6.55 (s, 1H), 6.96 (t, 1H), 7.08 (m, 1H) and 7.41 (m, 1H) | C1 |
| 235 | 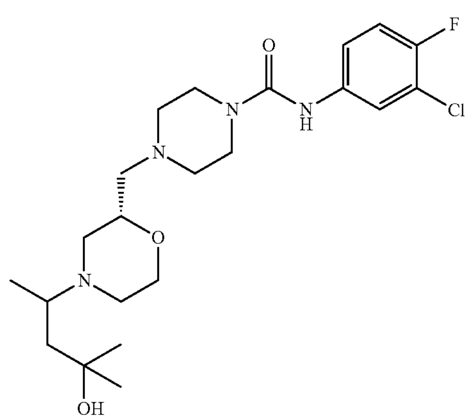 | N-(3-chloro-4-fluorophenyl)-4-({(2S)-4-[(1S)-3-hydroxy-1,3-dimethylbutyl]morpholin-2-yl}methyl)piperazine-1-carboxamide<br>LCMS M/z(+) 494.79 (M + H$^+$) | C1 |
| 236 | 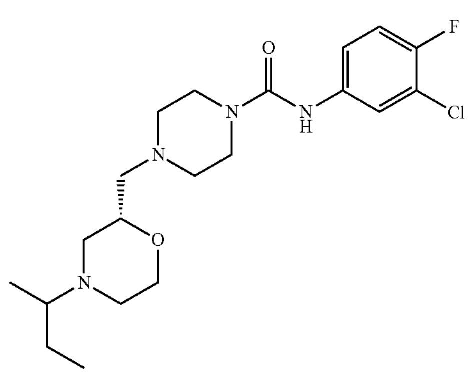 [SMILES: CCC(C)N1CCO[C@@H](CN2CCN(C(=O)Nc3ccc(F)c(Cl)c3)CC2)C1] | N-(3-chloro-4-fluorophenyl)-4-({(2R)-4-[(1R)-1-methylpropyl]morpholin-2-yl}methyl)piperazine-1-carboxamide<br>LCMS M/z(+) 413.25 (M + H$^+$)<br>$^1$H-NMR (400.132 MHz, DMSO-d$_6$) 0.80-0.94 (m, 6H), 1.18-1.30 (m, 1H), 1.40-1.53 (m, 1H), 2.01-2.66 (m, 10H), 3.10-3.52 (m, 6H + water), 3.74 (m, 1H), 7.28 (t, 1H), 7.40 (m, 1H) and 7.74 (m, 1H) | C1 |

| Example No. | Structure | Characterisation Data | Chemistry Route |
|---|---|---|---|
| 237 | 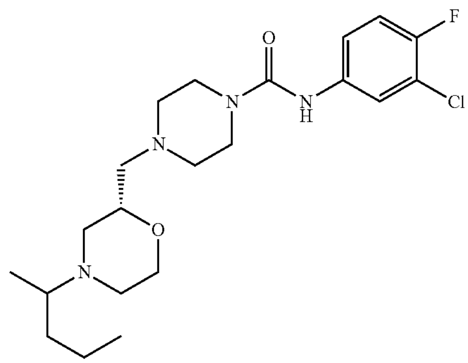 [SMILES: CCCC(C)N1CCO[C@@H](CN2CCN(C(=O)Nc3ccc(F)c(Cl)c3)CC2)C1] | N-(3-chloro-4-fluorophenyl)-4-({(2R)-4-[(1S)-1-methylbutyl]morpholin-2-yl}methyl)piperazine-1-carboxamide<br>LCMS M/z(+) 427.35 (M + H⁺)<br>¹H-NMR (400.132 MHz, DMSO-d₆) 0.83-0.94 (m, 6H), 1.13-1.49 (m, 4H), 1.86-2.69 (m, 10H), 3.35-3.60 (m, 6H + water), 3.74 (m, 1H), 7.28 (t, 1H), 7.40 (m, 1H) and 7.74 (m, 1H) | C1 |
| 238 | 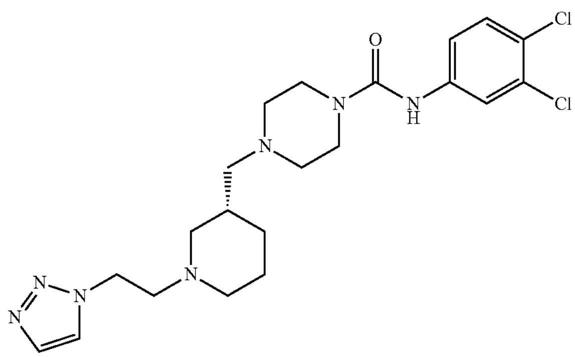 [SMILES: O=C(Nc1ccc(Cl)c(Cl)c1)N1CCN(C[C@@H]2CCCN(CCn3ccnn3)C2)CC1] | N-(3,4-dichlorophenyl)-4-({(3R)-1-[2-(1H-1,2,3-triazol-1-yl)ethyl]piperidin-3-yl}methyl)piperazine-1-carboxamide<br>LCMS M/z(+) 466.25, 468.15 (M + H⁺)<br>LCMS M/z(−) 464.23, 466.21 (M − H⁻)<br>¹H-NMR (400.132 MHz, DMSO-d₆) 0.90 (1H, m), 1.41 (1H, m), 1.55 to 1.81 (4H, m), 2.02 (1H, t), 2.03 to 2.18 (2H, m), 2.26 to 2.37 (4H, m), 2.67 to 2.78 (4H, m), 3.43 (4H, t), 4.48 (2H, t), 7.46 (2H, m), 7.70 (1H, d), 7.84 (1H, m), 8.10 (1H, d), 8.75 (1H, s) | C1 |
| 239 | 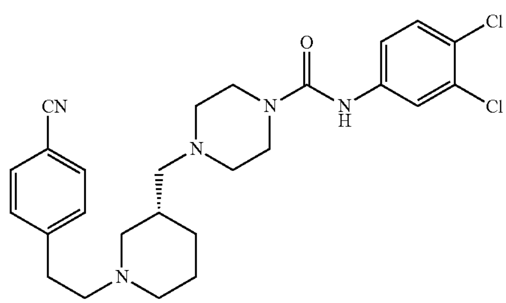 [SMILES: N#Cc1ccc(CCN2CCC[C@@H](CN3CCN(C(=O)Nc4ccc(Cl)c(Cl)c4)CC3)C2)cc1] | 4-({(3R)-1-[2-(4-cyanophenyl)ethyl]piperidin-3-yl}methyl)-N-(3,4-dichlorophenyl)piperazine-1-carboxamide<br>LCMS M/z(+) 500.22, 502.20 (M + H⁺)<br>LCMS M/z(−) 498.26, 500.25 (M − H⁻)<br>¹H-NMR (400.132 MHz, DMSO-d₆) 0.91 (1H, m), 1.44 (1H, m), 1.59 to 1.68 (4H, m), 2.02 (1H, m), 2.14 (2H, m), 2.27 to 2.38 (4H, m), 2.56 (2H, d), 2.83 (4H, m), 3.44 (4H, t), 7.44 to 7.46 (4H, m), 7.73 (2H, d), 7.84 (1H, d), 8.76 (1H, s) | C1 |
| 240 | 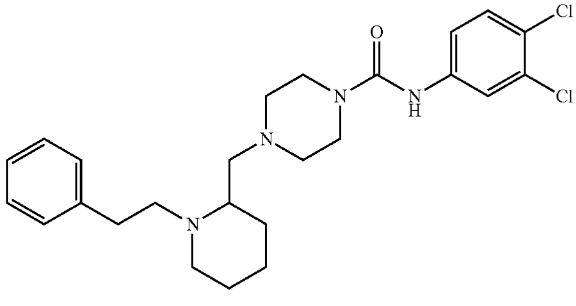 [SMILES: O=C(Nc1ccc(Cl)c(Cl)c1)N1CCN(CC2CCCCN2CCc2ccccc2)CC1] | N-(3,4-dichlorophenyl)-4-{[1-(2-phenylethyl)piperidin-2-yl]methyl}piperazine-1-carboxamide<br>LCMS M/z(+) 475.24, 477.24 (M + H⁺)<br>LCMS M/z(−) 473.24, 475.26 (M − H⁻)<br>¹H-NMR (400.132 MHz, DMSO-d₆) 1.25 to 1.73 (6H, m), 2.22 (1H, m), 2.39 (4H, m), 2.75 (2H, br s), 3.30 (5H, m), 3.43 (4H, t), 3.49 (1H, m), 7.16 to 7.31 (5H, m), 7.43 to 7.48 (2H, m), 7.84 (1H, s), 8.76 (1H, s) | C1 |

| Example No. | Structure | Characterisation Data | Chemistry Route |
|---|---|---|---|
| 241 | 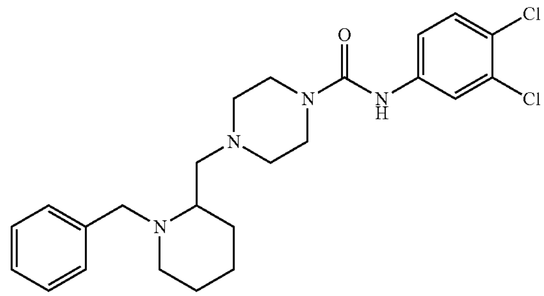 [SMILES: O=C(Nc1ccc(Cl)c(Cl)c1)N1CCN(CC2CCCCN2Cc2ccccc2)CC1] | 4-[(1-benzylpiperidin-2-yl)methyl]-N-(3,4-dichlorophenyl)piperazine-1-carboxamide<br>LCMS M/z(+) 461.25, 462.93 (M + H$^+$)<br>LCMS M/z(−) 459.24, 491.24 (M − H$^-$)<br>$^1$H-NMR (400.132 MHz, DMSO-d$_6$) 1.28 to 1.50 (4H, m), 1.62 (1H, m), 1.69 (1H, m), 2.09 (1H, s), 2.29 to 2.42 (5H, m), 2.64 (2H, m), 3.40 to 3.53 (6H, m), 4.09 (1H, d), 7.22 (1H, m), 7.32 (4H, m), 7.43 to 7.48 (2H, m), 7.84 (1H, s), 8.75 (1H, s) | C1 |
| 242 | 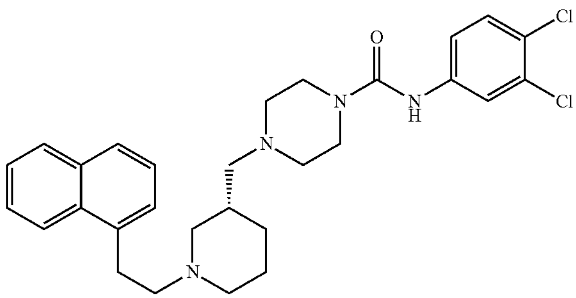 [SMILES: O=C(Nc1ccc(Cl)c(Cl)c1)N1CCN(C[C@@H]2CCCN(CCc3cccc4ccccc34)C2)CC1] | N-(3,4-dichlorophenyl)-4-({(3R)-1-[2-(1-naphthyl)ethyl]piperidin-3-methyl)piperazine-1-carboxamide<br>LCMS M/z(+) 525.22, 527.27 (M + H$^+$)<br>$^1$H-NMR (400.132 MHz, DMSO-d$_6$) 0.96 (1H, m), 1.55 (1H, m), 1.70 (2H, m), 1.86 (1H, s), 2.12 to 2.23 (3H, m), 2.31 to 2.40 (4H, m), 2.69 (1H, br s), 2.99 (2H, br s), 3.30 (4H, br s), 3.45 (4H, t), 7.41 to 7.59 (6H, m), 7.79 (1H, d), 7.85 (1H, s), 7.93 (1H, d), 8.08 (1H, d), 8.75 (1H, s) | C1 |
| 243 | 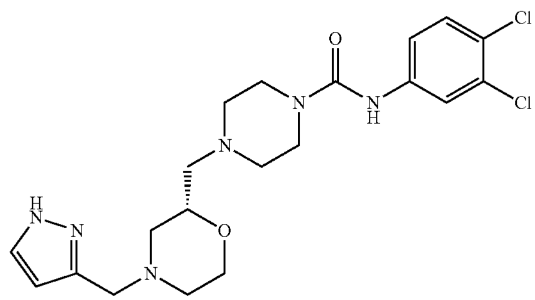 [SMILES: O=C(Nc1ccc(Cl)c(Cl)c1)N1CCN(C[C@H]2CN(Cc3cc[nH]n3)CCO2)CC1] | N-(3,4-dichlorophenyl)-4-{[(2S)-4-(1H-pyrazol-3-ylmethyl)morpholin-2-yl]methyl}piperazine-1-carboxamide<br>LCMS M/z(+) 453.19, 455.09 (M + H$^+$)<br>LCMS M/z(−) 451.20, 453.19 (M − H$^-$)<br>$^1$H-NMR (400.132 MHz, DMSO-d$_6$) 1.80 (1H, t), 2.04 (1H, m), 2.29 to 2.45 (6H, m), 2.60 (1H, d), 2.76 (1H, d), 3.41 (4H, t), 3.49 (3H, m), 3.60 (1H, m), 3.74 (1H, d), 6.14 (1H, s), 7.40 & 7.63 (1H, d), 7.43 to 7.48 (2H, t), 7.84 (1H, s), 8.75 (1H, s), 12.55 & 12.66 (1H, d) | C1 |
| 244 | 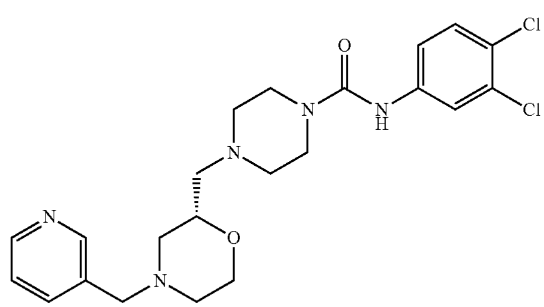 [SMILES: O=C(Nc1ccc(Cl)c(Cl)c1)N1CCN(C[C@H]2CN(Cc3cccnc3)CCO2)CC1] | N-(3,4-dichlorophenyl)-4-{[(2S)-4-(pyridin-3-ylmethyl)morpholin-2-yl]methyl}piperazine-1-carboxamide<br>LCMS M/z(+) 464.18, 466.04 (M + H$^+$)<br>LCMS M/z(−) 462.21, 464.20 (M − H$^-$)<br>$^1$H-NMR (400.132 MHz, DMSO-d$_6$) 1.85 (1H, t), 2.06 (1H, m), 2.30 to 2.46 (6H, m), 2.58 (1H, d), 2.74 (1H, d), 3.40 (4H, t), 3.46 to 3.56 (3H, m), 3.62 (1H, m), 3.75 (1H, m), 7.37 (1H, dd), 7.43 to 7.48 (2H, m), 7.72 (1H, m), 7.83 (1H, d), 8.47 (1H, dd), 8.50 (1H, d), 8.75 (1H, s) | C1 |

-continued

Examples

| Example No. | Structure | Characterisation Data | Chemistry Route |
|---|---|---|---|
| 245 | 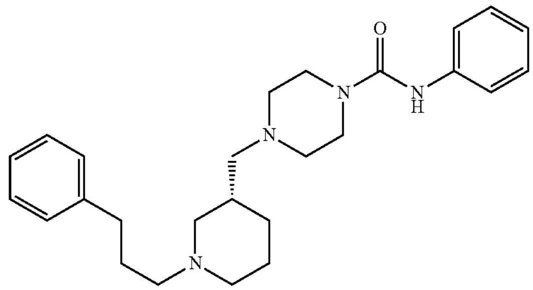 [SMILES: O=C(Nc1ccccc1)N1CCN(C[C@@H]2CCCN(CCCc3ccccc3)C2)CC1] | N-phenyl-4-[[(3R)-1-(3-phenylpropyl)-3-piperidyl]methyl]piperazine-1-carboxamide<br>LCMS M/z(+) 421 (M + H)<br>$^1$H NMR (400.132 MHz, CDCl$_3$) 0.90 (1H, m), 1.73 (4H, m), 1.91 (4H, m), 2.04 (2H, m), 2.16 (2H, m), 2.32 (2H, m), 2.50 (2H, m), 2.63 (2H, m), 3.11 (2H, m), 3.46 (4H, m), 6.89 (1H, m), 7.00 (1H, m), 7.22 (7H, m), 7.37 (2H, m) | C1 |
| 246 | 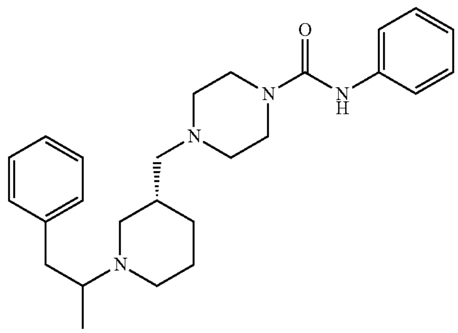 [SMILES: CC(Cc1ccccc1)N1CCC[C@@H](CN2CCN(C(=O)Nc3ccccc3)CC2)C1] | 4-[[(3R)-1-(1-methyl-2-phenyl-ethyl)-3-piperidyl]methyl]-N-phenyl-piperazine-1-carboxamide<br>LCMS M/z(+) 421 (M + H)<br>$^1$H NMR (400.132 MHz, CDCl$_3$) 0.99 (3H, m), 1.79 (4H, m), 2.16 (4H, m), 2.43 (6H, m), 3.11 (4H, m), 3.48 (4H, m), 6.72 (1H, m), 7.00 (1H, m), 7.25 (7H, m), 7.38 (2H, m) | C1 |
| 247 | 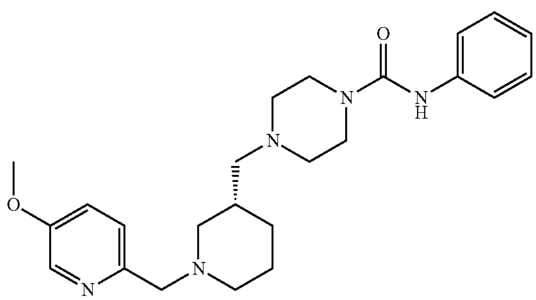 [SMILES: COc1ccc(CN2CCC[C@@H](CN3CCN(C(=O)Nc4ccccc4)CC3)C2)nc1] | 4-({(3R)-1-[(6-methoxypyridin-3-yl)methyl]piperidin-3-yl}methyl)-N-phenyl piperazine-1-carboxamide<br>LCMS M/z(+) 424 (M + H)<br>$^1$H NMR (400.132 MHz, CDCl$_3$) 0.92 (1H, m), 1.75 (2H, m), 1.90 (1H, m), 2.15 (4H, m), 2.41 (4H, m), 3.01 (1H, m), 3.22 (1H, m), 3.47 (4H, m), 3.71 (3H, m), 3.95 (3H, m), 6.58 (1H, m), 6.76 (1H, m), 7.03 (1H, m), 7.29 (2H, m), 7.37 (2H, m), 7.68 (1H, m), 8.06 (1H, m) | C1 |
| 248 | 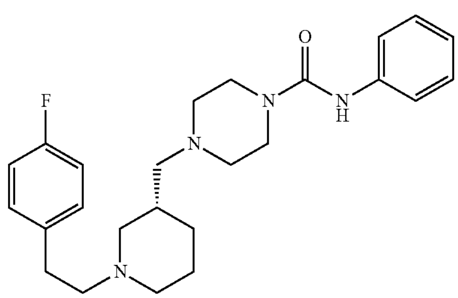 [SMILES: O=C(Nc1ccccc1)N1CCN(C[C@@H]2CCCN(CCc3ccc(F)cc3)C2)CC1] | 4-[[(3R)-1-[2-(4-fluorophenyl)ethyl]-3-piperidyl]methyl]-N-phenyl-piperazine-1-carboxamide<br>LCMS M/z(+) 425.5 (M + H) | C1 |
| 249 | 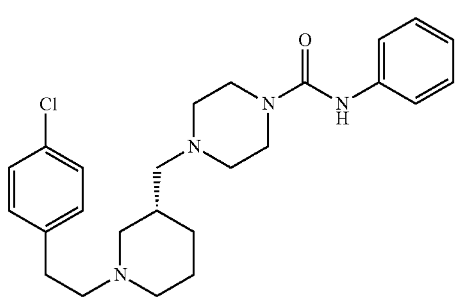 [SMILES: O=C(Nc1ccccc1)N1CCN(C[C@@H]2CCCN(CCc3ccc(Cl)cc3)C2)CC1] | 4-[[(3R)-1-[2-(4-chlorophenyl)ethyl]-3-piperidyl]methyl]-N-phenyl-piperazine-1-carboxamide<br>LCMS M/z(+) 441.4 (M + H) | C1 |

-continued

Examples

| Example No. | Structure | Characterisation Data | Chemistry Route |
|---|---|---|---|
| 250 | 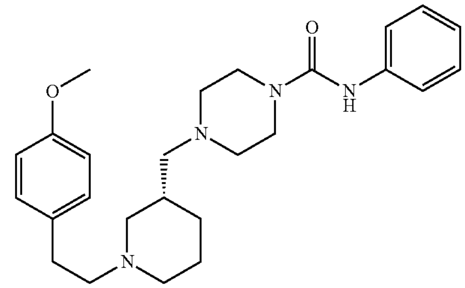 [SMILES: COc1ccc(CCN2CCC[C@@H](CN3CCN(C(=O)Nc4ccccc4)CC3)C2)cc1] | 4-[[(3R)-1-[2-(4-methoxyphenyl)ethyl]-3-piperidyl]methyl]-N-phenyl-piperazine-1-carboxamide<br>LCMS M/z(+) 437.5 (M + H) | C1 |
| 251 | 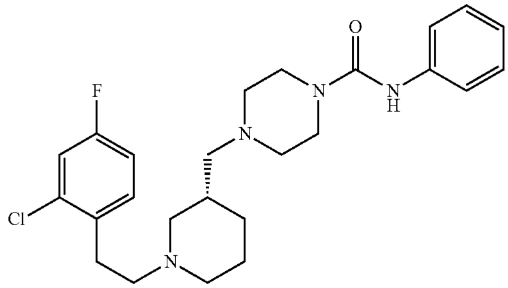 [SMILES: O=C(Nc1ccccc1)N1CCN(C[C@@H]2CCCN(CCc3ccc(F)cc3Cl)C2)CC1] | 4-[[(3R)-1-[2-(2-chloro-4-fluoro-phenyl)ethyl]-3-piperidyl]methyl]-N-phenyl-piperazine-1-carboxamide<br>LCMS M/z(+) 459.4 (M + H) | C1 |
| 252 | 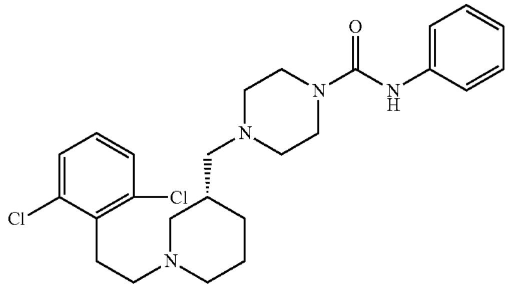 [SMILES: O=C(Nc1ccccc1)N1CCN(C[C@@H]2CCCN(CCc3c(Cl)cccc3Cl)C2)CC1] | 4-[[(3R)-1-[2-(2,6-dichlorophenyl)ethyl]-3-piperidyl]methyl]-N-phenyl-piperazine-1-carboxamide<br>LCMS M/z(+) 475.4 (M + H) | C1 |
| 253 | 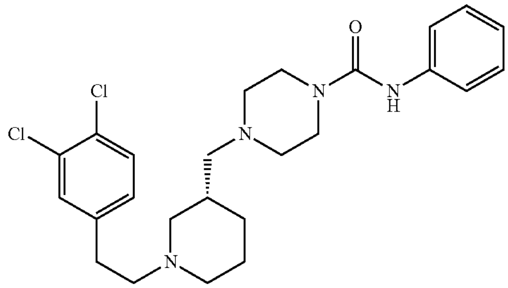 [SMILES: O=C(Nc1ccccc1)N1CCN(C[C@@H]2CCCN(CCc3ccc(Cl)c(Cl)c3)C2)CC1] | 4-[[(3R)-1-[2-(3,4-dichlorophenyl)ethyl]-3-piperidyl]methyl]-N-phenyl piperazine-1-carboxamide<br>LCMS M/z(+) 475.4 (M + H) | C1 |
| 254 | 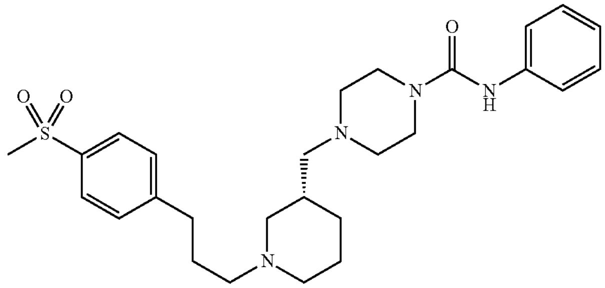 [SMILES: CS(=O)(=O)c1ccc(CCCN2CCC[C@@H](CN3CCN(C(=O)Nc4ccccc4)CC3)C2)cc1] | 4-[[(3R)-1-[3-(4-methylsulfonylphenyl)propyl]-3-piperidyl]methyl]-N-phenyl-piperazine-1-carboxamide<br>LCMS M/z(+) 499.5 (M + H) | C1 |

-continued

Examples

| Example No. | Structure | Characterisation Data | Chemistry Route |
|---|---|---|---|
| 255 | 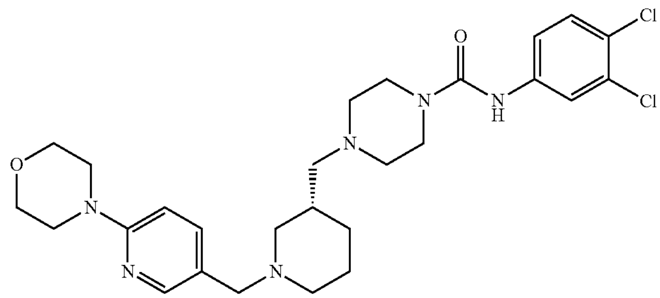 [SMILES: O=C(Nc1ccc(Cl)c(Cl)c1)N1CCN(C[C@@H]2CCCN(Cc3ccc(N4CCOCC4)nc3)C2)CC1] | N-(3,4-dichlorophenyl)-4-[[(3R)-1-[(6-morpholin-4-ylpyridin-3-yl)methyl]-3-piperidyl]methyl]piperazine-1-carboxamide<br>LCMS M/z(−) 544.9 (M − H) | C1 |
| 256 | 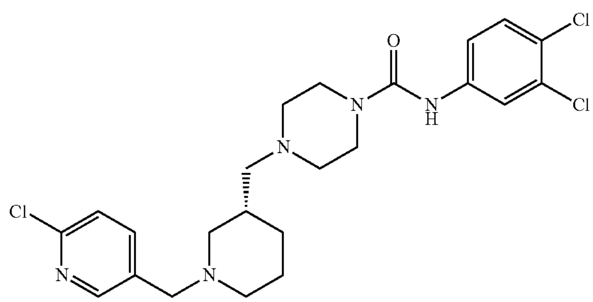 [SMILES: O=C(Nc1ccc(Cl)c(Cl)c1)N1CCN(C[C@@H]2CCCN(Cc3ccc(Cl)nc3)C2)CC1] | 4-({(3R)-1-[(6-chloropyridin-3-yl)methyl]piperidin-3-yl}methyl)-N-(3,4-dichlorophenyl)piperazine-1-carboxamide<br>LCMS M/z(+) 498 (M + H)<br>$^1$H NMR (399.902 MHz, DMSO-$d_6$) (373K) 1.00 (1H, m), 1.48 (1H, m), 1.61 (1H, m), 1.68 (1H, m), 1.79 (1H, m), 1.87 (1H, m), 2.09 (1H, m), 2.20 (2H, m), 2.35 (4H, m), 2.62 (1H, m), 2.73 (1H, m), 3.40 (4H, m), 7.40 (1H, d), 7.43 (1H, d), 7.45 (1H, d), 7.73 (1H, d), 8.30 (1H, d), 8.48 (1H, s) | C1 |
| 257 | 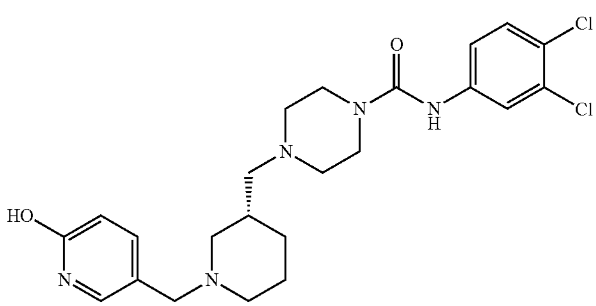 [SMILES: O=C(Nc1ccc(Cl)c(Cl)c1)N1CCN(C[C@@H]2CCCN(Cc3ccc(O)nc3)C2)CC1] | N-(3,4-dichlorophenyl)-4-({(3R)-1-[(6-hydroxypyridin-3-yl)methyl]piperidin-3-yl}methyl)piperazine-1-carboxamide<br>LCMS M/z(−) 475 (M − H) | C1 |
| 258 | 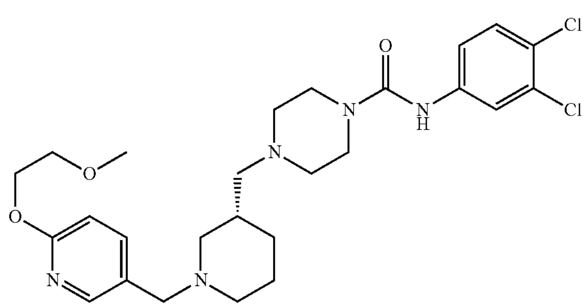 [SMILES: COCCOc1ccc(CN2CCC[C@@H](CN3CCN(C(=O)Nc4ccc(Cl)c(Cl)c4)CC3)C2)cn1] | N-(3,4-dichlorophenyl)-4-[((3R)-1-{[6-(2-methoxyethoxy)pyridin-3-yl]methyl}piperidin-3-yl)methyl]piperazine-1-carboxamide<br>LCMS M/z(+) 535.9 (M + H) | C1 |

-continued

Examples

| Example No. | Structure | Characterisation Data | Chemistry Route |
|---|---|---|---|
| 259 | 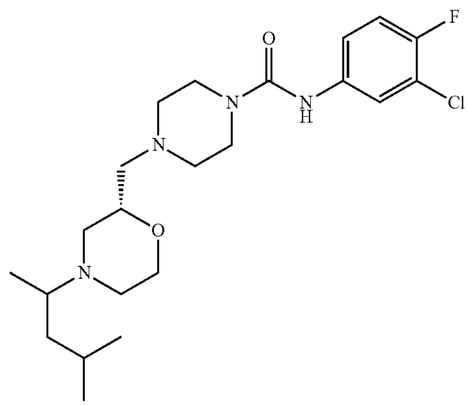 [SMILES: CC(C)CC(C)N1CCO[C@@H](CN2CCN(C(=O)Nc3ccc(F)c(Cl)c3)CC2)C1] | N-(3-chloro-4-fluorophenyl)-4-({(2R)-4-[(1R)-1,3-dimethylbutyl]morpholin-2-yl}methyl)piperazine-1-carboxamide<br>LCMS M/z(+) 439.79 (M − H$^+$)<br>$^1$H-NMR (400.132 MHz, CDCl$_3$) 0.84-0.98 (m, 6H), 1.07-1.42 (m, 5H), 2.00-2.08 (m, 1H), 2.15-2.36 (m, 2H), 2.50-2.69 (m, 7H), 3.59-3.79 (m, 2H), 3.85-3.92 (m, 1H), 6.38 (s, 1H), 7.05 (t, 1H), 7.16 (m, 1H) and 7.52 (m, 1H) | C1 |
| 260 | 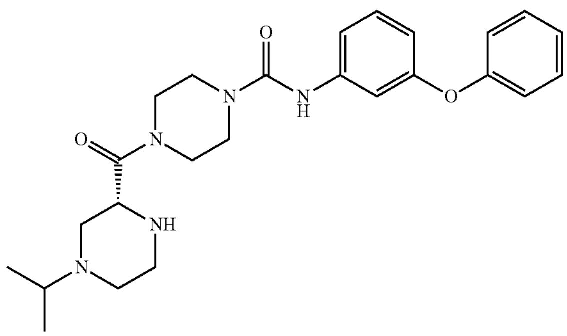 [SMILES: CC(C)N1CCN[C@@H](C(=O)N2CCN(C(=O)Nc3cccc(Oc4ccccc4)c3)CC2)C1] | 4-{[(2R)-4-Isopropylpiperazin-2-yl]carbonyl}-N-(3-phenoxyphenyl)piperazine-1-carboxamide<br>LCMS M/z(+) 452 (M + H$^+$)<br>$^1$H NMR (400.132 MHz, DMSO-d$_6$) 0.93-1.01 (m, 6H), 2.02-2.22 (m, 2H), 2.61-2.84 (m, 4H), 2.93-2.98 (m, 1H), 3.31-3.67 (m, 8H), 3.77-3.84 (m, 1H), 6.58-6.64 (m, 1H), 7.01 (d, 2H), 7.14 (t, 1H), 7.21-7.28 (m, 3H), 7.40 (t, 2H), 8.65 (s, 1H) | A1 |
| 261 | 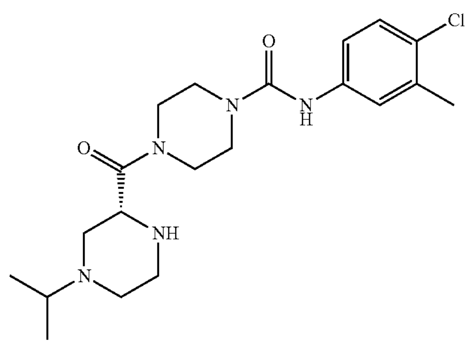 | N-(3-Chloro-4-methylphenyl)-4-{[(2R)-4-isopropylpiperazin-2-yl]carbonyl}piperazine-1-carboxamide<br>LCMS M/z(+) 408 (M + H$^+$)<br>$^1$H NMR (400.132 MHz, DMSO-d$_6$) 1.00 (m, 6H), 2.30 (m, 3H), 2.45 (m, 3H), 2.85 (m, 2H), 3.05 (m, 3H), 3.30-3.82 (m, 8H), 4.48 (m, 1H), 7.20 (d, 1H), 7.42 (d, 1H), 7.64 (s, 1H), 8.70 (s, 1H) | A1 |
| 262 | 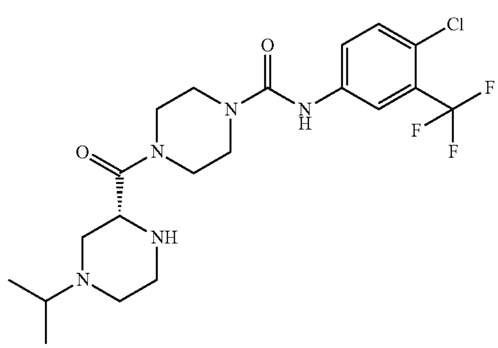 | N-[3-Chloro-4-(trifluoromethyl)phenyl]-4-{[(2R)-4-isopropylpiperazin-2-yl]carbonyl}piperazine-1-carboxamide<br>LCMS M/z(+) 462 (M + H$^+$)<br>$^1$H NMR (400.132 MHz, DMSO-d$_6$) 0.98 (m, 6H), 2.10-2.25 (m, 2H), 2.65-2.84 (m, 4H), 3.00 (d, 1H), 3.35-3.70 (m, 8H), 3.90 (d, 1H), 7.61 (d, 1H), 7.71 (d, 1H), 7.90 (s, 1H), 9.14 (s, 1H) | A1 |

-continued

Examples

| Example No. | Structure | Characterisation Data | Chemistry Route |
|---|---|---|---|
| 263 | 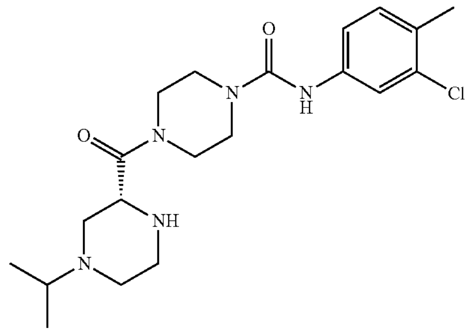 [SMILES: Cc1ccc(NC(=O)N2CCN(C(=O)[C@H]3CN(C(C)C)CCN3)CC2)cc1Cl] | N-(4-Chloro-3-methylphenyl)-4-{[(2R)-4-isopropylpiperazin-2-yl]carbonyl}piperazine-1-carboxamide<br>LCMS M/z(+) 408 (M + H$^+$)<br>$^1$H NMR (400.132 MHz, DMSO-d$_6$) 0.81 (m, 6H), 1.95-2.15 (m, 3H), 2.55-2.72 (m, 4H), 2.88 (d, 1H), 3.10-3.48 (m, 8H), 3.80 (d, 1H), 7.05 (d, 1H), 7.14 (dd, 1H), 7.28 (d, 1H), 8.45 (s, 1H) | A1 |
| 264 | 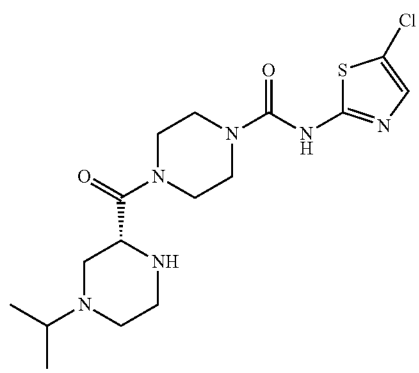 [SMILES: CC(C)N1CCN[C@@H](C(=O)N2CCN(C(=O)Nc3ncc(Cl)s3)CC2)C1] | N-(5-Chloro-1,3-thiazol-2-yl)-4-{[(2R)-4-isopropylpiperazin-2-yl]carbonyl}piperazine-1-carboxamide<br>LCMS M/z(+) 401 (M + H$^+$)<br>$^1$H NMR (400.132 MHz, DMSO-d$_6$) 0.81 (m, 6H), 2.17 (m, 1H), 2.27 (t, 1H), 2.75-3.06 (m, 4H), 3.12 (d, 1H), 3.40-3.93 (m, 9H), 7.12 (s, 1H) | E |
| 265 | 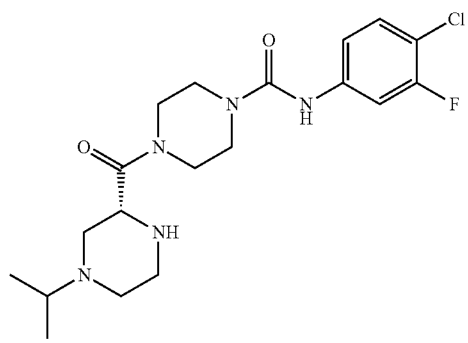 [SMILES: CC(C)N1CCN[C@@H](C(=O)N2CCN(C(=O)Nc3ccc(Cl)c(F)c3)CC2)C1] | N-(4-Chloro-3-fluorophenyl)-4-{[(2R)-4-isopropylpiperazin-2-yl]carbonyl}piperazine-1-carboxamide<br>LCMS M/z(+) 412 (M + H$^+$)<br>$^1$H NMR (400.132 MHz, DMSO-d$_6$) 1.30 (m, 6H), 2.65 (m, 1H), 2.79 (t, 1H), 3.20-3.81 (m, 13H), 4.45 (d, 1H), 7.03 (m, 2H), 7.27 (d, 1H), 7.46 (d, 1H) | E |
| 266 | 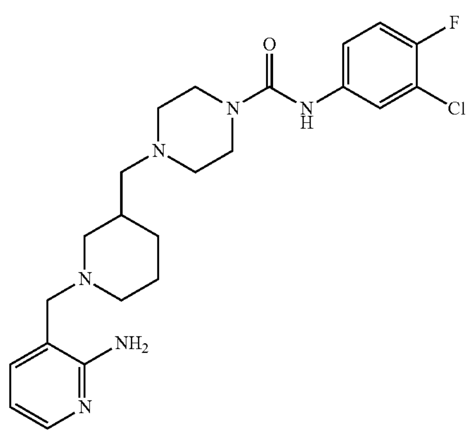 [SMILES: Nc1ncccc1CN1CCCC(CN2CCN(C(=O)Nc3ccc(F)c(Cl)c3)CC2)C1] | 4-({1-[(2-aminopyridin-3-yl)methyl]piperidin-3-yl}methyl)-N-(3-chloro-4-fluorophenyl)piperazine-1-carboxamide<br>LCMS M/z(+) 460.88 (M + H$^+$)<br>$^1$H NMR (300 MHz, DMSO-d$_6$) 1.0-1.9 (5H, m), 2.2-3.5 (16H, m), 6.5 (1H, m), 7.3 (2H, m), 7.7 (1H, m), 7.9 (1H, m), 8.65 (1H, s) | C1 |

-continued

Examples

| Example No. | Structure | Characterisation Data | Chemistry Route |
|---|---|---|---|
| 267 | 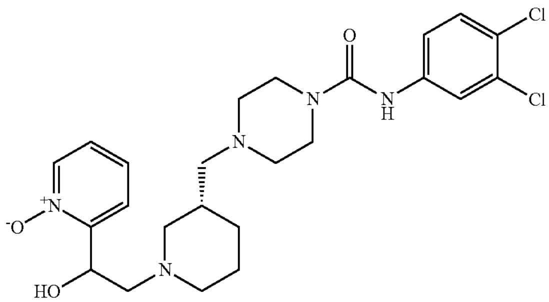 | N-(3,4-dichlorophenyl)-4-({(3R)-1-[2-hydroxy-2-(1-oxidopyridin-2-yl)ethyl]piperidin-3-yl}methyl)piperazine-1-carboxamide<br>LCMS M/z(+) 507.83 (M + H⁺)<br>¹H NMR (300 MHz, DMSO-d₆) 1.0 (5H, m), 1.8-4.0 (17H, m), 5.2 (1H, s), 7.4 (4H, m), 7.6 (1H, d), 7.85 (1H, s), 8.2 (1H, d), 8.8 (1H, m) | C1 |
| 268 | 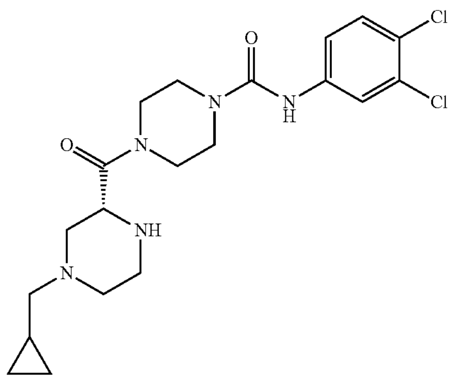 [SMILES: O=C(Nc1ccc(Cl)c(Cl)c1)N1CCN(C(=O)[C@H]2CN(CC3CC3)CCN2)CC1] | 4-{[(2R)-4-(cyclopropylmethyl)piperazin-2-yl]carbonyl}-N-(3,4-dichlorophenyl)piperazine-1-carboxamide<br>LCMS M/z(+) 439.99 (M + H⁺)<br>¹H NMR (300 MHz, DMSO-d₆) 0.0 (2H, d), 0.35 (2H, d), 0.75 (1H, m), 2.1-3.6 (16H, m), 4.1 (1H, d), 7.3 (2H, m), 7.7 (1H, s), 8.8 (1H, s) | C3 |
| 269 | 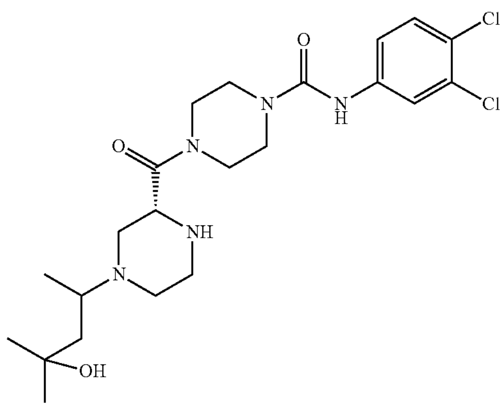 [SMILES: CC(CC(C)(C)O)N1CCN[C@@H](C(=O)N2CCN(C(=O)Nc3ccc(Cl)c(Cl)c3)CC2)C1] | N-(3,4-dichlorophenyl)-4-{[(2R)-4-(3-hydroxy-1,3-dimethylbutyl)piperazin-2-yl]carbonyl}piperazine-1-carboxamide<br>LCMS M/z(+) 486.0 (M + H⁺)<br>¹H NMR (300 MHz, DMSO-d₆) 0.9 (3H, d), 1.1 (3H, s), 1.15 (3H, s), 1.4 (2H, m), 2.05 (1H, m), 2.4-3.6 (14H, m), 3.75 (1H, d), 7.45 (2H, m), 7.8 (1H, s), 8.85 (1H, s) | C3 |
| 270 | 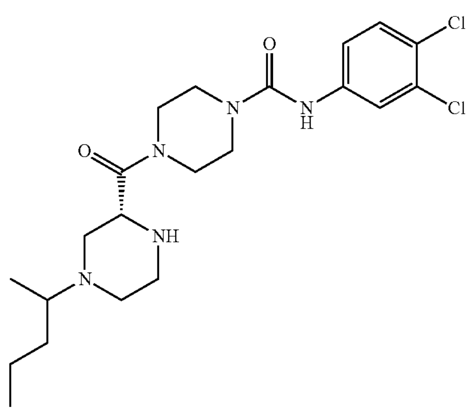 [SMILES: CCCC(C)N1CCN[C@@H](C(=O)N2CCN(C(=O)Nc3ccc(Cl)c(Cl)c3)CC2)C1] | N-(3,4-dichlorophenyl)-4-{[(2R)-4-(1-methylbutyl)piperazin-2-yl]carbonyl}piperazine-1-carboxamide<br>LCMS M/z(+) 456.01 (M + H⁺)<br>¹H NMR (300 MHz, DMSO-d₆) 0.9 (6H, m), 1.3 (3H, m), 1.5 (1H, m), 2.3-3.7 (15H, m), 4.05 (1H, m), 7.45 (2H, m), 7.8 (1H, s), 8.85 (1H, s) | C3 |

-continued

Examples

| Example No. | Structure | Characterisation Data | Chemistry Route |
|---|---|---|---|
| 271 | 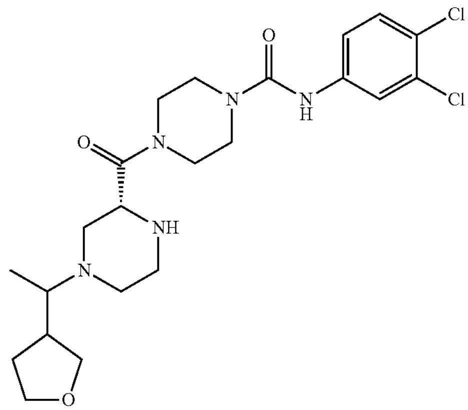 | N-(3,4-dichlorophenyl)-4-{[(2R)-4-(tetrahydrofuran-3-ylmethyl)piperazin-2-yl]carbonyl}piperazine-1-carboxamide<br>LCMS M/z(+) 469.94 (M + H$^+$)<br>$^1$H NMR (300 MHz, DMSO-d$_6$) 1.5 (2H, m), 1.9 (1H, m), 2.2-3.8 (20H, m), 4.55 (1H, m), 7.5 (2H, m), 7.8 (1H, s), 8.95 (1H, s) | C3 |
| 272 | 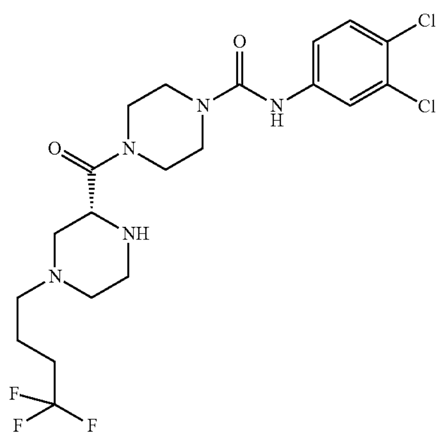 [SMILES: O=C(Nc1ccc(Cl)c(Cl)c1)N1CCN(C(=O)[C@H]2CN(CCCC(F)(F)F)CCN2)CC1] | N-(3,4-dichlorophenyl)-4-{[(2R)-4-(4,4,4-trifluorobutyl)piperazin-2-yl]carbonyl}piperazine-1-carboxamide<br>LCMS M/z(+) 495.90 (M + H$^+$)<br>$^1$H NMR (300 MHz, DMSO-d$_6$) 1.65 (2H, m), 2.2-3.5 (14H, m), 3.7 (4H, m), 4.55 (1H, m), 7.45 (2H, m), 7.8 (1H, s), 8.95 (1H, s) | C3 |
| 273 | 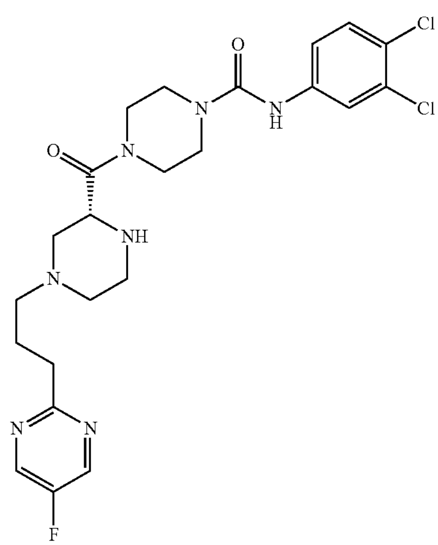 [SMILES: O=C(Nc1ccc(Cl)c(Cl)c1)N1CCN(C(=O)[C@H]2CN(CCCc3ncc(F)cn3)CCN2)CC1] | N-(3,4-dichlorophenyl)-4-({(2R)-4-[3-(5-fluoropyrimidin-2-yl)propyl]piperazin-2-yl}carbonyl)piperazine-1-carboxamide<br>LCMS M/z(+) 523.93 (M + H$^+$)<br>$^1$H NMR (300 MHz, DMSO-d$_6$) 1.9 (2H, m), 2.2-3.7 (18H, m), 4.5 (1H, m), 7.45 (m, 2H), 7.8 (1H, s), 8.85 (2H, s), 8.95 (1H, s) | C3 |

-continued

Examples

| Example No. | Structure | Characterisation Data | Chemistry Route |
|---|---|---|---|
| 274 | 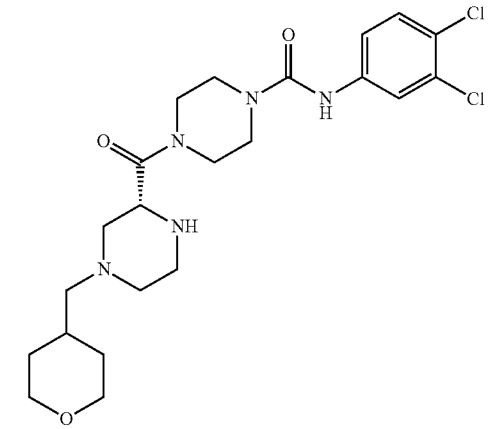 [SMILES: O=C(Nc1ccc(Cl)c(Cl)c1)N1CCN(C(=O)[C@H]2CN(CC3CCOCC3)CCN2)CC1] | N-(3,4-dichlorophenyl)-4-{[(2R)-4-(tetrahydro-2H-pyran-4-ylmethyl)piperazin-2-yl]carbonyl}piperazine-1-carboxamide<br>LCMS M/z(+) 483.93 (M + H$^+$)<br>$^1$H NMR (300 MHz, DMSO-d$_6$) 1.1 (2H, m), 1.6 (2H, m), 1.75 (1H, m), 2.2-3.8 (20H, m), 4.55 (1H, m), 7.45 (2H, m), 7.8 (1H, s), 8.95 (1H, s) | C3 |
| 275 | 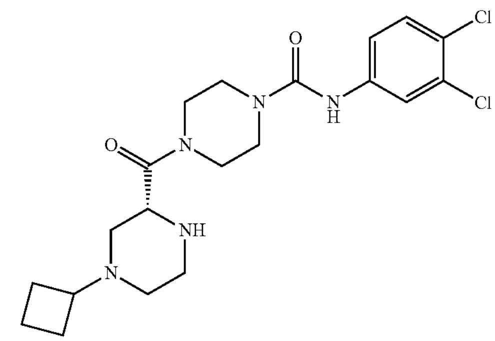 [SMILES: O=C(Nc1ccc(Cl)c(Cl)c1)N1CCN(C(=O)[C@H]2CN(C3CCC3)CCN2)CC1] | 4-{[(2R)-4-Cyclobutylpiperazin-2-yl]carbonyl}-N-(3,4-dichlorophenyl)piperazine-1-carboxamide<br>LCMS M/z(+) 439.98 (M + H$^+$)<br>$^1$H NMR (300 MHz, DMSO-d$_6$) 1.6 (2H, m), 1.8 (4H, m), 1.95 (2H, m), 2.2-3.7 (13H, m), 3.95 (1H, d), 7.4 (2H, m), 7.8 (1H, s), 8.85 (1H, s) | C3 |
| 276 | 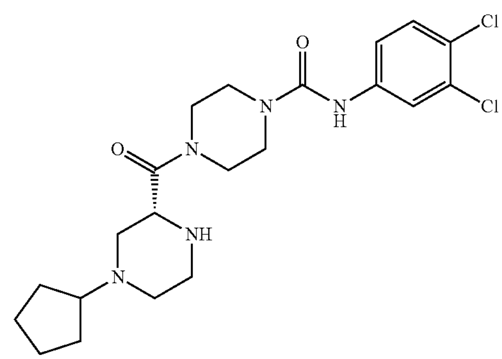 [SMILES: O=C(Nc1ccc(Cl)c(Cl)c1)N1CCN(C(=O)[C@H]2CN(C3CCCC3)CCN2)CC1] | 4-{[(2R)-4-Cyclopentylpiperazin-2-yl]carbonyl}-N-(3,4-dichlorophenyl)piperazine-1-carboxamide<br>LCMS M/z(+) 453.99 (M + H$^+$)<br>$^1$H NMR (300 MHz, DMSO-d$_6$) 1.35 (2H, m), 1.5 (4H, m), 1.8 (2H, m), 2.05 (2H, m), 2.25-3.7 (13H, m), 4.05 (1H, m), 7.4 (2H, m), 7.85 (1H, s), 8.85 (1H, s) | C3 |
| 277 | 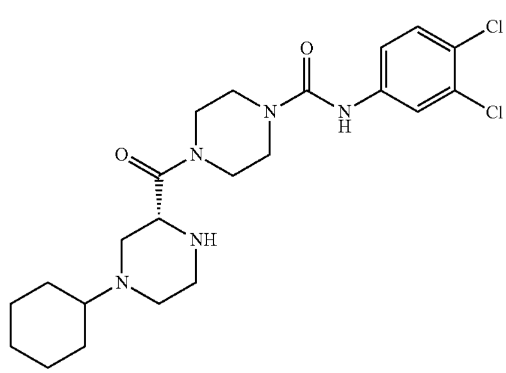 [SMILES: O=C(Nc1ccc(Cl)c(Cl)c1)N1CCN(C(=O)[C@H]2CN(C3CCCCC3)CCN2)CC1] | 4-{[(2R)-4-Cyclohexylpiperazin-2-yl]carbonyl}-N-(3,4-dichlorophenyl)piperazine-1-carboxamide<br>LCMS M/z(+) 468.00 (M + H$^+$)<br>$^1$H NMR (300 MHz, DMSO-d$_6$) 1.2 (5H, m), 1.6 (1H, d), 1.75 (4H, m), 2.25-3.8 (15H, m), 4.3 (1H, d), 7.45 (2H, m), 7.85 (1H, s), 8.9 (1H, s) | C3 |

| Example No. | Structure | Characterisation Data | Chemistry Route |
|---|---|---|---|
| 278 | 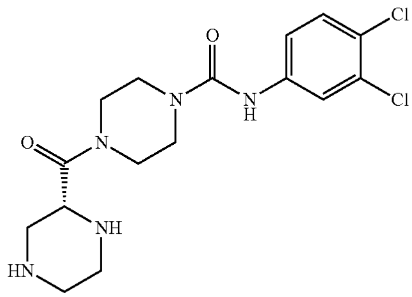 [SMILES: O=C(Nc1ccc(Cl)c(Cl)c1)N1CCN(C(=O)[C@H]2CNCCN2)CC1] | N-(3,4-dichlorophenyl)-4-[(2R)-piperazin-2-ylcarbonyl]piperazine-1-carboxamide<br>LCMS M/z(+) 385.96 (M + H$^+$)<br>$^1$H NMR (300 MHz, DMSO-d$_6$) 2.4-3.7 (14H, m), 4.1 (1H, m), 7.45 (2H, m), 7.8 (1H, s), 8.85 (1H, s) | E |
| 279 | 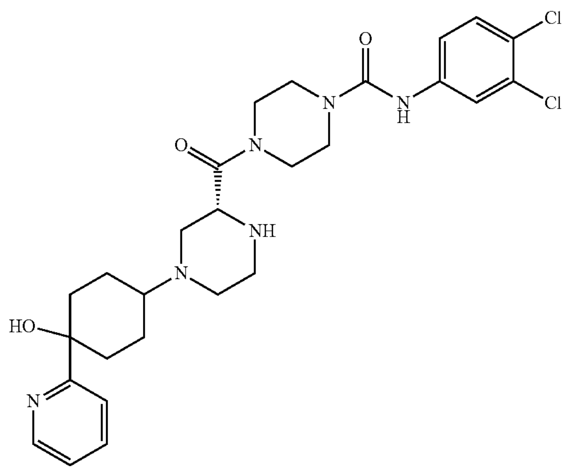 [SMILES: O=C(Nc1ccc(Cl)c(Cl)c1)N1CCN(C(=O)[C@H]2CN(C3CCC(O)(c4ccccn4)CC3)CCN2)CC1] | N-(3,4-Dichlorophenyl)-4-{[(2R)-4-(4-hydroxy-4-pyridin-2-ylcyclohexyl)piperazin-2-yl]carbonyl}piperazine-1-carboxamide<br>LCMS M/z(+) 560.97 (M + H$^+$)<br>$^1$H NMR (300 MHz, DMSO-d$_6$) 1.1-1.8 (6H, m), 1.9 (2H, m), 2.2-3.7 (15H, m), 3.8 (1H, d), 4.95 (1H, s), 7.2 (1H, m), 7.45 (2H, m), 7.6 (1H, m), 7.8 (2H, m), 8.45 (1H, m), 8.9 (1H, s) | C3 |
| 280 | 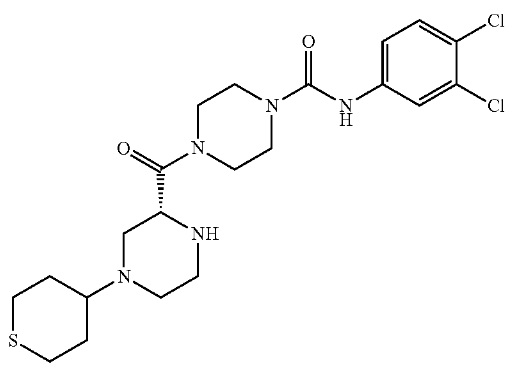 [SMILES: O=C(Nc1ccc(Cl)c(Cl)c1)N1CCN(C(=O)[C@H]2CN(C3CCSCC3)CCN2)CC1] | N-(3,4-Dichlorophenyl)-4-{[(2R)-4-(tetrahydro-2H-thiopyran-4-yl)piperazin-2-yl]carbonyl}piperazine-1-carboxamide<br>LCMS M/z(+) 485.91 (M + H$^+$)<br>$^1$H NMR (300 MHz, DMSO-d$_6$) 1.55 (2H, m), 1.95 (2H, m), 2.2-3.6 (19H, m), 3.75 (1H, m), 7.45 (2H, m), 7.8 (1H, s), 8.85 (1H, s) | C3 |
| 281 | 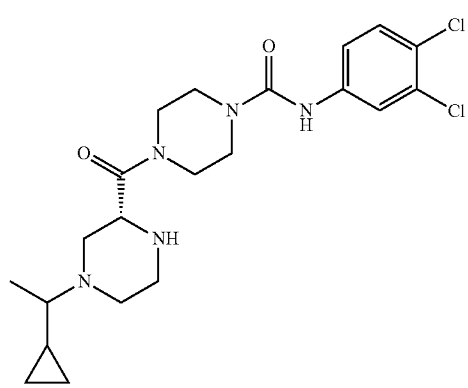 [SMILES: CC(C1CC1)N1CCN[C@@H](C(=O)N2CCN(C(=O)Nc3ccc(Cl)c(Cl)c3)CC2)C1] | 4-{[(2R)-4-(1-Cyclopropylethyl)piperazin-2-yl]carbonyl}-N-(3,4-dichlorophenyl)piperazine-1-carboxamide<br>LCMS M/z(+) 453.95 (M + H$^+$)<br>$^1$H NMR (300 MHz, DMSO-d$_6$) 0.0-0.75 (5H, m), 1.00 (3H, d), 2.3-3.7 (15H, m), 3.95 (1H, m), 7.45 (2H, m), 7.8 (1H, m), 8.85 (1H, s) | C3 |

| Ex-ample No. | Structure | Characterisation Data | Chemistry Route |
|---|---|---|---|
| 282 | 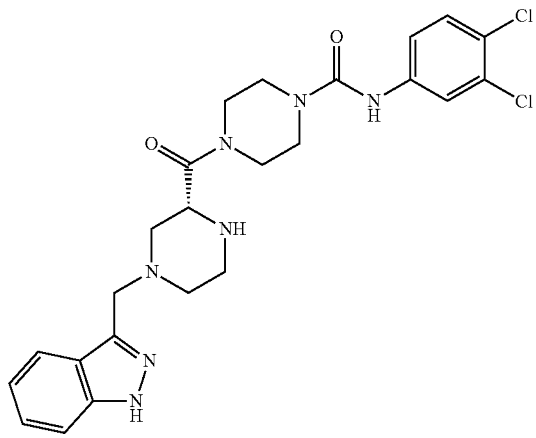 [SMILES: O=C(Nc1ccc(Cl)c(Cl)c1)N1CCN(C(=O)[C@H]2CN(Cc3n[nH]c4ccccc34)CCN2)CC1] | N-(3,4-Dichlorophenyl)-4-{[(2R)-4-(1H-indazol-3-ylmethyl)piperazin-2-yl]carbonyl}piperazine-1-carboxamide<br>LCMS M/z(+) 515.91 (M + H$^+$)<br>$^1$H NMR (300 MHz, DMSO-d$_6$) 2.0 (2H, m), 2.5-3.8 (15H, m), 7.1 (1H, t), 7.3 (1H, t), 7.5 (3H, m), 7.85 (2H, m), 8.8 (1H, s), 12.8 (1H, m) | C3 |
| 283 | 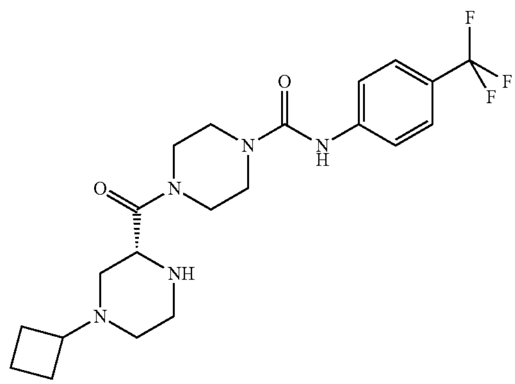 [SMILES: O=C(Nc1ccc(C(F)(F)F)cc1)N1CCN(C(=O)[C@H]2CN(C3CCC3)CCN2)CC1] | 4-{[(2R)-4-Cyclobutylpiperazin-2-yl]carbonyl}-N-[4-(trifluoromethyl)phenyl]piperazine-1-carboxamide<br>LCMS M/z(+) 439.94 (M + H$^+$)<br>$^1$H NMR (300 MHz, DMSO-d$_6$) 1.65 (2H, m), 1.8 (2H, m), 2.0 (2H, m), 2.25 (1H, m), 2.8-3.5 (10H, m), 3.7 (4H, m), 4.5 (1H, m), 7.55 (2H, d), 7.7 (2H, d), 9.0 (1H, s) | A9 |
| 284 | 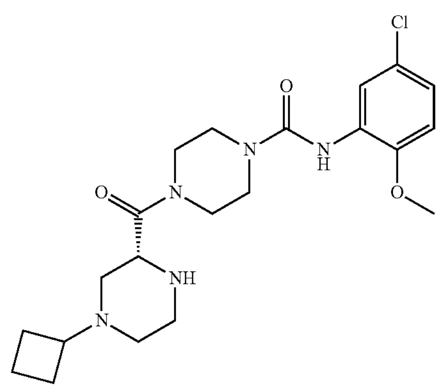 [SMILES: COc1ccc(Cl)cc1NC(=O)N1CCN(C(=O)[C@H]2CN(C3CCC3)CCN2)CC1] | N-(5-chloro-2-methoxyphenyl)-4-{[(2R)-4-cyclobutylpiperazin-2-yl]carbonyl}piperazine-1-carboxamide<br>LCMS M/z(+) 435.91 (M + H$^+$)<br>$^1$H NMR (300 MHz, DMSO-d$_6$) 1.65 (2H, m), 1.75 (2H, m), 1.95 (2H, m), 2.5-3.7 (16H, m), 3.8 (3H, m), 7.0 (2H, m), 7.8 (2H, m) | A9 |
| 285 | 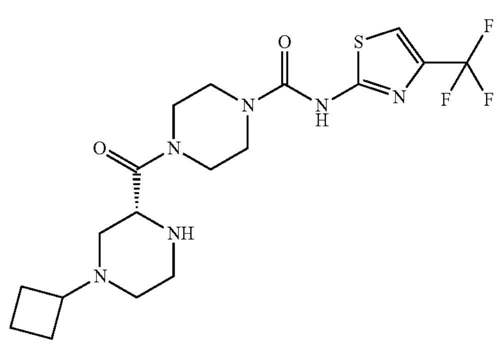 [SMILES: O=C(Nc1nc(C(F)(F)F)cs1)N1CCN(C(=O)[C@H]2CN(C3CCC3)CCN2)CC1] | 4-{[(2R)-4-Cyclobutylpiperazin-2-yl]carbonyl}-N-[4-(trifluoromethyl)-1,3-thiazol-2-yl]piperazine-1-carboxamide<br>LCMS M/z(+) 446.87 (M + H$^+$)<br>$^1$H NMR (300 MHz, DMSO-d$_6$) 1.7 (6H, m), 2.0 (2H, m), 2.5-3.7 (14H, m), 7.75 (1H, s) | A9 |

-continued

| Example No. | Structure | Characterisation Data | Chemistry Route |
|---|---|---|---|
| 286 | 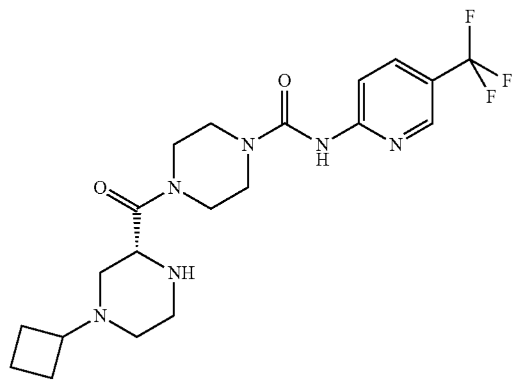 [SMILES: O=C(Nc1ccc(C(F)(F)F)cn1)N1CCN(C(=O)[C@H]2CN(C3CCC3)CCN2)CC1] | 4-{[(2R)-4-cyclobutylpiperazin-2-yl]carbonyl}-N-[5-(trifluoromethyl)pyridin-2-yl]piperazine-1-carboxamide<br>LCMS M/z(+) 440.91 (M + H⁺)<br>$^1$H NMR (300 MHz, DMSO-d$_6$) 1.7 (6H, m), 1.95 (2H, m), 2.4-3.7 (14H, m), 7.9 (1H, d), 8.1 (1H, d), 8.6 (1H, s), 9.8 (1H, s) | A9 |
| 287 | 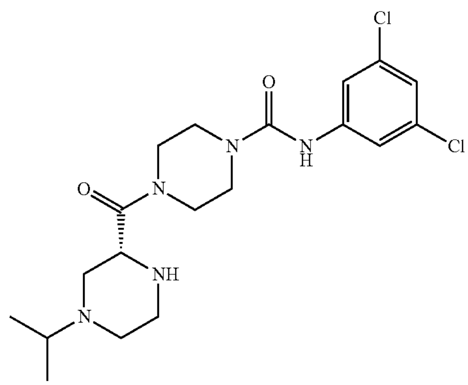 [SMILES: CC(C)N1CCN[C@@H](C(=O)N2CCN(C(=O)Nc3cc(Cl)cc(Cl)c3)CC2)C1] | N-(3,5-Dichlorophenyl)-4-{[(2R)-4-isopropylpiperazin-2-yl]carbonyl}piperazine-1-carboxamide<br>LCMS M/z(+) 428/30 (M + H⁺).<br>$^1$H NMR (400.132 MHz, DMSO-d$_6$) 0.93-1.00 (m, 6H), 2.00-2.12 (m, 2H), 2.57-2.79 (m, 7H), 2.93 (d, 1H), 3.33-3.76 (m, 9H), 7.12 (s, 1H), 7.61 (s, 2H), 8.91 (s, 1H) | A9 |
| 288 | 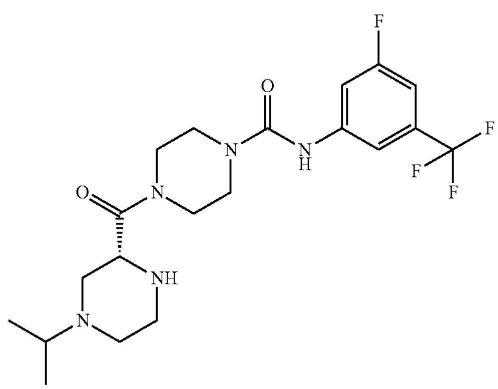 [SMILES: CC(C)N1CCN[C@@H](C(=O)N2CCN(C(=O)Nc3cc(F)cc(C(F)(F)F)c3)CC2)C1] | N-[3-Fluoro-5-(trifluoromethyl)phenyl]-4-{[(2R)-4-isopropylpiperazin-2-yl]carbonyl}piperazine-1-carboxamide<br>LCMS M/z(+) 446 (M + H⁺)<br>$^1$H NMR (400.132 MHz, DMSO-d$_6$) 0.77-0.87 (m, 6H), 1.85-2.02 (m, 2H), 2.43-2.68 (m, 4H), 2.79 (d, 1H), 3.17-3.70 (m, 9H), 7.04 (s, 1H), 7.51-7.66 (m, 2H), 8.96 (s, 1H) | A9 |
| 289 | 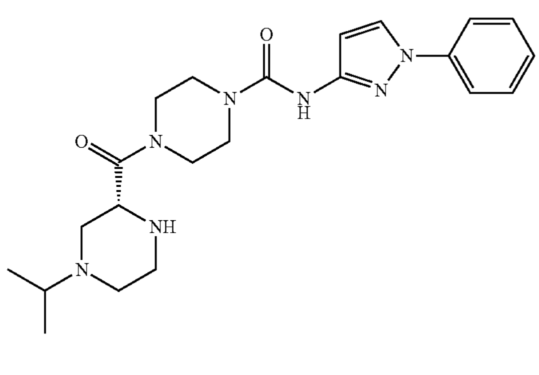 [SMILES: CC(C)N1CCN[C@@H](C(=O)N2CCN(C(=O)Nc3ccn(-c4ccccc4)n3)CC2)C1] | 4-{[(2R)-4-Isopropylpiperazin-2-yl]carbonyl}-N-(1-phenyl-1H-pyrazol-3-yl)piperazine-1-carboxamide<br>LCMS M/z(+) 426 (M + H⁺)<br>$^1$H NMR (400.132 MHz, CDCl$_3$) 1.03-1.06 (6H, m), 2.12 (td, 1H), 2.22 (t, 1H), 2.68-2.80 (m, 2H), 2.81-2.97 (m, 2H), 3.09 (d, 1H), 3.39-3.87 (m, 9H), 6.80 (s, 1H), 7.21 (d, 1H), 7.41 (m, 2H), 7.58 (d, 1H), 7.81 (s, 1H) | A9 |

-continued

Examples

| Example No. | Structure | Characterisation Data | Chemistry Route |
|---|---|---|---|
| 290 | 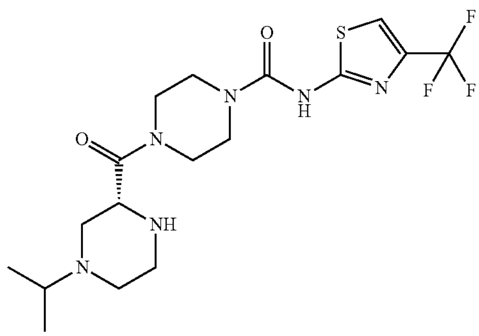 [SMILES: CC(C)N1CCN[C@@H](C(=O)N2CCN(C(=O)Nc3nc(C(F)(F)F)cs3)CC2)C1] | 4-{[(2R)-4-Isopropylpiperazin-2-yl]carbonyl}-N-[4-(trifluoromethyl)-1,3-thiazol-2-yl]piperazine-1-carboxamide<br>LCMS M/z(+) 435 (M + H$^+$)<br>$^1$H NMR (400.132 MHz, CDCl$_3$) 1.03-1.06 (6H, m), 2.12 (td, 1H), 2.20 (t, 1H), 2.71 (t, 1H), 2.75 (d, 1H), 2.80-2.93 (m, 2H), 3.08 (d, 1H), 3.41-3.91 (m, 9H), 7.31 (s, 1H) | A9 |
| 291 | 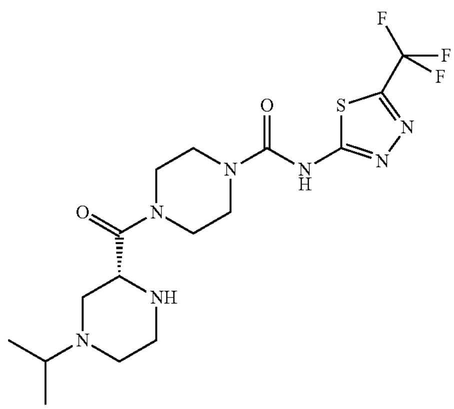 [SMILES: CC(C)N1CCN[C@@H](C(=O)N2CCN(C(=O)Nc3nnc(C(F)(F)F)s3)CC2)C1] | 4-{[(2R)-4-Isopropylpiperazin-2-yl]carbonyl}-N-[5-(trifluoromethyl)-1,3,4-thiadiazol-2-yl]piperazine-1-carboxamide<br>LCMS M/z(+) 436 (M + H$^+$)<br>$^1$H NMR (400.132 MHz, CDCl$_3$) 0.90-1.16 (m, 6H), 2.17 (t, 1H), 2.27 (t, 1H), 2.72-2.82 (m, 2H), 2.86-2.97 (m, 2H), 3.10 (d, 1H), 3.51-3.99 (m, 9H) | A9 |
| 292 | 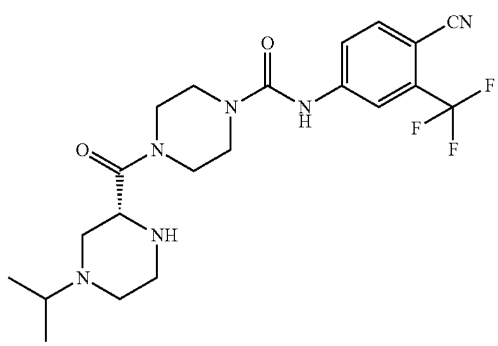 [SMILES: CC(C)N1CCN[C@@H](C(=O)N2CCN(C(=O)Nc3ccc(C#N)c(C(F)(F)F)c3)CC2)C1] | N-[4-Cyano-3-(trifluoromethyl)phenyl]-4-{[(2R)-4-isopropylpiperazin-2-yl]carbonyl}piperazine-1-carboxamide<br>LCMS M/z(+) 453 (M + H$^+$)<br>$^1$H NMR (400.132 MHz, CDCl$_3$) 1.04-1.10 (m, 6H), 2.11-2.29 (m, 2H), 2.70-2.97 (m, 4H), 3.09 (d, 1H), 3.40-3.93 (m, 9H), 6.94 (s, 1H), 7.69-7.80 (m, 2H), 7.86 (s, 1H) | A9 |
| 293 | 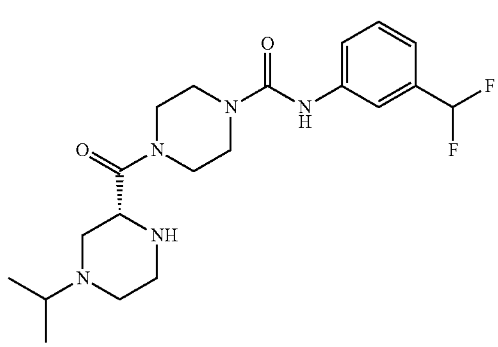 [SMILES: CC(C)N1CCN[C@@H](C(=O)N2CCN(C(=O)Nc3cccc(C(F)F)c3)CC2)C1] | N-[3-(Difluoromethyl)phenyl]-4-{[(2R)-4-isopropylpiperazin-2-yl]carbonyl}piperazine-1-carboxamide<br>LCMS M/z(+) 410 (M + H$^+$)<br>$^1$H NMR (400.132 MHz, CDCl$_3$) 1.03-1.11 (m, 6H), 2.12-2.29 (m, 2H), 2.69-2.83 (m, 2H), 2.84-2.99 (m, 2H), 3.10 (d, 1H), 3.39-3.91 (m, 9H), 6.49 (s, 1H), 6.61 (t, 1H), 7.20 (d, 1H), 7.38 (t, 1H), 7.47 (d, 1H), 7.56 (s, 1H) | A9 |

-continued

| Example No. | Structure | Characterisation Data | Chemistry Route |
|---|---|---|---|
| 294 | 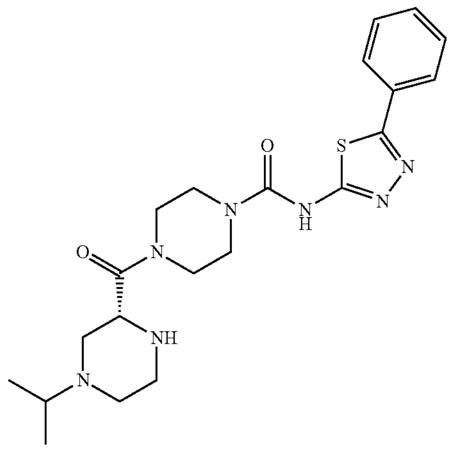 [SMILES: CC(C)N1CCN[C@@H](C(=O)N2CCN(C(=O)Nc3nnc(-c4ccccc4)s3)CC2)C1] | 4-{[(2R)-4-Isopropylpiperazin-2-yl]carbonyl}-N-(5-phenyl-1,3,4-thiadiazol-2-yl)piperazine-1-carboxamide<br>LCMS M/z(+) 444 (M + H$^+$)<br>$^1$H NMR (400.132 MHz, DMSO-d$_6$) 0.79-0.85 (m, 6H), 1.88-1.99 (m, 2H), 2.44-2.65 (m, 4H), 2.79 (d, 1H), 3.21-3.64 (m, 9H), 7.31-7.42 (m, 3H), 7.71 (d, 2H) | A9 |
| 295 | 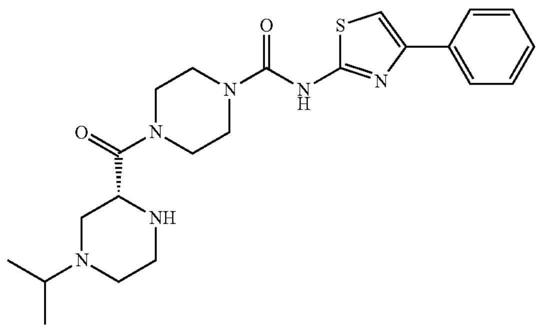 [SMILES: CC(C)N1CCN[C@@H](C(=O)N2CCN(C(=O)Nc3nc(-c4ccccc4)cs3)CC2)C1] | 4-{[(2R)-4-Isopropylpiperazin-2-yl]carbonyl}-N-(4-phenyl-1,3-thiazol-2-yl)piperazine-1-carboxamide<br>LCMS M/z(+) 443 (M + H$^+$)<br>$^1$H NMR (400.132 MHz, DMSO-d$_6$) 0.92-1.01 (m, 6H), 1.98-2.11 (m, 2H), 2.42-2.79 (m, 4H), 2.92 (d, 1H), 3.36-3.74 (m, 9H), 7.31 (t, 1H), 7.42 (t, 2H), 7.47 (s, 1H), 7.89 (d, 2H) | A9 |
| 296 | 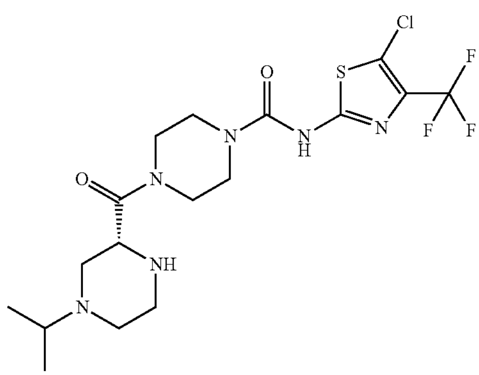 [SMILES: CC(C)N1CCN[C@@H](C(=O)N2CCN(C(=O)Nc3nc(C(F)(F)F)c(Cl)s3)CC2)C1] | N-[5-Chloro-4-(trifluoromethyl)-1,3-thiazol-2-yl]-4-{[(2R)-4-isopropylpiperazin-2-yl]carbonyl}piperazine-1-carboxamide<br>LCMS M/z(+) 469/471 (M + H$^+$)<br>$^1$H NMR (400.132 MHz, DMSO-d$_6$) 1.00-1.08 (m, 6H), 2.15-2.35 (m, 2H), 2.70-2.95 (m, 4H), 3.09 (d, J = 16.5 Hz, 1H), 3.25-3.77 (m, 8H), 4.01 (d, J = 11.2 Hz, 1H) | A9 |
| 297 | 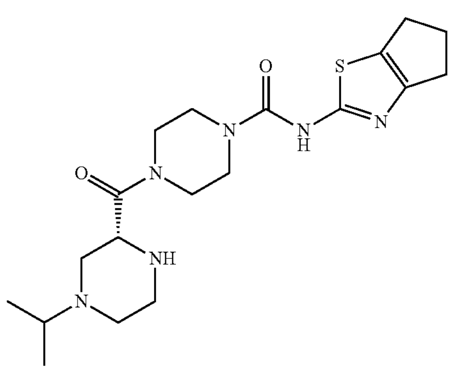 [SMILES: CC(C)N1CCN[C@@H](C(=O)N2CCN(C(=O)Nc3nc4c(s3)CCC4)CC2)C1] | N-(5,6-Dihydro-4H-cyclopenta[d][1,3]thiazol-2-yl)-4-{[(2R)-4-isopropylpiperazin-2-yl]carbonyl}piperazine-1-carboxamide<br>LCMS M/z(+) 407 (M + H$^+$)<br>$^1$H NMR (400.132 MHz, DMSO-d$_6$) 0.92-0.99 (m, 6H), 1.99-2.10 (m, 2H), 2.30-2.40 (m, 2H), 2.58-2.81 (m, 8H), 2.91 (d, 1H), 3.35-3.71 (m, 9H) | A9 |

-continued

Examples

| Example No. | Structure | Characterisation Data | Chemistry Route |
|---|---|---|---|
| 298 | 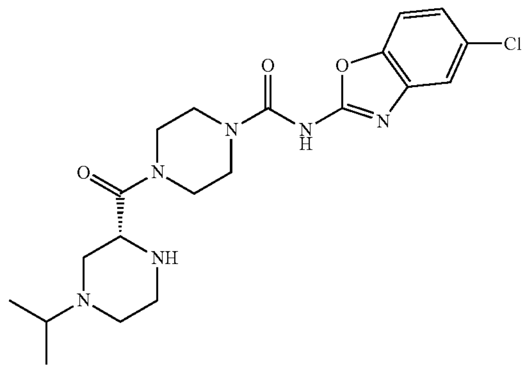 [SMILES: CC(C)N1CCN[C@@H](C(=O)N2CCN(C(=O)Nc3nc4cc(Cl)ccc4o3)CC2)C1] | N-(5-Chloro-1,3-benzoxazol-2-yl)-4-{[(2R)-4-isopropylpiperazin-2-yl]carbonyl}piperazine-1-carboxamide<br>LCMS M/z(+) 435/437 (M + H$^+$)<br>$^1$H NMR (400.132 MHz, DMSO-d$_6$) 0.92-1.01 (m, 6H), 2.02-2.14 (m, 2H), 2.58-2.80 (m, 4H), 2.95 (d, 1H), 3.35-3.79 (m, 9H), 7.15-7.24 (m, 1H), 7.33-7.38 (m, 1H), 7.41-7.49 (m, 1H), 7.54-7.60 (m, 1H) | A9 |
| 299 | 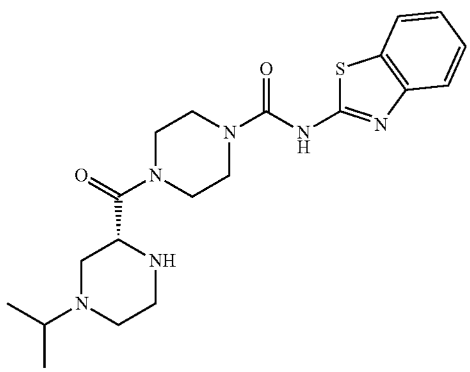 [SMILES: CC(C)N1CCN[C@@H](C(=O)N2CCN(C(=O)Nc3nc4ccccc4s3)CC2)C1] | N-1,3-Benzothiazol-2-yl-4-{[(2R)-4-isopropylpiperazin-2-yl]carbonyl}piperazine-1-carboxamide<br>LCMS M/z(+) 417 (M + H$^+$)<br>$^1$H NMR (400.132 MHz, DMSO-d$_6$) 0.94-1.00 (m, 6H), 2.02-2.13 (m, 2H), 2.59-2.78 (m, 4H), 2.93 (d, 1H), 3.37-3.75 (m, 9H), 7.21 (t, 1H), 7.36 (t, 1H), 7.50 (d, 1H), 7.81 (d, 1H) | A9 |
| 300 | 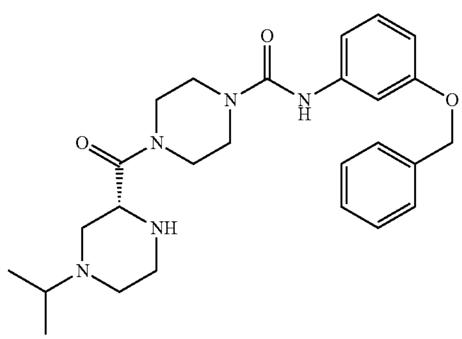 [SMILES: CC(C)N1CCN[C@@H](C(=O)N2CCN(C(=O)Nc3cccc(OCc4ccccc4)c3)CC2)C1] | N-[3-(benzyloxy)phenyl]-4-{[(2R)-4-isopropylpiperazin-2-yl]carbonyl}piperazine-1-carboxamide<br>LCMS M/z(+) 466.83 (M − H$^+$)<br>$^1$H NMR (400.132 MHz, CDCl$_3$) 1.04 (t, 6H), 2.08-2.23 (m, 2H), 2.66-2.93 (m, 4H), 3.09 (d, 2H), 3.48-3.64 (m, 6H), 3.69-3.87 (m, 3H), 5.06 (s, 2H), 6.35 (s, 1H), 6.69 (d, 1H), 6.84 (d, 1H), 7.14-7.21 (m, 2H) and 7.29-7.44 (m, 5H) | A9 |
| 301 | 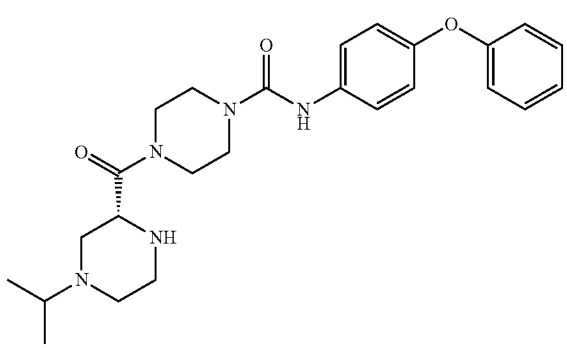 [SMILES: CC(C)N1CCN[C@@H](C(=O)N2CCN(C(=O)Nc3ccc(Oc4ccccc4)cc3)CC2)C1] | 4-{[(2R)-4-isopropylpiperazin-2-yl]carbonyl}-N-(4-phenoxyphenyl)piperazine-1-carboxamide<br>LCMS M/z(+) 452.81 (M + H)<br>$^1$H NMR (400.132 MHz, CDCl$_3$) 1.05 (t, 6H), 2.08-2.23 (m, 2H), 2.64-2.94 (m, 4H), 3.09 (d, 2H), 3.40-3.53 (m, 6H), 3.70-3.88 (m, 3H), 6.29 (s, 1H), 6.98 (d, 4H), 7.07 (t, 1H) and 7.28-7.35 (m, 4H) | A9 |

| Example No. | Structure | Characterisation Data | Chemistry Route |
|---|---|---|---|
| 302 | 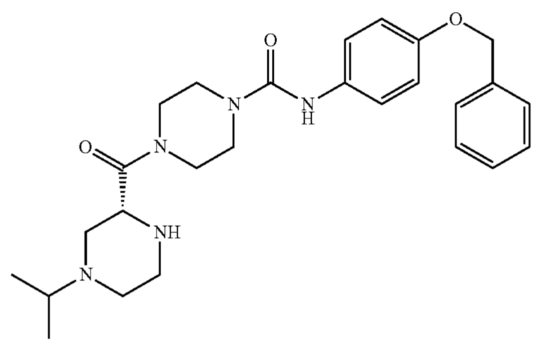 [SMILES: CC(C)N1CCN[C@@H](C(=O)N2CCN(C(=O)Nc3ccc(OCc4ccccc4)cc3)CC2)C1] | N-[4-(benzyloxy)phenyl]-4-{[(2R)-4-isopropylpiperazin-2-yl]carbonyl}piperazine-1-carboxamide<br>LCMS M/z(+) 466.86 (M + H)<br>$^1$H NMR (400.132 MHz, CDCl$_3$) 1.07 (t, 6H), 2.10-2.25 (m, 2H), 2.68-2.96 (m, 4H), 3.09 (d, 2H), 3.36-3.61 (m, 6H), 3.67-3.84 (m, 3H), 5.03 (s, 2H), 6.33 (s, 1H), 6.92 (d, 2H), 7.23 (d, 1H) and 7.29-7.45 (m, 5H) | A9 |
| 303 | 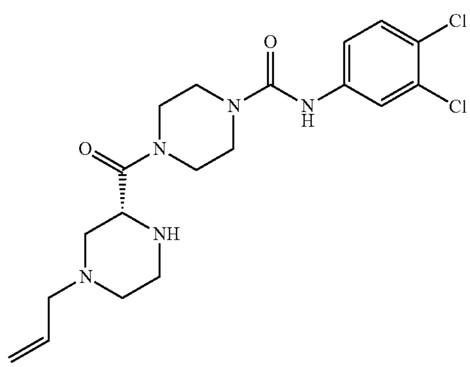 [SMILES: C=CCN1CCN[C@@H](C(=O)N2CCN(C(=O)Nc3ccc(Cl)c(Cl)c3)CC2)C1] | N-(3,4-dichlorophenyl)-4-{[(2R)-4-(prop-2-en-1-yl)piperazin-2-yl]carbonyl}piperazine-1-carboxamide<br>LCMS M/z(+) 426.36 (M + H$^+$)<br>$^1$H NMR (400.132 MHz, DMSO-d$_6$) 1.84 (2H, t), 2.64-2.73 (2H, m), 2.78 (1H, brd), 2.88-2.95 (3H, m), 3.26-3.33 (obscured, m), 3.35-3.67 (5H, m), 3.73 (1H, brd), 5.12 (1H, dd), 5.18 (1H, dd), 5.75-5.84 (1H, m), 7.44 (1H, dd), 7.48 (1H, d), 7.83 (1H, d), 8.85 (1H, s) | E1 |
| 304 | 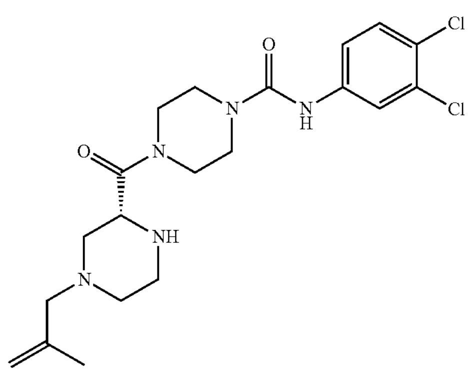 [SMILES: C=C(C)CN1CCN[C@@H](C(=O)N2CCN(C(=O)Nc3ccc(Cl)c(Cl)c3)CC2)C1] | N-(3,4-dichlorophenyl)-4-{[(2R)-4-(2-methylprop-2-en-1-yl)piperazin-2-yl]carbonyl}piperazine-1-carboxamide<br>LCMS M/z(+) 440.27 (M + H$^+$)<br>$^1$H NMR (500 MHz, DMSO-d$_6$) 1.72 (3H, s), 1.81 (2H, t), 2.55-2.7 (1H, m), 2.73 (2H, m), 2.83 (2H, s), 2.92 (1H, d), 3.35-3.6 (8H, m), 3.6-3.7 (2H, m), 4.89 (2H, d), 7.43-7.48 (2H, m), 7.84 (1H, d), 8.88 (1H, s) | E1 |
| 305 | 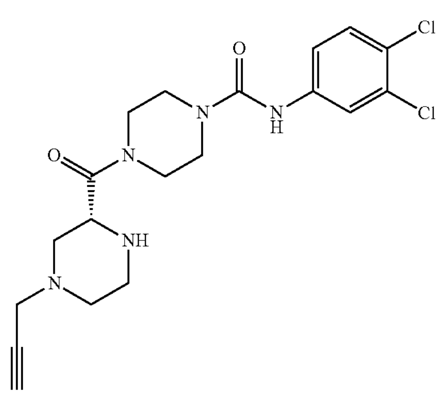 [SMILES: C#CCN1CCN[C@@H](C(=O)N2CCN(C(=O)Nc3ccc(Cl)c(Cl)c3)CC2)C1] | N-(3,4-dichlorophenyl)-4-{[(2R)-4-(prop-2-yn-1-yl)piperazin-2-yl]carbonyl}piperazine-1-carboxamide<br>LCMS M/z(+) 424.36 (M + H$^+$)<br>$^1$H NMR (500 MHz, DMSO-d$_6$) 2.05 (2H, t), 2.59 (1H, d), 2.65-2.74 (2H, m), 2.91 (1H, brd), 3.13 (1H, t), 3.26 (partially obscured, d), 3.35-3.57 (7H, m), 3.60-3.67 (1H, br), 3.69 (1H, dd), 7.43-7.48 (2H, m), 7.83 (1H, d), 8.85 (1H, s). | E1 |

-continued

Examples

| Example No. | Structure | Characterisation Data | Chemistry Route |
|---|---|---|---|
| 306 | 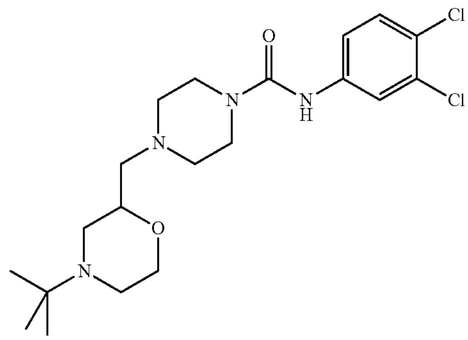 [SMILES: CC(C)(C)N1CCOC(CN2CCN(C(=O)Nc3ccc(Cl)c(Cl)c3)CC2)C1] | 4-[(4-tert-butylmorpholin-2-yl)methyl]-N-(3,4-dichlorophenyl)piperazine-1-carboxamide<br>LCMS M/z(+) 428.96 (M + H$^+$)<br>$^1$H NMR (400.132 MHz, CDCl$_3$) 1.07 (s, 9H), 1.93-2.04 (m, 1H), 2.28-2.35 (m, 2H), 2.48-2.61 (m, 5H), 2.70-2.89 (m, 2H), 3.44-3.57 (m, 4H), 3.57-3.75 (m, 2H), 3.92 (d, 1H), 6.31 (s, 1H), 7.19 (dd, 1H), 7.32 (d, 1H), 7.59 (d, 1H) | E1 |
| 307 | 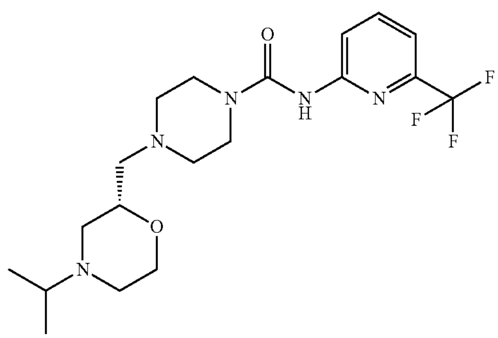 [SMILES: CC(C)N1CCO[C@@H](CN2CCN(C(=O)Nc3cccc(C(F)(F)F)n3)CC2)C1] | 4-{[(2S)-4-isopropylmorpholin-2-yl]methyl}-N-[6-(trifluoromethyl)pyridin-2-yl]piperazine-1-carboxamide<br>LCMS M/z(+) 415.96 (M + H$^+$)<br>$^1$H NMR (400.132 MHz, CDCl$_3$) 1.07 (t, 6H), 1.92-2.09 (m, 1H), 2.25-2.37 (m, 2H), 2.48-2.84 (m, 8H), 3.35-3.83 (m, 6H), 3.93 (dd, 1H), 7.29-7.34 (m, 2H), 7.80 (t, 1H), 8.23 (d, 1H) | A1 |
| 308 | 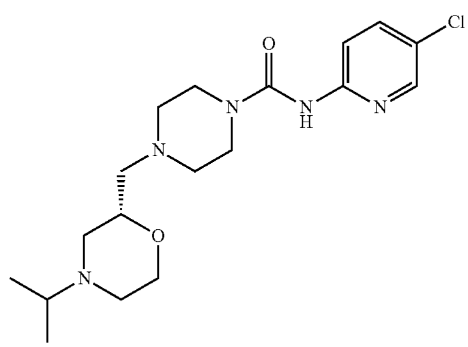 [SMILES: CC(C)N1CCO[C@@H](CN2CCN(C(=O)Nc3ccc(Cl)cn3)CC2)C1] | N-(5-chloropyridin-2-yl)-4-{[(2S)-4-isopropylmorpholin-2-yl]methyl}piperazine-1-carboxamide<br>LCMS M/z(+) 381.94 (M + H$^+$)<br>$^1$H NMR (400.132 MHz, CDCl$_3$) 1.07 (t, 6H), 2.01 (t, 1H), 2.24-2.35 (m, 2H), 2.46-2.81 (m, 8H), 3.47-3.61 (m, 4H), 3.62-3.79 (m 2H), 3.88-3.96 (m, 1H), 7.18 (s, 1H), 7.61 (dd, 1H), 8.01 (d, 1H), 8.14 (d, 1H) | A1 |
| 309 | 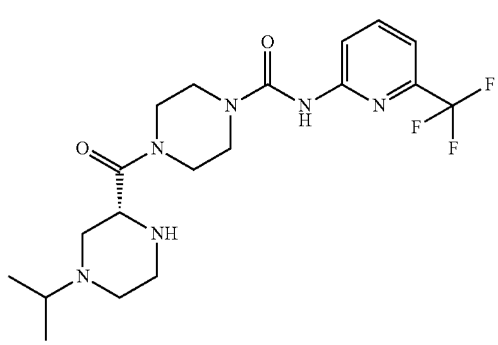 [SMILES: CC(C)N1CCN[C@@H](C(=O)N2CCN(C(=O)Nc3cccc(C(F)(F)F)n3)CC2)C1] | 4-{[(2R)-4-isopropylpiperazin-2-yl]carbonyl}-N-[6-(trifluoromethyl)pyridin-2-yl]piperazine-1-carboxamide<br>LCMS M/z(+) 428.96 (M + H$^+$)<br>$^1$H NMR (400.132 MHz, CDCl$_3$) 1.07 (t, 6H), 2.15 (td, 1H), 2.24 (t, 1H), 2.68-2.99 (m, 4H), 3.06-3.13 (m, 1H), 3.43-3.90 (m, 9H), 7.31 (s, 1H), 7.33 (d, 1H), 7.81 (t, 1H), 8.22 (d, 1H) | A9 |

-continued

Examples

| Example No. | Structure | Characterisation Data | Chemistry Route |
|---|---|---|---|
| 310 | 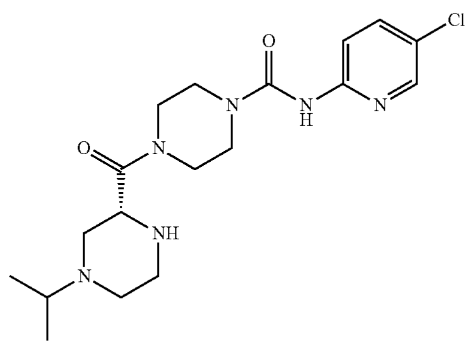 [SMILES: CC(C)N1CCN[C@@H](C(=O)N2CCN(C(=O)Nc3ccc(Cl)cn3)CC2)C1] | N-(5-chloropyridin-2-yl)-4-{[(2R)-4-isopropylpiperazin-2-yl]carbonyl}piperazine-1-carboxamide<br>LCMS M/z(+) 394.97 (M + H$^+$)<br>$^1$H NMR (400.132 MHz, CDCl$_3$) 1.04 (d, 3H), 1.06 (d, 3H), 2.13 (td, 1H), 2.22 (t, 1H), 2.67-2.79 (m, 2H), 2.81-2.96 (m, 2H), 3.05-3.12 (m, 1H), 3.40-3.89 (m, 9H), 7.16 (s, 1H), 7.62 (m, 1H), 7.98-8.01 (m, 1H), 8.15-8.17 (m, 1H) | A9 |
| 311 | 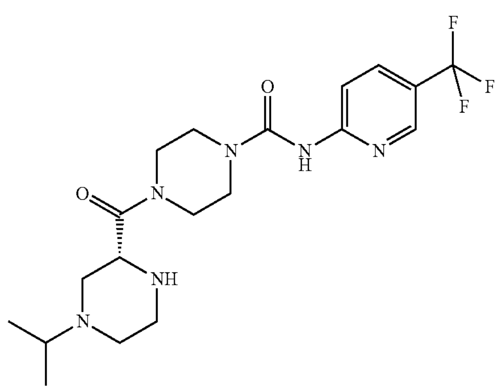 [SMILES: CC(C)N1CCN[C@@H](C(=O)N2CCN(C(=O)Nc3ccc(C(F)(F)F)cn3)CC2)C1] | 4-{[(2R)-4-isopropylpiperazin-2-yl]carbonyl}-N-[5-(trifluoromethyl)pyridin-2-yl]piperazine-1-carboxamide<br>LCMS M/z(+) 428.96 (M + H$^+$)<br>$^1$H NMR (400.132 MHz, CDCl$_3$) 1.07 (d, 3H), 1.10 (d, 3H), 2.17 (t, 1H), 2.27 (t, 1H), 2.70-3.03 (m, 4H), 3.11 (d, 1H), 3.43-3.72 (m, 7H), 3.74-3.95 (m, 3H), 7.39 (s, 1H), 7.88 (dd, 1H), 8.15 (d, 1H), 8.47 (s, 1H) | A9 |
| 312 | 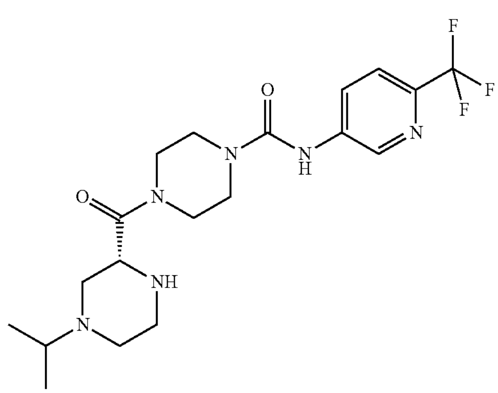 [SMILES: CC(C)N1CCN[C@@H](C(=O)N2CCN(C(=O)Nc3ccc(C(F)(F)F)nc3)CC2)C1] | 4-{[(2R)-4-isopropylpiperazin-2-yl]carbonyl}-N-[6-(trifluoromethyl)pyridin-3-yl]piperazine-1-carboxamide<br>LCMS M/z(+) 428.96 (M + H$^+$)<br>$^1$H NMR (400.132 MHz, CDCl$_3$) 1.07 (d, 3H), 1.10 (d, 3H), 2.18 (t, 1H), 2.27 (t, 1H), 2.72-3.02 (m, 4H), 3.11 (d, 1H), 3.43-3.96 (m, 10H), 6.88 (s, 1H), 7.64 (d, 1H), 8.23 (dd, 1H), 8.56 (d, 1H) | A9 |
| 313 | 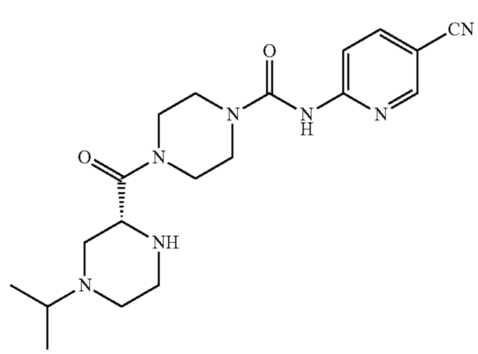 [SMILES: CC(C)N1CCN[C@@H](C(=O)N2CCN(C(=O)Nc3ccc(C#N)cn3)CC2)C1] | N-(5-cyanopyridin-2-yl)-4-{[(2R)-4-isopropylpiperazin-2-yl]carbonyl}piperazine-1-carboxamide<br>LCMS M/z(+) 386.01 (M + H$^+$)<br>$^1$H NMR (400.132 MHz, CDCl$_3$) 1.06 (d, 3H), 1.09 (d, 3H), 2.16 (t, 1H), 2.25 (t, 1H), 2.69-3.00 (m, 4H), 3.10 (d, 1H), 3.42-3.95 (m, 10H), 7.42 (s, 1H), 7.89 (dd, 1H), 8.16 (dd, 1H), 8.50 (dd, 1H) | A9 |

-continued

Examples

| Example No. | Structure | Characterisation Data | Chemistry Route |
|---|---|---|---|
| 314 | 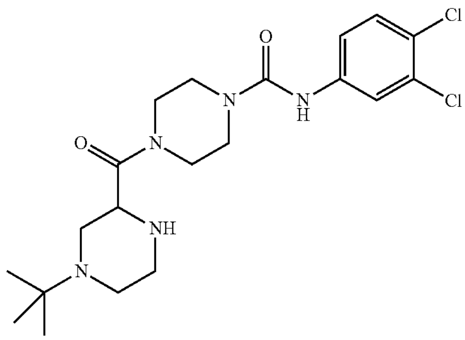 [SMILES: CC(C)(C)N1CCNC(C(=O)N2CCN(C(=O)Nc3ccc(Cl)c(Cl)c3)CC2)C1] | 4-[(4-tert-butylpiperazin-2-yl)carbonyl]-N-(3,4-dichlorophenyl)piperazine-1-carboxamide<br>LCMS M/z(+) 442.10 (M + H$^+$)<br>$^1$H NMR (400.132 MHz, CDCl$_3$) 1.08 (s, 9H), 2.04-2.18 (m, 2H), 2.84-2.95 (m, 2H), 2.99-3.13 (m, 2H), 3.36-3.91 (m, 10H), 6.49 (s, 1H), 7.21 (dd, 1H), 7.33 (d, 1H), 7.59 (d, 1H) | E1 |
| 315 | 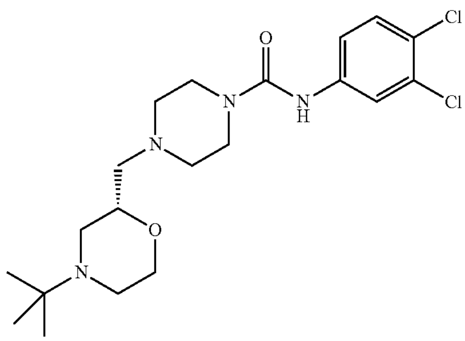 [SMILES: CC(C)(C)N1CCO[C@@H](CN2CCN(C(=O)Nc3ccc(Cl)c(Cl)c3)CC2)C1] | 4-{[(2S)-4-tert-butylmorpholin-2-yl]methyl}-N-(3,4-dichlorophenyl)piperazine-1-carboxamide<br>LCMS M/z(+) 428.96 (M + H$^+$)<br>$^1$H NMR (400.132 MHz, CDCl$_3$) 1.07 (s, 9H), 1.93-2.04 (m, 1H), 2.28-2.35 (m, 2H), 2.48-2.61 (m, 5H), 2.70-2.89 (m, 2H), 3.44-3.57 (m, 4H), 3.57-3.75 (m, 2H), 3.92 (d, 1H), 6.31 (s, 1H), 7.19 (dd, 1H), 7.32 (d, 1H), 7.59 (d, 1H) | E1 |
| 316 | 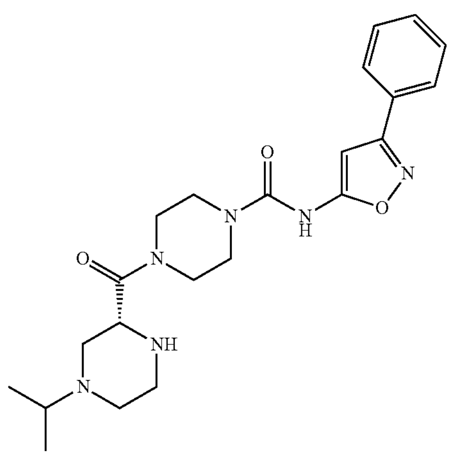 [SMILES: CC(C)N1CCN[C@@H](C(=O)N2CCN(C(=O)Nc3cc(-c4ccccc4)no3)CC2)C1] | 4-{[(2R)-4-Isopropylpiperazin-2-yl]carbonyl}-N-(3-phenylisoxazol-5-yl)piperazine-1-carboxamide<br>LCMS M/z(+) 427 (M + H$^+$)<br>$^1$H NMR (400.132 MHz, DMSO-d$_6$) 0.99-1.06 (m, 6H), 2.07-2.21 (m, 2H), 2.64-2.86 (m, 4H), 2.99 (d, 1H), 3.41-3.82 (m, 10H), 4.07-4.14 (m, 1H), 6.57 (s, 1H), 7.53-7.57 (m, 3H), 7.85-7.90 (m, 2H) | A9 |
| 317 | 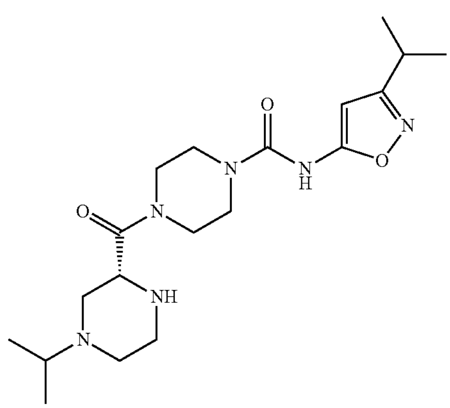 [SMILES: CC(C)c1cc(NC(=O)N2CCN(C(=O)[C@H]3CN(C(C)C)CCN3)CC2)on1] | N-(3-Isopropylisoxazol-5-yl)-4-{[(2R)-4-isopropylpiperazin-2-yl]carbonyl}piperazine-1-carboxamide<br>LCMS M/z(+) 393 (M + H$^+$)<br>$^1$H NMR (400.132 MHz, DMSO-d$_6$) 1.03 (t, 6H), 1.25 (d, 6H), 2.10-2.24 (m, 2H), 2.67-3.06 (m, 6H), 3.39-3.72 (m, 8H), 3.85 (d, 1H), 10.07-10.54 (m, 1H) | A9 |

-continued

Examples

| Example No. | Structure | Characterisation Data | Chemistry Route |
|---|---|---|---|
| 318 | 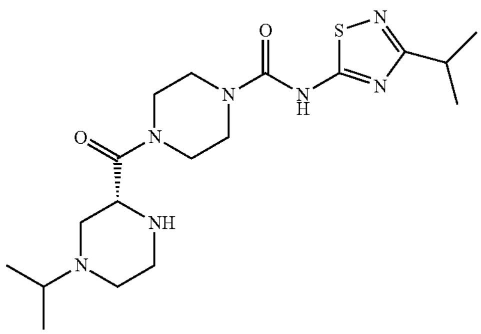 [SMILES: CC(C)c1nsc(NC(=O)N2CCN(C(=O)[C@H]3CN(C(C)C)CCN3)CC2)n1] | 4-{[(2R)-4-Isopropylpiperazin-2-yl]carbonyl}-N-(3-isopropyl-1,2,4-thiadiazol-5-yl)piperazine-1-carboxamide<br>LCMS M/z(+) 410 (M + H$^+$)<br>$^1$H NMR (400.132 MHz, DMSO-d$_6$) 0.94-0.99 (m, 6H), 1.26 (d, 6H), 2.01-2.10 (m, 2H), 2.57-2.78 (m, 4H), 2.92 (d, 1H), 2.96-3.08 (m, 1H), 3.35-3.77 (m, 9H) | A9 |
| 319 | 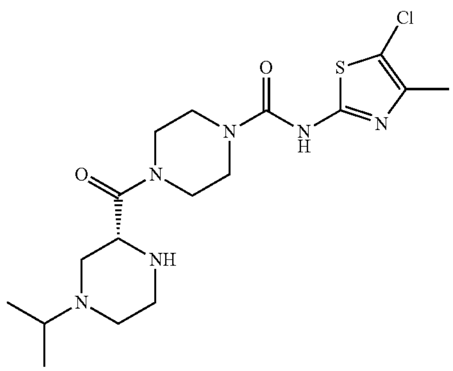 [SMILES: Cc1nc(NC(=O)N2CCN(C(=O)[C@H]3CN(C(C)C)CCN3)CC2)sc1Cl] | N-(5-Chloro-4-methyl-1,3-thiazol-2-yl)-4-{[(2R)-4-isopropylpiperazin-2-yl]carbonyl}piperazine-1-carboxamide<br>LCMS M/z(+) 415/417 (M + H$^+$)<br>$^1$H NMR (400.132 MHz, DMSO-d$_6$) 0.94-0.99 (m, 6H), 2.00-2.11 (m, 2H), 2.17 (s, 3H), 2.57-2.76 (m, 4H), 2.91 (d, 1H), 3.32-3.71 (m, 9H) | A9 |
| 320 | 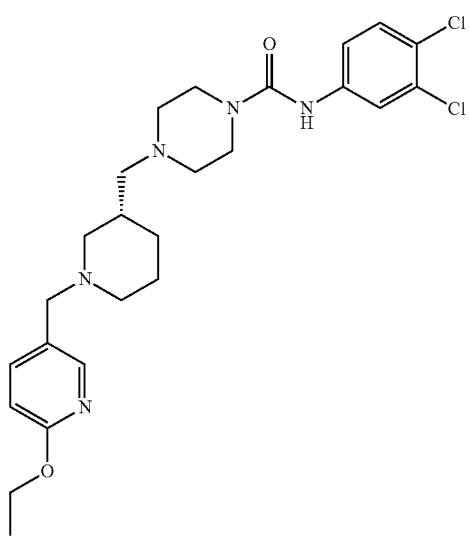 [SMILES: CCOc1ccc(CN2CCC[C@@H](CN3CCN(C(=O)Nc4ccc(Cl)c(Cl)c4)CC3)C2)cn1] | N-(3,4-Dichlorophenyl)-4-({(3S)-1-[(5-ethoxypyridin-2-yl)methyl]piperidin-3-yl}methyl)piperazine-1-carboxamide<br>LCMS M/z(+) 506 (M + H$^+$)<br>$^1$H NMR (500.133 MHz, DMSO-d$_6$) 1.30 (3H, t), 1.50 (1H, m), 1.66 (2H, m), 1.82 (1H, m), 1.93 (1H, m), 2.19 (3H, m), 2.36 (4H, m), 2.70 (1H, m), 2.81 (1H, m), 3.40 (4H, m), 4.31 (2H, q), 6.71 (1H, d), 7.39 (1H, d), 7.79 (1H, d), 8.03 (1H, d) | C1 |

| Examples | | |
|---|---|---|
| Example No. | Structure | Characterisation Data | Chemistry Route |
| 321 | | N-(3,4-Dichlorophenyl)-4-({(3R)-1-[(6-isopropoxypyridin-3-yl)methyl]piperidin-3-yl}methyl)piperazine-1-carboxamide<br>LCMS M/z(+) 520 (M + H$^+$)<br>$^1$H NMR (500.133 MHz, DMSO-d$_6$) 1.00 (1H, m), 1.28 (6H, d), 1.51 (1H, m), 1.65 (2H, m), 1.85 (2H, m), 2.10 (1H, m), 2.21 (2H, m), 2.36 (4H, m), 2.65 (1H, m), 2.75 (1H, m), 3.40 (4H, m), 3.40 (2H, m), 5.25 (1H, septet), 6.65 (1H, d), 7.40 (1H, d), 7.45 (1H, d), 7.60 (1H, d), 7.80 (1H, d), 8.03 (1H, d), 8.48 (1H, s) | C1 |
| 322 | | 4-({(3R)-1-[2-Chloro-4-(methylsulfonyl)benzyl]piperidin-3-yl}methyl)-N-(3,4-dichlorophenyl)piperazine-1-carboxamide<br>LCMS M/z(+) 571 (M − H)<br>$^1$H NMR (400.133 MHz, DMSO-d$_6$) 1.04 (1H, m), 1.52 (1H, m), 1.66 (2H, m), 1.83 (1H, m), 1.98 (1H, m), 2.22 (3H, m), 2.37 (4H, m), 2.66 (1H, m), 2.78 (1H, m), 3.21 (3H, s), 3.40 (4H, t), 3.63 (2H, s), 7.40 (1H, d), 7.44 (1H, dd), 7.77 (1H, d), 7.79 (1H, d), 7.85 (1H, dd), 7.91 (1H, d), 8.47 (1H, s) | C1 |

Examples

| Example No. | Structure | Characterisation Data | Chemistry Route |
|---|---|---|---|
| 323 | 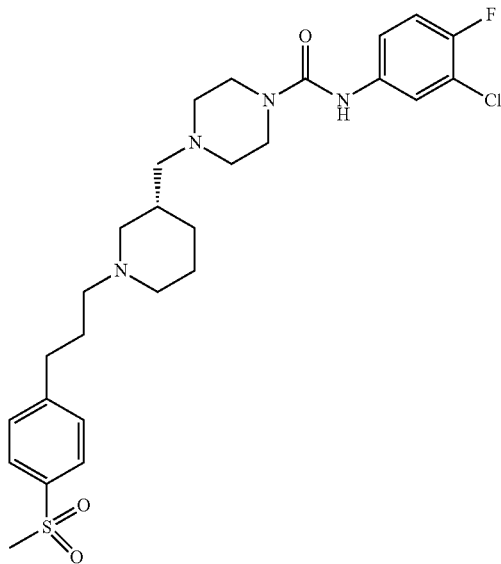 [SMILES: CS(=O)(=O)c1ccc(CCCN2CCC[C@@H](CN3CCN(C(=O)Nc4ccc(F)c(Cl)c4)CC3)C2)cc1] | N-(3-Chloro-4-fluorophenyl)-4-[((3R)-1-{3-[4-(methylsulfonyl)phenyl]propyl}piperidin-3-yl)methyl]piperazine-1-carboxamide<br>LCMS M/z(+) 551 (M + H$^+$)<br>$^1$H NMR (400.133 MHz, DMSO-d$_6$) 0.97 (16H, m), 1.47 (16H, m), 1.64 (1H, m), 1.78 (1H, m), 2.01 (2H, m), 2.20 (2H, m), 2.36 (6H, m), 2.67 (2H, m), 2.74 (2H, m), 3.13 (3H, s), 3.43 (4H, ABq), 7.20 (1H, m), 7.41 (1H, m), 7.46 (2H, d), 7.71 (1H, dd), 7.81 (2H, d), 8.38 (1H, s) | A1 |
| 324 | 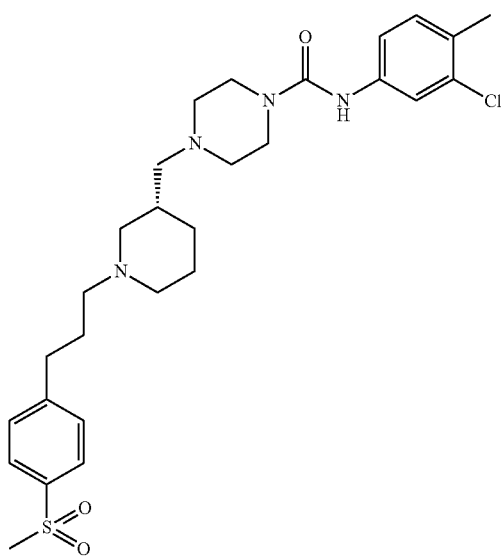 [SMILES: Cc1ccc(NC(=O)N2CCN(C[C@@H]3CCCN(CCCc4ccc(S(C)(=O)=O)cc4)C3)CC2)cc1Cl] | N-(3-Chloro-4-methylphenyl)-4-[((3R)-1-{3-[4-(methylsulfonyl)phenyl]propyl}piperidin-3-yl)methyl]piperazine-1-carboxamide<br>LCMS M/z(+) 547 (M + H$^+$)<br>$^1$H NMR (400.133 MHz, DMSO-d$_6$) 0.98 (1H, m), 1.47 (1H, m), 1.65 (2H, m), 1.79 (4H, m), 2.02 (1H, m), 2.20 (2H, m), 2.26 (3H, s), 2.36 (6H, m), 2.72 (4H, m), 3.12 (3H, s), 3.42 (4H, ABq), 7.15 (1H, d), 7.30 (1H, dd), 7.46 (2H, d), 7.60 (1H, d), 7.81 (2H, d), 8.26 (1H, s) | A1 |

| Example No. | Structure | Characterisation Data | Chemistry Route |
|---|---|---|---|
| 325 | 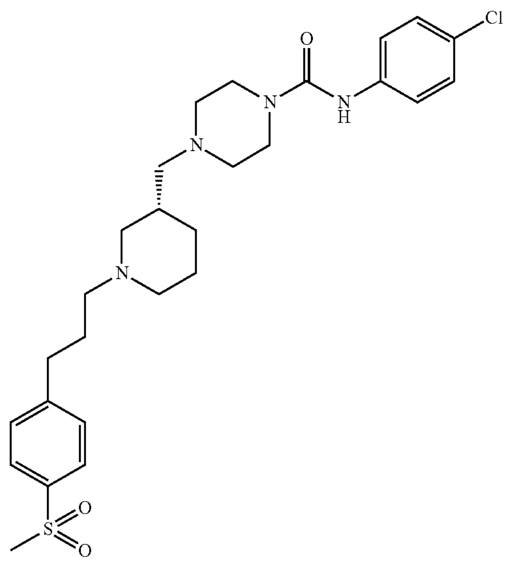 [SMILES: CS(=O)(=O)c1ccc(CCCN2CCC[C@@H](CN3CCN(C(=O)Nc4ccc(Cl)cc4)CC3)C2)cc1] | N-(4-Chlorophenyl)-4-[((3R)-1-{3-[4-(methylsulfonyl)phenyl]propyl}piperidin-3-yl)methyl]piperazine-1-carboxamide<br>LCMS M/z(+) 534 (M + H$^+$)<br>$^1$H NMR (400.133 MHz, DMSO-d$_6$) 0.90 (1H, m), 1.25 (2H, m), 1.87 (4H, m), 1.96 (2H, m), 2.17 (2H, m), 2.35 (4H, m), 2.42 (2H, m), 2.74 (2H, m), 2.85 (2H, m), 3.05 (3H, s), 3.46-3.49 (4H, m), 7.24 (2H, d), 7.33 (2H, d), 7.40 (2H, d), 7.84 (2H, d) | A1 |
| 326 | 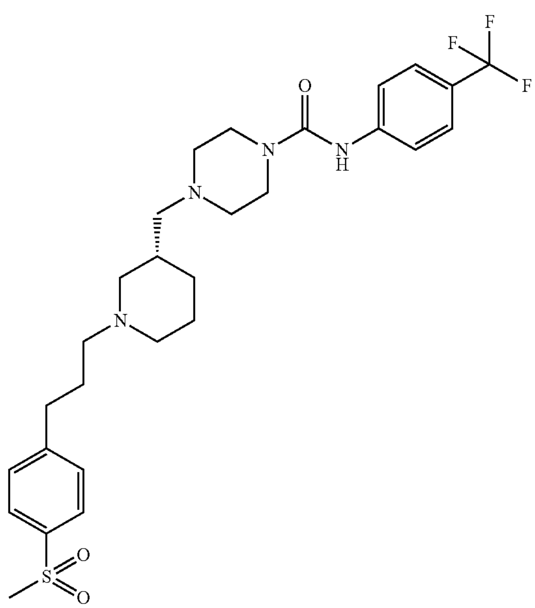 [SMILES: CS(=O)(=O)c1ccc(CCCN2CCC[C@@H](CN3CCN(C(=O)Nc4ccc(C(F)(F)F)cc4)CC3)C2)cc1] | 4-[((3R)-1-{3-[4-(Methylsulfonyl)phenyl]propyl}piperidin-3-yl)methyl]-N-[4-(trifluoromethyl)phenyl]piperazine-1-carboxamide<br>LCMS M/z(+) 567 (M + H$^+$)<br>$^1$H NMR (400.133 MHz, DMSO-d$_6$) 0.90 (1H, m) 1.60-1.62 (1H, m), 1.65-1.72 (2H, m), 1.74 (1H, d), 1.82-1.91 (1H, m), 1.80-1.93 (1H, m), 1.85-1.90 (2H, m), 2.14-2.19 (2H, m), 2.34-2.38 (4H, m), 2.42-2.47 (2H, m), 2.74 (2H, t), 2.88 (2H, d), 3.06 (3H, s), 3.43-3.56 (4H, m), 6.72 (1H, s), 7.39 (2H, m), 7.49-7.54 (4H, m), 7.84 (2H, d) | A1 |

Examples

| Example No. | Structure | Characterisation Data | Chemistry Route |
|---|---|---|---|
| 327 | 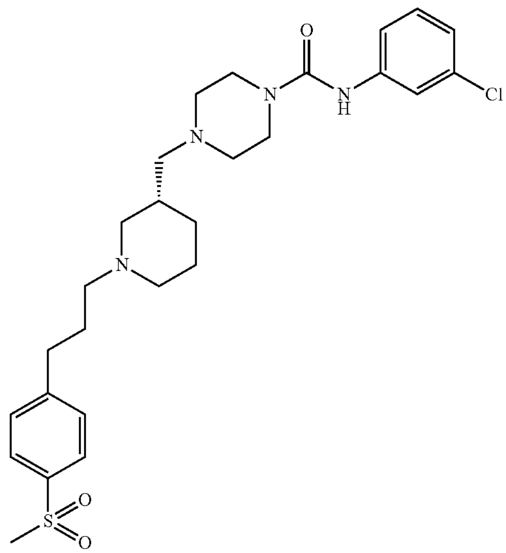 [SMILES: CS(=O)(=O)c1ccc(CCCN2CCC[C@@H](CN3CCN(C(=O)Nc4cccc(Cl)c4)CC3)C2)cc1] | N-(3-Chlorophenyl)-4-[((3R)-1-{3-[4-(methylsulfonyl)phenyl]propyl}piperidin-3-yl)methyl]piperazine-1-carboxamide<br>LCMS M/z(+) 533/535 (M + H$^+$)<br>$^1$H NMR (400.133 MHz, DMSO-d$_6$) 0.90 (d, 1H), 1.46 (d, 1H), 1.55-1.71 (m, 3H), 1.77 (d, 3H), 2.09-2.23 (m, 2H), 2.33 (dd, 5H), 2.65-2.89 (m, 4H), 3.19 (s, 3H), 3.33 (d, 2H), 3.43 (t, 4H), 6.97 (ddd, 1H), 7.24 (t, 1H), 7.39 (ddd, 1H), 7.49 (d, 2H), 7.65 (t, 1H), 7.83 (d, 2H), 8.68 (s, 1H) | A1 |
| 328 | 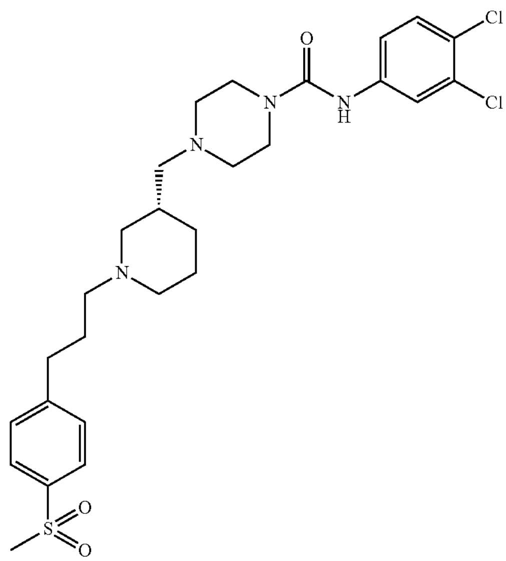 [SMILES: CS(=O)(=O)c1ccc(CCCN2CCC[C@@H](CN3CCN(C(=O)Nc4ccc(Cl)c(Cl)c4)CC3)C2)cc1] | N-(3,4-Dichlorophenyl)-4-[((3R)-1-{3-[4-(methylsulfonyl)phenyl]propyl}piperidin-3-yl)methyl]piperazine-1-carboxamide<br>LCMS M/z(+) 565/569/571 (M + H$^+$)<br>$^1$H NMR (400.133 MHz, DMSO-d$_6$) 0.91 (s, 1H), 1.48 (s, 1H), 1.67 (d, 3H), 1.77 (s, 3H), 2.16 (d, 2H), 2.34 (dd, 5H), 2.65-2.93 (m, 4H), 3.19 (s, 3H), 3.32 (d, 2H), 3.43 (d, 4H), 7.43-7.52 (m, 4H), 7.81-7.86 (m, 3H), 8.79 (s, 1H) | A1 |
| 329 | 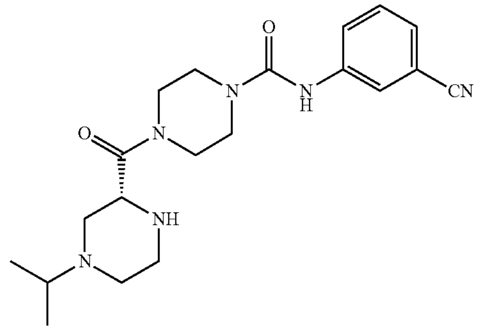 [SMILES: CC(C)N1CCN[C@@H](C(=O)N2CCN(C(=O)Nc3cccc(C#N)c3)CC2)C1] | N-(3-cyanophenyl)-4-{[(2R)-4-isopropylpiperazin-2-yl]carbonyl}piperazine-1-carboxamide<br>LCMS M/z(+) 385.46 (M + H$^+$)<br>$^1$H NMR (500.133 MHz, CDCl$_3$) 0.98 (6H, m), 2.09 (2H, m), 2.70 (4H, m), 3.57 (8H, m), 7.32 (1H, m), 7.43 (1H, m), 7.76 (1H, m), 7.91 (1H, m), 8.61 (1H, m) 3H under DMSO/water | A9 |

-continued

Examples

| Example No. | Structure | Characterisation Data | Chemistry Route |
|---|---|---|---|
| 330 | 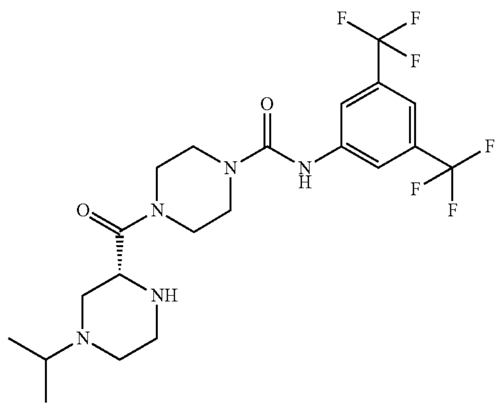 [SMILES: CC(C)N1CCN[C@@H](C(=O)N2CCN(C(=O)Nc3cc(C(F)(F)F)cc(C(F)(F)F)c3)CC2)C1] | N-[3,5-bis(trifluoromethyl)phenyl]-4-{[(2R)-4-isopropylpiperazin-2-yl]carbonyl}piperazine-1-carboxamide<br>LCMS M/z(+) 496.34 (M + H$^+$)<br>$^1$H NMR (499.803 MHz, DMSO-d$_6$) 1.13 (6H, m), 2.70 (1H, m), 3.09 (4H, m), 3.60 (4H, m), 3.74 (2H, m), 4.28 (1H, m), 6.96 (1H, m), 7.13 (1H, m), 7.51 (1H, m), 8.18 (2H, m), 9.52-11.23 (1H, m) 3H under DMSO or water | A9 |
| 331 | 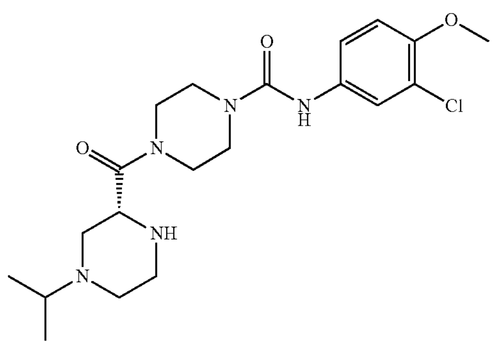 [SMILES: COc1ccc(NC(=O)N2CCN(C(=O)[C@H]3CN(C(C)C)CCN3)CC2)cc1Cl] | N-(3-chloro-4-methoxyphenyl)-4-{[(2R)-4-isopropylpiperazin-2-yl]carbonyl}piperazine-1-carboxamide<br>LCMS M/z(+) 424.40 (M + H$^+$)<br>$^1$H NMR (499.803 MHz, DMSO-d$_6$) 0.96 (6H, m), 2.05 (2H, m), 2.67 (4H, m), 2.92 (1H, m), 3.49 (4H, m), 3.71 (1H, m), 3.78 (3H, m), 7.04 (1H, m), 7.33 (1H, m), 7.59 (1H, m), 8.55 (1H, s) 2H under DMSO | A9 |
| 332 | 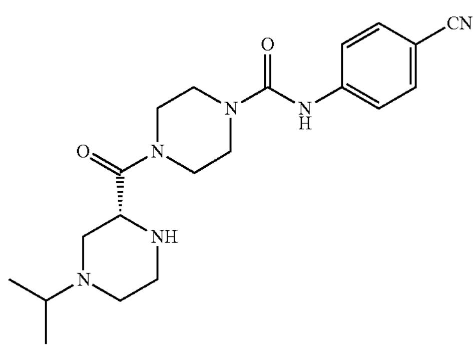 [SMILES: CC(C)N1CCN[C@@H](C(=O)N2CCN(C(=O)Nc3ccc(C#N)cc3)CC2)C1] | N-(4-cyanophenyl)-4-{[(2R)-4-isopropylpiperazin-2-yl]carbonyl}piperazine-1-carboxamide<br>LCMS M/z(+) 385.41 (M + H$^+$)<br>$^1$H NMR (500.133 MHz, DMSO-d$_6$) 0.98 (6H, m), 2.11 (2H, m), 2.70 (5H, m), 3.42 (1H, m), 3.54 (8H, m), 3.66 (1H, m), 7.61 (2H, m), 7.66 (2H, m), 8.75 (1H, m) | A9 |
| 333 | 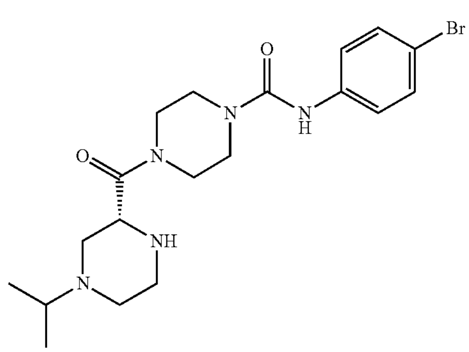 [SMILES: CC(C)N1CCN[C@@H](C(=O)N2CCN(C(=O)Nc3ccc(Br)cc3)CC2)C1] | N-(4-bromophenyl)-4-{[(2R)-4-isopropylpiperazin-2-yl]carbonyl}piperazine-1-carboxamide<br>LCMS M/z(+) 440.22 (M + H$^+$)<br>$^1$H NMR (500.133 MHz, CDCl$_3$) 0.95 (6H, m), 2.05 (2H, m), 2.64 (3H, m), 2.74 (1H, m), 2.92 (1H, m), 3.49 (9H, m), 3.71 (1H, m), 7.39 (2H, m), 7.44 (2H, m), 8.71 (1H, s) | A9 |

| Example No. | Structure | Characterisation Data | Chemistry Route |
|---|---|---|---|
| 334 | 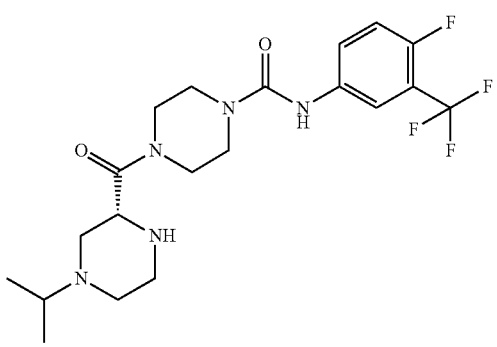 [SMILES: CC(C)N1CCN[C@@H](C(=O)N2CCN(C(=O)Nc3ccc(F)c(C(F)(F)F)c3)CC2)C1] | N-[4-fluoro-3-(trifluoromethyl)phenyl]-4-{[(2R)-4-isopropylpiperazin-2-yl]carbonyl}piperazine-1-carboxamide<br>LCMS M/z(+) 446.16 (M + H$^+$)<br>$^1$H NMR (499.803 MHz, DMSO-d$_6$) 0.94 (6H, m), 2.02 (2H, m), 2.64 (4H, m), 2.89 (1H, m), 3.50 (10H, m), 7.38 (1H, m), 7.77 (1H, m), 7.91 (1H, m), 8.90 (1H, s) | A9 |
| 335 | 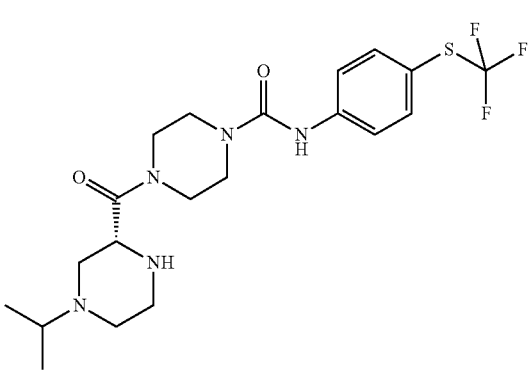 [SMILES: CC(C)N1CCN[C@@H](C(=O)N2CCN(C(=O)Nc3ccc(SC(F)(F)F)cc3)CC2)C1] | 4-{[(2R)-4-isopropylpiperazin-2-yl]carbonyl}-N-{4-[(trifluoromethyl)thio]phenyl}piperazine-1-carboxamide<br>LCMS M/z(+) 460.30 (M + H$^+$)<br>$^1$H NMR (499.803 MHz, DMSO-d$_6$) 0.99 (6H, m), 2.14 (2H, m), 2.71 (5H, m), 3.54 (9H, m), 3.71 (1H, m), 7.54 (2H, m), 7.63 (2H, m), 8.64 (1H, m) | A9 |
| 336 | 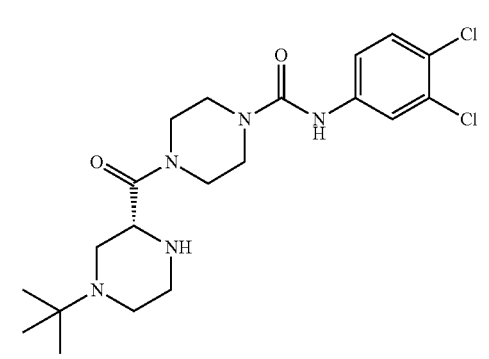 [SMILES: CC(C)(C)N1CCN[C@@H](C(=O)N2CCN(C(=O)Nc3ccc(Cl)c(Cl)c3)CC2)C1] | 4-{[(2R)-4-tert-butylpiperazin-2-yl]carbonyl}-N-(3,4-dichlorophenyl)piperazine-1-carboxamide<br>LCMS M/z(+) 442.10 (M + H$^+$)<br>$^1$H NMR (400.132 MHz, CDCl$_3$) 1.08 (s, 9H), 2.04-2.18 (m, 2H), 2.84-2.95 (m, 2H), 2.99-3.13 (m, 2H), 3.36-3.91 (m, 10H), 6.49 (s, 1H), 7.21 (dd, 1H), 7.33 (d, 1H), 7.59 (d, 1H) | E1 |
| 337 | 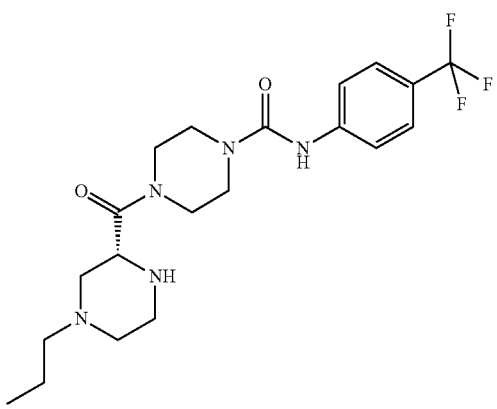 [SMILES: CCCN1CCN[C@@H](C(=O)N2CCN(C(=O)Nc3ccc(C(F)(F)F)cc3)CC2)C1] | 4-{[(2R)-4-(prop-1-yl)piperazin-2-yl]carbonyl}-N-(4-trifluoromethyl-phenyl)piperazine-1-carboxamide<br>LCMS M/z(+) 428.32 (M + H$^+$)<br>$^1$H-NMR (500.133 MHz, DMSO-d$_6$) 0.87 (3H, t), 1.46 (2H, sextet), 1.85-1.95 (2H, m), 2.26 (2H, t), 2.62-2.80 (2H, m), 2.9-2.94 (obscured, m), 3.4-3.6 (8H, m), 3.67 (1H, dd), 7.55 (2H, d), 7.69 (2H, d), 8.66 (1H, s) | E1 |

Examples -continued

| Example No. | Structure | Characterisation Data | Chemistry Route |
|---|---|---|---|
| 338 | 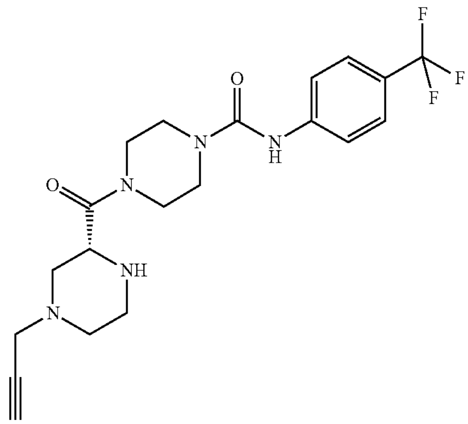 [SMILES: C#CCN1CCN[C@@H](C(=O)N2CCN(C(=O)Nc3ccc(C(F)(F)F)cc3)CC2)C1] | 4-{[(2R)-4-(prop-2-yn-1-yl)piperazin-2-yl]carbonyl}-N-(4-trifluoromethyl-phenyl)piperazine-1-carboxamide<br>LCMS M/z(+) 423.94 (M + H⁺)<br>¹H-NMR (500.133 MHz, DMSO-d6, 373K) 2.19 (1H, dt), 2.13 (1H, q), 2.64 (1H, m), 2.72-2.80 (2H, m), 2.9-2.98 (2H partially obscured, m), 3.26 (2H, d), 3.49-3.60 (8H, m), 3.69 (1H, dd), 7.55 (2H, d), 7.68 (2H, d), 8.65 (1H, s) | E1 |
| 339 | 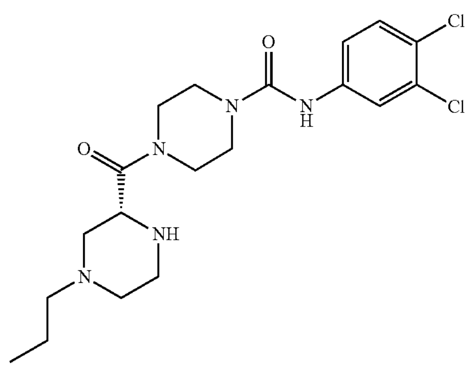 [SMILES: CCCN1CCN[C@@H](C(=O)N2CCN(C(=O)Nc3ccc(Cl)c(Cl)c3)CC2)C1] | N-(3,4-dichlorophenyl)-4-{[(2R)-4-(prop-1-yl)piperazin-2-yl]carbonyl}piperazine-1-carboxamide<br>LCMS M/z(+) 429.83 (M + H⁺)<br>¹H-NMR (500.133 MHz, DMSO-d6, 373K) 0.86 (3H, t), 1.45 (2H, hextet), 1.88 (1H, dt), 1.93 (1H, t), 2.26 (2H, t), 2.62-2.79 (4H, m), 3.40-3.59 (8H, m), 3.68 (1H, dd), 7.42 (1H, d), 7.47 (1H, dd), 7.72 (1H, d), 8.57 (1H, s) | E1 |

The chemical routes used to synthesise the examples and certain intermediates in their preparation are designated A-E and illustrated hereinafter.

Route A1

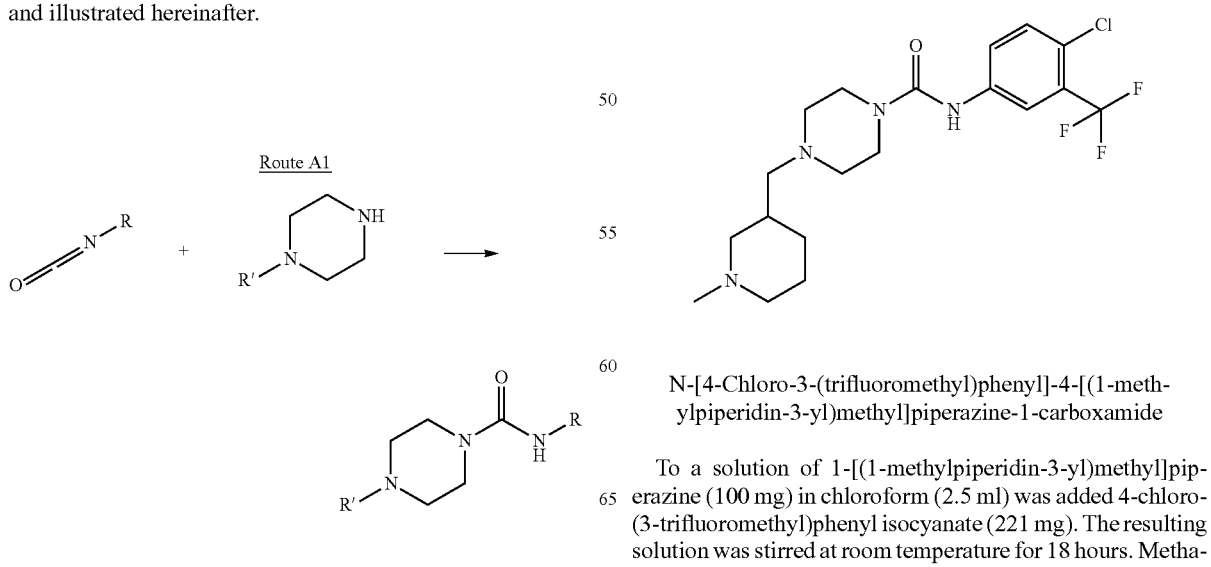

Experimental

N-[4-Chloro-3-(trifluoromethyl)phenyl]-4-[(1-methylpiperidin-3-yl)methyl]piperazine-1-carboxamide To a solution of 1-[(1-methylpiperidin-3-yl)methyl]piperazine (100 mg) in chloroform (2.5 ml) was added 4-chloro-(3-trifluoromethyl)phenyl isocyanate (221 mg). The resulting solution was stirred at room temperature for 18 hours. Methanol (1 ml) and silica gel (0.5 g) was added and the mixture concentrated in vacuo. The resulting powder was purified by column chromatography on silica gel (20 g) using a gradient of 100% dichloromethane through to 20% methanolic ammonia in dichloromethane to give the title compound (204.4 mg).

LCMS M/z(+) 419.28, 421.37 (M+H$^+$).

$^1$H-NMR (400.132 MHz, DMSO-d$_6$) 0.84 (1H, m), 1.40 to 1.66 (4H, m), 1.72 to 1.86 (2H, m), 2.15 (5H, m), 2.28 to 2.40 (4H, m), 2.62 (1H, d), 2.77 (1H, d), 3.45 (4H, t), 7.56 (1H, d), 7.79 (1H, dd), 8.05 (1H, d), 8.92 (1H, s).

The following compounds were prepared in an analogous fashion.

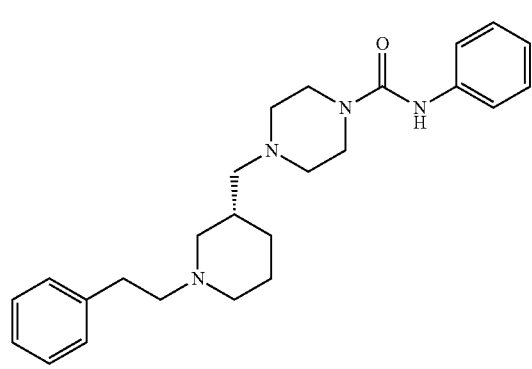 [SMILES: O=C(Nc1ccccc1)N1CCN(C[C@@H]2CCCN(CCc3ccccc3)C2)CC1]

N-Phenyl-4-{[(3R)-1-(2-phenylethyl)piperidin-3-yl]methyl}piperazine-1-carboxamide LCMS M/z(+) 406.97 (M+H$^+$).

$^1$H-NMR (400.132 MHz, DMSO-d$_6$) 1.4 (3H, m), 2.1 (2H, m), 2.3-3.5 (18H, m), 6.9 (1H, t), 7.25 (7H, m), 7.45 (2H, d), 8.45 (1H, s).

The 1-{[(3R)-1-Phenylethylpiperidin-3-yl]methyl}piperazine used to make the above molecule through Route A1 was prepared using the following procedure.

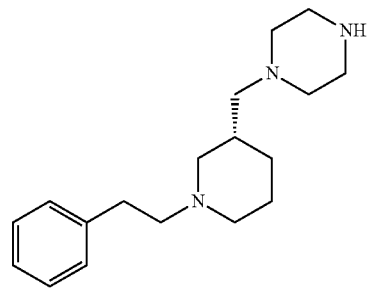 [SMILES: c1ccc(CCN2CCC[C@@H](CN3CCNCC3)C2)cc1]

1-{[(3R)-1-Phenylethylpiperidin-3-yl]methyl}piperazine

Water (5 ml), 10% palladium on carbon (900 mg) and ethanol (50 ml) were added to benzyl 4-{[(3R)-1-phenylethylpiperidin-3-yl]methyl}piperazine-1-carboxylate (950 mg) under an argon atmosphere. The mixture was stirred overnight under a hydrogen filled balloon. The catalyst was remove by filtration through celite and the filtrate concentrated in vacuo and azeotroped once with toluene to give 1-{[(3R)-1-phenylethylpiperidin-3-yl]methyl}piperazine as a yellow oil (650 mg).

$^1$H-NMR (400.132 MHz, DMSO-d$_6$) 1.4 (5H, m), 2.0 to 4.0 (18H, m), 7.2 (5H, m).

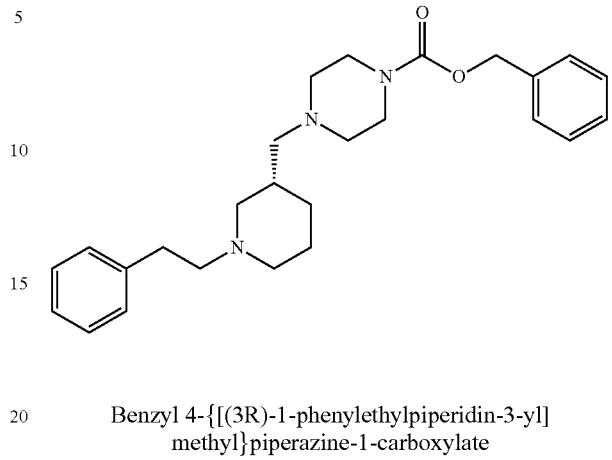

Benzyl 4-{[(3R)-1-phenylethylpiperidin-3-yl]methyl}piperazine-1-carboxylate

Benzyl 4-[(3R)-piperidin-3-ylmethyl]piperazine-1-carboxylate dihydrochloride (1.5 g) was suspended in THF (45 ml) and stirred at room temperature. N,N-Diisopropylethylamine (3.3 ml) was added followed by phenylacetaldehyde (0.9 ml) and magnesium sulphate (300 mg). After 20 minutes sodium triacetoxyborohydride (1.6 g) was added and stirring continued overnight. Inorganic residues were removed by filtration and the filtrate was adsorbed onto silica for purification by chromatography eluting with 0-7% methanol/dichloromethane. This gave benzyl 4-{[(3R)-1-phenylethylpiperidin-3-yl]methyl}piperazine-1-carboxylate as a pale yellow gum (960 mg).

LCMS M/z(+) 422.02 (M+H$^+$).

$^1$H-NMR (400.132 MHz, DMSO-d$_6$) 1.1 (1H, m), 2.3 (7H, m), 2.5 to 3.5 (11H, m), 5.05 (2H, s), 7.3 (10H, m).

Benzyl 4-[(3R)-piperidin-3-ylmethyl]piperazine-1-carboxylate dihydrochloride was prepared as detailed in Route A3.

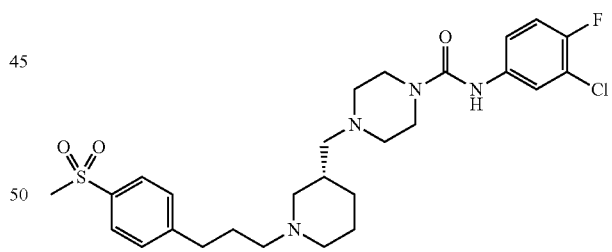

N-(3-Chloro-4-fluorophenyl)-4-[((3R)-1-{3-[4-(methylsulfonyl)phenyl]propyl}piperidin-3-yl)methyl]piperazine-1-carboxamide To a solution of 1-[((3R)-1-{3-[4-(methylsulfonyl)phenyl]propyl}piperidin-3-yl)methyl]piperazine (215 mg, 0.57 mmol) in toluene (15 ml) was added 3-chloro-4-fluorophenyl isocyanate (107 mg, 0.62 mmol) and the solution stirred for 18 hours. A further portion of 3-chloro-4-fluorophenyl isocyanate (54.0 mg, 0.31 mmol) was added and stirred for 30 minutes. The reaction was evaporated to an oil and flash column chromatography (silica, CH$_2$Cl$_2$ to 10% MeOH/CH$_2$Cl$_2$) gave N-(3-chloro-4-fluorophenyl)-4-[((3R)-1-{3-

[4-(methylsulfonyl)phenyl]propyl}piperidin-3-yl)methyl]piperazine-1-carboxamide as a white foam (155 mg, 50%).

LCMS M/z(+) 551 (M+H$^+$).

$^1$H NMR (399.902 MHz, DMSO-d$_6$) 0.97 (16H, m), 1.47 (16H, m), 1.64 (1H, m), 1.78 (1H, m), 2.01 (2H, m), 2.20 (2H, m), 2.36 (6H, m), 2.67 (2H, m), 2.74 (2H, m), 3.13 (3H, s), 3.43 (4H, ABq), 7.20 (1H, m), 7.41 (1H, m), 7.46 (2H, d), 7.71 (1H, dd), 7.81 (2H, d), 8.38 (1H, s).

The 1-[((3R)-1-{3-[4-(methylsulfonyl)phenyl]propyl}piperidin-3-yl)methyl]piperazine used in the above variant of Route A1 was prepared as detailed below.

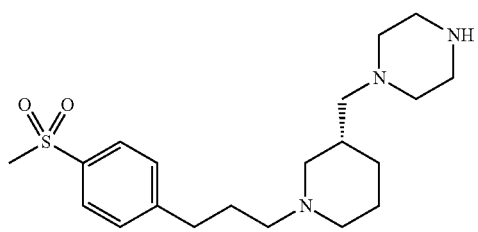 [SMILES: CS(=O)(=O)c1ccc(CCCN2CCC[C@@H](CN3CCNCC3)C2)cc1]

1-[((3R)-1-{3-[4-(methylsulfonyl)phenyl]propyl}piperidin-3-yl)methyl]piperazine

Benzyl 4-[((3R)-1-{3-[4-(methylsulfonyl)phenyl]propyl}piperidin-3-yl)methyl]piperazine-1-carboxylate (5.00 g, 9.70 mmol) was dissolved in methanol (30 ml) in a three-necked flask. The air was removed under reduced pressure and replaced with argon before the addition of 10% Pd/C (1.00 g). A balloon of hydrogen was then added and the reaction stirred at room temperature for 18 h. The hydrogen was evacuated and replaced with argon. The catalyst was then filtered using a nylon whatman autocup and the solvent removed under reduced pressure to afford the desired product as a yellow gum (3.50 g, 95% crude yield).

LCMS M/z(+) 380 (M+H$^+$).

$^1$H NMR (400.132 MHz, CDCl$_3$) 0.90 (1H, m), 1.70 (8H, m), 2.13 (2H, m), 2.30 (2H, t), 2.35 (2H, m), 2.71 (2H, t), 2.79 (4H, m), 3.04 (3H, s), 3.48 (4H, m), 7.47 (2H, d), 7.80 (2H, d).

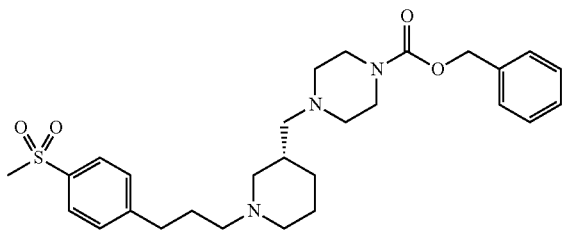 [SMILES: CS(=O)(=O)c1ccc(CCCN2CCC[C@@H](CN3CCN(C(=O)OCc4ccccc4)CC3)C2)cc1]

Benzyl 4-[((3R)-1-{3-[4-(methylsulfonyl)phenyl]propyl}piperidin-3-yl)methyl]piperazine-1-carboxylate 3-[4-(Methylsulfonyl)phenyl]propan-1-ol (4.02 g, 18.8 mmol) and Dess-Martin periodate (8.49 g, 20.0 mmol) were stirred in DCM (50 ml) at room temperature overnight. The reaction was washed with NaOH solution (1N, 3×25 ml). Sodium triacetoxyborohydide (5.28 g, 25 mmol) was added to the mixture followed by benzyl 4-[(3R)-piperidin-3-ylmethyl]piperazine-1-carboxylate (3.97 g, 12.5 mmol) and magnesium sulphate (20.0 mg). The reaction was stirred at room temperature overnight then washed with water (20 ml) and dried using a phase separation cartridge. Silica was added and the solvent removed under reduced pressure to provide a cake which was added to the top of a silica column. Flash column chromatography (silica, 1%-10% MeOH: DCM) gave the title compound as a yellow oil (5.47 g, 85%).

LCMS M/z(+) 514 (M+H$^+$).

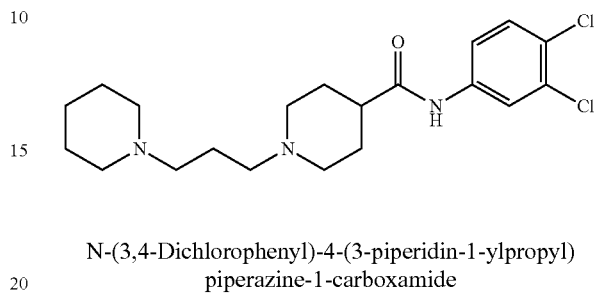

N-(3,4-Dichlorophenyl)-4-(3-piperidin-1-ylpropyl)piperazine-1-carboxamide

A solution of 3,4-dichlorophenylisocyanate (0.3 g; 1.5 mmol) in a mixture of DMF (0.5 ml) and dichloromethane (5 ml) was added to 1-(3-piperidinopropyl)-piperazine (0.21 g; 1 mmol) at room temperature. The resulting mixture was stirred at room temperature overnight.

The reaction mixture was evaporated to dryness and purified using reverse phase chromatography; eluting with a mixture of 25-75% acetonitrile in water.

LCMS M/z(+) 399 (M+H$^+$).

As a variation of route A1 the following example was prepared as shown below.

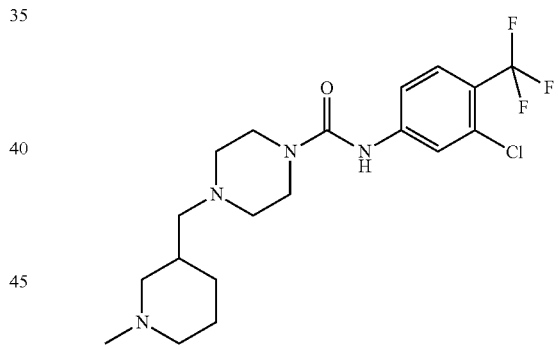

N-[3-Chloro-4-(trifluoromethyl)phenyl]-4-[(1-methylpiperidin-3-yl)methyl]piperazine-1-carboxamide To a solution of di-tert-butyl dicarbonate (114.6 mg) in chloroform (2 ml) was added 4-dimethylaminopyridine (6 mg). A solution of 4-amino-2-chlorobenzotrifluoride (98.1 mg) in chloroform (2 ml) was added and the reaction mixture stirred for 20 minutes at room temperature. A solution of 1-[(1-methylpiperidin-3-yl)methyl]piperazine (98.5 mg) in chloroform (2 ml) was added and the resulting solution was stirred at reflux for 18 hours. The reaction mixture was purified by column chromatography on silica gel (20 g) using a gradient of 100% dichloromethane through to 20% methanolic ammonia in dichloromethane to give the title compound (14 mg).

LCMS M/z(+) 369.37, 371.36 (M+H$^+$).
LCMS M/z(−) 367.39, 369.37 (M−H$^−$).

$^1$H-NMR (400.132 MHz, DMSO-d$_6$) 0.93 (1H, m), 1.55 (1H, m), 1.38 (2H, d), 1.92 (1H, m), 2.17 to 2.38 (11H, m), 2.94 to 3.03 (2H, d), 3.45 (4H, t), 7.29 to 7.32 (1H, dd), 7.41 (1H, t), 7.63 to 7.67 (1H, dd), 8.83 (1H, s).

As an additional variation of route A1 the following example was prepared as shown below.

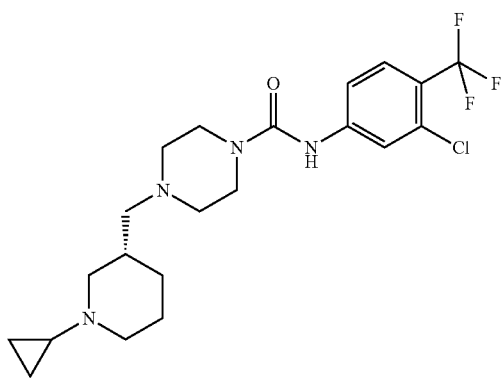 [SMILES: O=C(Nc1ccc(C(F)(F)F)c(Cl)c1)N1CCN(C[C@@H]2CCCN(C3CC3)C2)CC1]

N-[3-Chloro-4-(trifluoromethyl)phenyl]-4-{[(3S)-1-cyclopropylpiperidin-3-yl]methyl}piperazine-1-carboxamide A mixture of 1-{[(3S)-1-cyclopropylpiperidin-3-yl]methyl}piperazine (67 mg), 2,2,2-trichloro-N-[3-chloro-4-(trifluoromethyl)phenyl]acetamide (102 mg) and DBU (46 mg) in acetonitrile (4 mL) was heated to 150° C. in the microwave for 10 minutes. The solution was concentrated at reduced pressure and purified by reverse phase prep HPLC eluting with a mixture of 5-95% acetonitrile in water and then SCX-2 column eluting with methanol then 7M NH$_3$ in methanol to give the title compound as a white solid (55 mg, 41%).

LCMS M/z(+) 444.92 (M+H$^+$).

$^1$H NMR (400.132 MHz, DMSO-d$_6$) 0.22-0.32 (m, 2H), 0.36-0.44 (m, 2H), 0.83-0.95 (m, 1H), 1.31-1.44 (m, 1H), 1.51-1.62 (m, 2H), 1.62-1.75 (m, 2H), 1.83 (t, 1H), 2.07-2.20 (m, 3H), 2.28-2.40 (m, 4H), 2.82 (d, 1H), 2.94 (d, 1H), 3.46 (t, 4H), 7.58-7.63 (m, 1H), 7.70 (d, 1H), 7.90 (d, 1H), 9.03 (s, 1H).

The 1-{[(3R)-1-cyclopropylpiperidin-3-yl]methyl}piperazine used in Route A1 was prepared using the following procedure.

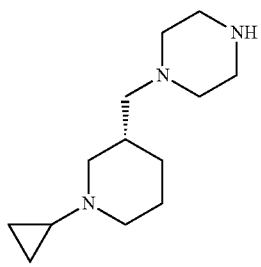 [SMILES: C1C[C@@H](CN2CCNCC2)CN(C2CC2)C1]

1-{[(3R)-1-Cyclopropylpiperidin-3-yl]methyl}piperazine

Benzyl 4-{[(3R)-1-cyclopropylpiperidin-3-yl]methyl}piperazine-1-carboxylate (45 mg) was dissolved in ethanol (6 ml). 10% Palladium on carbon (Degussa) (72 mg) was added and the mixture stirred for 60 hours at room temperature under an atmosphere of hydrogen. A further amount of catalyst (60 mg) was added and the mixture stirred for 40 hours at room temperature under an atmosphere of hydrogen. The reaction mixture was filtered through a pad of Celite, washed with ethanol and the filtrate concentrated in vacuo to give the title compound as a white solid (27.5 mg).

LCMS M/z(+) 224.41 (M+H$^+$).

$^1$H-NMR (400.132 MHz, CDCl$_3$) 0.45 (4H, m), 0.9 (1H obscured, m), 1.45-1.58 (2H, m), 1.68 (1H, m), 1.74-1.85 (3H, m), 2.07-2.55 (10H, m), 2.89 (2H, m), 2.99 (1H, d), 3.09 (1H, d).

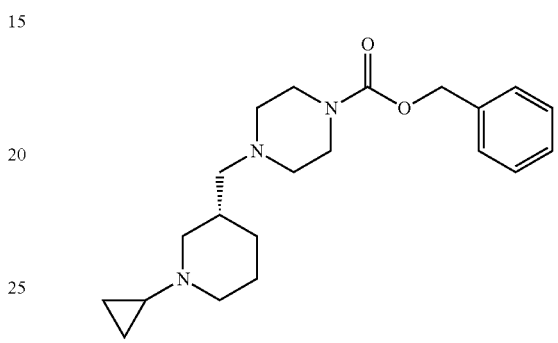

Benzyl 4-{[(3R)-1-cyclopropylpiperidin-3-yl]methyl}piperazine-1-carboxylate

Benzyl 4-[(3R)-piperidin-3-ylmethyl]piperazine-1-carboxylate dihydrochloride (389 mg) was dissolved in MeOH (5 mL) and diisopropylethylamine (0.52 mL) added under argon. Freshly dried 3 Å molecular sieves (413 mg) was added, followed sequentially by glacial acetic acid (0.2 mL), 1-ethoxy-1-trimethylsilyloxycyclopropane (1.2 mL) and sodium cyanoborohydride as a 1M solution in THF (4.5 mL). The mixture was heated at 81° C. for 2 hours, allowed to cool, filtered through Celite, washed through with 1:1 MeOH-THF (10 mL) and evaporated. The residue was partitioned between ethyl acetate and 1M aqueous sodium hydroxide solution, the organic extract washed with brine, dried over MgSO$_4$ and evaporated. The residue was purified by silica column chromatography, eluting with a gradient of 0 to 10% MeOH in dichloromethane to give the title compound as a white solid (222 mg, 62%).

LCMS M/z(+) 358.41 (M+H$^+$).

$^1$H-NMR (400.132 MHz, CDCl$_3$) 0.46 (4H, m), 0.9-1.1 (1H obscured, m), 1.5-1.7 (4H, m), 1.7-1.8 (3H, m), 2.14 (2H, d), 2.23-2.43 (4H, m), 3.02 (1H, d), 3.12 (1H, d), 3.50 (4H, m), 5.13 (2H, s), 7.28-7.38 (5H, m).

The 2,2,2-trichloro-N-[3-chloro-4-(trifluoromethyl)phenyl]acetamide used in Route A1 was prepared using the following procedure.

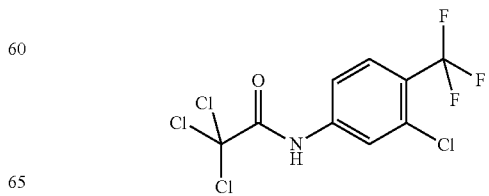

2,2,2-Trichloro-N-[3-chloro-4-(trifluoromethyl)phenyl]acetamide

To a solution of 4-amino-2-chlorobenzotrifluoride (300 mg) and pyridine (243 mg) in dichloromethane (10 mL) was added a solution of trichloroacetyl chloride (279 mg) in dichloromethane (5 mL) dropwise. The solution was stirred for 2 hrs and then concentrated at reduced pressure. The residue was purified by silica gel chromatography eluting with 0-10% ethyl acetate in hexane to give the title compound as a white solid (360 mg, 69%).

LCMS M/z(+) 339.59 (M+H$^+$).

$^1$H NMR (400.132 MHz, CDCl$_3$) 7.59 (dd, 1H), 7.72 (d, 1H), 7.86 (d, 1H), 8.42 (s, 1H).

As an additional variation of route A1 the following examples were prepared as shown below.

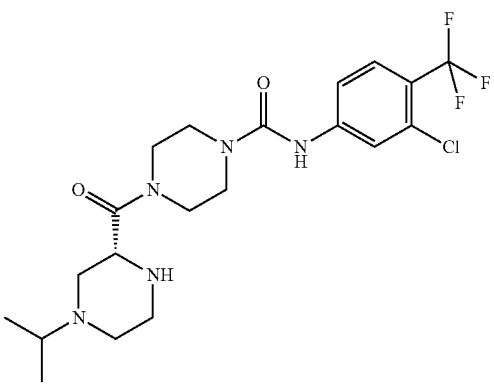 [SMILES: CC(C)N1CCN[C@@H](C(=O)N2CCN(C(=O)Nc3ccc(C(F)(F)F)c(Cl)c3)CC2)C1]

N-[3-Chloro-4-(trifluoromethyl)phenyl]-4-{[(2R)-4-isopropylpiperazin-2-yl]carbonyl}piperazine-1-carboxamide To phenyl [3-chloro-4-(trifluoromethyl)phenyl]carbamate (112 mg) under an argon atmosphere was added tert-butyl (2R)-4-isopropyl-2-(piperazin-1-ylcarbonyl)piperazine-1-carboxylate in dry THF (5 mL) followed by triethylamine (0.052 mL) and the reaction was stirred for 18 h at 25° C. and then 2 h at 50° C. The reaction mixture was taken up in 1M NaOH (10 mL) and DCM (30 mL) and organic layer was separated through a phase separation cartridge and evaporated. Trituration with 1:9 EtOAc:isohexane (3 mL) followed by filtration of the resulting solid afforded the intermediate protected compound (185 mg) as a white solid. TFA/DCM (1:1, 10 mL) was added and the reaction stirred under argon for 1 h. The solvent was then removed in vacuo. The residue was then dissolved in MeOH (10 mL) and placed onto SCX-2 column. The column was then washed with 15 mL MeOH before elution of the product with 7M NH$_3$/MeOH (20 mL) and more MeOH (20 mL). The basic fraction was evaporated in vacuo to afford the title compound (143 mg) as a white foam.

LCMS M/z(+) 462 (M+H$^+$).

$^1$H NMR (400.132 MHz, DMSO-d$_6$) 0.98 (m, 6H), 2.10-2.25 (m, 2H), 2.65-2.84 (m, 4H), 3.00 (d, 1H), 3.35-3.70 (m, 8H), 3.90 (d, 1H), 7.61 (d, 1H), 7.71 (d, 1H), 7.90 (s, 1H), 9.14 (s, 1H).

The phenyl [3-chloro-4-(trifluoromethyl)phenyl]carbamate used in the above variant of Route A1 was prepared according to the following procedure.

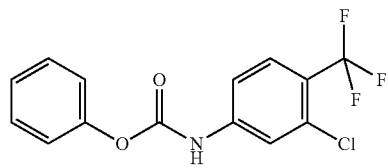 [SMILES: O=C(Nc1ccc(C(F)(F)F)c(Cl)c1)Oc1ccccc1]

Phenyl [3-chloro-4-(trifluoromethyl)phenyl]carbamate

Phenyl chloroformate (0.86 mL) was added slowly to a stirring solution of 3-chloro-4-trifluoromethyl aniline (933 mg) in THF (10 mL) containing pyridine (1.07 mL) under an argon atmosphere. The reaction was stirred for 18 h then diluted with ethyl acetate (35 mL) and 1M HCl (20 mL). The

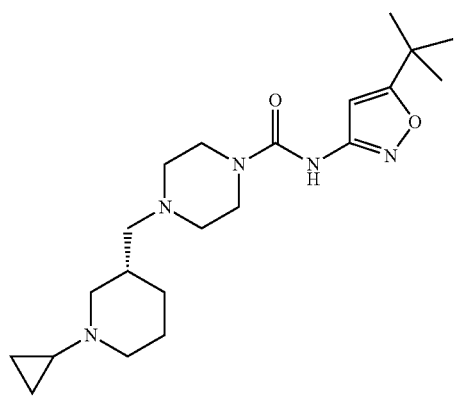

N-(5-tert-Butylisoxazol-3-yl)-4-{[(3S)-1-cyclopropylpiperidin-3-yl]methyl}piperazine-1-carboxamide A mixture of 1-{[(3S)-1-cyclopropylpiperidin-3-yl]methyl}piperazine (60 mg), phenyl(5-tert-butylisoxazol-3-yl)carbamate (84 mg) and triethylamine (54 mg) in tetrahydrofuran (4 mL) was heated to 60° C. in the microwave for 1 hour. The solution was concentrated at reduced pressure and then purified by reverse phase prep HPLC eluting with a mixture of 5-95% acetonitrile in water and then SCX-2 column eluting with methanol then 7M NH$_3$ in methanol to give the title compound as a white solid (55 mg, 52%).

LCMS M/z(+) 390.06 (M+H$^+$).

$^1$H NMR (400.132 MHz, DMSO-d$_6$) 0.20-0.32 (m, 2H), 0.35-0.45 (m, 2H), 0.81-0.94 (m, 1H), 1.28 (s, 9H), 1.30-1.45 (m, 1H), 1.49-1.60 (m, 2H), 1.61-1.73 (m, 2H), 1.81 (t, 1H), 2.06-2.18 (m, 3H), 2.23-2.36 (m, 4H), 2.76-2.86 (m, 1H), 2.88-2.97 (m, 1H), 3.42 (t, 4H), 6.43 (s, 1H), 9.57 (s, 1H).

organic layer was separated and washed with saturated aqueous NaHCO₃ then dried (MgSO₄), filtered and evaporated. Trituration with 1:9 EtOAc:isohexanes (10 mL) at reflux followed by cooling to RT afforded a solid which was filtered to afford 1.15 g of the title compound.

LCMS M/z(+) 314, 316 (M−H⁻).

¹H NMR (400.132 MHz, CDCl₃) 7.10 (br. s, 1H), 7.20 (m, 2H), 7.26 (t, 1H), 7.42 (m, 3H), 7.65 (d, 1H), 7.70 (s, 1H).

All additional starting materials used for generating compounds under Route A1 were obtained form commercial sources; for example, 1-[(1-methylpiperidin-3-yl)methyl]piperazine is available commercially from CHESS Gmbh, Max-Planck-Str. 1, D-68169 Mannheim, Germany and all isocyanates are available from either Sigma, Avocado, ACROS or Lancaster.

Route A2

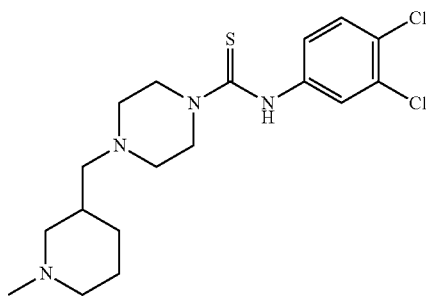 [SMILES: CN1CCCC(CN2CCN(C(=S)Nc3ccc(Cl)c(Cl)c3)CC2)C1]

N-(3,4-Dichlorophenyl)-4-[(1-methylpiperidin-3-yl)methyl]piperazine-1-carbothioamide To a solution of 1-[(1-methylpiperidin-3-yl)methyl]piperazine (400 mg) in chloroform (10 ml) was added a 2M solution of sodium(trimethylsilyl)amide in THF (2.2 ml). The resulting solution was stirred at room temperature for 10 minutes. 3,4-Dichlorophenylisothiocyanate (0.44 ml) was added and mixture stirred at room temperature for 1 hour. The reaction was quench with water (1 ml) then concentrated in vacuo before being separated between ethyl acetate (100 ml) and saturated sodium bicarbonate solution (100 ml). The ethyl acetate layer was separated, dried over magnesium sulphate, filtered then concentrated in vacuo onto silica gel (1.0 g). The resulting powder was purified by column chromatography on silica gel (50 g) using a gradient of 100% dichloromethane through to 10% methanolic ammonia in dichloromethane to give the title compound (726 mg).

LCMS M/z(+) 401.20, 403.17 (M+H⁺).

LCMS M/z(−) 399.23, 401.22 (M−H⁻).

¹H-NMR (400.132 MHz, DMSO-d₆) 0.85 (1H, m), 1.41 to 1.67 (4H, m), 1.73 to 1.87 (2H, m), 2.12 to 2.21 (5H, m), 2.34 to 2.46 (4H, m), 2.65 (1H, d), 2.78 (1H, d), 3.89 (4H, t), 7.33 (1H, dd), 7.53 (1H, d), 7.62 (1H, d), 9.43 (1H, s).

The 3,4-Dichlorophenylisothiocyanate used in the above procedure is commercially available and was purchased from Lancaster Synthesis Ltd, UK.

Route A3

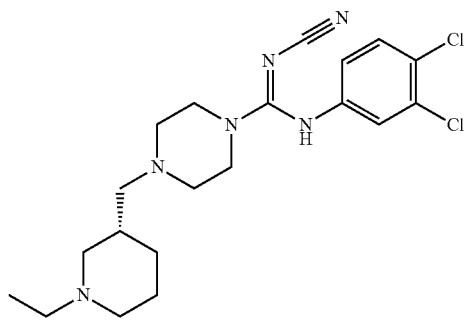 [SMILES: CCN1CCC[C@@H](CN2CCN(/C(=N/C#N)Nc3ccc(Cl)c(Cl)c3)CC2)C1]

N'-Cyano-N-(3,4-dichlorophenyl)-4-{[(3R)-1-ethylpiperidin-3-yl]methyl}piperazine-1-carboximidamide 3,4-Dichlorophenylisothiocyanate (204 mg) and sodium hydrogen cyanamide (70 mg) were refluxed in ethanol (20 ml) for three hours. The mixture was allowed to cool to room temperature then 1-(3-dimethylaminopropyl)-3-ethylcarbodiimide hydrochloride (211 mg), 1-{[(3R)-1-ethylpiperidin-3-yl]methyl}piperazine (220 mg) and N,N-dimethylformamide (2 ml) were added and the reaction left to stir for 18 hours then concentrated in vacuo. The crude product was subjected to reverse phase HPLC using a gradient of 95% water/acetonitrile/0.1% TFA through to 50% water/acetonitrile/0.1% TFA. The combined product fractions were concentrated in vacuo then separated between dichloromethane (50 ml) and saturated sodium bicarbonate solution (100 ml). The dichloromethane layer was separated, dried over magnesium sulphate, filtered and concentrated in vacuo to give the title compound (159 mg).

LCMS M/z(+) 423.29, 425.23 (M+H⁺)

LCMS M/z(−) 421.29, 423.27 (M−H⁻).

¹H-NMR (400.132 MHz, DMSO-d₆) 0.83 (1H, m), 0.99 (3H, t), 1.43 (1H, q), 1.59 to 1.80 (4H, m), 1.88 (1H, t), 2.12 to 2.20 (2H, m), 2.25 to 2.45 (6H, m), 2.74 to 2.90 (2H, m), 3.50 (4H, t), 7.05 (1H, dd), 7.29 (1H, d), 7.55 (1H, d), 9.49 (1H, s).

The 1-{[(3R)-1-ethylpiperidin-3-yl]methyl}piperazine used in Route A3 was prepared using the following procedure.

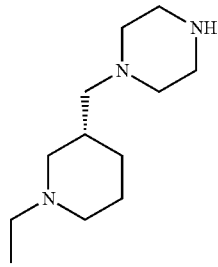

1-{[(3R)-1-Ethylpiperidin-3-yl]methyl}piperazine

Benzyl 4-{[(3R)-1-ethylpiperidin-3-yl]methyl}piperazine-1-carboxylate (352 mg) was dissolved in ethanol (50 ml). 10% Palladium on carbon (35 mg) was added and the mixture stirred for 18 hours at room temperature under an atmosphere of hydrogen. The reaction mixture was filtered through a pad of celite and the filtrate concentrated in vacuo to give the title compound (225 mg).

LCMS M/z(+) 212.42 (M+H$^+$).

$^1$H-NMR (400.132 MHz, DMSO-d$_6$) 1.02 (1H, q), 1.36 (3H, t), 1.85 (2H, d), 2.07 (2H, t), 2.26 (2H, m), 2.44 (4H, m), 2.64 (2H, d), 2.81 to 2.94 (2H, m), 3.01 (4H, m), 3.33 (1H, d), 3.41 (1H, d), 5.00 (1H, s).

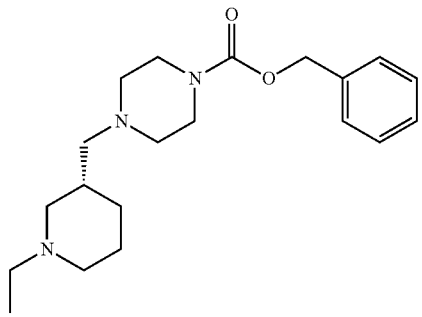 [SMILES: CCN1CCC[C@@H](CN2CCN(C(=O)OCc3ccccc3)CC2)C1]

Benzyl 4-{[(3R)-1-ethylpiperidin-3-yl]methyl}piperazine-1-carboxylate

Benzyl 4-[(3R)-piperidin-3-ylmethyl]piperazine-1-carboxylate (1.8 g), bromoethane (1.3 ml) and potassium carbonate (3.9 g) was refluxed in acetone (50 ml) for seven hours. The reaction mixture was allowed to cool to room temperature then filtered. The filtrate was concentrated in vacuo and the resulting oil separated between dichloromethane (100 ml) and water (100 ml). The dichloromethane layer was separated, dried over magnesium sulphate, filtered then concentrated in vacuo onto silica gel (5 g). The resulting powder was subjected to chromatography on silica gel (50 g) using a gradient of 100% dichloromethane through to 20% methanolic ammonia in dichloromethane to give the title compound (352 mg).

LCMS M/z(+) 346.36 (M+H$^+$).

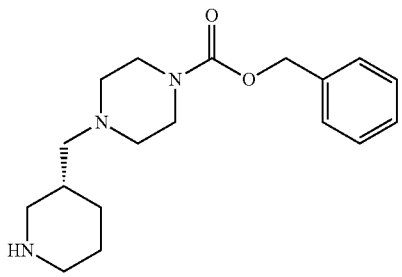 [SMILES: O=C(OCc1ccccc1)N1CCN(C[C@@H]2CCCNC2)CC1]

Benzyl 4-[(3R)-piperidin-3-ylmethyl]piperazine-1-carboxylate

Benzyl 4-{[(3S)-1-(tert-butoxycarbonyl)piperidin-3-yl]methyl}piperazine-1-carboxylate (4.46 g) was stirred in a mixture of trifluoroacetic acid (20 ml) and dichloromethane (200 ml) for two hours at room temperature. The reaction mixture was concentrated in vacuo and the resulting oil separated between ethyl acetate (200 ml) and saturated aqueous sodium bicarbonate solution (500 ml). The ethyl acetate layer was separated, dried over magnesium sulphate, filtered then concentrated in vacuo to give the title compound (3.6 g).

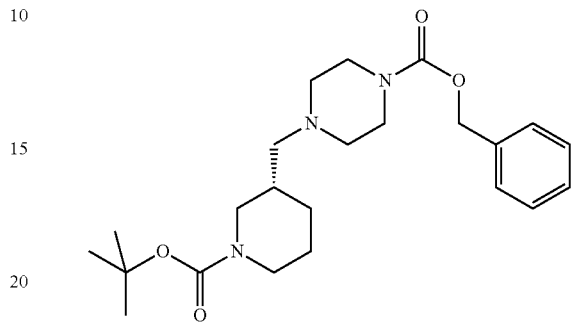

Benzyl 4-{[(3S)-1-(tert-butoxycarbonyl)piperidin-3-yl]methyl}piperazine-1-carboxylate tert-Butyl (3R)-3-(hydroxymethyl)piperidine-1-carboxylate (2.31 g) and Dess-Martin periodinane (5.0 g) were stirred in dichloromethane (30 ml) for 2 hours at room temperature. 2N aqueous sodium hydroxide (100 ml) was added and the mixture stirred for 10 minutes. The dichloromethane layer was separated, dried over magnesium sulphate then filtered. This solution of tert-butyl (3R)-3-formylpiperidine-1-carboxylate was added to a solution of benzyl piperazine-1-carboxylate (2.36 g) in dichloromethane (70 ml). Sodium triacetoxyborohydride (5.67 g) was added and the reaction left to stir at room temperature for 18 hours. Saturated aqueous sodium bicarbonate solution (500 ml). The dichloromethane layer was separated, dried over magnesium sulphate, filtered then concentrated in vacuo to give the title compound (4.46 g).

LCMS M/z(+) 418.33 (M+H$^+$).

The tert-Butyl (3R)-3-(hydroxymethyl)piperidine-1-carboxylate used in the above procedure was commercially available and purchased from Arch Chemical Corporation, New Jersey, USA.

Route A4

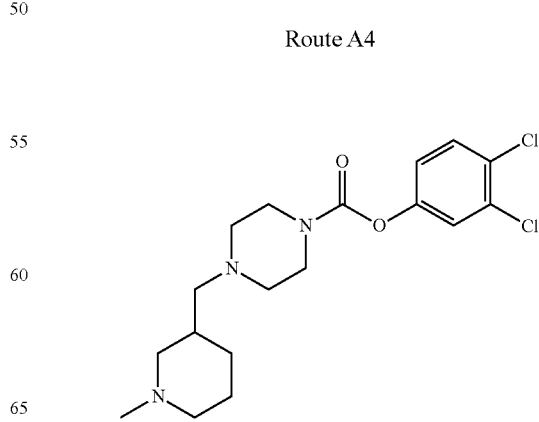

3,4-Dichlorophenyl 4-[(1-methylpiperidin-3-yl)methyl]piperazine-1-carboxylate 3,4-Dichlorophenyl chloroformate (282 mg) in dichloromethane (10 ml) was added to a solution of 1-[(1-methylpiperidin-3-yl)methyl]piperazine (246 mg) in dichloromethane (2 ml) at room temperature. N,N-Diisopropylethylamine (0.44 ml) was added and the mixture stirred for 18 hours. Saturated aqueous sodium bicarbonate solution (5 ml) was added and the dichloromethane layer separated then concentrated in vacuo onto silica gel (0.5 g). The resulting powder was subjected to chromatography on silica gel (20 g) using a gradient of 100% dichloromethane through to 20% methanolic ammonia in dichloromethane to give the title compound (292 mg).

LCMS M/z(+) 386.30, 388.28 (M+H$^+$).
LCMS M/z(−) 386.28, 388.26 (M−H$^−$).
$^1$H-NMR (400.132 MHz, DMSO-d$_6$) 1.04 (1H, m), 1.72 (3H, q), 2.07 (1H, s), 2.33 (2H, m), 2.36 (2H, m), 2.46 (2H, m), 2.60 (3H, s), 3.18 (2H, t), 3.44 (2H, s), 3.57 (2H, s), 7.20 (1H, dd), 7.54 (1H, d), 7.66 (1H, d).

The 3,4-dichlorophenyl chloroformate used in Route A4 was prepared using the following procedure.

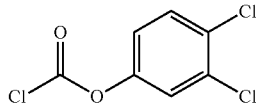 [SMILES: O=C(Cl)Oc1ccc(Cl)c(Cl)c1]

3,4-Dichlorophenyl chloroformate 3,4-Dichlorophenol (2.35 g) was dissolved in anhydrous dichloromethane (50 ml) at room temperature under an atmosphere of argon. The mixture was cooled to −30° C. and diphosgene (3.92 g) and N,N-Diisopropylethylamine (2.51 ml) were added slowly in the order specified. The resulting solution was then stirred at 0° C. for 3 hours, then at room temperature for 18 hours and finally at reflux for 2 hours. The solution volume was measured and used accordingly.

Route A5

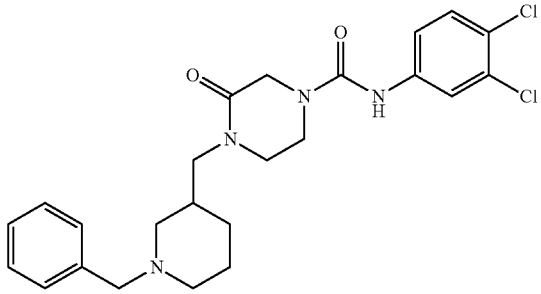 [SMILES: O=C1CN(C(=O)Nc2ccc(Cl)c(Cl)c2)CCN1CC1CCCN(Cc2ccccc2)C1]

4-[(1-Benzylpiperidin-3-yl)methyl]-N-(3,4-dichlorophenyl)-3-oxopiperazine-1-carboxamide To a mixture of 1-[(1-benzylpiperidin-3-yl)methyl]piperazin-2-one dihydrochloride (83 mg) in dichloromethane (10 mL) was added N,N-di-iso-propylethylamine (0.1 mL). After 1 minute dimethylformamide (1 mL) was added followed by 3,4-dichlorophenyl isocyanate (47 mg). The solution was stirred for 5 minutes and then partitioned between dichloromethane and water. The organic layer was separated, dried over sodium sulfate and evaporated. The residue was purified by silica column chromatography, eluting with a gradient of 0 to 10% MeOH in dichloromethane to give the title compound as a white solid (92 mg, 84%).

LCMS M/z(+) 475 (M+H$^+$).
$^1$H-NMR (400.132 MHz, CDCl$_3$) 1.00-1.16 (1H, m), 1.45-1.74 (3H, m), 1.80-1.91 (1H, m), 1.96-2.12 (2H, m), 2.58-2.75 (2H, m), 3.25-3.54 (6H, m), 3.58-3.72 (2H, m), 4.15 (2H, s), 7.01 (1H, s), 7.19-7.37 (7H, m), 7.70 (1H, t).

The 1-[(1-benzylpiperidin-3-yl)methyl]piperazin-2-one dihydrochloride used in Route A5 was prepared using the following procedure.

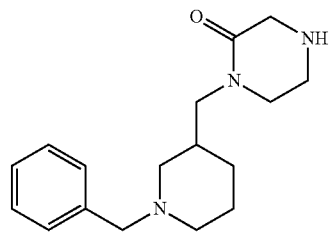 [SMILES: O=C1CNCCN1CC1CCCN(Cc2ccccc2)C1]

1-[(1-Benzylpiperidin-3-yl)methyl]piperazin-2-one dihydrochloride

To a solution of tert-butyl 4-[(1-benzylpiperidin-3-yl)methyl]-3-oxopiperazine-1-carboxylate (95 mg) in dichloromethane (1 mL) was added 4M hydrochloric acid in dioxane (1 mL). The mixture was stirred at room temperature for 15 minutes and then evaporated to give the title compound as a sticky white solid (89 mg, 100%).

LCMS M/z(+) 288 (M+H$^+$).

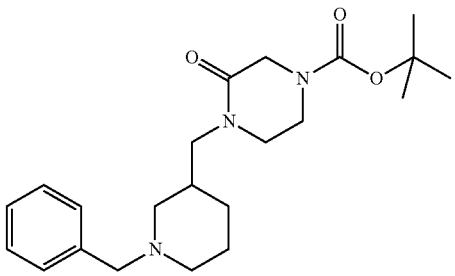 [SMILES: CC(C)(C)OC(=O)N1CCN(CC2CCCN(Cc3ccccc3)C2)C(=O)C1]

tert-Butyl 4-[(1-benzylpiperidin-3-yl)methyl]-3-oxopiperazine-1-carboxylate

To a solution of tert-butyl-3-oxopiperazine-1-carboxylate (250 mg) in dimethylformamide (10 mL) was added sodium hydride (55 mg) at room temperature under argon. The mixture was stirred at room temperature 15 minutes before a solution of (1-benzylpiperidin-3-yl)methyl 4-methylbenzenesulfonate (492 mg) in dimethylformamide (5 mL) was added. The mixture was stirred overnight at room temperature before sodium hydride (60 mg) was added and the mixture was stirred for 48 hours. A further quantity of sodium hydride (60 mg) was added and the mixture was stirred for 5 hours and then quenched by the addition of water. The mixture was then partitioned between water and ethyl acetate. The layers were separated and the organic layer washed twice with water and once with brine. The organic layer was then dried over sodium sulfate and evaporated. The residue was purified by silica column chromatography, eluting with a gradient of 0 to 70% ethyl acetate in hexane to give the title compound as a colourless oil (95 mg, 20%).

LCMS M/z(+) 388 (M+H$^+$).

The tert-butyl-3-oxopiperazine-1-carboxylate used in the above procedure is commercially available and was purchased from Tyger Scientifc Inc.

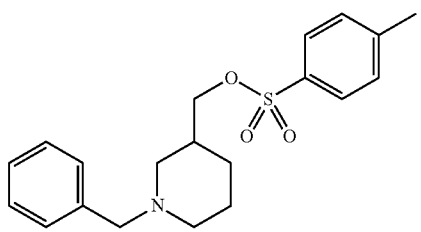 [SMILES: Cc1ccc(S(=O)(=O)OCC2CCCN(Cc3ccccc3)C2)cc1]

(1-Benzylpiperidin-3-yl)methyl 4-methylbenzenesulfonate

To a solution of (1-benzylpiperidin-3-yl)methanol (820 mg) and triethylamine (0.84 mL) in dichloromethane (10 mL) was added para-toluenesulfonyl chloride (846 mg). The solution was stirred overnight at room temperature. The mixture was partitioned between dichloromethane and water. The layers were separated and the organic layer was dried over sodium sulfate and evaporated. The residue was purified by silica column chromatography, eluting with a gradient of 0 to 50% ethyl acetate in hexane to give the title compound as a colourless oil (1.15 g, 80%).

LCMS M/z(+) 360 (M+H$^+$).

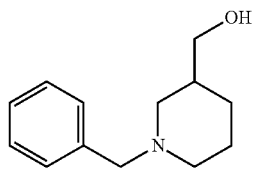 [SMILES: OCC1CCCN(Cc2ccccc2)C1]

(1-Benzylpiperidin-3-yl)methanol

To a solution of ethyl 1-benzylpiperidine-3-carboxylate (1.0 g) in tetrahydrofuran (10 mL) at 5° C. under argon was added a 1M solution of lithium aluminium hydride (4.04 mL) dropwise. The mixture was stirred for 1 hour at 5° C. and then quenched by the dropwise addition of ethyl acetate (5 mL). The mixture was warmed to room temperature and dichloromethane (150 mL) was added followed by saturated aqueous sodium potassium tartrate (50 mL). The mixture was stirred vigorously overnight. The layers were separated and the organic layer was dried over magnesium sulfate and evaporated to give the title compound as a colourless oil (0.82 g, 99%).

LCMS M/z(+) 206 (M+H$^+$).

The ethyl 1-benzylpiperidine-3-carboxylate used in the above procedure is commercially available and was purchased from CHESS Gmbh, Max-Planck-Str. 1, D-68169 Mannheim, Germany.

Route A6

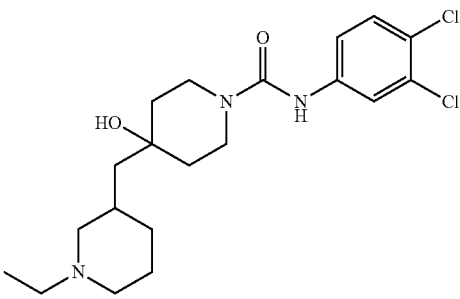 [SMILES: CCN1CCCC(CC2(O)CCN(C(=O)Nc3ccc(Cl)c(Cl)c3)CC2)C1]

N-(3,4-Dichlorophenyl)-4-[(1-ethylpiperidin-3-yl)methyl]-4-hydroxypiperidine-1-carboxamide To a mixture of 4-[(1-ethylpiperidin-3-yl)methyl]piperidin-4-ol dihydrochloride (80 mg) in dichloromethane (10 mL) was added di-iso-propylethylamine (0.12 mL), dimethylformamide (1 mL) and 3,4-dichlorophenylisocyanate (55 mg). After 10 minutes the mixture was evaporated and the residue was purified by silica column chromatography, eluting with a gradient of 0 to 10% 7M NH$_3$/MeOH in dichloromethane to give the title compound as a white solid (110 mg, 100%).

LCMS M/z(+) 414 (M+H$^+$).
$^1$H-NMR (400.132 MHz, CDCl$_3$) 0.80-0.90 (1H, m), 0.96-1.98 (13H, m), 1.07 (3H, t), 2.30-2.45 (2H, m), 2.74-2.87 (2H, m), 3.27-3.37 (2H, m), 3.73-3.82 (2H, m), 6.38 (1H, s), 7.19 (1H, dd), 7.32 (1H, d), 7.59 (1H, d).

The 4-[(1-ethylpiperidin-3-yl)methyl]piperidin-4-ol dihydrochloride used in Route A6 was prepared using the following procedure.

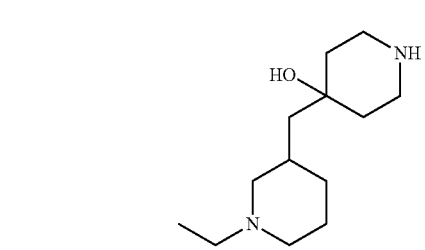 [SMILES: CCN1CCCC(CC2(O)CCNCC2)C1]

4-[(1-Ethylpiperidin-3-yl)methyl]piperidin-4-ol dihydrochloride

To a mixture of 3-(bromomethyl)-1-ethylpiperidine (369 mg) and tert-butyl 4-oxo-1-piperidine carboxylate (375 mg) in diethyl ether (5 mL) at −78° C. under argon was added a 1.7M solution of tert-butyl lithium in pentane (2.11 mL) dropwise. After stirring for 30 minutes at −78° C. the reaction was quenched by the addition of saturated aqueous ammonium chloride and warmed to ambient temperature. The mixture was then partitioned between water and dichloromethane. The layers were separated and the organic layer dried over sodium sulfate and evaporated. The residue was purified by silica column chromatography, eluting with a gradient of 0 to 5% 7M NH$_3$/MeOH in dichloromethane. To a solution of the isolated residue (91 mg) in methanol (15 mL) was added 4M HCl in dioxane (1 mL). The mixture was stirred overnight and evaporated to give the title compound as a yellow oil (84 mg, 16%).

LCMS M/z(+) 227 (M+H$^+$).

The tert-butyl 4-oxo-1-piperidine carboxylate used in the above procedure is commercially available and was purchased from Aldrich Chemical Company, Inc.

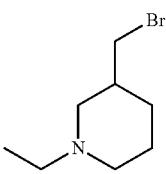

3-(Bromomethyl)-1-ethylpiperidine

To mixture of (1-ethylpiperidin-3-yl)methanol (430 mg) and polymer bound triphenylphoshphine (2 g) in tetrahydrofuran (30 mL) was added carbon tetrabromide (1 g). The mixture was stirred for 8 hours before polymer bound triphenylphoshphine (1 g) and carbon tetrabromide (0.5 g) were added. The reaction was stirred overnight at room temperature. The mixture was filtered and evaporated and the residue was purified by silica column chromatography, eluting with a gradient of 0 to 5% 7M NH$_3$/MeOH in dichloromethane to give the title compound as a yellow oil (430 mg, 69%).

$^1$H-NMR (400.132 MHz, CDCl$_3$) 1.00-1.17 (1H, m), 1.08 (3H, t), 1.52-2.03 (6H, m), 2.40 (2H, dq), 2.75-2.85 (1H, m), 2.93-3.03 (1H, m), 3.30 (2H, dq).

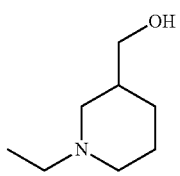

(1-Ethylpiperidin-3-yl)methanol

To a solution of piperidin-3-ylmethanol (3.88 g) in dimethylformamide (50 mL) was added potassium carbonate (9.3 g) and ethyl bromide (2.52 mL). The reaction was stirred overnight at room temperature. The mixture was filtered and the filtrate evaporated. The residue was filtered through a short pad of silica eluting with 10% 7M NH$_3$/MeOH in dichloromethane. The filtrate was evaporated to give the title compound as an orange oil (4.8 g, 99%).

$^1$H-NMR (400.132 MHz, CDCl$_3$) 1.02-1.19 (1H, m), 1.08 (3H, t), 1.53-1.85 (4H, m), 1.94 (1H, t), 2.08 (1H, t), 2.39 (2H, q), 2.63-2.74 (1H, m), 2.82-2.90 (1H, m), 3.51 (1H, dd), 3.63 (1H, dd).

Route A7

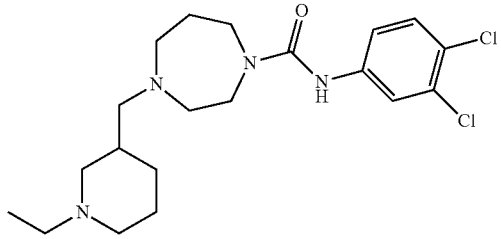 [SMILES: CCN1CCCC(CN2CCCN(C(=O)Nc3ccc(Cl)c(Cl)c3)CC2)C1]

N-(3,4-Dichlorophenyl)-4-[(1-ethylpiperidin-3-yl)methyl]-1,4-diazepane-1-carboxamide A mixture of tert-butyl 1,4-diazepane-1-carboxylate (81 mg), (1-ethylpiperidin-3-yl)methyl 4-methylbenzenesulfonate (100 mg) and potassium carbonate (186 mg) in acetonitrile (3 mL) was heated to 100° C. in the microwave for 1 hour 15 minutes. The mixture was filtered and evaporated. The residue was purified by silica column chromatography, eluting with a gradient of 0 to 5% 7M NH$_3$/MeOH in dichloromethane. To a solution of the isolated material (100 mg) in methanol (5 mL) was added 4M hydrochloric acid in dioxane (2 mL). The mixture was stirred for 6 hours at room temperature and then evaporated to give a colourless oil. To a mixture of this oil (150 mg) in dichloromethane (10 mL) and dimethylformamide (1 mL) was added di-iso-propylethylamine (0.31 mL) and 3,4-dichlorophenylisocyanate (100 mg). The mixture was stirred for 15 minutes and then evaporated. The residue was purified using reverse phase HPLC eluting with a mixture of 5-95% acetonitrile in water to give the title compound as a white solid (78 mg, 56%).

LCMS M/z(+) 413 (M+H$^+$).

$^1$H-NMR (400.132 MHz, CDCl$_3$) 0.78-0.93 (1H, m), 1.07 (3H, t), 1.50-1.94 (8H, m), 2.23-2.47 (4H, m), 2.55-2.79 (4H, m), 2.89 (1H, d), 2.99 (1H, d), 3.48-3.64 (4H, m), 6.30 (1H, s), 7.22 (1H, dd), 7.31 (1H, d), 7.64 (1H, d).

The tert-butyl 1,4-diazepane-1-carboxylate used in Route A7 is commercially available and was purchased from Aldrich Chemical Company, Inc.

The (1-ethylpiperidin-3-yl)methyl 4-methylbenzenesulfonate used in Route A7 was prepared in an analogous manner to (1-benzylpiperidin-3-yl)methyl 4-methylbenzenesulfonate.

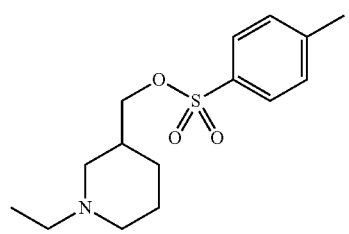 [SMILES: CCN1CCCC(COS(=O)(=O)c2ccc(C)cc2)C1]

(1-Ethylpiperidin-3-yl)methyl 4-methylbenzenesulfonate

LCMS M/z(+) 298 (M+H$^+$).

$^1$H-NMR (400.132 MHz, CDCl$_3$) 0.93-1.06 (1H, m), 1.03 (3H, t), 1.46-1.79 (4H, m), 1.84-2.02 (2H, m), 2.35 (2H, q), 2.45 (3H, s), 2.71-2.84 (2H, m), 3.85-3.95 (2H, m), 7.34 (2H, d), 7.78 (2H, d).

Route A8

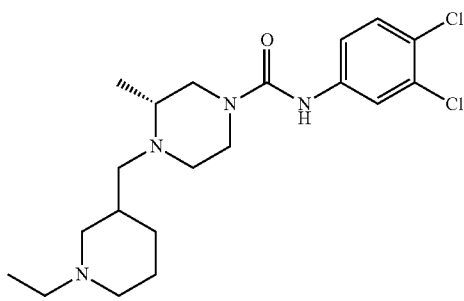 [SMILES: CCN1CCCC(CN2CCN(C(=O)Nc3ccc(Cl)c(Cl)c3)C[C@H]2C)C1]

(3R)—N-(3,4-Dichlorophenyl)-4-[(1-ethylpiperidin-3-yl)methyl]-3-methylpiperazine-1-carboxamide To a solution of tert-butyl (3R)-3-methylpiperazine-1-carboxylate (84 mg) and (1-ethylpiperidin-3-yl)methyl 4-methylbenzenesulfonate (150 mg) in acetonitrile (3 mL) was added potassium carbonate (233 mg). The mixture was heated to 100° C. in the microwave for 2 hours and then evaporated. The residue was purified by silica column chromatography, eluting with a gradient of 0 to 5% 7M NH$_3$/MeOH in dichloromethane. To a solution of the isolated material (50 mg) in methanol (5 mL) was added 4M HCl in dioxane (0.5 mL). The mixture was stirred overnight at room temperature and then evaporated to give a colourless oil. To a mixture of this oil in dichloromethane (10 mL) was added di-iso-propylethylamine (0.11 mL) and 3,4-dichlorophenyl-isocyanate (35 mg). The mixture was stirred for 15 minutes and then evaporated. The residue was purified using reverse phase HPLC eluting with a mixture of 5-95% acetonitrile in water to give the title compound as a white foam (52 mg, 30%).

LCMS M/z(+) 413 (M+H$^+$).

$^1$H-NMR (400.132 MHz, CDCl$_3$) 0.80-0.95 (1H, m), 1.04 (1.5H, d), 1.06 (1.5H, d), 0.61-0.68 (3H, m), 1.43-1.76 (4H, m), 1.77-1.95 (2H, m), 1.97-2.05 (1H, m), 2.12-2.21 (0.5H, m), 2.23-2.32 (0.5H, m), 2.33-2.57 (4H, m), 2.78-3.04 (3.5H, m), 3.08-3.16 (0.5H, m), 3.19-3.34 (1H, m), 3.57-3.73 (2H, m), 6.33 (1H, s), 7.21 (1H, d), 7.33 (1H, d), 7.60 (1H, s).

The tert-butyl (3R)-3-methylpiperazine-1-carboxylate used in Route A8 is commercially available and was purchased from Arch Chemical Corporation, New Jersey, USA.

Route A9

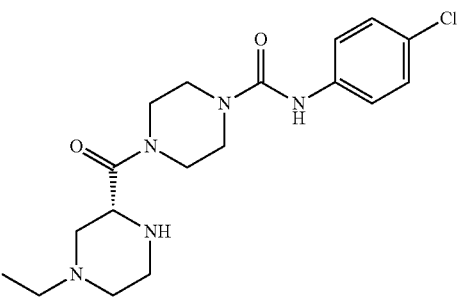 [SMILES: CCN1CCN[C@@H](C(=O)N2CCN(C(=O)Nc3ccc(Cl)cc3)CC2)C1]

N-(4-Chlorophenyl)-4-{[(2R)-4-ethylpiperazin-2-yl]carbonyl}piperazine-1-carboxamide Triethylamine (29 uL) was added to a solution of tert-butyl (2R)-4-ethyl-2-(piperazin-1-ylcarbonyl)piperazine-1-carboxylate (67.5 mg) in dry dichloromethane (5 ml) followed by 4-chloro phenylisocyanate (35 mg) and the reaction was stirred for 18 h under argon. Methanol (1 ml) was added, the solvent was evaporated and the product purified by chromatography (3-15% MeOH-DCM) to afford the homologated product (91 mg) as a foam. The foam was then dissolved in TFA/DCM (1:1, 6 ml) and stirred for 1 h. The solvent was removed under reduced pressure then taken up in 1M. aqueous sodium hydroxide (30 ml) and extracted with dichloromethane (2×30 ml). The combined organic layers were dried (MgSO$_4$), filtered and evaporated to form the title compound (70 mg) as a white foam.

LCMS M/z(+) 380, 382 (M+H$^+$).

$^1$H NMR (400.132 MHz, CDCl$_3$) 1.18 (3H, t), 2.12 (1H, t), 2.22 (1H, t), 2.62 (2H, m), 3.10 (3.57 (6H, m), 3.78 (2H, m), 4.01 (1H, d), 6.42 (1H, s), 7.30 (4H, m).

The tert-butyl (2R)-4-ethyl-2-(piperazin-1-ylcarbonyl)piperazine-1-carboxylate used in Route A9 was prepared using the following procedures.

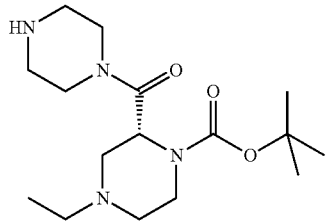 [SMILES: CCN1CCN(C(=O)OC(C)(C)C)[C@@H](C(=O)N2CCNCC2)C1]

tert-Butyl (2R)-4-ethyl-2-(piperazin-1-ylcarbonyl)piperazine-1-carboxylate 4-(4,6-Dimethoxy[1.3.5]triazin-2-yl)-4-methylmorpholinium chloride hydrate (253 mg, Acros chemicals) was added to a solution of (2R)-1-(tert-butoxycarbonyl)-4-ethylpiperazine-2-carboxylic acid (212 mg) in dry dichloromethane (6 ml) followed by addition on N-methyl morpholine (0.28 ml) and stirring under argon for 1 h. piperazine (234 mg) was then added and stirring was continued for 18 h. Dichloromethane (30 ml) was added and extracted with 1M NaOH (2×10 mL). The organic layer was dried (MgSO₄), filtered and evaporated. Purification by chromatography (5-50% MeOH:DCM) afforded the title compound (135 mg) as a foam.

LCMS M/z(+) 327 (M+H⁺).

¹H NMR (400.132 MHz, CDCl₃) 1.05 (3H, t), 1.42 (9H, s), 2.04 (1H, m), 2.20 (1H, m), 2.31 (1H, m), 2.47 (1H, m), 2.79 (1H, d), 2.87 (3H, m), 3.02 (1H, m), 3.52 (5H, m), 3.75 (2H, m), 4.83 (1H, br. s).

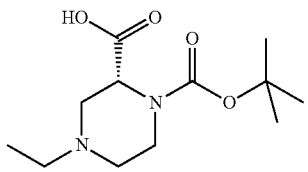 [SMILES: CCN1CCN(C(=O)OC(C)(C)C)[C@@H](C(=O)O)C1]

(2R)-1-(tert-Butoxycarbonyl)-4-ethylpiperazine-2-carboxylic acid

To (2R)-1-(tert-butoxycarbonyl)piperazine-2-carboxylic acid (1.406 g) and Na₂CO₃ (2.59 g) was added dry EtOH (28 ml) then ethyl iodide (0.54 ml) and the mixture heated at reflux for 18 h under argon. The solvent was then removed under reduced pressure and 5% MeOH/DCM (40 ml) was added and stirred for 1 hour in a sealed flask. The solution was filtered and washed with dichloromethane (2×10 mL). The filtrate was then placed directly onto a 120 g-silica cartridge and was purified using eluent 10-70% MeOH/DCM. After evaporation, the product was isolated as a white foam (1.00 g), which was used without further purification.

¹H NMR (400.132 MHz, DMSO-d₆) 0.95 (3H, t), 1.35+1.42 (9H, 2×s (rotameric)), 1.81 (1H, m), 2.03 (1H, m), 2.29 (2H, m), 2.78 (1H, m), 3.02+3.16 (1H, 2×t, rotameric), 3.28 (1H, m), 3.63 (1H, appt. d), 4.35+4.42 (1H, 2×appt. s., rotameric), 13.00 (1H, br. s).

The (2R)-1-(tert-butoxycarbonyl)piperazine-2-carboxylic acid used in Route C3 is commercially available and was purchased from Arch Chemical Corporation, New Jersey, USA.

The following compounds were made in an analogous manner.

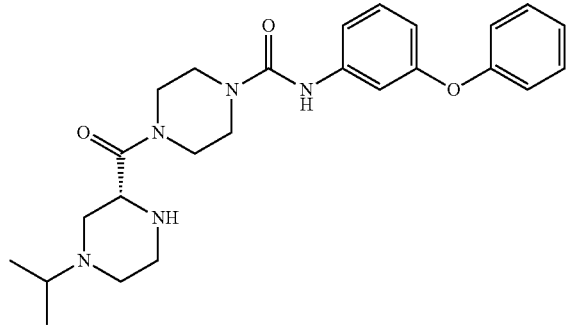 [SMILES: CC(C)N1CCN[C@@H](C(=O)N2CCN(C(=O)Nc3cccc(Oc4ccccc4)c3)CC2)C1]

4-{[(2R)-4-Isopropylpiperazin-2-yl]carbonyl}-N-(3-phenoxyphenyl)piperazine-1-carboxamide LCMS M/z(+) 452 (M+H⁺).

¹H NMR (400.132 MHz, DMSO-d₆) 0.93-1.01 (m, 6H), 2.02-2.22 (m, 2H), 2.61-2.84 (m, 4H), 2.93-2.98 (m, 1H), 3.31-3.67 (m, 8H), 3.77-3.84 (m, 1H), 6.58-6.64 (m, 1H), 7.01 (d, 2H), 7.14 (t, 1H), 7.21-7.28 (m, 3H), 7.40 (t, 2H), 8.65 (s, 1H).

The tert-butyl (2R)-4-isopropyl-2-(piperazin-1-ylcarbonyl)piperazine-1-carboxylate used in Route A9 was prepared using the following procedures.

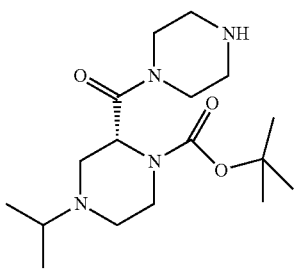 [SMILES: CC(C)N1CCN(C(=O)OC(C)(C)C)[C@@H](C(=O)N2CCNCC2)C1]

tert-Butyl (2R)-4-isopropyl-2-(piperazin-1-ylcarbonyl)piperazine-1-carboxylate

To tert-butyl (2R)-2-({4-[(benzyloxy)carbonyl]piperazin-1-yl}carbonyl)-4-isopropylpiperazine-1-carboxylate (660 mg) in ethyl acetatec (20 mL, degassed) was added Pd/C (10%) (200 mg) and the mixture was degassed again. The reaction was placed under an H₂ atmosphere and stirred vigorously for 16 h. The reaction was filtered and 500 mg of 10% Pd/C added and place under hydrogen atmosphere and stirred for an additional 5 h. The reaction was filtered through a PTFE filter and evaporated to give the title compound (462 mg) as a solid on further drying.

¹H NMR (400.132 MHz, DMSO-d₆) 0.93 (m, 6H), 1.37 (s, 9H), 2.12 (t, 1H), 2.32 (m, 1H), 2.60-2.75 (m, 6H), 2.90 (m, 1H), 3.25-3.62 (m, 6H), 4.72 (m, 1H).

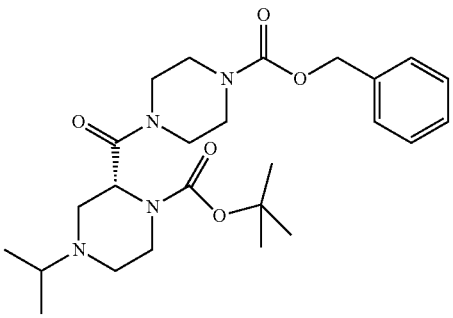 [SMILES: CC(C)N1CCN(C(=O)OC(C)(C)C)[C@@H](C(=O)N2CCN(C(=O)OCc3ccccc3)CC2)C1]

tert-Butyl (2R)-2-({4-[(benzyloxy)carbonyl]piperazin-1-yl}carbonyl)-4-isopropyl piperazine-1-carboxylate To (2R)-1-(tert-butoxycarbonyl)-4-isopropylpiperazine-2-carboxylic acid (513 mg) in dry THF was added benzyl piperazine-1-carboxylate (0.364 mL) followed by 1-hydroxybenzotriazole (289 mg), EDCI (361 mg) and N,N-diisopropylethylamine (0.329 mL) under an argon atmosphere. The reaction was stirred for 60 h and then the solvent was evaporated in vacuo. The residue was taken up in dichloromethane (50 mL) and 1M NaOH (25 mL) and the organic layer was dried (MgSO₄), filtered and evaporated to dryness. Purification by column chromatography 5% MeOH/DCM afforded the title compound (624 mg) as a foam.

LCMS M/z(+) 475 (M+H⁺).

¹H NMR (400.132 MHz, CDCl₃) 0.99 (m, 6H), 1.48 (s, 9H), 2.23-2.34 (m, 1H), 2.39-2.48 (m, 1H), 2.64-2.79 (m, 2H), 2.86-2.99 (m, 1H), 3.58 (s, 8H), 3.57-3.84 (m, 2H), 4.87 (s, 1H), 5.19 (s, 2H), 7.29-7.46 (m, 5H).

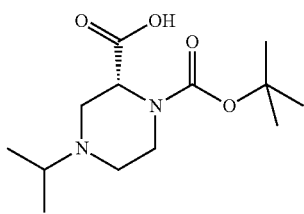 [SMILES: CC(C)N1CCN(C(=O)OC(C)(C)C)[C@@H](C(=O)O)C1]

(2R)-1-(tert-Butoxycarbonyl)-4-isopropylpiperazine-2-carboxylic acid

To (2R)-1-(tert-butoxycarbonyl)piperazine-2-carboxylic acid (500 mg) in dry methanol (10 mL) was added sodium cyanoborohydride (1.0 M in THF, 2.28 mL.) and the suspension was stirred for 18 h at 20° C. The reaction was now in solution. The solvent was then removed under reduced pressure and was purified using eluent 10-70% MeOH/DCM. After evaporation, the product was isolated as a white foam (513 mg), which was used without further purification.

¹H NMR (400.132 MHz, DMSO-d₆) 0.95 (m, 6H), 1.40 (2×s, 9H), 2.30 (m, 2H), 2.75 (m, 2H), 2.95 (t, 1H), 3.12 (t, 1H,), 3.70 (m, 1H), 4.48 (d, 1H), 12.60 (br. s, 1H). Trace contamination of sodium cyanoborohydride is present in 1H n.m.r. 0.45 (q(J$_{BH}$), 3H).

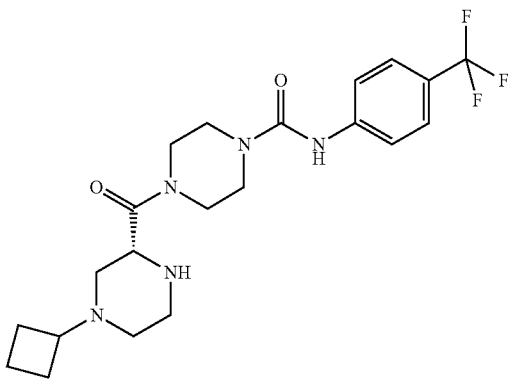 [SMILES: O=C(Nc1ccc(C(F)(F)F)cc1)N1CCN(C(=O)[C@H]2CN(C3CCC3)CCN2)CC1]

4-{[(2R)-4-Cyclobutylpiperazin-2-yl]carbonyl}-N-[4-(trifluoromethyl)phenyl]piperazine-1-carboxamide LCMS M/z(+)-439.94 (M+H⁺).

¹H NMR (300 MHz, DMSO-d₆) 1.65 (2H, m), 1.8 (2H, m), 2.0 (2H, m), 2.25 (1H, m), 2.8-3.5 (10H, m), 3.7 (4H, m), 4.5 (1H, m), 7.55 (2H, d), 7.7 (2H, d), 9.0 (1H, s).

The tert-Butyl (2R)-4-cyclobutyl-2-{[4-({[4(trifluoromethyl)phenyl]amino}carbonyl)piperazin-1-yl]carbonyl}piperazine-1-carboxylate used to make 4-{[(2R)-4-Cyclobutylpiperazin-2-yl]carbonyl}-N-[4-(trifluoromethyl)phenyl]piperazine-1-carboxamide was prepared according to the following procedure.

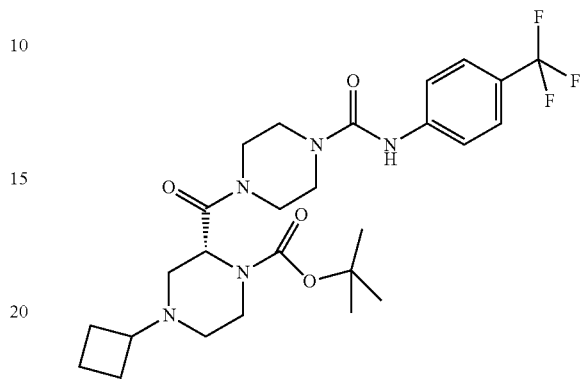

tert-Butyl (2R)-4-cyclobutyl-2-{[4-({[4-(trifluoromethyl)phenyl]amino}carbonyl)piperazin-1-yl]carbonyl}piperazine-1-carboxylate tert-Butyl (2R)-4-cyclobutyl-2-(piperazin-1-ylcarbonyl)piperazine-1-carboxylate (350 mg) was stirred at room temperature in dichloromethane (15 ml). Triethylamine (0.14 ml) was added followed by 4-(trifluoromethyl)phenyl isocyanate (0.14 ml) and the solution stirred overnight. The solvent was removed in vacuo and the residue adsorbed onto silica for purification by chromatography eluting with 0-7.5% methanol/dichloromethane. This gave tert-butyl (2R)-4-cyclobutyl-2-{[4-({[4-(trifluoromethyl)phenyl]amino}carbonyl)piperazin-1-yl]carbonyl}piperazine-1-carboxylate as a white glass (370 mg).

LCMS M/z(+) 539.96 (M+H⁺).

¹H NMR (300 MHz, DMSO-d₆) 1.2-2.0 (15H, m), 2.5-3.7 (15H, m), 4.05 (1H, m), 7.55 (2H, d), 7.65 (2H, d), 8.95 (1H, s).

The tert-butyl (2R)-4-cyclobutyl-2-(piperazin-1-ylcarbonyl)piperazine-1-carboxylate used in the above procedure was prepared as detailed below.

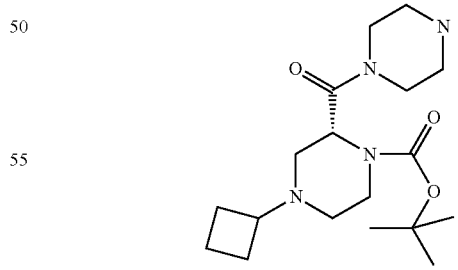

tert-Butyl (2R)-4-cyclobutyl-2-(piperazin-1-ylcarbonyl)piperazine-1-carboxylate

10% Palladium on carbon (900 mg) was added to tert-butyl (2R)-2-[(4-benzylpiperazin-1-yl)carbonyl]-4-cyclobutylpiperazine-1-carboxylate (5.12 g) and water (10 ml). Under an argon atmosphere, ethanol (250 ml) was added and the mixture stirred at room temperature under a hydrogen filled balloon. After 4 hours the catalyst was removed by filtration and washed with a small quantity of non-flammable solvent (dichloromethane). The combined filtrate was concentrated in vacuo, azeotroped once with toluene and dried under vacuum to give tert-butyl (2R)-4-cyclobutyl-2-(piperazin-1-ylcarbonyl)piperazine-1-carboxylate as an off-white foam (4.08 g).

LCMS M/z(+) 353.05 (M+H+).
$^1$H NMR (300 MHz, DMSO-$d_6$) 1.2-1.9 (15H, m), 2.1-3.7 (15H, m), 4.8 (1H, m).

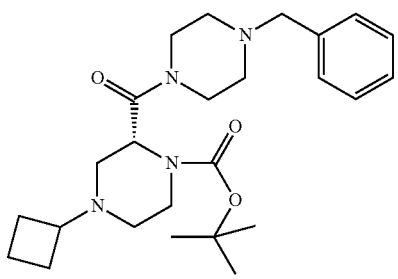 [SMILES: CC(C)(C)OC(=O)N1CCN(C2CCC2)C[C@@H]1C(=O)N1CCN(Cc2ccccc2)CC1]

tert-Butyl (2R)-2-[(4-benzylpiperazin-1-yl)carbonyl]-4-cyclobutylpiperazine-1-carboxylate tert-Butyl (2R)-2-[(4-benzylpiperazin-1-yl)carbonyl]piperazine-1-carboxylate (4.5 g) was dissolved in tetrahydrofuran (300 ml) and stirred at room temperature. N,N-Diisopropyl-ethylamine (5.95 ml) was added followed by cyclobutanone (3.25 g) and magnesium sulphate (300 mg). After 45 minutes, sodium triacetoxyborohydride (9.78 g) was added and stirring continued overnight. Inorganic residues were removed by filtration and the filtrate concentrated in vacuo. The residue was purified by chromatography eluting with 0-10% methanol/dichloromethane. This gave tert-butyl (2R)-2-[(4-benzylpiperazin-1-yl)carbonyl]-4-cyclobutylpiperazine-1-carboxylate as a colourless gum (5.12 g).

LCMS M/z(+) 443.04 (M+H+).
$^1$H NMR (300 MHz, DMSO-$d_6$) 1.2-1.8 (15H, m), 2.0-4.0 (18H, m), 7.3 (5H, m).

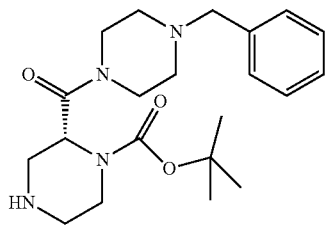 [SMILES: CC(C)(C)OC(=O)N1CCNC[C@@H]1C(=O)N1CCN(Cc2ccccc2)CC1]

tert-Butyl (2R)-2-[(4-benzylpiperazin-1-yl)carbonyl]piperazine-1-carboxylate

1-Benzylpiperazine (2.7 ml) and (2R)-1-BOC-piperazine-2-carboxylic acid (3.571 g) were suspended in DMF (150 ml) and stirred at 0° C. Triethylamine (4.33 ml) was added followed by PyBOP reagent (8.08 g). The mixture was allowed to warm to room temperature overnight, concentrated to approximately a third of the volume in vacuo and partitioned between brine (75 ml) and ethyl acetate (2×200 ml). Combined organic extracts were treated with saturated aqueous sodium bicarbonate (75 ml) and brine (75 ml), dried (sodium sulphate), concentrated in vacuo using high vacuum to remove DMF traces and purified by chromatography eluting with 0-15% methanol/dichloromethane. This gave tert-butyl (2R)-2-[(4-benzylpiperazin-1-yl)carbonyl]piperazine-1-carboxylate as a white glass (5.01 g).

LCMS M/z(+) 389.05 (M+H+).
$^1$H NMR (300 MHz, DMSO-$d_6$) 1.4 (9H, s), 2.2-4.0 (17H, m), 7.3 (5H, m).

The 1-Benzylpiperazine used in the above procedure is commercially available and was purchased from Aldrich Chemical Company, Inc.

As an alternative of Route A9, the following compounds were prepared as detailed below.

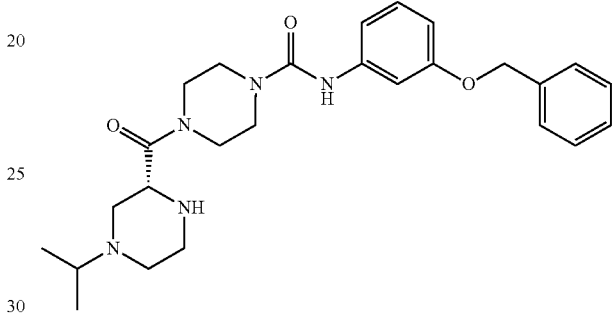

N-[3-(Benzyloxy)phenyl]-4-{[(2R)-4-isopropylpiperazin-2-yl]carbonyl}piperazine-1-carboxamide To a stirred solution of tert-butyl (2R)-4-isopropyl-2-(piperazin-1-ylcarbonyl)piperazine-1-carboxylate (0.2 g, 0.59 mmol) and phenyl [3-(benzyloxy)phenyl]carbamate (0.189 g, 0.59 mmol) in THF (5 mL) was added triethylamine (91 uL, 0.65 mmol) and the reaction heated to 60° C. for 6 hours. The solvents were then removed in vacuo and the residue dissolved in DCM (3 ml), added TFA (3 ml) and stirred at room temperature for a further 90 mins. The reaction mixture was then concentrated under reduced pressure, residue partitioned between DCM/1M NaOH, extracted twice, combined organics passed through phase separating cartridge and evaporated to dryness to give a yellow gum. This was then purified by silica gel chromatography (Isco Companion™; 12 g column; 10% methanolic ammonia/DCM) to give the product, as a pale yellow foam (153 mg, 0.33 mmol, 56%).

LCMS M/z(+) 466.83 (M−H+).
$^1$H-NMR (300 MHz, CDCl$_3$) 1.04 (t, 6H), 2.08-2.23 (m, 2H), 2.66-2.93 (m, 4H), 3.09 (d, 2H), 3.48-3.64 (m, 6H), 3.69-3.87 (m, 3H), 5.06 (s, 2H), 6.35 (s, 1H), 6.69 (d, 1H), 6.84 (d, 1H), 7.14-7.21 (m, 2H) and 7.29-7.44 (m, 5H).

The phenyl [3-(benzyloxy)phenyl]carbamate used in the above alternative of Route A9 was prepared as detailed below.

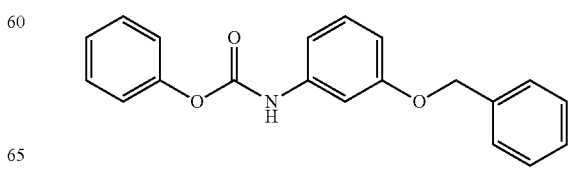

Phenyl [3-(benzyloxy)phenyl]carbamate

To a stirred solution of 3-benzyloxyaniline (0.999 g, 5.01 mmol) in DCM (10 mL) was added pyridine (1.22 ml, 15.03 mmol) and phenyl chloroformate (0.68 ml, 5.51 mmol) dropwise (Exotherm!). The reaction was then allowed to stir at room temperature for 2 hours. The reaction mixture was then partitioned between DCM and 1M HCl, extracted twice, combined organics passed through phase separating cartridge and filtrate evaporated to dryness to give an orange solid. This was then triturated in 10% ethyl acetate/hexanes, filtered and dried to give the product, phenyl [3-(benzyloxy)phenyl]carbamate, as beige solid (1.209 g, 3.78 mmol, 75% yield).

In addition, the following examples 289, 290, 291, 292, 293, 294, 295, 296, 297, 298, 299, 316, 317, 318 & 319 were prepared in an analogous manner to 300, from the following phenyl carbamates using dichloromethane, pyridine, phenyl chloroformate and the corresponding amine Purification was by chromatography, filtration of the precipitate from the reaction mixture or by trituration (1:9 EtOAc:isohexanes) from the crude product after work-up.

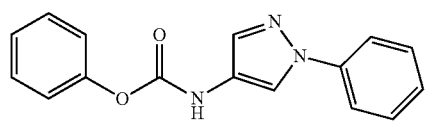 [SMILES: O=C(Nc1cnn(-c2ccccc2)c1)Oc1ccccc1]

Phenyl (1-phenyl-1H-pyrazol-4-yl)carbamate $^1$H NMR (400.132 MHz, DMSO-d$_6$) 6.62 (s, 1H), 7.17-7.32 (m, 4H), 7.41-7.54 (m, 4H), 7.78 (d, J=11.3 Hz, 2H), 8.42 (s, 1H), 10.80 (s, 1H).

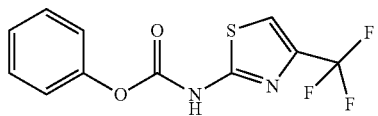 [SMILES: O=C(Nc1nc(C(F)(F)F)cs1)Oc1ccccc1]

Phenyl [4-(trifluoromethyl)-1,3-thiazol-2-yl]carbamate $^1$H NMR (400.132 MHz, DMSO-d$_6$) 7.26-7.35 (m, 3H), 7.45 (t, 2H), 8.00 (s, 1H), 12.71 (s, 1H).

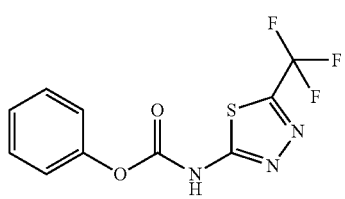 [SMILES: O=C(Nc1nnc(C(F)(F)F)s1)Oc1ccccc1]

Phenyl [5-(trifluoromethyl)-1,3,4-thiadiazol-2-yl]carbamate $^1$H NMR (400.132 MHz, DMSO-d$_6$) 7.30-7.38 (m, 3H), 7.48 (t, 2H), 12.51 (br. s, 1H).

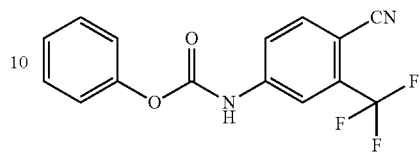

Phenyl [4-cyano-3-(trifluoromethyl)phenyl]carbamate $^1$H NMR (400.132 MHz, DMSO-d$_6$) 7.24-7.35 (m, 3H), 7.46 (t, 2H), 7.92 (d, J=8.0 Hz, 1H), 8.10-8.17 (m, 2H), 11.10 (s, 1H).

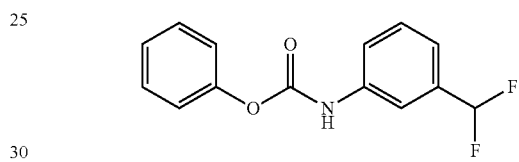

Phenyl [3-(difluoromethyl)phenyl]carbamate $^1$H NMR (400.132 MHz, DMSO-d$_6$) 7.02 (t, 1H), 7.21-7.32 (m, 4H), 7.40-7.53 (m, 3H), 7.61-7.68 (m, 1H), 7.79 (s, 1H), 10.44 (s, 1H).

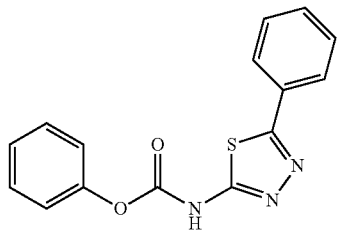 [SMILES: O=C(Nc1nnc(-c2ccccc2)s1)Oc1ccccc1]

Phenyl (5-phenyl-1,3,4-thiadiazol-2-yl)carbamate

LCMS M/z(+) 298 (M+H$^+$).

$^1$H NMR (400.132 MHz, DMSO-d$_6$) 7.27-7.36 (m, 3H), 7.48 (t, 2H), 7.51-7.57 (m, 3H), 7.90-7.96 (m, 2H), 12.21-13.13 (m, 1H).

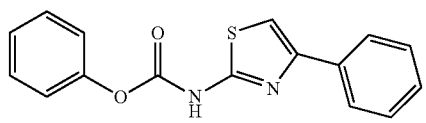 [SMILES: O=C(Nc1nc(-c2ccccc2)cs1)Oc1ccccc1]

Phenyl (4-phenyl-1,3-thiazol-2-yl)carbamate

LCMS M/z(+) 297 (M+H⁺).
¹H NMR (400.132 MHz, DMSO-d₆) 7.25-7.37 (m, 4H), 7.41-7.50 (m, 4H), 7.66 (s, 1H), 7.91 (d, 2H), 12.42 (s, 1H).

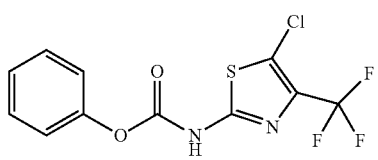 [SMILES: O=C(Nc1nc(C(F)(F)F)c(Cl)s1)Oc1ccccc1]

Phenyl [5-chloro-4-(trifluoromethyl)-1,3-thiazol-2-yl]carbamate

LCMS M/z(+) 321/323 (M+H⁺). ¹H NMR (400.132 MHz, DMSO-d₆) 7.28-7.39 (m, 3H), 7.45-7.55 (m, 2H), 13.01 (br. s, 1H).

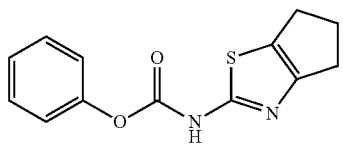 [SMILES: O=C(Nc1nc2c(s1)CCC2)Oc1ccccc1]

Phenyl 5,6-dihydro-4H-cyclopenta[d][1,3]thiazol-2-ylcarbamate

LCMS M/z(+) 261 (M+H⁺).
¹H NMR (400.132 MHz, DMSO-d₆) 2.36-2.48 (m, 2H), 2.68-2.78 (m, 2H), 2.83-2.91 (m, 2H), 7.27-7.38 (m, 3H), 7.50 (t, 2H), 11.55-12.58 (m, 1H).

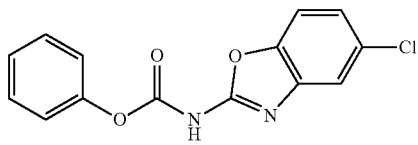 [SMILES: O=C(Nc1nc2cc(Cl)ccc2o1)Oc1ccccc1]

Phenyl (5-chloro-1,3-benzoxazol-2-yl)carbamate

LCMS M/z(+) 289 (M+H⁺).
¹H NMR (400.132 MHz, DMSO-d₆) 7.31-7.41 (m, 4H), 7.53 (t, 2H), 7.72 (d, 2H), 12.76 (s, 1H).

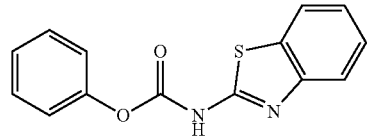 [SMILES: O=C(Nc1nc2ccccc2s1)Oc1ccccc1]

Phenyl 1,3-benzothiazol-2-ylcarbamate

LCMS M/z(+) 271 (M+H⁺).
¹H NMR (400.132 MHz, DMSO-d₆) 7.26-7.36 (m, 4H), 7.41-7.52 (m, 3H), 7.74 (d, 1H), 7.98 (d, 1H), 13.01 (s, 1H).

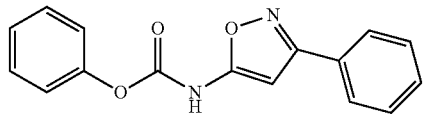 [SMILES: O=C(Nc1cc(-c2ccccc2)no1)Oc1ccccc1]

Phenyl (3-phenylisoxazol-5-yl)carbamate

LCMS M/z(+) 281 (M+H⁺).

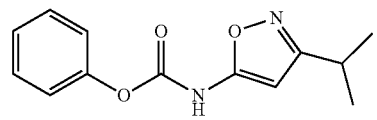 [SMILES: CC(C)c1cc(NC(=O)Oc2ccccc2)on1]

Phenyl (3-isopropylisoxazol-5-yl)carbamate

LCMS M/z(+) 247 (M+H⁺).

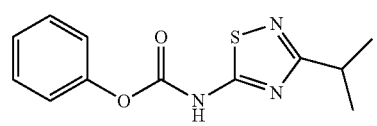 [SMILES: CC(C)c1nsc(NC(=O)Oc2ccccc2)n1]

Phenyl (3-isopropyl-1,2,4-thiadiazol-5-yl)carbamate

LCMS M/z(+) 264 (M+H⁺).

Phenyl (5-chloro-4-methyl-1,3-thiazol-2-yl)carbamate

LCMS M/z(+) 269/271 (M+H⁺).
¹H NMR (400.132 MHz, DMSO-d₆) 2.22 (s, 3H), 7.28 (d, 2H), 7.32 (t, 1H), 7.45 (t, 2H), 12.41 (br. s, 1H).

The (2R)-1-(tert-butoxycarbonyl)piperazine-2-carboxylic acid used in the above procedure is commercially available and was purchased from Arch Chemical Corporation, New Jersey, USA.

Route B1

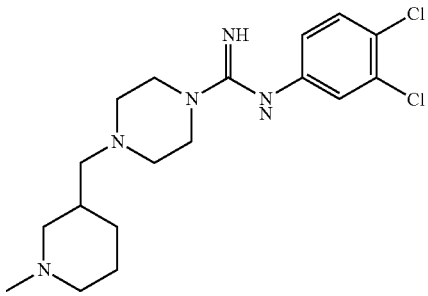

N-(3,4-Dichlorophenyl)-4-[(1-methylpiperidin-3-yl)methyl]piperazine-1-carboximidamide N-(3,4-Dichlorophenyl)-4-[(1-methylpiperidin-3-yl)methyl]piperazine-1-carbothioamide (0.53 g) was dissolved in a mixture of saturated ammonia in THF (1 ml) and dichloromethane (20 ml). The reaction mixture was cooled to −30° C. under an atmosphere of argon then silver triflate (0.34 g) was added. The reaction mixture was allowed to warm to room temperature then methanol (4 ml) was added. The soluble material was separated the concentrated in vacuo. The crude product was subjected to reverse phase HPLC using a gradient of 95% water/acetonitrile/0.1% TFA through to 50% water/acetonitrile/0.1% TFA. The combined product fractions were concentrated in vacuo then separated between dichloromethane (50 ml) and saturated sodium bicarbonate solution (100 ml). The dichloromethane layer was separated, dried over magnesium sulphate, filtered and concentrated in vacuo to give the title compound (209.1 mg).

LCMS M/z(+) 385.30, 387.27 (M+H$^+$).
LCMS M/z(−) 383.31, 385.29 (M−H$^-$).
$^1$H-NMR (400.132 MHz, DMSO-d$_6$) 0.83 (1H, m), 1.40 to 1.66 (4H, m), 1.72 to 1.86 (2H, m), 2.10 to 2.18 (5H, m), 2.27 to 2.39 (4H, m), 2.63 (1H, d), 2.76 (1H, d), 3.44 (4H, t), 7.46 (2H, t), 7.84 (1H, s), 8.76 (1H, s).

Route C1

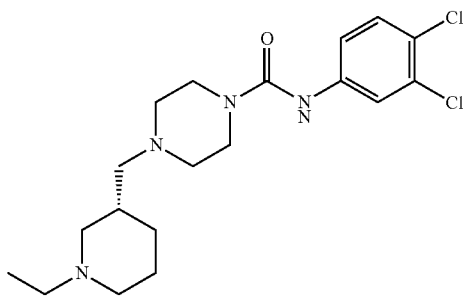

N-(3,4-Dichlorophenyl)-4-{[(3R)-1-ethylpiperidin-3-yl]methyl}piperazine-1-carboxamide N-(3,4-Dichlorophenyl)-4-[(3R)-piperidin-3-ylmethyl]piperazine-1-carboxamide (0.30 g), bromoethane (0.12 ml) and potassium carbonate (0.56 g) was refluxed in acetone (70 ml) for 18 hours. The reaction mixture was allowed to cool to room temperature then filtered. The filtrate was concentrated in vacuo and the resulting oil separated between ethyl acetate (100 ml) and water (100 ml). The ethyl acetate layer was separated, dried over magnesium sulphate, filtered then concentrated in vacuo onto silica gel (5 g). The resulting powder was subjected to chromatography on silica gel (50 g) using a gradient of 100% dichloromethane through to 20% methanolic ammonia in dichloromethane to give the title compound (24.9 mg).

LCMS M/z(+) 399.26, 401.20 (M+H$^+$).
$^1$H-NMR (400.132 MHz, DMSO-d$_6$) 0.88 (1H, m), 1.00 (3H, t), 1.45 (1H, m), 1.60 to 1.70 (3H, m), 1.77 (1H, m), 1.89 (1H, m), 2.11 to 2.19 (2H, m), 2.28 to 2.39 (6H, m), 2.78 (1H, d), 2.87 (1H, d), 3.44 (4H, t), 7.44 to 7.48 (2H, m), 7.84 (1H, s), 8.76 (1H, s).

The following compounds were prepared in an analogous fashion.

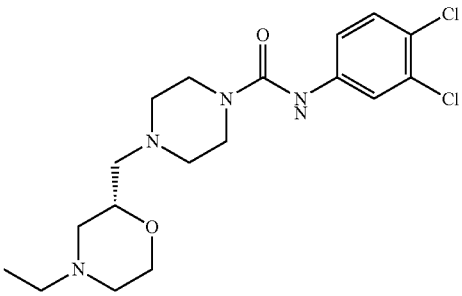

N-(3,4-Dichlorophenyl)-4-{[(2S)-4-ethylmorpholin-2-yl]methyl}piperazine-1-carboxamide LCMS M/z(+) 401.24, 403.19 (M+H$^+$).
LCMS M/z(−) 399.24, 401.25 (M−H$^-$).
$^1$H-NMR (400.132 MHz, DMSO-d$_6$) 1.00 (3H, t), 1.70 (1H, m), 1.94 (1H, m), 2.27 to 2.48 (8H, m), 2.67 (1H, m), 2.79 (1H, m), 3.37 to 3.51 (5H, m), 3.59 (1H, m), 3.75 (1H, m), 7.43 to 7.48 (2H, m), 7.84 (1H, m), 8.75 (1H, s).

The N-(3,4-dichlorophenyl)-4-[(2R)-morpholin-2-ylmethyl]piperazine-1-carboxamide (bis TFA salt) used in the preparation of N-(3,4-dichlorophenyl)-4-{[(2S)-4-ethylmorpholin-2-yl]methyl}piperazine-1-carboxamide was made using the following procedure.

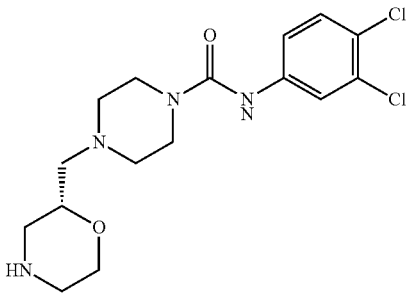

N-(3,4-Dichlorophenyl)-4-[(2R)-morpholin-2-ylinethyl]piperazine-1-carboxamide (bis TFA salt)

Trifluoroacetic acid/Dichloromethane (20 ml, 1:1) was added to tert-butyl (2S)-2-[(4-{[(3,4-dichlorophenyl)amino]- carbonyl}piperazin-1-yl)methyl]morpholine-4-carboxylate (2.10 g) under argon and stirred for 1 h. The solvent was then removed on a rotavapor and azeotroped (2×20 ml) with toluene and dried for 24 h under high vacuum to afford the title compound (2.67 g) as a brown oil which was used without further purification.

LCMS M/z(+) 371, 373 (M+H⁺).

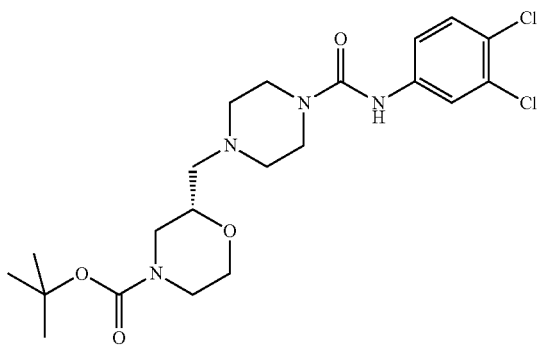 [SMILES: CC(C)(C)OC(=O)N1CCO[C@@H](CN2CCN(C(=O)Nc3ccc(Cl)c(Cl)c3)CC2)C1]

tert-Butyl (2S)-2-[(4-{[(3,4-dichlorophenyl)amino]carbonyl}piperazin-1-yl)methyl]-morpholine-4-carboxylate Dess-Martin periodinane (8.60 g) was added to tert-butyl (2R)-2-(hydroxymethyl)morpholine-4-carboxylate (4.00 g) in dry DCM at 0° C. The reaction was warmed to RT and stirred for a further 2 h. Aqueous sodium thiosulfate (10% w/v, 50 ml) was added and the DCM layer was removed then dried (MgSO₄), filtered and evaporated to form the crude aldehyde. The residue was then dissolved in dry dichloromethane (100 ml) followed by addition of N-(3,4-dichlorophenyl)piperazine-1-carboxamide hydrochloride (5.72 g), N, N-diisopropylethylamine (3.17 mL) and NaBH(OAc)₃ (9.76 g) and the reaction was stirred under argon for 18 h. 1M NaOH (50 mL) was added followed by vigorous stirring and the dichloromethane layer was extracted. The organic layer was dried (MgSO₄), filtered and evaporated. Purification by chromatography (EtOAc neat) afforded the title compound (2.10 g) as a white foam.

LCMS M/z(+) 471, 473 (M+H⁺).

¹H-NMR (400.132 MHz, CDCl₃) 1.45 (9H, s) 2.37 (1H, dd), 2.56 (6H, m), 2.92 (1H, m), 3.53 (6H, m), 3.90 (3H, m), 6.37 (1H, s), 7.20 (1H, dd), 7.32 (1H, d), 7.59 (1H, d).

The tert-butyl (2R)-2-(hydroxymethyl)morpholine-4-carboxylate used in the above procedure was prepared as detailed in the following reference; Heterocycles 35; 1; 1993; 105-109.

The following compounds were prepared in an analogous fashion.

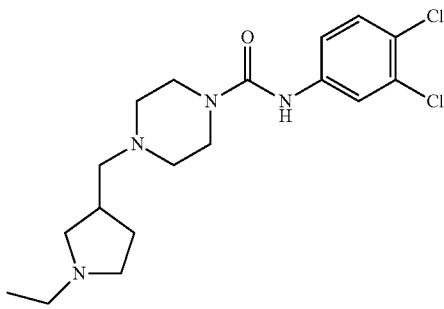 [SMILES: CCN1CCC(CN2CCN(C(=O)Nc3ccc(Cl)c(Cl)c3)CC2)C1]

N-(3,4-Dichlorophenyl)-4-[(1-ethylpyrrolidin-3-yl)methyl]piperazine-1-carboxamide LCMS M/z(+) 385.29, 387.27 (M+H⁺).
LCMS M/z(-) 383.36, 385.31 (M-H⁻).
¹H-NMR (400.132 MHz, DMSO-d₆) 1.13 (3H, t), 1.52 (1H, m), 1.97 (1H, m), 2.27 to 2.45 (7H, m), 2.82 (2H, s), 2.90 (1H, s), 3.03 (1H, s), 3.44 (4H, t), 7.47 (2H, m), 7.85 (1H, s), 8.79 (1H, s).

The N-(3,4-dichlorophenyl)-4-(pyrrolidin-3-ylmethyl)piperazine-1-carboxamide used in Route C1 was prepared using the following procedure.

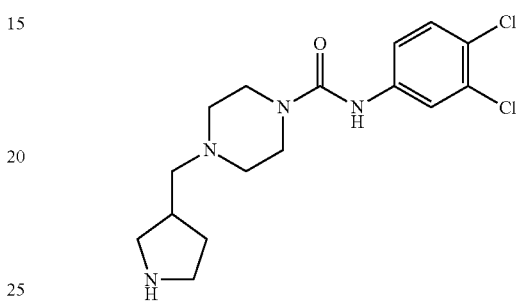

N-(3,4-Dichlorophenyl)-4-(pyrrolidin-3-ylmethyl)piperazine-1-carboxamide tert-Butyl 3-[(4-{[(3,4-dichlorophenyl)amino]carbonyl}piperazin-1-yl)methyl]pyrrolidine-1-carboxylate (440 mg) was stirred in a mixture of trifluoroacetic acid (5 ml) and dichloromethane (10 ml) for one hour at room temperature. The reaction mixture was concentrated in vacuo to give the title compound as a trifluoro acetate salt (350 mg).

LCMS M/z(+) 357.25, 359.24 (M+H⁺).

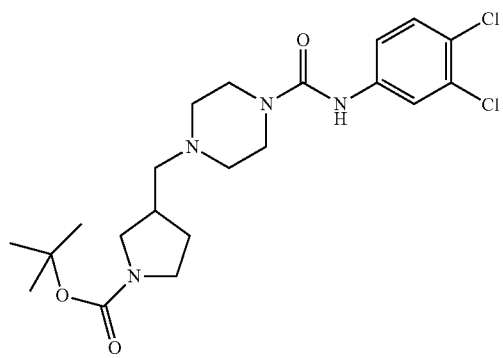 [SMILES: CC(C)(C)OC(=O)N1CCC(CN2CCN(C(=O)Nc3ccc(Cl)c(Cl)c3)CC2)C1]

tert-Butyl 3-[(4-{[(3,4-dichlorophenyl)amino]carbonyl}piperazin-1-yl)methyl]pyrrolidine-1-carboxylate tert-Butyl 3-(hydroxymethyl)pyrrolidine-1-carboxylate (281 mg) and Dess-Martin periodinane (652 mg) were stirred in dichloromethane (10 ml) for 1 hour at room temperature. 1N aqueous sodium hydroxide (50 ml) was added and the mixture stirred for 1 hour. The dichloromethane layer was separated. This solution of tert-butyl 3-formylpyrrolidine-1-carboxylate was added to a solution of N-(3,4-dichlorophenyl)piperazine-1-carboxamide (369 mg) in dichloromethane (20 ml). Sodium triacetoxyborohydride (713 mg) was added and the reaction left to stir at room temperature for 18 hours. Saturated aqueous sodium bicarbonate solution (500 ml) was added and the dichloromethane layer was separated then concentrated in vacuo to give the title compound (444 mg).

LCMS M/z(+) 479.21, 481.16 (M+Na$^+$).

LCMS M/z(−) 357.29, 359.25 (M−H$^-$).

$^1$H-NMR (400.132 MHz, DMSO-d$_6$) 1.40 (10H, s), 1.52 (1H, m), 1.91 (1H, m), 2.29 to 2.45 (6H, m), 2.90 (1H, q), 3.19 (1H, t), 3.39 (1H, dd), 3.45 (4H, t), 7.46 (2H, m), 7.84 (1H, s), 8.77 (1H, s).

The tert-Butyl 3-(hydroxymethyl)pyrrolidine-1-carboxylate used in the above procedure was commercially available and purchased from Arch Chemical Corporation, New Jersey, USA.

As a variation of Route C1 the following example was prepared as shown below.

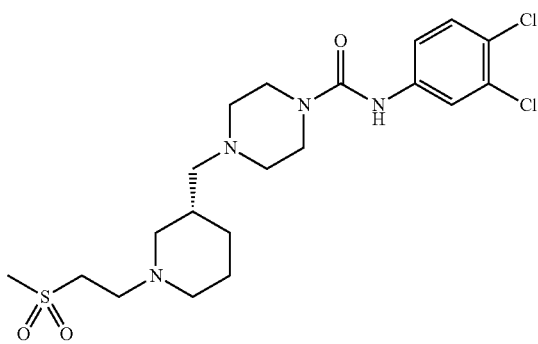 [SMILES: CS(=O)(=O)CCN1CCC[C@@H](CN2CCN(C(=O)Nc3ccc(Cl)c(Cl)c3)CC2)C1]

N-(3,4-Dichlorophenyl)-4-({(3S)-1-[2-(methylsulfonyl)ethyl]piperidin-3-yl}methyl)piperazine-1-carboxamide A solution of N-(3,4-dichlorophenyl)-4-[(3R)-piperidin-3-ylmethyl]piperazine-1-carboxamide (0.15 g; 0.33 mmol) in acetonitrile (10 ml) was added to methyl vinyl sulphone (0.08 g; 0.75 mmol and the resulting solution stirred at room temperature overnight. The mixture was then partitioned between water and ethyl acetate. The dried organic layer was evaporated and the residue purified by reverse phase HPLC eluting with a gradient of 25-75% acetonitrile in water. After evaporation of the relevant fractions, the pure product was dissolved in ethyl acetate (0.5 ml) and HCl in dioxan (0.5 ml) was added. After standing at room temp for 15 minutes the solvent was removed to give the hydrochloride salt (0.045 g; 27%).

LCMS M/z(+) 477 (M+H$^+$).

$^1$H-NMR (400.132 MHz, DMSO-d$_6$) 1.05-1.2 (1H, m); 1.7-1.8 (2H, m); 2.3.2.4 (2H, m); 2.6-2.75 (4H, m); 2.75-2.85 (2H, m); 3.1 (3H, s); 3.05-3.2 (4H, m); 3.4-3.5 (4H, m); 3.6-3.8 (4H, m); 6.6 (1H, d); 6.77 (1H, s); 7.13 (1H, d); 7.4 (1H, q).

As an additional variation of Route C1 the following example was prepared as follows.

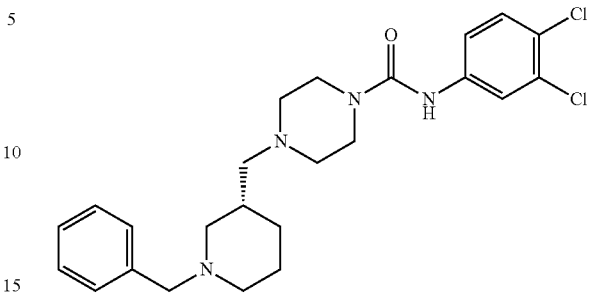

1-{[(3R)-1-Benzylpiperidin-3-yl]methyl}-N-(3,4-dichlorophenyl)piperazine-4-carboxamide To a mixture of N-(3,4-dichlorophenyl)-1-[(3R)-piperidin-3-ylmethyl]piperazine-4-carboxamide dihydrochloride (800 mg) in dichloromethane (25 mL) was added N,N-di-iso-propylethylamine (0.94 mL) under argon. The mixture was stirred at room temperature for 5 minutes before benzaldehyde (0.22 mL) and sodium triacetoxyborohydride (573 mg) were added. The reaction mixture was stirred at room temperature under argon for 4 hours. The reaction was quenched with water and then partitioned between dichloromethane and water. The organic extract was washed with brine, dried over magnesium sulfate and evaporated. The residue was purified by silica column chromatography, eluting with a gradient of 0 to 10% MeOH in dichloromethane to give the title compound as a white solid (550 mg, 66%).

LCMS M/z(+) 461 (M+H$^+$).

$^1$H-NMR (400.132 MHz, CDCl$_3$) 0.86-1.01 (1H, m), 1.58-1.88 (4H, m), 1.91-2.11 (2H, m), 2.12-2.24 (2H, m), 2.33 (2H, quintet), 2.42 (2H, quintet), 2.85 (1H, d), 3.01 (1H, d), 3.37-3.48 (4H, m), 3.52 (1H, d), 3.70 (1H, d), 6.82 (1H, s), 7.23-7.38 (7H, m), 7.63 (1H, d).

The following compounds were pillared in an analogous fashion.

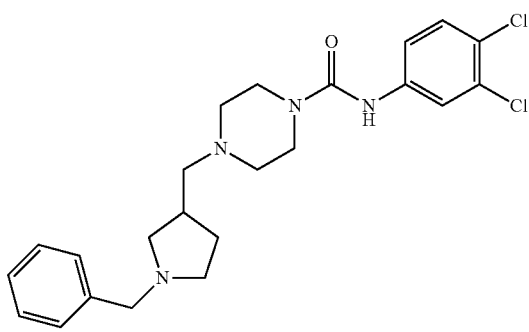 [SMILES: O=C(Nc1ccc(Cl)c(Cl)c1)N1CCN(CC2CCN(Cc3ccccc3)C2)CC1]

4-[(1-Benzylpyrrolidin-3-yl)methyl]-N-(3,4-dichlorophenyl)piperazine-1-carboxamide LCMS M/z(+) 447.26, 449.24 (M+H$^+$).
LCMS M/z(−) 445.26, 447.27 (M−H$^-$).
$^1$H-NMR (400.132 MHz, DMSO-d$_6$) 1.25 (6H, s), 1.49 (1H, s), 1.95 (1H, s), 2.26 to 2.43 (7H, m), 3.15 (1H, s), 3.42

(4H, t), 3.61 (1H, s), 3.81 (1H, s), 7.30 to 7.38 (5H, m), 7.46 (2H, m), 7.83 (1H, d), 8.77 (1H, s).

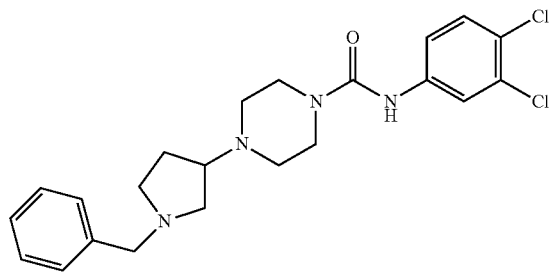 [SMILES: O=C(Nc1ccc(Cl)c(Cl)c1)N1CCN(C2CCN(Cc3ccccc3)C2)CC1]

4-(1-Benzylpyrrolidin-3-yl)-N-(3,4-dichlorophenyl) piperazine-1-carboxamide

LCMS M/z(+) 433.32, 435.30 (M+H⁺).
LCMS M/z(−) 431.31, 433.32 (M−H⁻).
¹H-NMR (400.132 MHz, DMSO-d₆) 1.71 (1H, s), 1.92 (1H, s), 2.34 to 2.47 (5H, m), 3.30 (4H, s), 3.42 (4H, t), 3.63 (2H, s) 7.28 (1H, m), 7.33 (4H, m), 7.46 (2H, m), 7.83 (1H, d), 8.76 (1H, s).

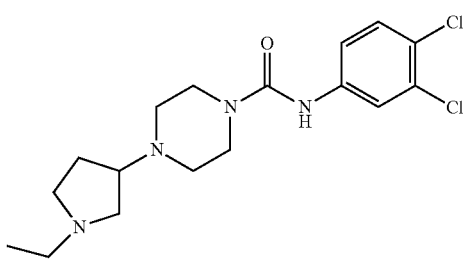 [SMILES: CCN1CCC(N2CCN(C(=O)Nc3ccc(Cl)c(Cl)c3)CC2)C1]

N-(3,4-Dichlorophenyl)-4-(1-ethylpyrrolidin-3-yl) piperazine-1-carboxamide

N-(3,4-dichlorophenyl)-4-pyrrolidin-3-ylpiperazine-1-carboxamide (95.0 mg, 0.29 mmols) and acetaldehyde (0.016 ml, 0.29 mmols) were stirred at room temperature in dichloromethane (5 ml) for approximately 15 minutes. Added to this mixture was sodium triacetoxyborohydride (154 mg, 0.73 mmols) and the reaction stirred overnight at room temperature. Saturated sodium bicarbonate solution (5 ml) was added and the mixture stirred for 1 hour then poured onto a hydromatrix column and the product eluted with dichloromethane (100 ml). The crude product was subjected to chromatography on silica gel (20 g) using a gradient of 100% dichloromethane through to 20% methanolic ammonia in dichloromethane to give impure product. This was dissolved in a mixture of DMSO/acetonitrile/water 7:3:1 (2 ml) and subjected to reverse phase preparative HPLC to yield the trifluoroacetate salt of the desired compound. This was dissolved in dichloromethane (50 ml) and washed with saturated sodium bicarbonate solution (50 ml). The organic layer was separated, dried (MgSO₄), filtered then concentrated in vacuo to give the title compound as a white solid (23.5 mg).
LCMS M/z(+) 371.30, 373.28 (M+H⁺).
LCMS M/z(−) 369.31, 371.30 (M−H⁻).
¹H-NMR (400.132 MHz, DMSO-d₆) 1.01 (3H, t), 1.63 (1H, m), 1.85 (1H, m), 2.29-2.46 (8H, m), 2.56 (1H, q), 2.69 (1H, t), 2.81 (1H, m), 3.43 (4H, t), 7.46 (2H, m), 7.84 (1H, s), 8.75 (1H, s).

The N-(3,4-dichlorophenyl)-4-pyrrolidin-3-ylpiperazine-1-carboxamide used for this preparation was made as follows.

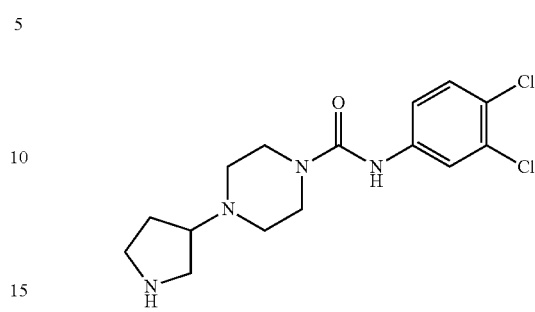

N-(3,4-Dichlorophenyl)-4-pyrrolidin-3-ylpiperazine-1-carboxamide tert-butyl 3-(4-{[(3,4-dichlorophenyl)amino] carbonyl}piperazin-1-yl)pyrrolidine-1-carboxylate (690 mg, 1.6 mmol) was dissolved in dichloromethane (50 ml) at room temperature. Trifluoroacetic acid (3 ml) was added and the mixture left to stir for 2 hours then concentrated in vacuo.
¹H-NMR (400.132 MHz, DMSO-d₆) 1.40 (9H, s), 1.70 (1H, m), 2.04 (1H, m), 2.38 (2H, m), 2.47 (2H, m), 2.80 (1H, m), 2.98 (1H, q), 3.17 (1H, m), 3.39 (1H, m), 3.44 (4H, t), 3.52 (1H, m), 7.46 (2H, m), 7.84 (1H, s), 8.78 (1H, s)

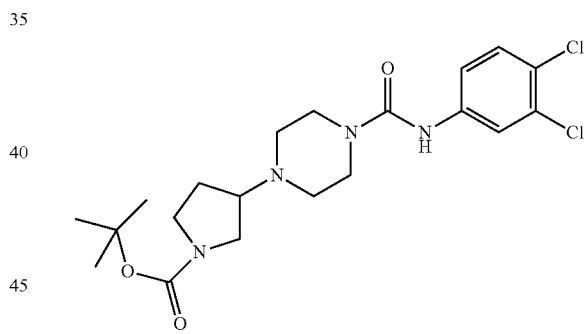

tert-Butyl 3-(4-{[(3,4-dichlorophenyl)amino] carbonyl}piperazin-1-yl)pyrrolidine-1-carboxylate N-(3,4-dichlorophenyl)piperazine-1-carboxamide (0.548 g, 2 mmols) and 1-N-BOC-3-pyrrolidinone (370 mg, 2 mmols) were stirred at room temperature in dichloromethane (20 ml) for approximately 15 minutes. Added to this mixture was sodium triacetoxyborohydride (1.06 g, 5 mmols) and the reaction stirred overnight at room temperature. Saturated sodium bicarbonate solution (5 ml) was added and the mixture stirred for 1 hour then poured onto a hydromatrix column and the product eluted with dichloromethane (100 ml). The crude product was subjected to chromatography on silica gel (50 g) using a gradient of 100% dichloromethane through to 10% methanolic ammonia in dichloromethane to give the title compound as a white solid (780 mg).
LCMS M/z(−) 441.25, 443.24 (M−H⁻).

The 1-N-tert-butoxy-3-pyrrolidinone used in the above procedure is commercially available and was purchased from Aldrich Chemical Company, Inc.

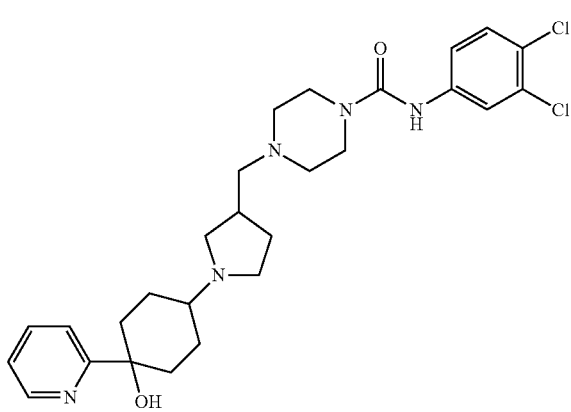 [SMILES: O=C(Nc1ccc(Cl)c(Cl)c1)N1CCN(CC2CCN(C3CCC(O)(c4ccccn4)CC3)C2)CC1]

N-(3,4-dichlorophenyl)-4-{[1-(4-hydroxy-2-pyridin-2-ylcyclohexyl)pyrrolidin-3-yl]methyl}piperazine-1-carboxamide LCMS M/z(+) 532.91 (M+H$^+$).
$^1$H-NMR (400.132 MHz, CDCl$_3$) 1.34-1.49 (m, 3H), 1.86-2.02 (m, 4H), 2.11-2.60 (m, 14H), 2.68-2.75 (m, 1H), 3.40 (t, 4H), 6.30 (s, 1H), 7.11-7.14 (m, 2H), 7.28 (d, 1H), 7.53 (d, 1H), 7.63 (t, 1H) and 8.46 (d, 1H).

The starting material, N-(3,4-dichlorophenyl)-4-(pyrrolidin-3-ylmethyl)piperazine-1-carboxamide, was prepared as follows.

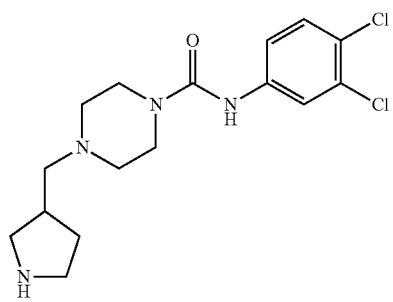 [SMILES: O=C(Nc1ccc(Cl)c(Cl)c1)N1CCN(CC2CCNC2)CC1]

N-(3,4-dichlorophenyl)-4-(pyrrolidin-3-ylmethyl)piperazine-1-carboxamide

To a stirred solution of tert-butyl 3-[(4-{[(3,4-dichlorophenyl)amino]carbonyl}piperazin-1-yl)carbonyl]pyrrolidine-1-carboxylate (3.39 g, 7.19 mmol) in THF (60 ml) was added a 1M solution of borane in THF (21.6 ml, 21.6 mmol) and the reaction heated to reflux for 4 hours. The cooled reaction mixture was then cautiously quenched by addition of methanol then solvents removed in vacuo to give a white solid. To this was then added saturated HCl in methanol (150 ml) and heated to reflux for 1 hour. The reaction mixture was then evaporated to dryness, partitioned between 2M NaOH and DCM, extracted twice, combined organics dried (Na$_2$SO$_4$), filtered and evaporated to a colorless oil. This was then purified on Isco™ Companion (40 g column: 20% methanolic ammonia/DCM) to give the product N-(3,4-dichlorophenyl)-4-(pyrrolidin-3-ylmethyl)piperazine-1-carboxamide as a white foam (444 mg, 1.24 mmol, 17%).
LCMS M/z(+) 357.21 (M+H$^+$).

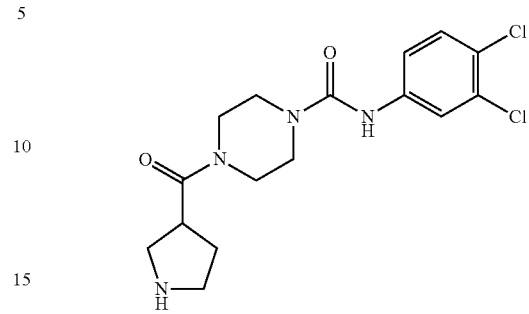

N-(3,4-Dichlorophenyl)-4-(pyrrolidin-3-ylcarbonyl)piperazine-1-carboxamide

To a stirred solution of tert-butyl 3-[(4-{[(3,4-dichlorophenyl)amino]carbonyl}piperazin-1-yl)carbonyl]pyrrolidine-1-carboxylate (3.485 g, 7.39 mmol) in DCM (30 ml) was added TFA (30 ml). The reaction was allowed to stir at ambient temperature for 1 hour. The solvents were then removed in vacuo, residue partitioned between DCM and 2M NaOH, extracted twice and the combined organics dried (Na$_2$SO$_4$), filtered and evaporated to dryness to give the product, N-(3,4-dichlorophenyl)-4-(pyrrolidin-3-ylcarbonyl)piperazine-1-carboxamide, as a pale yellow foam (2.745 g, 7.39 mmol, 100%).
LCMS M/z(+) 372.02 (M+H$^+$).

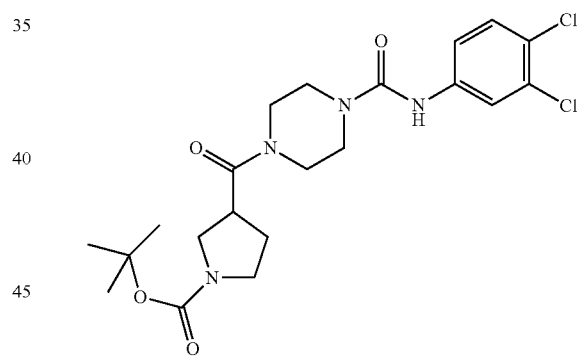

tert-Butyl 3-[(4-{[(3,4-dichlorophenyl)amino]carbonyl}piperazin-1-yl)carbonyl]pyrrolidine-1-carboxylate To a stirred solution of N-(3,4-dichlorophenyl)piperazine-1-carboxamide (2.00 g, 7.30 mmol) in DMF (150 ml) was added DIPEA (3.8 ml, 21.9 mmol), 3-carboxy-N-boc-proline (Arch Corporation) (1.727 g, 8.02 mmol) and HATU (3.051 g, 8.02 mmol) and the reaction stirred at ambient temperature for overnight (convenience). The solvents were then removed under reduced pressure. The resulting gum was then partitioned between EtOAc and water, extracted, the organic phase washed with saturated sodium bicarbonate solution and evaporated to dryness. The resulting foam was then purified on Isco™ Companion (40 g column. EtOAc) to give the product tert-butyl 3-[(4-{[(3,4-dichlorophenyl)amino]carbonyl}piperazin-1-yl)carbonyl]pyrrolidine-1-carboxylate as a pale yellow foam (3.396 g, 7.20 mmol, 99%).
LCMS M/z(−) 469.30 (M−H$^+$).

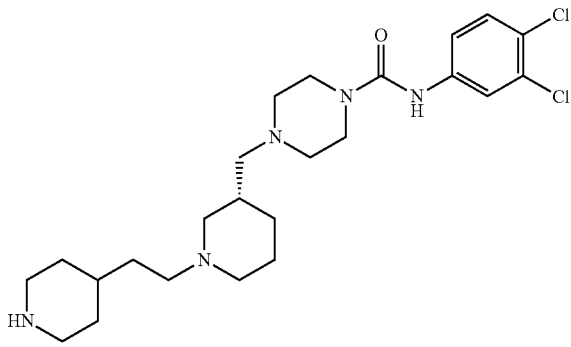 [SMILES: O=C(Nc1ccc(Cl)c(Cl)c1)N1CCN(C[C@@H]2CCCN(CCC3CCNCC3)C2)CC1]

N-(3,4-Dichlorophenyl)-4-{[(3R)-1-(2-piperidin-4-ylethyl)piperidin-3-yl]methyl}piperazine-1-carboxamide To benzyl 4-(2-{(3R)-3-[(4-{[(3,4-dichlorophenyl)amino]carbonyl}piperazin-1-yl)methyl]piperidin-1-yl}ethyl)piperidine-1-carboxylate (805 mg) was added 4M HCl in dioxane (5 ml). After removal of the solvent, 1-methyl-2-pyrrolidinone (5 ml) and zinc bromide (20 mg) were added, the mixture purged with Argon, 10% Pd/C (100 mg) added and stirred under hydrogen for 60 hours. Catalyst was filtered off through Celite, fresh catalyst and zinc bromide added and stirring continued for a further 48 hours under hydrogen. After filtration, the mixture was purified on a SCX2 50 g column, eluting sequentially with isohexane, ethyl acetate, 50% ethyl acetate/MeOH, MeOH and finally with 10% ammonia in MeOH to give the title compound (205 mg, 34%).

$^1$H-NMR (400.132 MHz, DMSO-$d_6$) 0.88 (1H, m), 1.02 (3H, m), 1.33 (2H, m), 1.45 (1H, m), 1.61 (4H, m), 1.75 (1H, m), 1.85 (1H, m), 2.28 (8H, m), 2.68 (1H, m), 2.77 (1H, m), 2.91 (2H, m), 3.45 (8H, m), 7.45 (2H, m), 7.84 (1H, m), 8.76 (1H, m).

The benzyl 4-(2-{(3R)-3-[(4-{[(3,4-dichlorophenyl)amino]carbonyl}piperazin-1-yl)methyl]piperidin-1-yl}ethyl)piperidine-1-carboxylate used in the above procedure was prepared as described above.

Benzyl 4-(2-{(3R)-3-[(4-{[(3,4-dichlorophenyl)amino]carbonyl}piperazin-1-yl)methyl]piperidin-1-yl}ethyl)piperidine-1-carboxylate LCMS M/z(−) 613.92 (M−H$^-$), M/z(+) 616.20 (M+H$^+$).

$^1$H-NMR (400.132 MHz, DMSO-$d_6$) 0.87 (2H, m), 1.02 (2H, m), 1.35 (2H, m), 1.45 (2H, m), 1.66 (4H, m), 1.85 (2H, m), 2.14 (2H, m), 2.30 (6H, m), 2.75 (4H, m), 3.43 (4H, m), 3.97 (2H, m), 5.06 (2H, s), 7.35 (5H, m), 7.46 (2H, m), 7.84 (1H, m), 8.77 (1H, s).

In each case the N-(3,4-dichlorophenyl)-4-[(3R)-piperidin-3-ylmethyl]piperazine-1-carboxamide used for the preparation of compounds via Route C1 was made by the following procedure.

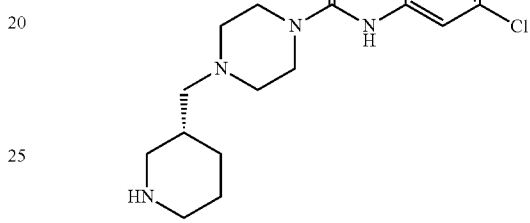

N-(3,4-Dichlorophenyl)-4-[(3R)-piperidin-3-ylmethyl]piperazine-1-carboxamide tert-Butyl (3S)-3-[(4-{[(3,4-dichlorophenyl)amino]carbonyl}piperazin-1-yl)methyl]piperidine-1-carboxylate (1 g), trifluoroacetic acid (10 ml) and dichloromethane (20 ml) were stirred at room temperature for one hour. The solvent was removed in vacuo to yield a dark brown oil. Water (20 ml) was added to this giving a milky solution and this was then basified to ~pH 6 by addition of solid NaHCO$_3$. This left a milky solution which was diluted with water (~50 ml) before extracting with ethyl acetate (3×75 ml). The combined organics were washed with brine (~100 ml) and separated then dried (MgSO$_4$) before removing solvent in vacuo to yield the title compound (531 mg).

LCMS M/z(+) 371.31, 373.30 (M+H$^+$).

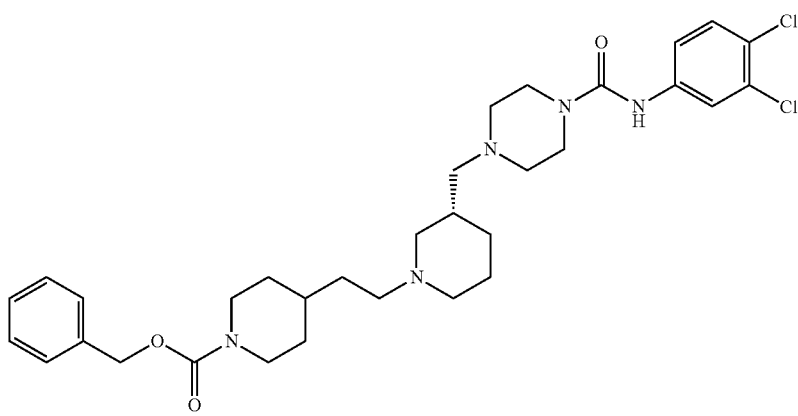 [SMILES: O=C(Nc1ccc(Cl)c(Cl)c1)N1CCN(C[C@@H]2CCCN(CCC3CCN(C(=O)OCc4ccccc4)CC3)C2)CC1]

¹H-NMR (400.132 MHz, DMSO-d₆) 2.75 (1H, m), 1.08-1.24 (1H, m), 1.53-2.10 (6H, m), 2.30-2.40 (4H, dq), 2.81-3.40 (8H, m), 7.45 (2H, m), 7.83 (1H, s), 8.81 (1H, s).

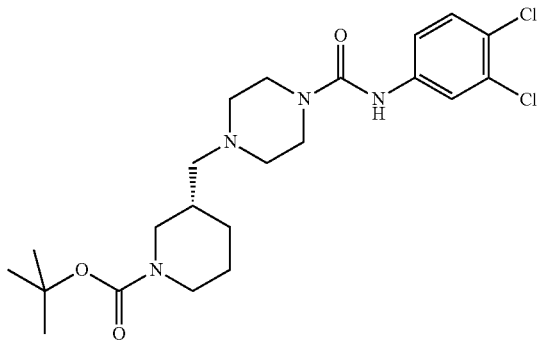

tert-Butyl (3S)-3-[(4-{[(3,4-dichlorophenyl)amino]carbonyl}piperazin-1-yl)methyl]piperidine-1-carboxylate tert-Butyl (3R)-3-(hydroxymethyl)piperidine-1-carboxylate (2.153 g) was added to Dess Martin Periodinane (4.67 g) and was stirred at room temperature in dichloromethane (50 ml) for 90 minutes. 2N Sodium hydroxide solution was added and the mixture filtered under reduced pressure before the filtrate separated using dichloromethane and the organic layer dried (MgSO₄). This was stirred at room temperature before filtering to remove drying agent. The solvent was removed in vacuo leaving the aldehyde product as a milky liquid. N-(3,4-dichlorophenyl)piperazine-1-carboxamide, (1.99 g) was added to the crude aldehyde (2.74 g) followed by sodium triacetoxyborohydride (5.30 g) and dichloromethane (50 ml) and stirred at room temperature for 18 hours. Saturated aqueous sodium bicarbonate solution (500 ml) was added and the dichloromethane layer was separated, dried over magnesium sulphate, filtered then concentrated in vacuo to yield the desired product as a white solid (3.05 g).

¹H-NMR (400.132 MHz, DMSO-d₆) 1.10 (1H, m), 1.31 (1H, d), 1.40 (9H, q), 1.60 (2H, m), 1.74 (1H, d), 2.13 (2H, m), 2.31 (2H, q), 2.39 (2H, d), 2.78 (1H, m), 3.44 (4H, d), 3.76 (1H, d), 3.93 (1H, d), 7.46 (2H, s), 8.76 (2H, s).

The tert-Butyl (3R)-3-(hydroxymethyl)piperidine-1-carboxylate used in the above procedure was commercially available and purchased from Arch Chemical Corporation, New Jersey, USA.

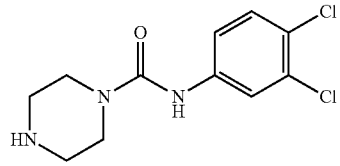 [SMILES: O=C(Nc1ccc(Cl)c(Cl)c1)N1CCNCC1]

N-(3,4-Dichlorophenyl)piperazine-1-carboxamide 3,4-Dichlorophenylisocyanate (3.43 g) and tert-butyl piperazine-1-carboxylate (3.40 g) were stirred for 18 hours in chloroform (20 ml) at room temperature. Trisamine resin (1 g) was added and the mixture stirred for 3 hours, then filtered off. Trifluoroacetic acid (10 ml) was added to the filtrate and this mixture was stirred for two hours. The reaction mixture was concentrated in vacuo and the resulting oil separated between ethyl acetate (100 ml) and saturated aqueous sodium bicarbonate solution (100 ml). The ethyl acetate layer was separated, dried over magnesium sulphate, filtered then concentrated in vacuo to give the title compound (5.47 g).

¹H-NMR (400.132 MHz, DMSO-d₆) 2.71 (4H, t), 3.38 (4H, t), 7.46 (2H, t), 7.84 (1H, d), 8.70 (1H, s).

As an additional variation of Route C1 the following examples were prepared as shown below.

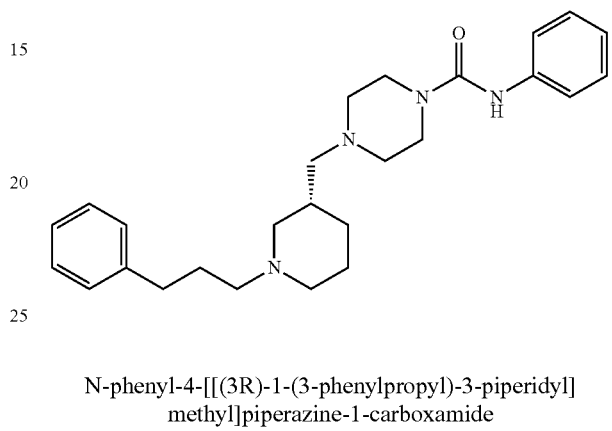

N-phenyl-4-[[(3R)-1-(3-phenylpropyl)-3-piperidyl]methyl]piperazine-1-carboxamide To a solution of 3-phenylpropanal (0.75 mmol) in dichloromethane (5 ml) was added N-phenyl-4-[(3R)-piperidin-3-ylmethyl]piperazine-1-carboxamide (151 mg, 0.50 mmol) and the reaction mixture stirred at room temperature for 30 min. Titanium tetraisopropoxide (710 mg, 2.50 mmol) and sodium triacetoxyborohydride (317 mg, 1.00 mmol) were then added and the mixture stirred for a further 24 hours. The mixture was then washed with water and dried using a phase separation cartridge. Silica was added and the solvent removed under reduced pressure then loaded onto a silica isolute column. Flash column chromatography (1%-10% methanol:dichloromethane) yielded the desire product as a gum.

LCMS M/z(+) 421 (M+H).

¹H NMR (400.132 MHz, CDCl₃) 0.90 (1H, m), 1.73 (4H, m), 1.91 (4H, m), 2.04 (2H, m), 2.16 (2H, m), 2.32 (2H, m), 2.50 (2H, m), 2.63 (2H, m), 3.11 (2H, m), 3.46 (4H, m), 6.89 (1H, m), 7.00 (1H, m), 7.22 (7H, m), 7.37 (2H, m).

The N-phenyl-4-[(3R)-piperidin-3-ylmethyl]piperazine-1-carboxamide used in Route C1 was prepared using the following procedures.

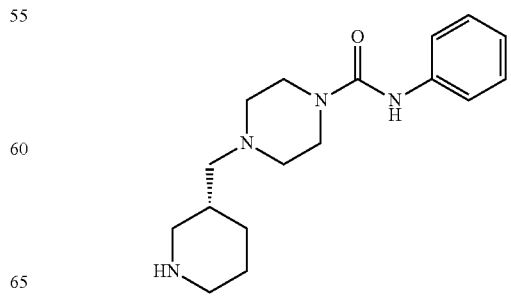

N-Phenyl-4-[(3R)-piperidin-3-ylmethyl]piperazine-1-carboxamide tert-Butyl (3S)-3-{[4-(anilinocarbonyl)piperazin-1-yl]methyl}piperidine-1-carboxylate (4.0 g) was added to a mixture of dichloromethane (20 ml) and TFA (20 ml) and the reaction mixture stirred for 2 h. The solvent was removed in-vacuo and the residue dissolved in dichloromethane (20 ml) and subsequently poured into hydrochloric acid solution (1N, 20 ml). The aqueous layer was basified using potassium carbonate and extracted with dichloromethane (3×15 ml). The organic layer was dried using a phase separation cartridge and the solvent removed under reduced pressure to afford the desired compound as a white foam white (2.0 g), which was used without further purification.

LCMS M/z(+) 303 (M+H).

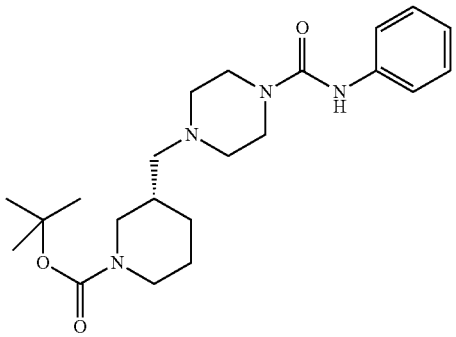 [SMILES: CC(C)(C)OC(=O)N1CCC[C@@H](CN2CCN(C(=O)Nc3ccccc3)CC2)C1]

tert-Butyl (3S)-3-{[4-(anilinocarbonyl)piperazin-1-yl]methyl}piperidine-1-carboxylate tert-Butyl (3S)-3-(piperazin-1-ylmethyl)piperidine-1-carboxylate (3.5 g) and phenyl isocyanate (1.62 g) were stirred in toluene (50 ml) at room temperature for 20 h. The solvent was then concentrated in-vacuo to afford a white solid. The solid was dissolved in methanol and passed through an SCX2 column. The SCX2 column was then flushed with 5% ammonia in methanol solution. The solution was collected and the solvent removed under reduced pressure. The resultant solid was re-crystalised from EtOAc and isoHexane, to afford the desired product as a white solid (4 g).

LCMS M/z(-) 401 (M-H).

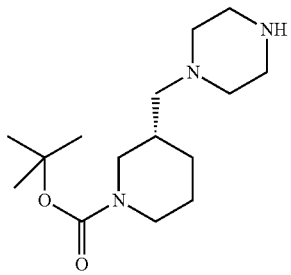 [SMILES: CC(C)(C)OC(=O)N1CCC[C@@H](CN2CCNCC2)C1]

tert-butyl (3S)-3-(piperazin-1-ylmethyl)piperidine-1-carboxylate

Benzyl 4-{[(3S)-1-(tert-butoxycarbonyl)piperidin-3-yl]methyl}piperazine-1-carboxylate (5.0 g, 12.4 mmol) was dissolved in methanol (50 ml) in a three-necked flask. The air was removed under reduced pressure and replaced with argon before the addition of 10% Pd/C (1.24 g). A balloon of hydrogen was then added and the reaction stirred at room temperature for 18 h. The hydrogen was evacuated and replaced with argon. The catalyst was then filtered and the solvent removed under reduced pressure to afford the desired product as a white foam (3.5 g). The compound was used without further purification.

Details for the preparation of benzyl 4-{[(3S)-1-(tert-butoxycarbonyl)piperidin-3-yl]methyl}piperazine-1-carboxylate have already been provided in Route A3.

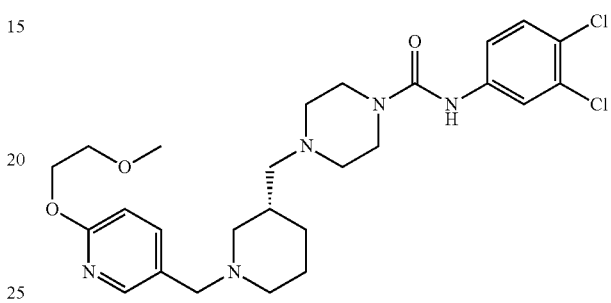

N-(3,4-dichlorophenyl)-4-[((3R)-1-{[6-(2-methoxyethoxy)pyridin-3-yl]methyl}piperidin-3-yl)methyl]piperazine-1-carboxamide To a suspension of the hydrochloride salt of N-(3,4-dichlorophenyl)-4-[(3R)-piperidin-3-ylmethyl]piperazine-1-carboxamide (442 mg, 1.00 mmol) in dichloromethane (40 ml) was added 6-(2-methoxyethoxy)nicotinaldehyde (199 mg, 1.00 mmol) and the cloudy mixture stirred at room temperature for 10 minutes. Polymer supported sodium triacetoxyborohydride (555 mg, 1.50 mmol) was added and the reaction stirred at room temperature overnight. The mixture was filtered, the filtrate washed with water (20 ml), organic extract dried (Na$_2$SO$_4$), filtered and evaporated to an oil. Flash column chromatography (10 gram Isolute silica column eluting; CH$_2$Cl$_2$ to 10% MeOH/CH$_2$Cl$_2$) yielded N-(3,4-dichlorophenyl)-4-[((3R)-1-{[6-(2-methoxyethoxy)pyridin-3-yl]methyl}piperidin-3-yl)methyl]piperazine-1-carboxamide (145 mg, 27%) as a white foam.

LCMS M/z(+) 535.9 (M+H).

The 6-(2-methoxyethoxy)nicotinaldehyde used in Route C1 was prepared using the following procedure.

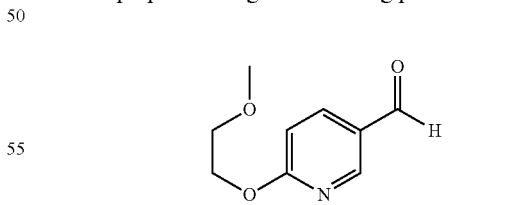

6-(2-Methoxyethoxy)nicotinaldehyde

[6-(2-methoxyethoxy)pyridine-3-yl]methanol (1.83 g 10.0 mmol) was dissolved in toluene (50 ml) and heated to reflux under an air condenser. Finely powdered MnO$_2$ (4.0 g) was added portion wise over 2 hours. After a further 2 and a half hours of heating the mixture was taken off the boil allowed to cool slightly then filtered through celite and washed with toluene. The filtrate was concentrated in-vacuo to yield a pale yellow oil which crystallized under high vacuum to yield the crude product (1.50 g).

LCMS M/z(+) 182 (M+H).

¹H NMR (400.132 MHz, CDCl₃) 3.45 (3H, s), 3.77 (2H, t), 4.48 (2H, t), 6.92 (1H, d), 8.08 (1H, dd), 8.63 (1H, s), 9.96 (1H, s).

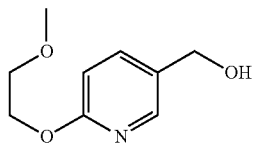

[6-(2-methoxyethoxy)pyridin-3-yl]methanol 6-(2-methoxyethoxy)nicotinic acid (3.94 g 20.0 mmol) was dissolved in anhydrous THF (80 ml) and cooled to 0° C., and stirred under argon while a solution of 1M borane in THF (80 ml) was added over a period of 1 hour. The mixture was allowed to warm to room temperature and left to stir for 4 hours to complete the reaction. The reaction was cooled to 0° C., and quenched by the careful addition of methanol (20 ml total) in small aliquots. The mixture was allowed to stir overnight to complete the quench, then concentrated to dryness in vacuo. The solids were partitioned between ethyl acetate (100 ml) and saturated Na₂CO₃ (50 ml), and separated, then the aqueous extracted again with ethyl acetate (100 ml). The combined organics were washed with brine (50 ml), then dried (MgSO₄) and concentrated in vacuo to give the crude product as clear oil (2.86 g).

LCMS M/z(+) 184 (M+H).

¹H NMR (400.132 MHz, CDCl₃) 3.46 (3H,$), 3.76 (2H, t), 4.49 (2H, t), 4.63 (2H, s); 6.81 (1H, d), 7.62 (1H, dd), 8.11 (1H, s).

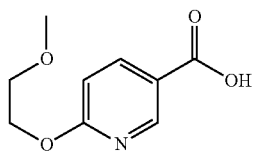

6-(2-methoxyethoxy)nicotinic acid

6-Chloronictotinic acid (7.91 g, 50.2 mmol) was suspended in dry toluene (100 ml) and 2-methoxymethanol (4.84 g, 5.0 ml) was added under an atmosphere of argon. Powdered sodium hydroxide (roughly 12 g, 300 mmol) and tetrabutylammonium bromide (1.58 g, 4.9 mmol) were added followed by additional toluene (110 ml). The thick white suspension was then heated at 120° C. under argon with slow stirring and swirling for 6 hours. The mixture was allowed to cool to room temperature overnight then heating resumed at 120° C. for a further 8 hours. The cooled mixture was treated with 1M HCl (cf 100 ml) and the aqueous separated. Additional 1M HCl was added until the mixture was acidic (cf 240 ml), then a yellow precipitate formed which was isolated by filtration and washed with toluene and dried to yield the crude product acid. (9.98 g).

LCMS M/z (M+H) 198 (M−H) 196.

¹H NMR (400.132 MHz, d6-DMSO) 3.69 (2H, m), 4.47 (2H, m), 6.92 (1H, d), 8.14 (1H, q), 8.72 (1H, s), 13.0 (1H, br).

6-Chloronicotinic acid is commercially available and was purchased from Lancaster Synthesis Ltd., UK.

The following compounds were also prepared in an identical manner to 6-(2-methoxy ethoxy)nicotinaldehyde from commercially available 6-chloronicotinic acid.

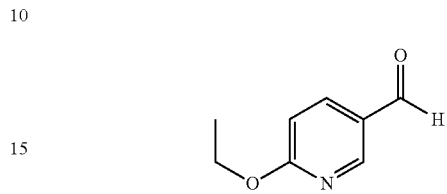

6-ethoxynicotinaldehyde

LCMS M/z (M+H) 152.

¹H NMR (400.132 MHz, CDCl₃) 1.43 (3H, t), 4.47 (2H, q), 6.82 (1H, d), 8.06 (1H, d), 8.62 (1H, d), 9.95 (1H, s).

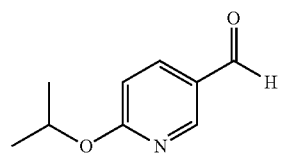

6-isopropoxynicotinaldehyde

LCMS M/z (M+H) 166.

¹H NMR (400.132 MHz, CDCl₃) 1.38 (6H, d), 5.44 (1H, septet), 6.76 (1H, d), 8.03 (1H, dd), 8.60 (1H, d), 9.93 (1H, s).

As an additional alternative to the above procedures, the following compounds were made in as detailed below.

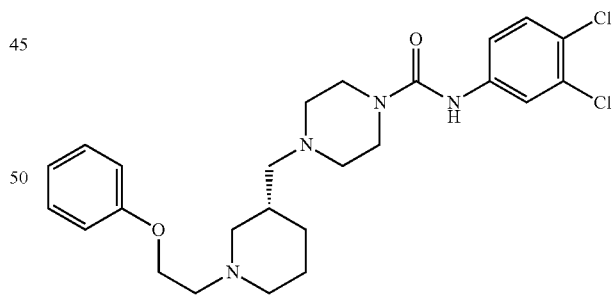

N-(3,4-Dichlorophenyl)-4-{[(3S)-1-(2-phenoxyethyl)piperidin-3-yl]methyl}piperazine-1-carboxamide N-(3,4-Dichlorophenyl)-4-{[(3S)-1-(2-hydroxyethyl)piperidin-3-yl]methyl}piperazine-1-carboxamide (250 mg, 0.62 mmols) and phenol (58.35 mg, 0.62 mmols) were stirred at room temperature under an atmosphere of argon before addition of P(Bu)₃ (0.30 ml, 1.24 mmols) and 1,1-azodicarbonyl dipiperidine (312 mg, 1.24 mmols). This reaction mixture was stirred at room temperature overnight under an argon atmosphere. The reaction mixture was washed using brine and the organic layer dried (MgSO₄) filtered then concentrated in vacuo onto silica gel (1 g). The resulting solid was subjected to chromatography on silica gel (20 g) using a gradient of 100% dichloromethane through to 20% methanolic ammonia in dichloromethane to give the title compound (65.4 mg).

LCMS M/z(+) 491.21, 493.14 (M+H⁺).

LCMS M/z(−) 489.22, 491.21 (M−H⁻).

¹H NMR (400.132 MHz, DMSO-d₆) 0.90 (1H, m), 1.45 (1H, q), 1.59 (2H, m), 1.75 (2H, s), 2.00 (1H, m), 2.11 (2H, m), 2.31 (4H, m), 2.66 (2H, m), 2.87 (2H, m), 3.40 (4H, m), 4.04 (2H, m), 6.92 (3H, m), 7.28 (2H, m), 7.42 (2H, dd), 7.80 (1H, s), 8.72 (1H, s).

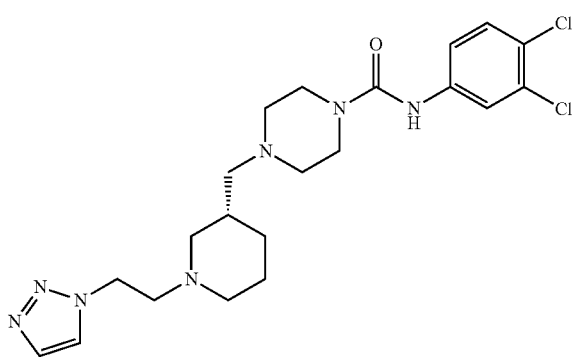 [SMILES: O=C(Nc1ccc(Cl)c(Cl)c1)N1CCN(C[C@@H]2CCCN(CCn3ccnn3)C2)CC1]

N-(3,4-dichlorophenyl)-4-({(3R)-1-[2-(1H-1,2,3-triazol-1-yl)ethyl]piperidin-3-yl}methyl)piperazine-1-carboxamide 4-{[(3R)-1-(2-Azidoethyl)piperidin-3-yl]methyl}-N-(3,4-dichlorophenyl)piperazine-1-carboxamide (100 mg, 0.23 mmol) was dissolved in 1,4-dioxane (4 ml). Bicyclo(2.2.1)hepta-2,5-diene (0.5 ml) was added and the mixture heated in the microwave at 180° C. for 20 minutes. The reaction mixture was poured onto a bond elut column (SiO₂, 20 g) and the product eluted with a gradient of dichloromethane through to 20% methanolic ammonia/dichloromethane to yield the title compound as a white solid (80.1 mg)

LCMS M/z(+) 466.25, 468.15 (M+H⁺)

LCMS M/z(−) 464.23, 466.21 (M−H⁻)

¹H NMR (400.132 MHz, DMSO-d₆) 0.90 (1H, m), 1.41 (1H, m), 1.55 to 1.81 (4H, m), 2.02 (1H, t), 2.03 to 2.18 (2H, m), 2.26 to 2.37 (4H, m), 2.67 to 2.78 (4H, m), 3.43 (4H, t), 4.48 (2H, t), 7.46 (2H, m), 7.70 (1H, d), 7.84 (1H, m), 8.10 (1H, d), 8.75 (1H, s).

The 4-{[(3R)-1-(2-Azidoethyl)piperidin-3-yl]methyl}-N-(3,4-dichlorophenyl)piperazine-1-carboxamide used in the above procedure was prepared as follows.

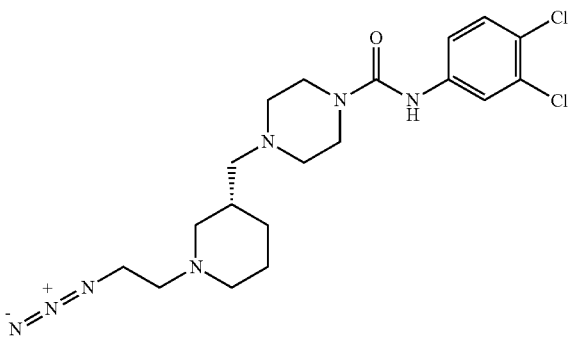

4-{[(3R)-1-(2-Azidoethyl)piperidin-3-yl]methyl}-N-(3,4-dichlorophenyl)piperazine-1-carboxamide Methane sulphonyl chloride (0.4 ml) was added to a solution of N-(3,4-dichlorophenyl)-4-{[(3S)-1-(2-hydroxyethyl)piperidin-3-yl]methyl}piperazine-1-carboxamide (1.85 g, 4.45 mmol) in triethylamine (0.75 ml, 5.3 mmol) and dichloromethane (50 ml) at 0° C. under an atmosphere of argon. The reaction mixture was stirred at this temperature for one hour then water (100 ml) was added. The organic layer was separated, dried over magnesium carbonate, filtered then concentrated in vacuo. This material was then dissolved in anhydrous DMF (10 ml). Sodium azide (435 mg, 6.7 mmol) was added and the reaction mixture stirred overnight at 60° C. The reaction mixture was concentrated in vacuo and the residue separated between ethyl acetate (150 ml) and water (150 ml). The organic layer was separated, dried over magnesium carbonate, filtered then concentrated in vacuo onto silica gel (3 g). The resulting powder was subjected to chromatography (SiO₂, 20 g) and the product eluted with a gradient of dichloromethane through to 10% methanolic ammonia/dichloromethane to yield the title compound as a white solid (105 mg)

LCMS M/z(+) 440.19, 442.11 (M+H⁺)

LCMS M/z(−) 438.21, 440.13 (M−H⁻)

¹H NMR (400.132 MHz, DMSO-d₆) 0.92 (1H, m), 1.45 (1H, m), 1.58 to 1.76 (4H, m), 2.00 (1H, t), 2.12 to 2.22 (2H, m), 2.28 to 2.40 (4H, m), 2.76 (1H, d), 2.86 (1H, d), 3.27 to 3.43 (4H, m), 3.44 (4H, t), 7.46 (2H, m), 7.84 (1H, m), 8.75 (1H, s).

The N-(3,4-dichlorophenyl)-4-{[(3S)-1-(2-hydroxyethyl)piperidin-3-yl]methyl}piperazine-1-carboxamide used in Route C1 was made using the following procedure.

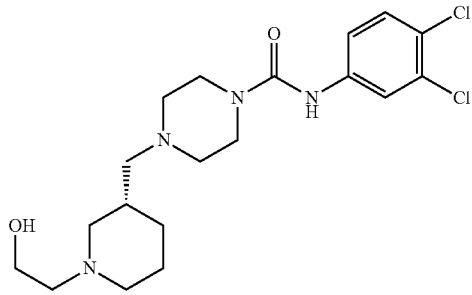 [SMILES: O=C(Nc1ccc(Cl)c(Cl)c1)N1CCN(C[C@@H]2CCCN(CCO)C2)CC1]

N-(3,4-Dichlorophenyl)-4-{[(3S)-1-(2-hydroxyethyl)piperidin-3-yl]methyl}piperazine-1-carboxamide N-(3,4-Dichlorophenyl)-4-[(3R)]-piperidin-3-ylmethylpiperazine-1-carboxamide (1.48 g, 4 mmols) and glycolaldehyde (300 mg, 5 mmols) were stirred at room temperature in dichloromethane (100 ml) for approximately 15 minutes. Added to this mixture was sodium triacetoxyborohydride (2.65 g, 12.5 mmols) and the reaction stirred overnight at room temperature. The reaction mixture was then washed using sodium bicarbonate solution and the organic layer dried (MgSO$_4$) filtered then concentrated in vacuo onto silica gel (1 g). The resulting solid was subjected to chromatography on silica gel (50 g) using a gradient of 100% dichloromethane through to 20% methanolic ammonia in dichloromethane to give the title compound as a white solid (440 mg)

LCMS M/z(+) 415.23, 417.13 (M+H$^+$).

LCMS M/z(−) 415.20, 413.30 (M−H$^−$).

$^1$H NMR (400.132 MHz, DMSO-d$_6$) 0.90 (1H, m), 1.45 (1H, m), 1.58 (1H, m), 1.67 (1H, m), 1.78 (1H, m), 1.91 (1H, m), 2.13 (2H, m), 2.39 (5H, m), 3.30 (5H, m), 3.46 (5H, m), 4.28 (1H, s), 7.43 (2H, dd), 7.82 (1H, s), 8.80 (1H, s).

As a variation of Route C1 the following example was prepared as shown below.

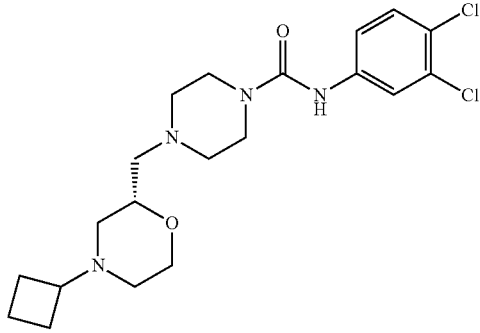 [SMILES: O=C(Nc1ccc(Cl)c(Cl)c1)N1CCN(C[C@H]2CN(C3CCC3)CCO2)CC1]

4-{[(2S)-4-Cyclobutylmorpholin-2-yl]methyl}-N-(3,4-dichlorophenyl)piperazine-1-carboxamide To a stirred solution of N-(3,4-Dichlorophenyl)-4-[(2R)-morpholin-2-ylmethyl]piperazine-1-carboxamide (bis TFA salt) (200 mg) in THF (10 ml) under an argon atmosphere was added MgSO$_4$ (100 mg), cyclobutyl ketone (41 uL), N,N-diisopropylethylamine (0.34 mL) then NaBH(OAc)$_3$ (155 mg) and the reaction was stirred for 18 h. The solvent was then removed under reduced pressure and dissolved in ethyl acetate (40 ml) and sat. aqueous NaHCO$_3$ (20 ml). The organic layer was separated, dried (MgSO$_4$) and evaporated. Purification by column chromatography 5-20% MeOH:DCM afforded the title compound (99 mg) as a white foam.

LCMS M/z(+) 427, 429 (M+H$^+$).

$^1$H NMR (400.132 MHz, CDCl$_3$) 1.50-2.15 (9H, m), 2.32 (1H, dd), 2.55 (5H, m), 2.80 (2H, m), 3.50 (4H, m), 3.75 (2H, m), 3.93 (1H, m), 6.32 (1H, s), 7.21 (1H, d), 7.30 (1H, d), 7.62 (1H, d).

The following examples were prepared by an analogous method from the corresponding ketones.

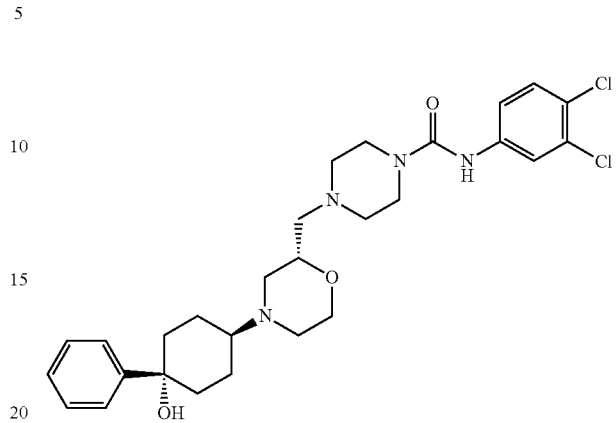

N-(3,4-Dichlorophenyl)-4-{[(2S)-4-(trans-4-hydroxy-4-phenylcyclohexyl)morpholin-2-yl]methyl}piperazine-1-carboxamide LCMS M/z(+) 547, 549 (M+H$^+$).

$^1$H NMR (400.132 MHz, CDCl$_3$) 1.60-2.60 (17H, m), 2.90 (2H, m), 3.50 (4H, m), 3.65 (2H, m), 3.78 (1H, m), 3.92 (1H, d), 6.48 (1H, s), 7.20 (1H, d), 7.30 (2H, m), 7.37 (2H, t), 7.55 (2H, d), 7.59 (1H, s).

The other diastereomer was also isolated from the same reaction.

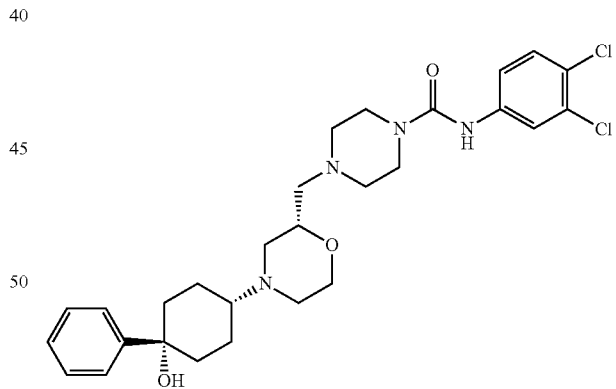

N-(3,4-Dichlorophenyl)-4-{[(2S)-4-(cis-4-hydroxy-4-phenylcyclohexyl)morpholin-2-yl]methyl}piperazine-1-carboxamide LCMS M/z(+) 547, 549 (M+H$^+$).

$^1$H NMR (400.132 MHz, CDCl$_3$) 1.55-2.62 (17H, m), 2.90 (2H, m), 3.50 (5H, m), 3.72 (2H, m), 3.95 (1H, d), 6.35 (1H, s), 7.20 (1H, dd), 7.28 (1H, m), 7.30 (3H, m), 7.46 (2H, d), 7.60 (1H, s).

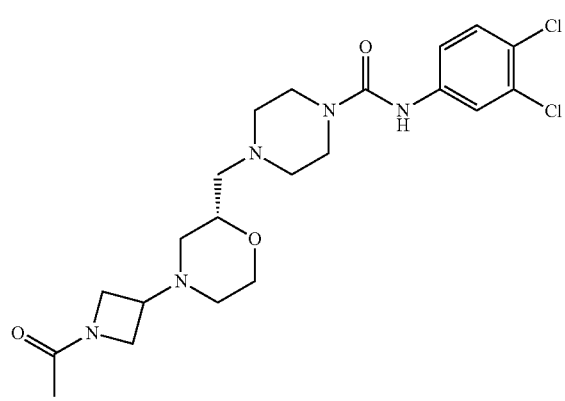 [SMILES: CC(=O)N1CC(N2CCO[C@@H](CN3CCN(C(=O)Nc4ccc(Cl)c(Cl)c4)CC3)C2)C1]

4-{[(2S)-4-(1-Acetylazetidin-3-yl)morpholin-2-yl]methyl}-N-(3,4-dichlorophenyl)-piperazine-1-carboxamide Standard reductive amination conditions using tert-butyl 3-oxoazetidine-1-carboxylate (Jpn. Kokai Tokkyo Koho, 2002255932, 11 Sep. 2002) as the ketone component afforded impure tert-butyl 3-{(2S)-2-[(4-{[(3,4-dichlorophenyl)amino]carbonyl}piperazin-1-yl)methyl]morpholin-4-yl}azetidine-1-carboxylate (250 mg, 70% purity). TFA/DCM (1:3, 30 mL) was then added to the crude material followed by stirring for 18 h. The solvent was then evaporated under reduced pressure. The reaction was then quenched by addition of 1M NaOH (aq.) (10 ml) and DCM (15 ml). The organic layer was separated and dried (MgSO$_4$), filtered and evaporated to afford the crude 4-{[(2S)-4-azetidin-3-ylmorpholin-2-yl]methyl}-N-(3,4-dichlorophenyl)piperazine-1-carboxamide product which was used without further purification.

Triethylamine (61 uL) was added to a stirring solution of 4-{[(2S)-4-azetidin-3-ylmorpholin-2-yl]methyl}-N-(3,4-dichlorophenyl)piperazine-1-carboxamide (125 mg) in DCM (5 ml) followed by Ac$_2$O (30 uL) and the reaction was stirred for 3 h. The reaction was then quenched by addition of 1M NaOH (aq.) (10 ml) and DCM (15 ml). The organic layer was separated and dried (MgSO$_4$), filtered and evaporated. Purification by column chromatography 5-10% MeOH:DCM afforded the title compound (31 mg) as a white foam.

LCMS M/z(+) 468, 470 (M+H$^+$).

$^1$H-NMR (400.132 MHz, CDCl$_3$) 1.51-1.82 (6H, m), 1.86 (3H, s), 2.22 (2H, m), 2.40 (2H, m), 2.50 (2H, m), 2.73 (1H, m), 2.88 (1H, m), 3.12 (2H, m), 3.50 (4H, m), 3.86 (1H, m), 4.02 (2H, m), 4.13 (1H, m), 6.47 (1H, s), 7.22 (1H, m, 7.31 (1H, d), 7.61 (1H, s).

The following examples were prepared by a similar method respectively from pyridin-3-ylacetaldehyde (J. Chem. Soc.; 1950; 1678-1681) and pyridin-4-ylacetaldehyde the latter being prepared by acid hydrolysis (3M. HCl/THF, reflux 2 h) of 3-[2-methoxyvinyl]pyridine (E/Z 1:1) (Chem. Europ. J.; 6; 11; 2000; 2053-2062) and was used without purification.

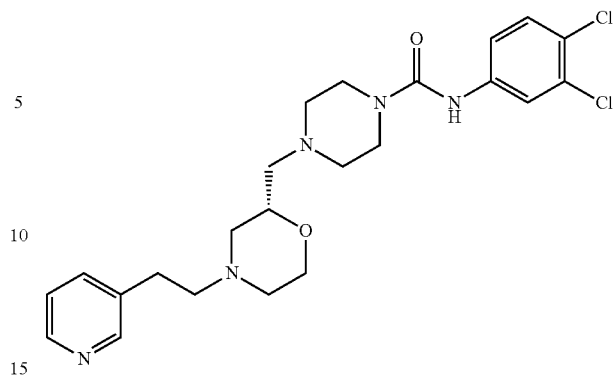

N-(3,4-Dichlorophenyl)-4-{[(2S)-4-(2-pyridin-3-ylethyl)morpholin-2-yl]methyl}piperazine-1-carboxamide LCMS M/z(+) 478, 480 (M+H$^+$).

$^1$H NMR (400.132 MHz, CDCl$_3$) 1.92 (1H, t), 2.20 (1H, m), 2.32 (1H, dd), 2.55 (7H, m), 2.80 (4H, m), 3.50 (4H, m), 3.65 (1H, m), 3.72 (1H, m), 3.90 (1H, d), 6.51 (1H, s), 7.20 (2H, m), 7.31 (1H, d), 7.53 (1H, d), 7.59 (1H, s), 8.47 (2H, m).

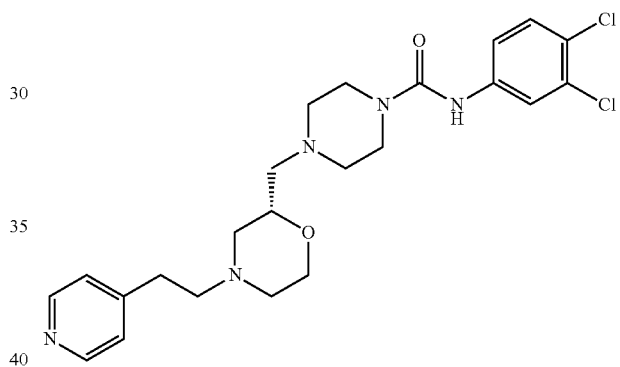

N-(3,4-Dichlorophenyl)-4-{[(2S)-4-(2-pyridin-4-ylethyl)morpholin-2-yl]methyl}piperazine-1-carboxamide LCMS M/z(+) 478, 480 (M+H$^+$).

$^1$H NMR (400.132 MHz, CDCl$_3$) 1.92 (1H, t), 2.20 (1H, m), 2.30 (1H, dd), 2.57 (7H, m), 2.78 (4H, m), 3.50 (4H, m), 3.70 (2H, m), 3.92 (1H, m), 6.38 (1H, s), 7.15 (2H, m), 7.19 (1H, d), 7.31 (1H, d), 7.50 (1H, s), 8.51 (2H, d).

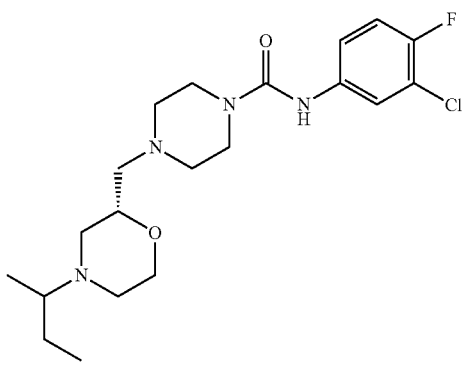 [SMILES: CCC(C)N1CCO[C@@H](CN2CCN(C(=O)Nc3ccc(F)c(Cl)c3)CC2)C1]

N-(3-chloro-4-fluorophenyl)-4-({(2R)-4-[(1R)-1-methylpropyl]morpholin-2-yl}methyl)piperazine-1-carboxamide To a stirred solution of N-(3-chloro-4-fluorophenyl)-4-[(2R)-morpholin-2-ylmethyl]piperazine-1-carboxamide (300 mg, 0.84 mmol) and 2-butanone (0.16 ml, 1.12 mmol) in THF:DCM, 1:1 (8 ml), was added titanium tetraisopropoxide (1.99 ml, 6.72 mmol) and the reaction stirred at ambient temperature for 3 hours. Sodium tris-acetoxyborohydride (356 mg, 1.68 mmol) was added and the reaction stirred overnight. 2M NaOH was then added and the cloudy mixture filtered through celite. The filtrate was then extracted with EtOAc (×2), organics dried ($Na_2SO_4$), filtered and evaporated to a yellow oil. This was then purified by reverse phase HPLC using basic modifier to give the product as a yellow gum (42 mg, 0.11 mmol, 13% yield).

LCMS M/z(+) 413.25 (M+H$^+$).

$^1$H-NMR (400.132 MHz, DMSO-d$_6$) 0.80-0.94 (m, 6H), 1.18-1.30 (m, 1H), 1.40-1.53 (m, 1H), 2.01-2.66 (m, 10H), 3.10-3.52 (m, 6H+water), 3.74 (m, 1H), 7.28 (t, 1H), 7.40 (m, 1H) and 7.74 (m, 1H).

The N-(3-chloro-4-fluorophenyl)-4-[(2R)-morpholin-2-ylmethyl]piperazine-1-carboxamide used in the above variant of Route C1 was prepared using the following procedures.

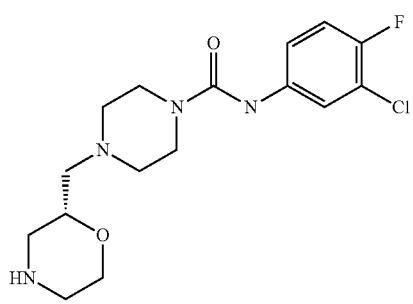 [SMILES: O=C(Nc1ccc(F)c(Cl)c1)N1CCN(C[C@H]2CNCCO2)CC1]

N-(3-chloro-4-fluorophenyl)-4-[(2R)-morpholin-2-ylmethyl]piperazine-1-carboxamide To a stirred solution of tert-butyl (2S)-2-[(4-{[(3-chloro-4-fluorophenyl)amino]carbonyl}piperazin-1-yl)methyl]morpholine-4-carboxylate (9.867 g, 21.6 mmol) in dichloromethane (100 ml) was added TFA (100 ml). The reaction was allowed to stir at ambient temperature for 2 hours. The solvents were then removed in vacuo, residue partitioned between DCM and 2M NaOH, extracted twice and the combined organics dried ($Na_2SO_4$), filtered and evaporated to dryness to give the product as an off white solid (7.69 g, 21.6 mmol, 100%).

LCMS M/z(+) 357.32 (M+H$^+$).

$^1$H-NMR (400.132 MHz, CDCl$_3$) 0.80-0.94 2.20-2.30 (m, 1H), 2.40-2.60 (m, 6H), 2.76-2.92 (m, 3H), 3.37-3.48 (m, 4H), 3.51-3.68 (m, 2H), 3.79-3.86 (m, 1H), 6.44 (s, 1H), 6.96 (t, 1H), 7.10 (m, 1H) and 7.40 (m, 1H).

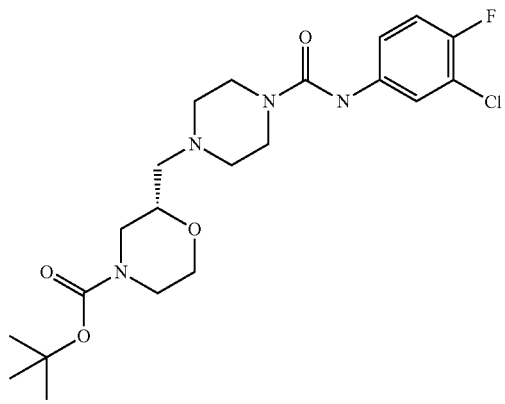 [SMILES: CC(C)(C)OC(=O)N1CCO[C@@H](CN2CCN(C(=O)Nc3ccc(F)c(Cl)c3)CC2)C1]

tert-butyl (2S)-2-[(4-{[(3-chloro-4-fluorophenyl)amino]carbonyl}piperazin-1-yl)methyl]morpholine-4-carboxylate To a stirred solution of tert-butyl (2S)-2-(piperazin-1-ylmethyl)morpholine-4-carboxylate (7.46 g, 26.1 mmol) in dichloromethane (100 ml) was added 3-chloro-4-fluoro phenylisocyanate (3.26 ml, 26.1 mmol) and the reaction stirred at ambient temperature overnight. After this time a white solid had precipitated out, this was filtered off and dried to give 16348-063-A (3.351 g, 7.33 mmol, 28%). The filtrate was then concentrated in vacuo and the residue purified on Isco™ Companion (120 g column: 5% MeOH/DCM) to give the product as an off white foam (6.59 g, 14.4 mmol, 55%).

LCMS M/z(+) 455.08 (M+H$^+$).

$^1$H-NMR (400.132 MHz, CDCl$_3$) 1.49 (s, 9H), 2.35 (dd, 1H), 2.49-2.70 (m, 6H), 2.92 (m, 1H), 3.42-3.61 (m, 6H), 3.80-4.10 (m, 3H), 6.65 (s, 1H), 7.10 (t, 1H), 7.17 (m, 1H), and 7.49 (dd, 1H).

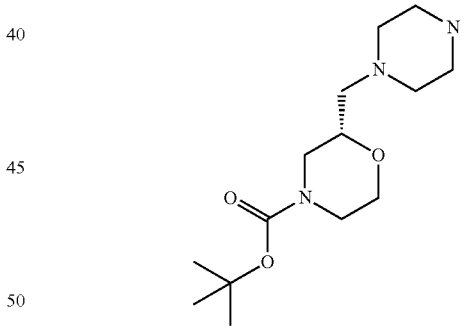

tert-butyl (2S)-2-(piperazin-1-ylmethyl)morpholine-4-carboxylate tert-Butyl (2S)-2-({4-[(benzyloxy)carbonyl]piperazin-1-yl}methyl)morpholine-4-carboxylate (11.16 g, 26.6 mmol) was hydrogenated over 10% palladium on carbon (500 mg) in ethanol (100 ml). The catalyst was then filtered off through a pad of celite and filtrate evaporated to dryness to give a dark yellow solid. This was then purified on Isco™ Companion (120 g column: 10% Methanolic ammonia/DCM) to give the product as a pale yellow solid (7.46 g, 26.1 mmol, 98%).

$^1$H-NMR (400.132 MHz, CDCl$_3$) 1.55 (s, 9H), 2.42 (dd, 1H), 2.56-2.68 (m, 1H), 2.72 (m, 4H), 2.96 (m, 3H), 3.14 (m, 4H), 3.48-3.68 (m, 2H), 3.80-4.08 (m, 3H) and 5.78 (bs, 1H).

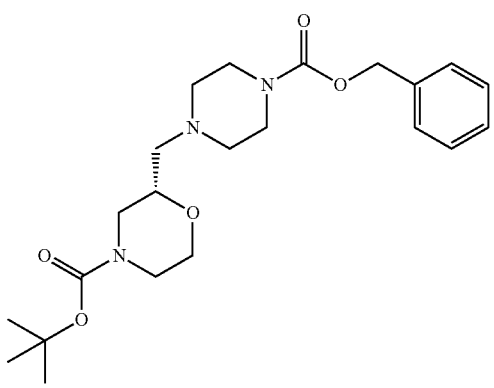 [SMILES: CC(C)(C)OC(=O)N1CCO[C@@H](CN2CCN(C(=O)OCc3ccccc3)CC2)C1]

tert-Butyl (2S)-2-({4-[(benzyloxy)carbonyl]piper-azin-1-yl}methyl)morpholine-4-carboxylate tert-Butyl (2R)-2-{[(methylsulfonyl)oxy]methyl}morpholine-4-carboxylate (75 g, 0.25 mol), sodium iodide (11.4 g, 76 mmol), potassium carbonate (38 g, 0.28 mol) and benzyl-1-piperazine carboxylate (54 mL, 0.28 mol) were heated together in butyronitrile (1.5 L) at 115° C. for 24 hours. Water (1.8 L) was added and the layers separated, the aqueous phase was washed with ethyl acetate (1 L) and the combined organics were washed with brine (1 L), dried ($MgSO_4$) and evaporated to give crude product as a yellow oil. Chromatography (5 kg column: 20% ethyl acetate to 50% ethyl acetate in isohexane) gave product as pale yellow gum (73 g, 0.17 mol, 70%).

$^1$H-NMR (400.132 MHz, $CDCl_3$) 1.46 (s, 9H), 2.33 (dd, 1H), 2.42-2.65 (m, 6H), 2.91 (m, 1H), 3.45-3.60 (m, 6H), 3.80-3.95 (m, 3H), 5.13 (s, 2H), 7.29-7.39 (m, 5H).

As a variation of Route C1 the following example was prepared as shown below.

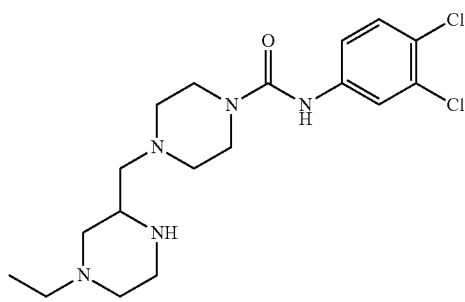

N-(3,4-Dichlorophenyl)-4-[(4-ethylpiperazin-2-yl)methyl]piperazine-1-carboxamide To benzyl 2-[(4-{[(3,4-dichlorophenyl)amino]carbonyl}piperazin-1-yl)methyl]-4-ethylpiperazine-1-carboxylate (20 mg) was added 4M HCl in dioxane (1 ml). The solvent was evaporated, 1-methyl-2-pyrrolidinone (1 ml), zinc bromide (10 mg) and 10% palladium on carbon (50 mg) added and the mixture stirred under hydrogen at RT for 72 hours. Evaporation to dryness and purification on a 10 g SCX2 column, eluting sequentially with ethyl acetate, MeOH and 1% ammonia/MeOH gave the title compound (9 mg, 60%) by precipitation from $CH_2Cl_2$ with isohexane.

LCMS M/z(+) 399 (M+H$^+$), 422.2 (M+Na$^+$).

$^1$H NMR (400.132 MHz, DMSO-$d_6$) 0.84 (3H, m), 0.99 (1H, m), 1.21 (2H, m), 2.34 (8H, m), 3.45 (8H, m), 7.46 (2H, m), 7.84 (1H, m), 8.00 (1H, m), 8.75 (1H, m).

The benzyl 2-[(4-{[(3,4-dichlorophenyl)amino]carbonyl}piperazin-1-yl)methyl]-4-ethylpiperazine-1-carboxylate used in the above procedure was prepared as follows.

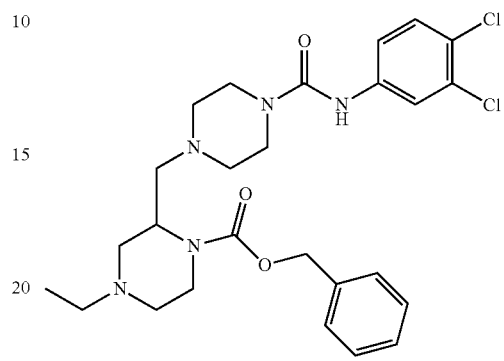

Benzyl 2-[(4-{[(3,4-dichlorophenyl)amino]carbonyl}piperazin-1-yl)methyl]-4-ethylpiperazine-1-carboxylate Benzyl 2-[(4-{[(3,4-dichlorophenyl)amino]carbonyl}piperazin-1-yl)methyl]piperazine-1-carboxylate and acetaldehyde were used in a similar manner to N-(3,4-dichlorophenyl)-4-{[(2S)-4-(2-pyridin-3-ylethyl)morpholin-2-yl]methyl}piperazine-1-carboxamide, except that after purification of the residue on a Redisep® silica column, eluting with ethyl acetate/MeOH (30:70), the solid, after precipitation from $CH_2Cl_2$ with isohexane, was further purified on an SCX column, eluting sequentially with ethyl acetate, MeOH and 1% ammonia/MeOH to give the title product (20 mg, 18%).

LCMS M/z(−) 532.2 (M−H$^−$), M/z(+) 534.2 (M+H$^+$).

$^1$H NMR (400.132 MHz, DMSO-$d_6$) 0.84 (2H, m), 0.99 (1H, m), 1.15 (1H, m), 1.27 (1H, m), 2.33 (6H, m), 3.66 (1H, m), 3.85 (1H, m), 4.13 (1H, m), 4.29 (1H, m), 5.11 (2H, m), 7.39 (5H, m), 7.84 (1H, s), 8.01 (1H, s), 8.03 (1H, s), 8.12 (1H, m), 8.72 (1H, m) (with 6H obscured).

The benzyl 2-[(4-{[(3,4-dichlorophenyl)amino]carbonyl}piperazin-1-yl)methyl]piperazine-1-carboxylate used in the above procedure was prepared as follows.

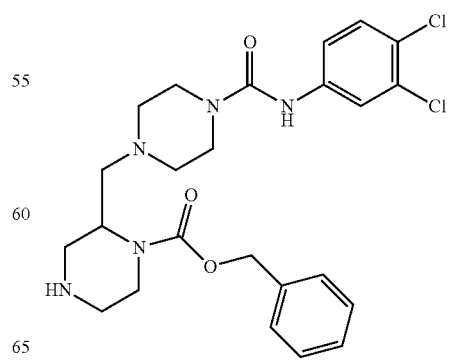

Benzyl 2-[(4-{[(3,4-dichlorophenyl)amino]carbonyl}piperazin-1-yl)methyl]piperazine-1-carboxylate To 1-benzyl 4-tert-butyl 2-[(4-{[(3,4-dichlorophenyl)amino]carbonyl}piperazin-1-yl)methyl]piperazine-1,4-dicarboxylate (332 mg) was added 4M HCl in dioxane (5 ml). The mixture was stirred at RT for 16 hours. Saturated aqueous sodium bicarbonate was added, followed by extraction into CH$_2$Cl$_2$ and evaporation. The residue was purified on a Redisep® SiO$_2$ column, eluting with 0-20% MeOH/CH$_2$Cl$_2$ to give, after precipitation from CH$_2$Cl$_2$ with isohexane, the title product as a solid (130 mg, 47%).

LCMS M/z(−) 504.25 (M−H⁻), M/z(+) 506.23 (M+H⁺).

$^1$H NMR (400.132 MHz, DMSO-d$_6$) 2.38 (4H, m), 2.91 (5H, m), 3.66 (1H, m), 3.88 (1H, m), 4.13 (1H, m), 4.28 (1H, m), 5.11 (2H, m), 7.35 (5H, m), 7.46 (2H, m), 7.84 (1H, s), 8.13 (1H, m), 8.74 (1H, m) (with 4H obscured).

The 1-benzyl 4-tert-butyl 2-[(4-{[(3,4-dichlorophenyl)amino]carbonyl}piperazin-1-yl)methyl]piperazine-1,4-dicarboxylate used in the above procedure was prepared as follows.

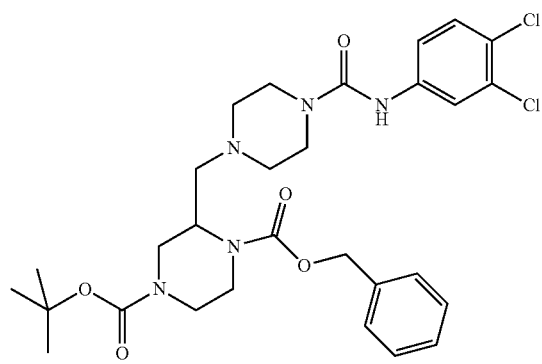 [SMILES: CC(C)(C)OC(=O)N1CCN(C(=O)OCc2ccccc2)C(CN2CCN(C(=O)Nc3ccc(Cl)c(Cl)c3)CC2)C1]

1-Benzyl 4-tert-butyl 2-[(4-{[(3,4-dichlorophenyl)amino]carbonyl}piperazin-1-yl)methyl]piperazine-1,4-dicarboxylate To 1-benzyl 4-tert-butyl 2-formylpiperazine-1,4-dicarboxylate (227 mg) in THF (20 ml) were added N-(3,4-dichlorophenyl)piperazine-1-carboxamide (179 mg), DIPEA (319 ul) DMF (1.6 ml) and MgSO$_4$ (30 mg) the mixture stirred at room temperature for 30 minutes, sodium triacetoxyborohydride (277 mg) added and stirring continued for 16 hours at room temperature. Saturated aqueous sodium bicarbonate and ethyl acetate were added. The organic phase was dried (MgSO4) and evaporated to give the title compound as a semi-solid gum (331 mg, 84%).

LCMS M/z(−) 604.25 (M−H⁻) M/z(+) 606.23 (M+H⁺).

$^1$H NMR (400.132 MHz, DMSO-d$_6$) 1.41 (9H, m), 1.92 (1H, m), 2.38 (4H, m), 2.96 (2H, m), 3.38 (6H, m), 3.97 (4H, m), 5.10 (2H, m), 7.35 (5H, m), 7.46 (2H, m), 7.84 (1H, m), 8.72 (1H, m).

The 1-benzyl 4-tert-butyl 2-formylpiperazine-1,4-dicarboxylate used in the above procedure was prepared as follows.

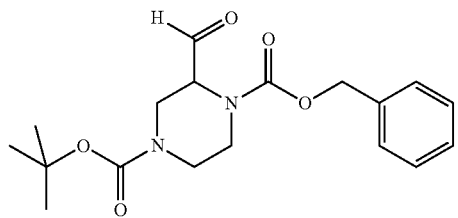 [SMILES: CC(C)(C)OC(=O)N1CCN(C(=O)OCc2ccccc2)C(C=O)C1]

1-Benzyl 4-tert-butyl 2-formylpiperazine-1,4-dicarboxylate

To 1-benzyl 4-tert-butyl 2-(hydroxymethyl)piperazine-1,4-dicarboxylate (0.4 g) in CH$_2$Cl$_2$ (10 ml) under argon was added Dess Martin periodinane (533 mg), the mixture stirred at room temperature for 16 hours, evaporated to half volume, saturated aqueous sodium bicarbonate and ethyl acetate added, the organic phase dried (MgSO$_4$), and evaporated to give the title compound (228 mg, 57%).

$^1$H NMR (400.132 MHz, DMSO-d$_6$) 1.38 (9H, m), 2.96 (2H, m), 3.20 (1H, m), 3.83 (2H, m), 4.47 (1H, m), 4.74 (1H, m), 5.12 (2H, m), 7.35 (5H, m), 9.56 (1H, s).

The 1-benzyl 4-tert-butyl 2-(hydroxymethyl)piperazine-1,4-dicarboxylate used in the above procedure was prepared as follows.

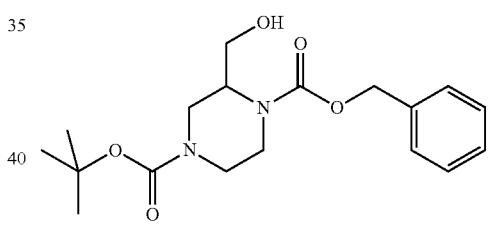

1-Benzyl 4-tert-butyl 2-(hydroxymethyl)piperazine-1,4-dicarboxylate

To 1-[(benzyloxy)carbonyl]-4-(tert-butoxycarbonyl)piperazine-2-carboxylic acid (1 g) in anhydrous THF (11 ml) under argon, cooled to 0° C. was added 1M borane in THF (11 ml) and the mixture allowed to warm to room temperature over 3.5 hours. After cooling to 0° C., MeOH was added and stirring continued for 72 hours. The solvents were evaporated, saturated aqueous sodium bicarbonate and ethyl acetate added, the organic phase dried (MgSO$_4$) and evaporated to give the title compound (0.88 g, 92%).

LCMS M/z(+) 373.12 (M+Na⁺).

$^1$H NMR (400.132 MHz, DMSO-d$_6$) 1.46 (9H, m), 2.95 (3H, m), 3.46 (2H, m), 3.87 (2H, m), 4.05 (2H, m), 4.85 (1H, m), 5.15 (2H, m), 7.39 (5H, m).

The 1-[(benzyloxy)carbonyl]-4-(tert-butoxycarbonyl)piperazine-2-carboxylic acid used in the above procedure is commercially available and was purchased from Astatech, Inc., USA.

As a variation of Route C1 the following example was prepared as shown below.

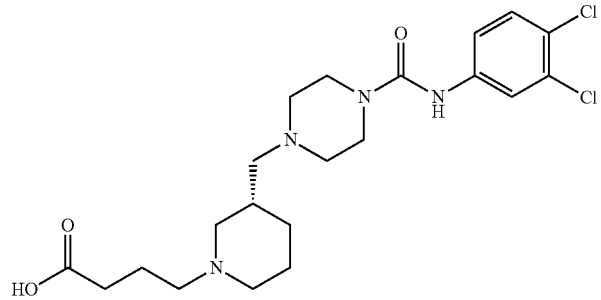

4-{(3R)-3-[(4-{[(3,4-Dichlorophenyl)amino]carbonyl}piperazin-1-yl)methyl]piperidin-1-yl}butanoic acid To a solution of methyl 4-{(3R)-3-[(4-{[(3,4-dichlorophenyl)amino]carbonyl}piperazin-1-yl)methyl]piperidin-1-yl}butanoate (80 mg) in tetrahydrofuran (5 mL) was added 1M aqueous lithium hydroxide (1 mL). The mixture was stirred overnight at room temperature. The mixture was then loaded directly onto an SCX-2 column and eluted with methanol then 7M $NH_3$ in methanol. The basic fraction was concentrated at reduced pressure and the residue was purified using reverse phase HPLC eluting with a mixture of 5-95% acetonitrile in water and then SCX-2 column eluting with methanol then 7M $NH_3$ in methanol to give the title compound as a white solid (60 mg, 77%).

LCMS M/z(+) 456.83 (M+H$^+$).

$^1$H NMR (400.132 MHz, DMSO-d$_6$) 0.83-1.00 (m, 1H), 1.40-1.53 (m, 1H), 1.58-1.72 (m, 4H), 1.74-1.83 (m, 2H), 2.01 (t, 1H), 2.10-2.23 (m, 2H), 2.26 (t, 2H), 2.28-2.41 (m, 6H), 2.80 (d, 1H), 2.87 (d, 1H), 3.38 (s, 1H), 3.44 (t, 4H), 7.43-7.49 (m, 2H), 7.83-7.85 (m, 1H), 8.76 (s, 1H).

The methyl 4-{(3R)-3-[(4-{[(3,4-dichlorophenyl)amino]carbonyl}piperazin-1-yl)methyl]piperidin-1-yl}butanoate was prepared using the following procedure.

Methyl 4-{(3R)-3-[(4-{[(3,4-dichlorophenyl)amino]carbonyl}piperazin-1-yl)methyl]piperidin-1-yl}butanoate To a solution of methyl 4-{(3S)-3-[(4-{[(3,4-dichlorophenyl)amino]carbonyl}piperazin-1-yl)methyl]piperidin-1-yl}-4-oxobutanoate (240 mg) in tetrahydrofuran (5 mL) at room temperature under argon was added a 1M solution of $BH_3$ in THF (1 mL). The solution was heated to reflux temperature for 1 hour and then cooled to ambient temperature. The reaction was quenched with methanol and then concentrated at reduced pressure. To the residue was added saturated HCl in methanol (10 mL) and the mixture was heated to reflux temperature for 1 hour and then cooled to ambient temperature. The mixture was stirred at ambient temperature overnight and then concentrated at reduced pressure. The residue was purified using reverse phase HPLC eluting with a mixture of 5-95% acetonitrile in water and then SCX-2 column eluting with methanol then 7M $NH_3$ in methanol to give methyl 4-{(3R)-3-[(4-{[(3,4-dichlorophenyl)amino]carbonyl}piperazin-1-yl)methyl]piperidin-1-yl}butanoate (80 mg, 34%).

LCMS M/z(+) 470.86 (M+H$^+$).

$^1$H NMR (400.132 MHz, DMSO-d$_6$) 0.80-0.96 (m, 1H), 1.34-1.50 (m, 1H), 1.54-1.81 (m, 6H), 1.89 (t, 1H), 2.08-2.42 (m, 10H), 2.62-2.72 (m, 1H), 2.77 (d, 1H), 3.44 (t, 4H), 3.59 (s, 3H), 7.43-7.49 (m, H), 7.83-7.85 (m, 1H), 8.75 (s, 1H).

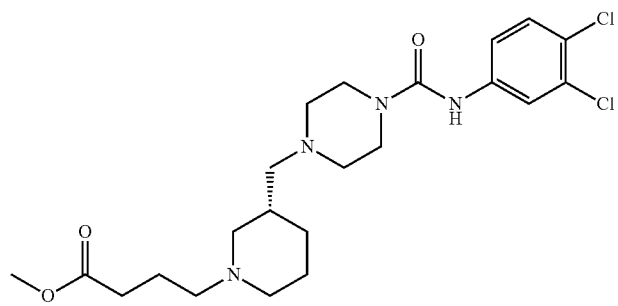

N-(3,4-dichlorophenyl)-4-{[(3R)-1-(4-hydroxybutyl)piperidin-3-yl]methyl}piperazine-1-carboxamide (28 mg, 13%) was also isolated under the above reaction conditions.

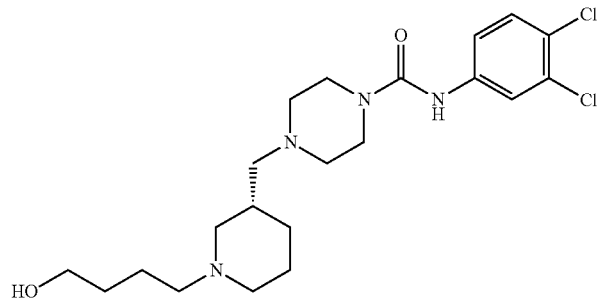

N-(3,4-Dichlorophenyl)-4-{[(3R)-1-(4-hydroxybutyl)piperidin-3-yl]methyl}piperazine-1-carboxamide LCMS M/z(+) 442.89 (M+H$^+$).

$^1$H NMR (400.132 MHz, DMSO-d$_6$) 0.80-0.95 (m, 1H), 1.35-1.50 (m, 4H), 1.52-1.94 (m, 6H), 2.09-2.40 (m, 8H), 2.66-2.87 (m, 2H), 3.19-3.49 (m, 7H), 7.43-7.49 (m, 2H), 7.83-7.85 (m, 1H), 8.76 (s, 1H).

The methyl 4-{(3S)-3-[(4-{[(3,4-dichlorophenyl)amino]carbonyl}piperazin-1-yl)methyl]piperidin-1-yl}-4-oxobutanoate was prepared using the following procedure.

The basic fraction was concentrated at reduced pressure and the residue was purified by silica column chromatography, eluting with a gradient of 0 to 10% methanol in dichloromethane to give the title compound as a white foam (252 mg, 96%).

LCMS M/z(+) 484.86 (M+H$^+$).

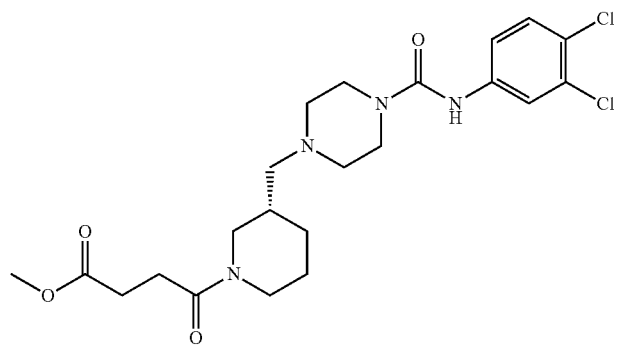

Methyl 4-{(3S)-3-[(4-{[(3,4-dichlorophenyl)amino]carbonyl}piperazin-1-yl)methyl]piperidin-1-yl}-4-oxobutanoate To a solution of N-(3,4-dichlorophenyl)-4-[3R)-piperidin-3-ylmethyl]piperazine-1-carboxamide (200 mg), N,N-di-isopropylethylamine (0.19 mL) and monomethyl succinate (79 mg) in dimethylformamide (5 mL) was added O-(7-Azabenzotriazol-1-Yl)—N,N,N',N'-Tetramethyluronium Hexafluoro-Phosphate. The solution was stirred at room temperature overnight and then loaded directly onto an SCX-2 column and eluted with methanol then 7M NH$_3$ in methanol.

The following compound was made in analogous fashion.

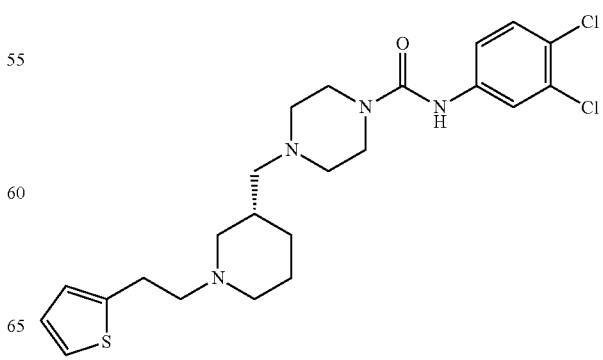

N-(3,4-Dichlorophenyl)-4-({(3R)-1-[2-(2-thienyl)ethyl]piperidin-3-yl}methyl)piperazine-1-carboxamide LCMS M/z(+) 481.06 (M+H+).

$^1$H NMR (400.132 MHz, CDCl$_3$) 0.84-1.01 (m, 1H), 1.36-2.15 (m, 7H), 2.16-2.27 (m, 2H), 2.33-2.43 (m, 2H), 2.45-2.54 (m, 2H), 2.61-2.80 (m, 2H), 2.85-3.21 (m, 3H), 3.42-3.53 (m, 4H), 6.37 (s, 1H), 6.83 (d, 1H), 6.89-6.94 (m, 1H), 7.10-7.14 (m, 1H), 7.20 (dd, 1H), 7.32 (d, 1H), 7.60 (d, 1H).

N-(3,4-dichlorophenyl)-4-{[(3S)-1-(2-thienylacetyl)piperidin-3-yl]methyl}piperazine-1-carboxamide was then reduced using an identical procedure as previously detailed in a variation of Route C1 to provide N-(3,4-dichlorophenyl)-4-({(3R)-1-[2-(2-thienyl)ethyl]piperidin-3-yl}methyl)piperazine-1-carboxamide.

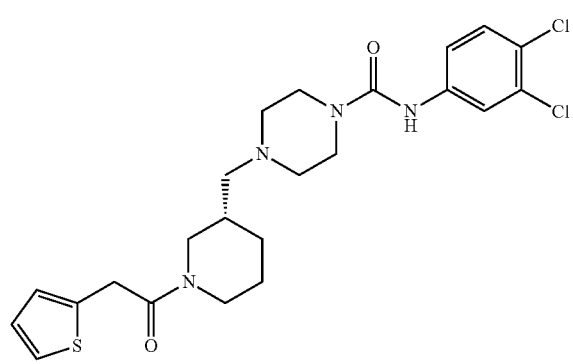 [SMILES: O=C(Cc1cccs1)N1CCC[C@@H](CN2CCN(C(=O)Nc3ccc(Cl)c(Cl)c3)CC2)C1]

N-(3,4-Dichlorophenyl)-4-{[(3S)-1-(2-thienylacetyl)piperidin-3-yl]methyl}piperazine-1-carboxamide To a solution of N-(3,4-dichlorophenyl)-4-[(3R)-piperidin-3-ylmethyl]piperazine-1-carboxamide (150 mg) and triethylamine (0.11 mL) in tetrahydrofuran (5 mL) at room temperature was added 2-thiopheneacetyl chloride under argon at room temperature. The solution was stirred for 30 minutes and then quenched with methanol. The mixture was loaded onto a SCX-2 column and eluted with methanol then 7M NH$_3$ in methanol. The basic fraction was concentrated and the residue purified by silica column chromatography, eluting with a gradient of 0 to 10% methanol in dichloromethane to give the title compound as a yellow oil (150 mg, 75%).

LCMS M/z(+) 496.88 (M+H+).

Route C2

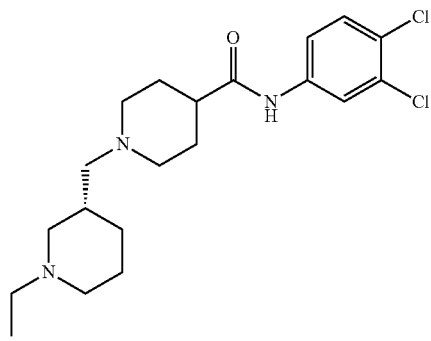 [SMILES: CCN1CCC[C@@H](CN2CCC(C(=O)Nc3ccc(Cl)c(Cl)c3)CC2)C1]

N-(3,4-Dichlorophenyl)-1-{[(3R)-1-ethylpiperidin-3-yl]methyl}piperidine-4-carboxamide A mixture of N-(3,4-dichlorophenyl)-1-[(3R)-piperidin-3-ylmethyl]piperidine-4-carboxamide (100 mg), potassium carbonate (41 mg) and ethyl bromide (0.022 mL) in dimethylformamide (4 ml) was stirred at room temperature for 24 hours. The reaction mixture was partitioned between dichloromethane and water. The organic layer was separated, dried over magnesium sulfate and evaporated. The residue was purified by silica column chromatography, eluting with a gradient of 0 to 10% 7M NH$_3$/MeOH in dichloromethane to give the title compound as a white solid (80 mg, 74%).

LCMS M/z(+) 398 (M+H+).

$^1$H NMR (400.132 MHz, CDCl$_3$): 0.78-0.94 (1H, m), 1.08 (3H, t), 1.49-2.03 (12H, m), 2.14 (2H, d), 2.12-2.27 (1H, m), 2.30-2.50 (2H, m), 2.89 (2H, d), 2.99 (2H, d), 7.16 (1H, s), 7.29-7.38 (2H, m), 7.77 (1H, d).

As a variation of Route C2 the following example was prepared as shown below.

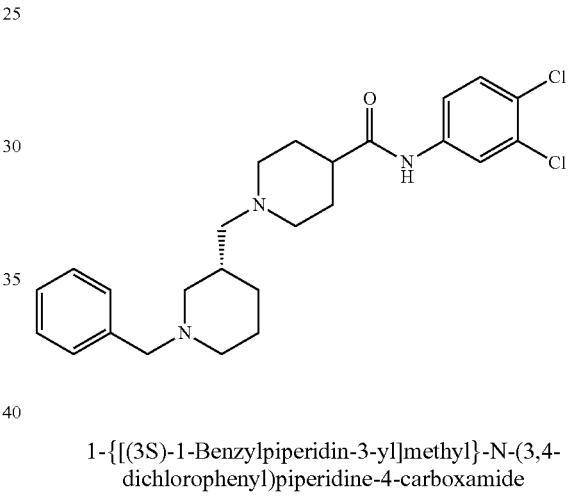

1-{[(3S)-1-Benzylpiperidin-3-yl]methyl}-N-(3,4-dichlorophenyl)piperidine-4-carboxamide To a mixture of N-(3,4-dichlorophenyl)-1-[(3R)-piperidin-3-ylmethyl]piperidine-4-carboxamide (150 mg) and benzaldehyde (0.04 mL) in dichloromethane was added sodium triacetoxyborohydride (103 mg). The reaction mixture was stirred at room temperature for 18 hours. The reaction was incomplete so sodium triacetoxyborohydride (50 mg) was added and the mixture was stirred for 48 hours. The reaction mixture was partitioned between dichloromethane and water and the organic layer was washed with brine. The organic extract was dried over magnesium sulfate and evaporated. The residue was purified by silica column chromatography, eluting with a gradient of 0 to 10% MeOH in dichloromethane to give the title compound as a white solid (28 mg, 15%)

LCMS M/z(+) 460 (M+H+).

$^1$H NMR (400.132 MHz, CDCl$_3$) 0.77-2.30 (14H, m), 2.80-3.09 (4H, m), 3.35-3.80 (3H, m), 7.20-7.41 (7H, m), 7.78 (1H, s).

The N-(3,4-dichlorophenyl)-1-[(3R)-piperidin-3-ylmethyl]piperidine-4-carboxamide used in Route C2 was prepared using the following procedure.

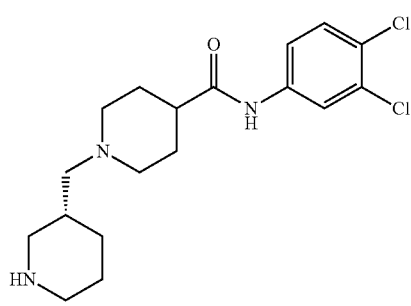 [SMILES: O=C(Nc1ccc(Cl)c(Cl)c1)C1CCN(C[C@@H]2CCCNC2)CC1]

N-(3,4-Dichlorophenyl)-1-[(3R)-piperidin-3-ylmethyl]piperidine-4-carboxamide To a solution of tert-butyl (3S)-3-[(4-{[(3,4-dichlorophenyl)amino]carbonyl}piperidin-1-yl)methyl]piperidine-1-carboxylate (2.3 g) in methanol (50 mL) was added 4M HCl in dioxane (15 mL). The mixture was stirred at room temperature for 18 hours and then evaporated. The residue was then partitioned between dichloromethane and saturated aqueous sodium hydrogen carbonate. The layers were separated and the organic extract was evaporated. The residue was triturated with dichloromethane and filtered to give the title compound as a white solid (1.5 g, 83%)

LCMS M/z(+) 370 (M+H$^+$).

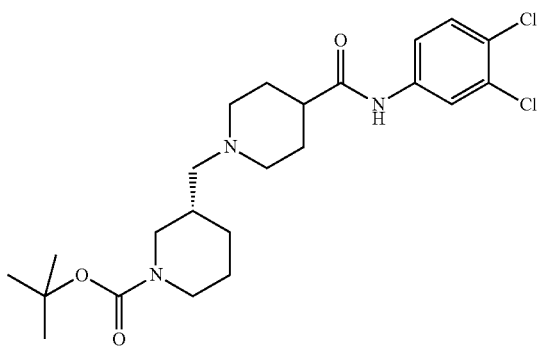 [SMILES: CC(C)(C)OC(=O)N1CCC[C@@H](CN2CCC(C(=O)Nc3ccc(Cl)c(Cl)c3)CC2)C1]

tert-Butyl (3S)-3-[(4-{[(3,4-dichlorophenyl)amino]carbonyl}piperidin-1-yl)methyl]piperidine-1-carboxylate To a mixture of N-(3,4-dichlorophenyl)piperidine-4-carboxamide hydrochloride (1.55 g) in dichloromethane (100 mL) was added di-iso-propylethylamine (1.3 mL). The solution was stirred for 15 minutes after which tert-butyl (3R)-3-formylpiperidine-1-carboxylate (1.17 g) and sodium triacetoxyborohydride (1.59 g) was added. The reaction was stirred at room temperature overnight. The reaction mixture was partitioned between dichloromethane and water and the aqueous layer extracted with dichloromethane. The combined organic layers were washed with brine, dried over magnesium sulfate and evaporated to give the title compound as a white foam (2.34 g, 100%).

LCMS M/z(+) 470 (M+H$^+$).

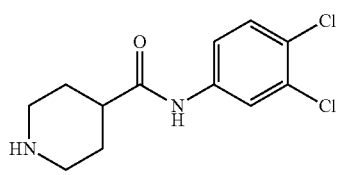 [SMILES: O=C(Nc1ccc(Cl)c(Cl)c1)C1CCNCC1]

N-(3,4-Dichlorophenyl)piperidine-4-carboxamide hydrochloride

To a solution of tert-butyl 4-{[(3,4-dichlorophenyl)amino]carbonyl}piperidine-1-carboxylate (3.0 g) in dichloromethane (15 mL) was added 4M HCl in dioxane (15 mL). The mixture was stirred at room temperature for 1 hour and then filtered to give the title compound as a white solid (2.2 g, 100%).

LCMS M/z(+) 273 (M+H$^+$).

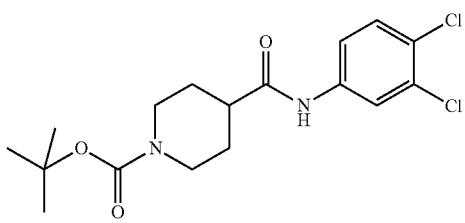 [SMILES: CC(C)(C)OC(=O)N1CCC(C(=O)Nc2ccc(Cl)c(Cl)c2)CC1]

tert-Butyl 4-{[(3,4-dichlorophenyl)amino]carbonyl}piperidine-1-carboxylate

To a solution of 1-(tert-butoxycarbonyl)piperidine-4-carboxylic acid (2 g) in dichloromethane (300 mL) was added the N-[3-(dimethylamino)propyl]-N'-ethylcarbodiimide (1.84 g) and 1-hydroxybenzotriazole (1.3 g). The mixture was stirred at room temperature for 15 minutes after which 3,4-dichloroanaline (1.55 g) was added. The reaction was stirred overnight at room temperature. The reaction mixture was partitioned between dichloromethane and water and the organic layer was washed with brine. The organic extract was dried over magnesium sulfate and evaporated. The residue was purified by silica column chromatography, eluting with a gradient of 0 to 40% ethyl acetate in hexane to give the title compound as a pink solid (3.1 g, 95%).

LCMS M/z(+) 273 (M-BOC+H$^+$).

The 1-(tert-butoxycarbonyl)piperidine-4-carboxylic acid used in the above procedure is commercially available and was purchased from Apollo Scientifc Ltd.

Route C3

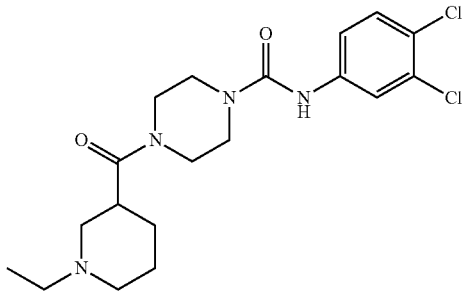 [SMILES: CCN1CCCC(C(=O)N2CCN(C(=O)Nc3ccc(Cl)c(Cl)c3)CC2)C1]

N-(3,4-Dichlorophenyl)-4-[(1-ethylpiperidin-3-yl)carbonyl]piperazine-1-carboxamide To a solution of N-(3,4-dichlorophenyl)-4-(piperidin-3-ylcarbonyl)piperazine-1-carboxamide hydrochloride (200 mg) in dimethylformamide (10 mL) was added potassium carbonate (138 mg) and ethyl bromide (0.035 mL). The reaction mixture was stirred overnight. The reaction mixture was partitioned between dichloromethane and water and the organic layer was washed with brine. The organic extract was dried over sodium sulfate and evaporated. The residue was purified by silica column chromatography, eluting with a gradient of 0 to 10% MeOH in dichloromethane to give the title compound as a white solid (94 mg, 48%).

LCMS M/z(+) 413 (M+H$^+$)

$^1$H NMR (400.132 MHz, CDCl$_3$) 1.08 (3H, t), 1.45-1.70 (2H, m), 1.73-1.96 (3H, m), 2.14 (1H, t), 2.44 (2H, q), 2.75-2.85 (1H, m), 2.87-3.00 (2H, m), 3.40-3.75 (8H, m), 6.72 (1H, s), 7.22 (1H, dd), 7.33 (1H, d), 7.56 (1H, d).

The N-(3,4-dichlorophenyl)-4-(piperidin-3-ylcarbonyl)piperazine-1-carboxamide hydrochloride used in Route C3 was prepared using the following procedures.

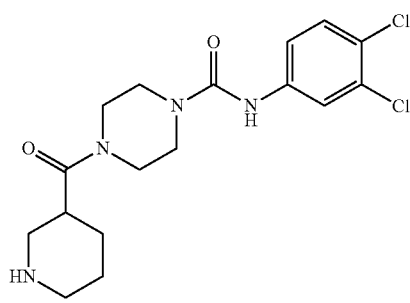 [SMILES: O=C(Nc1ccc(Cl)c(Cl)c1)N1CCN(C(=O)C2CCCNC2)CC1]

N-(3,4-Dichlorophenyl)-4-(piperidin-3-ylcarbonyl)piperazine-1-carboxamide hydrochloride To a solution of tert-butyl 3-[(4-{[(3,4-dichlorophenyl)amino]carbonyl}piperazin-1-yl)carbonyl]piperidine-1-carboxylate (1 g) in dichloromethane (40 mL) was added 4M HCl in dioxane (6 mL) and methanol (5 mL). The mixture was stirred at room temperature for 2 hours and then evaporated to give the title compound as a white foam (0.87 g, 100%).

LCMS M/z(+) 385 (M+H$^+$).

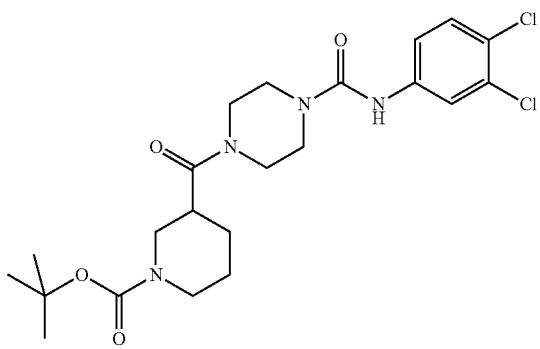 [SMILES: CC(C)(C)OC(=O)N1CCCC(C(=O)N2CCN(C(=O)Nc3ccc(Cl)c(Cl)c3)CC2)C1]

tert-Butyl 3-[(4-{[(3,4-dichlorophenyl)amino]carbonyl}piperazin-1-yl)carbonyl]piperidine-1-carboxylate To a mixture of N-(3,4-dichlorophenyl)piperazine-1-carboxamide hydrochloride (1.0 g) in dichloromethane (100 mL) was added N,N-di-iso-propylethylamine (0.56 mL) at room temperature. After 10 minutes N-[3-(dimethylamino)propyl]-N-ethylcarbodiimide (617 mg) was added followed by 1-(tert-butoxycarbonyl)piperidine-3-carboxylic acid (671 mg) and 1-hydroxybenzotriazole (435 mg). The reaction was stirred overnight at room temperature. The reaction mixture was partitioned between dichloromethane and water and the organic layer was washed with brine. The organic extract was dried over magnesium sulfate and evaporated. The residue was purified by silica column chromatography, eluting with a gradient of 0 to 15% ethyl acetate in hexane to give the title compound as a white foam (1.4 g, 99%).

LCMS M/z(+) 385 (M-BOC+H$^+$).

The 1-(tert-butoxycarbonyl)piperidine-3-carboxylic acid used in the above procedure is commercially available and was purchased from Aldrich Chemical Company, Inc.

As a variation of Route C3 the following example was prepared as shown below.

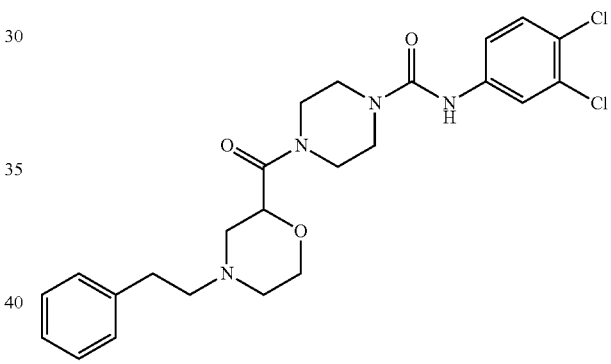

N-(3,4-Dichlorophenyl)-4-{[4-(2-phenylethyl)morpholin-2-yl]carbonyl}piperazine-1-carboxamide To a stirred solution of N-(3,4-dichlorophenyl)-4-(morpholin-2-ylcarbonyl)piperazine-1-carboxamide (350 mg) in dichloromethane (10 ml) under an argon atmosphere was added phenacetaldehyde (0.16 mL) then NaBH(OAc)$_3$ (383 mg) and the reaction was stirred for 3.5 h. The solvent was then removed under reduced pressure and dissolved in dichloromethane (40 ml) and 1M NaOH (20 ml). The organic layer was separated, dried (MgSO$_4$) and evaporated. Purification by column chromatography 3-7% MeOH:DCM afforded the title compound (170 mg) as a white foam.

LCMS M/z(+) 491, 493 (M+H$^+$).

$^1$H NMR (400.132 MHz, CDCl$_3$) 2.30 (1H, m), 2.46 (1H, t), 2.68 (2H, m), 2.80 (3H, m), 3.02 (1H, d), 3.70 (10H, m), 4.25 (1H, dd), 6.36 (1H, s), 7.30 (7H, m), 7.60 (1H, s).

The N-(3,4-dichlorophenyl)-4-(morpholin-2-ylcarbonyl)piperazine-1-carboxamide used in Route C3 was prepared using the following procedures.

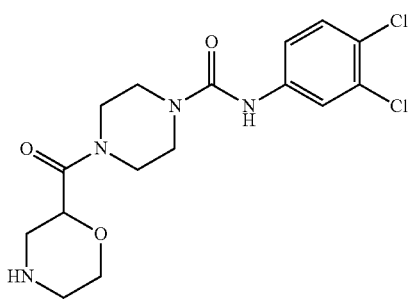 [SMILES: O=C(Nc1ccc(Cl)c(Cl)c1)N1CCN(C(=O)C2CNCCO2)CC1]

N-(3,4-Dichlorophenyl)-4-(morpholin-2-ylcarbonyl)piperazine-1-carboxamide

Trifluoroacetic acid/dichloromethane (1:1, 10 ml) was added to tert-butyl 2-[(4-{[(3,4-dichlorophenyl)amino]carbonyl}piperazin-1-yl)carbonyl]morpholine-4-carboxylate (900 mg, impure) followed by stirring for 30 min. The solvent was removed under reduced pressure then taken up in 1M. NaOH (aq.) (30 ml) and extracted with ethyl acetate (3×30 ml). The combined organic layers were dried (MgSO$_4$), filtered and evaporated to form the title compound (700 mg) as a white foam which was used without further purification.

LCMS M/z(+) 387, 389 (M+H$^+$).

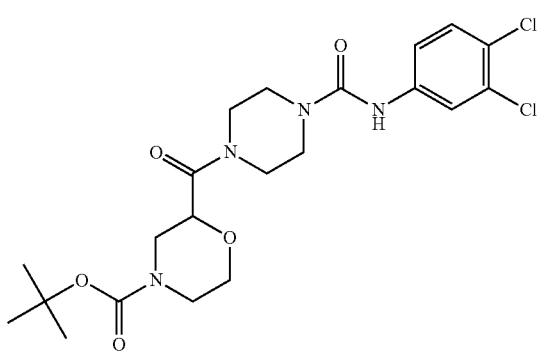 [SMILES: CC(C)(C)OC(=O)N1CCOC(C(=O)N2CCN(C(=O)Nc3ccc(Cl)c(Cl)c3)CC2)C1]

tert-Butyl 2-[(4-{[(3,4-dichlorophenyl)amino]carbonyl}piperazin-1-yl)carbonyl]morpholine-4-carboxylate N-(3,4-Dichlorophenyl)piperazine-1-carboxamide hydrochloride (467 mg) and 4-(tert-butoxycarbonyl)morpholine-2-carboxylic acid (347 mg) were dissolved in dry THF (10 mL) followed by addition of N,N-diisopropylethylamine (0.52 ml) and HATU (628 mg) and the reaction was stirred for 4 h. The solvent was evaporated under reduced pressure then redissolved in ethyl acetate (50 ml) followed by washing with sat. aqueous NaHCO$_3$ (20 ml), 10% w/v citric acid (aq.) (15 ml) and brine (15 ml). The organic layer was dried (MgSO$_4$), filtered and evaporated. Purification by chromatography (1:1 EtOAc:hexanes 1:1 to EtOAc neat) afforded the title compound (900 mg) as an impure foam contaminated with N,N,N',N'-tetramethylurea. The product was used without further purification.

LCMS M/z(+) 487, 489 (M+H$^+$).

$^1$H NMR (400.132 MHz, DMSO-d$_6$) 1.40 (9H, s), 3.45 (11H, m), 3.72 (1H, d), 3.81 (2H, m), 4.22 (1H, m), 7.43 (2H, m), 7.81 (1H, s), 8.82 (1H, s).

The 4-(tert-butoxycarbonyl)morpholine-2-carboxylic acid used in Route C3 is commercially available and was purchased from Neosystem Laboratoire.

As an additional alternative to Route C3, the following compounds were made as detailed below.

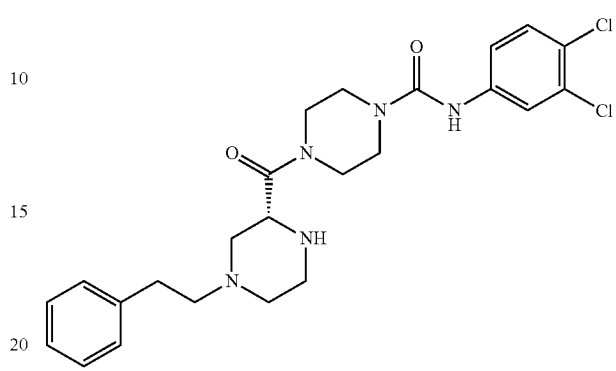

N-(3,4-Dichlorophenyl)-4-{[(2R)-4-(2-phenylethyl)piperazin-2-yl]carbonyl}piperazine-1-carboxamide In a similar manner to that described for N-(3,4-dichlorophenyl)-4-{[(3R)-1-(2-piperidin-4-ylethyl)piperidin-3-yl]methyl}piperazine-1-carboxamide, benzyl 2-[(4-{[(3,4-dichlorophenyl)amino]carbonyl}piperazin-1-yl)carbonyl]-4-(2-phenylethyl)piperazine-1-carboxylate (425 mg) was converted to N-(3,4-dichlorophenyl)-4-{[4-(2-phenylethyl)piperazin-2-yl]carbonyl}piperazine-1-carboxamide, obtained by precipitation from CH$_2$Cl$_2$ with isohexane to give the solid racemate (258 mg, 65%).

The racemate (100 mg) was separated using a Merck 50 mm 20 μm Chiralcel OJ column, eluting with MeOH, to give the title enantiomer which eluted first from the column (30 mg, 30%).

LCMS M/z(+) 488.21 (M−H$^−$), M/z(+) 490.23 (M+H$^+$).

$^1$H NMR (400.132 MHz, DMSO-d$_6$) 1.89 (2H, m), 2.70 (4H, m), 2.88 (2H, m), 3.52 (8H, m), 7.16 (1H, m), 7.21 (2H, m), 7.26 (2H, m), 7.46 (2H, m), 7.83 (1H, s), 8.85 (1H, s) (4 protons obscured).

The benzyl 2-[(4-{[(3,4-dichlorophenyl)amino]carbonyl}piperazin-1-yl)carbonyl]piperazine-1-carboxylate used above was prepared in a manner analogous to N-(3,4-dichlorophenyl)-4-{[(2S)-4-(2-pyridin-3-ylethyl)morpholin-2-yl]methyl}piperazine-1-carboxamide.

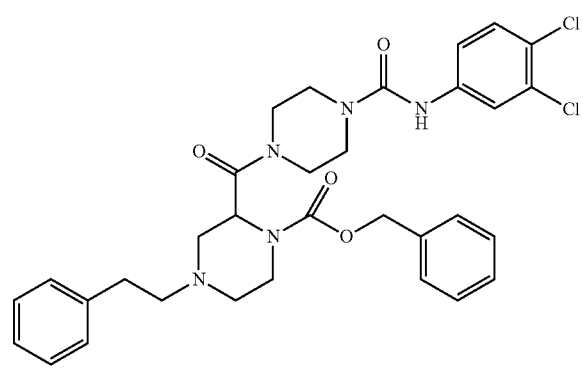 [SMILES: O=C(Nc1ccc(Cl)c(Cl)c1)N1CCN(C(=O)C2CN(CCc3ccccc3)CCN2C(=O)OCc2ccccc2)CC1]

Benzyl 2-[(4-{[(3,4-dichlorophenyl)amino]carbonyl}piperazin-1-yl)carbonyl]-4-(2-phenylethyl)piperazine-1-carboxylate LCMS M/z(−) 622.18 (M−H⁻), M/z(+) 624.19 (M+H⁺).
$^1$H NMR (400.132 MHz, DMSO-$d_6$) 2.03 (1H, m), 2.33 (1H, m), 2.69 (3H, m), 2.86 (2H, m), 3.08 (2H, m), 3.49 (8H, m), 3.72 (2H, m), 4.94 (1H, m), 5.12 (1H, m), 7.21 (10H, m), 7.48 (2H, m), 7.84 (1H, m), 8.85 (1H, m).

The benzyl 2-[(4-{[(3,4-dichlorophenyl)amino]carbonyl}piperazin-1-yl)carbonyl]piperazine-1-carboxylate used to prepare the above compound was prepared as detailed below.

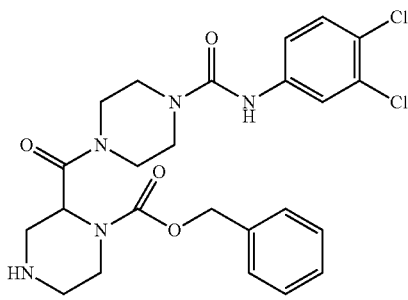 [SMILES: O=C(Nc1ccc(Cl)c(Cl)c1)N1CCN(C(=O)C2CNCCN2C(=O)OCc2ccccc2)CC1]

Benzyl 2-[(4-{[(3,4-dichlorophenyl)amino]carbonyl}piperazin-1-yl)carbonyl]piperazine-1-carboxylate To 1-benzyl 4-tert-butyl 2-[(4-{[(3,4-dichlorophenyl)amino]carbonyl}piperazin-1-yl)carbonyl]piperazine-1,4-dicarboxylate (6.61 g) in diethyl ether (50 ml) was added 4M HCl in dioxane (17.25 ml) and MeOH (10 ml) and the mixture heated at 65° C. for 16 hours. The mixture was allowed to cool, saturated aqueous sodium bicarbonate and ethyl acetate added and the organic phase separated, dried (MgSO4) and evaporated to a gum (4.8 g), used without further purification.

LCMS M/z(−) 518.17 (M−H⁻), M/z(+) 520.15 (M+H⁺).
$^1$H NMR (400.132 MHz, DMSO-$d_6$) 2.69 (3H, m), 2.89 (3H, m), 3.07 (2H, m), 3.47 (5H, m), 3.67 (2H, m), 4.82 (1H, m), 5.11 (2H, m), 7.31 (5H, m), 7.50 (2H, m), 7.85 (1H, m), 8.84 (1H, m).

The 1-benzyl 4-tert-butyl 2-[(4-{[(3,4-dichlorophenyl)amino]carbonyl}piperazin-1-yl)carbonyl]piperazine-1,4-dicarboxylate used in the above procedure was prepared as detailed below.

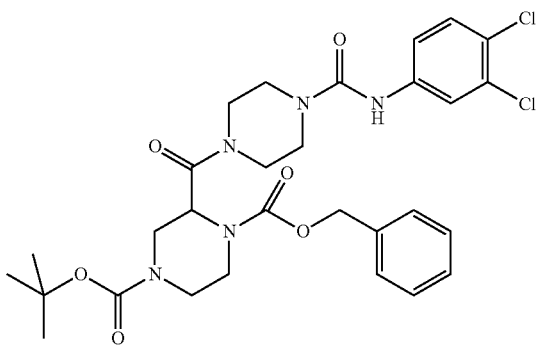 [SMILES: CC(C)(C)OC(=O)N1CCN(C(=O)OCc2ccccc2)C(C(=O)N2CCN(C(=O)Nc3ccc(Cl)c(Cl)c3)CC2)C1]

1-Benzyl 4-tert-butyl 2-[(4-{[(3,4-dichlorophenyl)amino]carbonyl}piperazin-1-yl)carbonyl]piperazine-1,4-dicarboxylate To N-(3,4-dichlorophenyl)piperazine-1-carboxamide (2.08 g) in DMF (30 ml) were added N,N-di-isopropylethylamine (3.69 ml), 1-benzyl 4-tert-butyl piperazine-1,2,4-tricarboxylic acid (2.76 g) and HATU (3.17 g) and the mixture stirred at room temperature for 16 hours. Saturated aqueous sodium bicarbonate and ethyl acetate were added, the organic phase washed with water, dried (MgSO4) and evaporated to give the title product which was used without further purification.

$^1$H NMR (400.132 MHz, DMSO-$d_6$) 1.36 (9H, m), 2.70 (2H, s), 3.18 (4H, m), 3.61 (5H, m), 4.06 (2H, m), 4.98 (2H, m), 5.11 (2H, m), 7.32 (5H, m), 7.48 (2H, m), 7.84 (1H, m), 8.87 (1H, m).

The 1-benzyl 4-tert-butyl piperazine-1,2,4-tricarboxylic acid used in the above procedure is commercially available and was purchased from Astatech, USA.

The following compounds were prepared in an analogous manner.

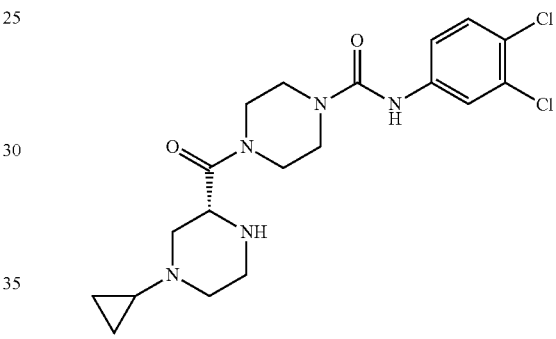

4-[(2R)(4-Cyclopropylpiperazin-2-yl)carbonyl]-N-(3,4-dichlorophenyl)piperazine-1-carboxamide In a similar manner to that described in N-(3,4-dichlorophenyl)-4-{[(3R)-1-(2-piperidin-4-ylethyl)piperidin-3-yl]methyl}piperazine-1-carboxamide, 4-{[(1-benzyloxycarbonyl-4-cyclopropyl)piperazin-2-yl]carbonyl}-N-(3,4-dichlorophenyl)piperazine-1-carboxamide (656 mg) gave after purification on a 20 g SCX column, eluting sequentially with isohexane, ethyl acetate and MeOH, followed by purification on a 12 g Redisep® SiO₂ column, eluting with 30-70% MeOH/ethyl acetate, after evaporation and trituration with isohexane, the product as a solid racemate (63 mg).

$^1$H NMR (400.132 MHz, DMSO-$d_6$) 0.29 (2H, m), 0.39 (2H, m), 0.83 (1H, m), 1.61 (1H, m), 2.09 (2H, m), 2.61 (2H, m), 2.74 (2H, m), 2.86 (3H, m), 3.51 (6H, m), 7.46 (2H, m), 7.83 (1H, s), 8.84 (1H, s).

The racemate (61 mg) was separated using a Chiralpak AD column, eluting with MeCN/MeOH (9:1), to give the title enantiomer (23 mg), which eluted first from the column.

LCMS M/z(−) 424.23 (M−H⁻), M/z(+) 426.23 (M+H⁺).
$^1$H NMR (400.132 MHz, DMSO-$d_6$) 0.50 (4H, m), 1.80 (1H, m), 2.40 (1H, m), 2.60 (1H, m), 3.00 (2H, m), 3.10 (1H, m) 3.50 (1H, m), 3.70 (4H, m), 4.50 (1H, m), 7.50 (2H, m), 7.80 (1H, m), 8.90 (1H, m), 9.20 (1H, m) (4H obscured)

The benzyl-4-cyclopropyl-2-[(4-{[(3,4-dichlorophenyl)amino]carbonyl}piperazin-1-yl)carbonyl]piperazine-1-carboxylate used in the above was prepared in a manner analogous to benzyl 4-{[(3R)-1-cyclopropylpiperidin-3-yl]methyl}piperazine-1-carboxylate.

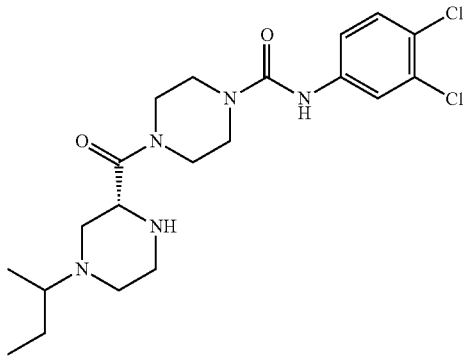 [SMILES: CCC(C)N1CCN[C@@H](C(=O)N2CCN(C(=O)Nc3ccc(Cl)c(Cl)c3)CC2)C1]

4-{[(2R)-4-sec-butylpiperazin-2-yl]carbonyl}-N-(3,4-dichlorophenyl)piperazine-1-carboxamide tert-Butyl (2R)-4-sec-butyl-2-[(4-{[(3,4-dichlorophenyl)amino]carbonyl}piperazin-1-yl)carbonyl]piperazine-1-carboxylate (75 mg) was dissolved in dichloromethane (5 ml), trifluoroacetic acid (1 ml) was added and the mixture stirred at room temperature overnight. The mixture was partitioned between dichloromethane (75 ml) and saturated aqueous sodium bicarbonate (15 ml) and the organic layer concentrated in vacuo and adsorbed onto silica for purification by chromatography eluting with 0-20% methanol/dichloromethane. This gave the product as a brittle white solid (41 mg).

LCMS M/z(+) 441.91 (M+H$^+$).

$^1$H NMR (300 MHz, DMSO-d$_6$) 0.85 (6H, m), 1.3 (1H, m), 1.5 (1H, m), 2.1-2.6 (4H, m), 2.75 (2H, d), 3.0 (1H, d), 3.2-3.7 (8H, m), 3.9 (1H, m), 7.5 (2H, m), 7.85 (1H, m), 8.9 (1H, s).

The tert-butyl (2R)-4-sec-butyl-2-[(4-{[(3,4-dichlorophenyl)amino]carbonyl}piperazin-1-yl)carbonyl]piperazine-1-carboxylate used in Route C3 was prepared using the following procedures.

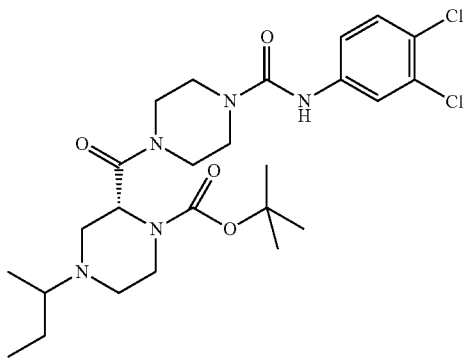 [SMILES: CCC(C)N1CCN(C(=O)OC(C)(C)C)[C@@H](C(=O)N2CCN(C(=O)Nc3ccc(Cl)c(Cl)c3)CC2)C1]

tert-Butyl (2R)-4-sec-butyl-2-[(4-{[(3,4-dichlorophenyl)amino]carbonyl}piperazin-1-yl)carbonyl]piperazine-1-carboxylate N-(3,4-Dichlorophenyl)-4-{[(2R)-4-tert-butoxycarbonylpiperazin-2-yl]carbonyl}piperazine-1-carboxamide (130 mg) was dissolved in THF (10 ml) and stirred at room temperature. Diisopropylethylamine (0.42 ml) was added followed by 2-butanone (0.8 ml) and magnesium sulphate (75 mg). After 45 minutes, sodium triacetoxyborohydride (1.82 g) was added and stirring continued overnight. Inorganic residues were removed by filtration and the filtrate concentrated in vacuo and adsorbed onto silica for purification by chromatography eluting with 0-10% methanol/dichloromethane. This gave the product as a white glass (80 mg).

LCMS M/z(+) 541.85 (M+H$^+$).

$^1$H NMR (300 MHz, DMSO-d$_6$) 0.6 (5H, m), 1.0 (3H, m), 1.2 (9H, m), 1.9-3.5 (15H, m), 4.6 (1H, m), 7.25 (2H, m), 7.6 (1H, s), 8.7 (1H, s).

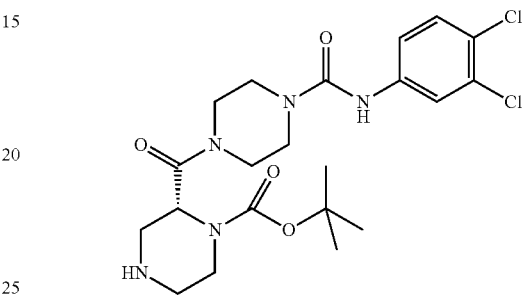

N-(3,4-Dichlorophenyl)-4-{[(2R)-4-tert-butoxycarbonylpiperazin-2-yl]carbonyl}piperazine-1-carboxamide N-(3,4-Dichlorophenyl)piperazine-1-carboxamide (596 mg) and (2R)-1-BOC-piperazine-2-carboxylic acid (500 mg) were dissolved in N,N-dimethylformamide (30 ml) and stirred at 0° C. Triethylamine (0.61 ml) was added followed by PYBOP reagent (1.13 g). The mixture was allowed to warm to room temperature overnight, poured into saturated aqueous sodium bicarbonate (60 ml) and extracted with ethyl acetate (2×100 ml), adding a little water during the process to dissolve precipitated sodium bicarbonate. The combined organic extracts were treated with brine (100 ml), dried (sodium sulphate), concentrated in vacuo and adsorbed onto silica for purification by chromatography eluting with 0-15% methanol/dichloromethane. This gave the product as a white glass (710 mg).

LCMS M/z(+) 485.96 (M+H$^+$).

$^1$H NMR (300 MHz, DMSO-d$_6$) 1.4 (9H, m), 2.7-3.7 (14H, m), 4.7 (1H, m), 7.4 (2H, m), 7.8 (1H, s), 8.9 (1H, s).

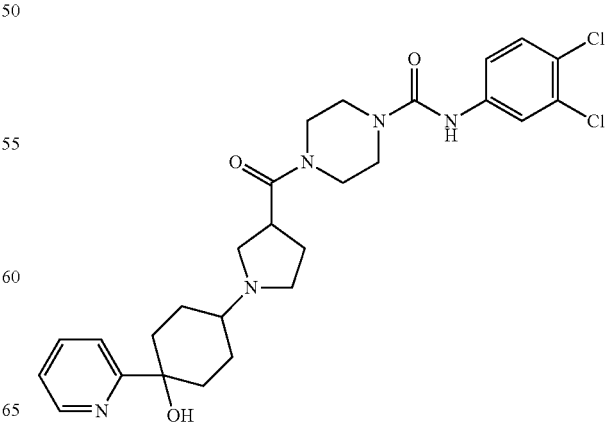

N-(3,4-dichlorophenyl)-4-{[1-(4-hydroxy-4-pyridin-2-ylcyclohexyl)pyrrolidin-3-yl]carbonyl}piperazine-1-carboxamide LCMS M/z(+) 546.81 (M+H⁺).

¹H NMR (400.132 MHz, CDCl₃) 1.51-1.80 (m, 4H), 1.91-2.00 (m, 2H), 2.05-2.16 (m, 2H), 2.23-2.40 (m, 3H), 2.06-2.13 (m, 1H), 2.75-2.85 (m, 2H), 2.84 (t, 1H), 3.22 (t, 1H), 3.49 (bs, 2H), 3.61 (bs, 4H), 3.75 (bs, 2H), 6.52 (s, 1H), 7.17-7.30 (m, 3H), 7.35 (d, 1H), 7.50 (s, 1H), 7.72 (t, 1H) and 8.52 (s, 1H).

Details for the preparation of the starting N-(3,4-Dichlorophenyl)-4-(pyrrolidin-3-ylcarbonyl)piperazine-1-carboxamide used to make N-(3,4-dichlorophenyl)-4-{[1-(4-hydroxy-4-pyridin-2-ylcyclohexyl)pyrrolidin-3-yl]carbonyl}piperazine-1-carboxamide are provided under Route C1.

Route D1

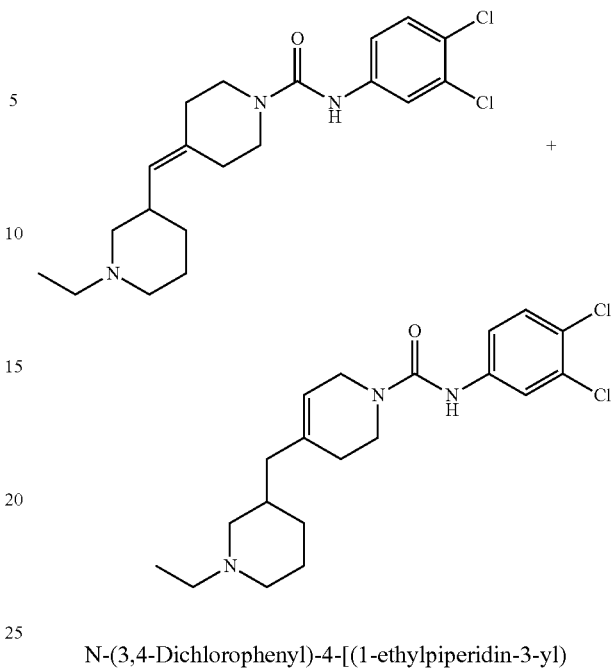

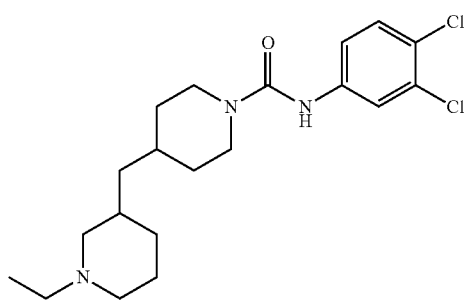 [SMILES: CCN1CCCC(CC2CCN(C(=O)Nc3ccc(Cl)c(Cl)c3)CC2)C1]

N-(3,4-Dichlorophenyl)-4-[(1-ethylpiperidin-3-yl)methyl]piperidine-1-carboxamide A mixture of the alkenes N-(3,4-dichlorophenyl)-4-[1-ethylpiperidin-3-yl)methyl]-3,6-dihydropyridine-1(2H)-carboxamide and N-(3,4-dichlorophenyl)-4-[(1-ethylpiperidin-3-yl)methylene]piperidine-1-carboxamide (3:1) (40 mg) and 10% palladium on charcoal (30 mg) in ethanol (5 mL) was evacuated and purged with hydrogen. The mixture was left under an atmosphere of hydrogen for 4 hrs and then filtered through celite. The celite pad was washed with ethanol and the filtrate evaporated. The residue was purified using reverse phase HPLC eluting with a mixture of 5-95% acetonitrile in water and then by silica column chromatography, eluting with a gradient of 0 to 5% 7M NH₃/MeOH in dichloromethane to give the title compound as a white solid (25 mg, 62%).

LCMS M/z(+) 398 (M+H⁺)

¹H NMR (400.132 MHz, CDCl₃) 0.85 (1H, dq), 1.08 (3H, t), 1.11-1.23 (1H, m), 1.14 (2H, t), 1.50-1.85 (10H, m), 3.30-2.46 (2H, m), 2.80-2.94 (4H, m), 4.01 (2H, d), 6.36 (1H, s), 7.19 (1H, dd), 7.31 (1H, d), 7.59 (1H, d).

The alkenes N-(3,4-dichlorophenyl)-4-[(1-ethylpiperidin-3-yl)methyl]-3,6-dihydropyridine-1(2H)-carboxamide and N-(3,4-dichlorophenyl)-4-[(1-ethylpiperidin-3-yl)methylene]piperidine-1-carboxamide (3:1) used in Route D1 were prepared using the following procedure.

N-(3,4-Dichlorophenyl)-4-[(1-ethylpiperidin-3-yl)methyl]-3,6-dihydropyridine-1(2H)-carboxamide and N-(3,4-dichlorophenyl)-4-[(1-ethylpiperidin-3-yl)methylene]piperidine-1-carboxamide (3:1 mixture respectively)

To a solution of N-(3,4-dichlorophenyl)-4-[(1-ethylpiperidin-3-yl)methyl]-4-hydroxypiperidine-1-carboxamide (93 mg) and triethylamine (0.08 mL) in dichloromethane (10 mL) at 5° C. was added methanesulfonyl chloride (0.02 mL) under argon. The mixture warmed to ambient temperature and was stirred overnight. Methanesulfonyl chloride (0.01 mL) and triethylamine (0.08 mL) were added to the mixture and stirring was continued for 5 hours. The mixture was then evaporated and the residue was purified by silica column chromatography, eluting with a gradient of 0 to 5% 7M NH₃/MeOH in dichloromethane to give the title compounds as a white solid (48 mg, 54%).

LCMS M/z(+) 396 (M+H⁺).

Route E1

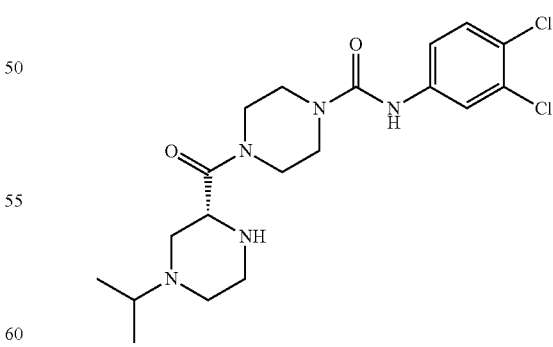

N-(3,4-Dichlorophenyl)-4-{[(2R)-4-isopropylpiperazin-2-yl]carbonyl}piperazine-1-carboxamide N-(3,4-Dichlorophenyl)piperazine-1-carboxamide hydrochloride (251 mg) and (2R)-1-(tert-Butoxycarbonyl)-4-isopropylpiperazine-2-carboxylic acid (200 mg) were dissolved in dry THF (10 mL) followed by addition of N,N-di-isopropylethylamine (0.26 ml) and HATU (335 mg) and the reaction was stirred for 4 h. A further 0.26 ml of N,N-di-iso-propylamine was added and the reaction was stirred for 18 h at rt. The solvent was evaporated under reduced pressure then redissolved in dichloromethane (50 ml) followed by washing with sat. aqueous NaHCO₃ (20 ml). The organic layer was separated on a phase separation cartridge and evaporated. Purification by chromatography (3-10% methanol:dichloromethane) afforded the crude product (180 mg) as a foam which was used without further purification. The foam was then dissolved in TFA/DCM (1:1, 10 ml) and stirred for 30 mins. The solvent was removed under reduced pressure then taken up in 1M. aqueous sodium hydroxide (30 ml) and extracted with dichloromethane (2×30 ml). The organic layer was separated on a phase separation cartridge and evaporated. Purification by chromatography (5-25% MeOH:DCM) afforded the title compound (95 mg) as a white foam.

LCMS M/z(+) 428, 430 (M+H⁺).

¹H NMR (400.132 MHz, CDCl₃) 1.30 (6H, m), 2.60 (1H, m), 2.75 (1H, m), 2.98 (1H, m), 3.20-3.83 (12H, m), 4.39 (1H, m), 6.55 (1H, s), 7.22 (1H, dd), 7.33 (1H, d), 7.63 (1H, d).

The (2R)-1-(tert-Butoxycarbonyl)-4-isopropylpiperazine-2-carboxylic acid used in Route E1 was prepared using the following procedure.

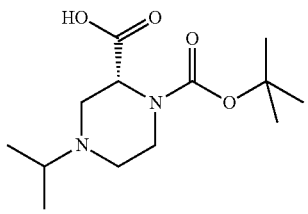 [SMILES: CC(C)N1CCN(C(=O)OC(C)(C)C)[C@@H](C(=O)O)C1]

(2R)-1-(tert-Butoxycarbonyl)-4-isopropylpiperazine-2-carboxylic acid

To (2R)-1-(tert-Butoxycarbonyl)piperazine-2-carboxylic acid (4.5 g) and Na₂CO₃ (8.32 g) was added dry ethanol (135 ml) then isopropyl iodide (2.16 ml) and the reaction heated at reflux for 18 h under argon. The solvent was then removed under reduced pressure and 5% MeOH/DCM (50 ml) was added and stirred for 1 hour in a sealed flask. The solution was filtered and washed through with dichloromethane (2×10 mL). The filtrate was then placed directly onto a 120 g-silica cartridge and was purified using eluent 10-70% MeOH/DCM. After evaporation, the product was isolated as a white foam (4.50 g), which was used without further purification.

¹H NMR (400.132 MHz, DMSO-d₆) 0.95 (6H, m), 1.40 (9H, 2×s), 2.30 (2H, m), 2.75 (2H, m), 2.95 (1H, t), 3.12 (1H, t), 3.70 (1H, m), 4.48 (1H, d), 12.60 (1H, br. s).

The following intermediates were used in the preparation of examples 303, 304 & 305.

(2R)-1-(tert-Butoxycarbonyl)-4-(prop-2-en-1-yl)piperazine-2-carboxylic acid used in Route E1 was prepared using the procedure described for (2R)-1-(tert-butoxycarbonyl)-4-isopropylpiperazine-2-carboxylic acid above but using prop-2-enyl bromide.

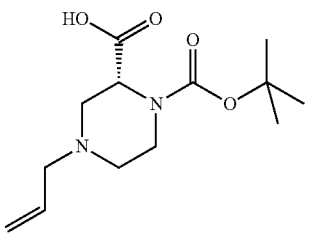 [SMILES: C=CCN1CCN(C(=O)OC(C)(C)C)[C@@H](C(=O)O)C1]

(2R)-1-(tert-Butoxycarbonyl)-4-(prop-2-en-1-yl)piperazine-2-carboxylic acid

LCMS M/z(−) 269.38 (M−H—).

¹H NMR (400.132 MHz, DMSO-d₆) 1.34, 1.38 (9H, 2×s), 1.83 (1H, dt), 1.97 (1H, m), 2.71 (1H, brt), 2.88 (2H, m), 3.05, 3.22, 3.31 (2H, rotamers, obscured), 3.62 (1H, d), 4.28 (1H, brd), 5.11 (1H, dd), 5.17 (1H, dd), 5.73 (1H, m). 2R)-1-(tert-Butoxycarbonyl)-4-(2-methylprop-2-en-1-yl)piperazine-2-carboxylic acid used in Route E1 was prepared using the procedure described for (2R)-1-(tert-butoxycarbonyl)-4-isopropylpiperazine-2-carboxylic acid above but using 2-methylprop-2-enyl bromide.

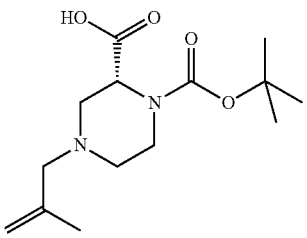 [SMILES: C=C(C)CN1CCN(C(=O)OC(C)(C)C)[C@@H](C(=O)O)C1]

(2R)-1-(tert-Butoxycarbonyl)-4-(2-methylprop-2-en-1-yl)piperazine-2-carboxylic acid LCMS M/z(−) 283.39 (M−H⁻).

¹H NMR (400.132 MHz, DMSO-d₆) 1.38, 1.42 (9H, 2×s), 1.66 (3H, s), 1.95 (2H, m), 2.72 (2H, m), 2.93 (1H, dd), 3.03 (1H, dt), 3.2 (obscured), 3.67 (1H, d), 4.43 (1H, d), 4.85 (2H, d).

(2R)-1-(tert-Butoxycarbonyl)-4-(prop-2-yn-1-yl)piperazine-2-carboxylic acid used in Route E1 was prepared using the procedure described for (2R)-1-(tert-butoxycarbonyl)-4-isopropylpiperazine-2-carboxylic acid above but using prop-2-ynyl bromide.

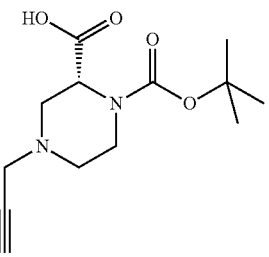 [SMILES: C#CCN1CCN(C(=O)OC(C)(C)C)[C@@H](C(=O)O)C1]

(2R)-1-(tert-Butoxycarbonyl)-4-(prop-2-yn-1-yl)piperazine-2-carboxylic acid

LCMS M/z(+) 269.36 (M+H⁺).
¹H NMR (400.132 MHz, DMSO-d₆) 1.35, 1.41 (9H, 2×s), 2.07 (1H, dt), 2.30 (1H, brm), 2.65-2.75 (1H, m), 3.01 (0.5H, t), 3.09 (1H, m), 3.1-3.24 (1.5H, m), 3.25 (2H, m), 3.68 (1H, d), 4.44 (1H, d).

(2R)-1-(tert-Butoxycarbonyl)-4-(propyl)piperazine-2-carboxylic acid used in Route E1 was prepared from the N-4-prop-2-yn-1-yl precursor as described below:—

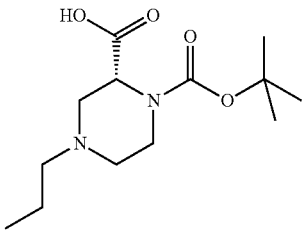 [SMILES: CCCN1CCN(C(=O)OC(C)(C)C)[C@@H](C(=O)O)C1]

(2R)-1-(tert-Butoxycarbonyl)-4-propylpiperazine-2-carboxylic acid

The N-prop-2-yn-1-yl compound (292 mg; 92% strength; ca. 1 mM) was dissolved in absolute ethanol (50 mL) and flushed with Argon. 10% Palladium on carbon (200 mg) was added and the mixture stirred under a hydrogen balloon for 20 hours, filtered through Celite and evaporated to give a solid (298 mg). Trituration with Et₂O gave a white solid (036/A1) (166 mg; 61%), containing 20% N⁴—H impurity, but from the ethereal solution was obtained the pure N-propyl product (96 mg; 35%) as a white solid, used without further purification.
¹H-NMR (DMSO-d₆) 0.81 (3H, t), 1.3-1.45 (>9H, 2×s), 1.88 (1H, m), 2.03 (1H, dt), 2.15-2.25 (2H, m), 2.74 (1H, dd), 2.98 (1H, dt), 3.15 (1H, dt), 3.2-3.3 (obscured, m), 3.64 (1H, d), 4.43 (1H, d), 12.4-12.8 (1H, br).

The following compound was made in an analogous fashion.

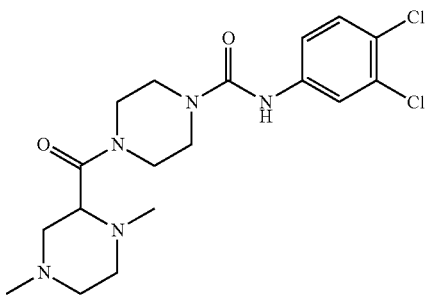 [SMILES: CN1CCN(C)C(C(=O)N2CCN(C(=O)Nc3ccc(Cl)c(Cl)c3)CC2)C1]

1-{[1,4-Dimethylpiperazin-3-yl]carbonyl}-N-(3,4-dichlorophenyl)piperazine-4-carboxamide LCMS M/z(+) 414.22 (M+H⁺).
¹H NMR (400.132 MHz, DMSO-d₆) 2.05-2.25 (3H, m, obscured), 2.13 (3H, s), 2.18 (3H, s), 2.56-2.68 (2H, m), 2.78 (1H, brd), 3.10-3.17 (<1H, m), 3.40-3.55 (6H, m), 3.8 (1H, brm), 3.86-3.98 (<1H, brm), 7.44 (1H, dd), 7.48 (1H, d), 7.83 (1H, d), 8.83 (1H, s).

The 1,4-dimethylpiperazin-2-yl carboxylic acid used in Route E1 was prepared using the following procedure.

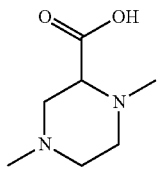

1,4-Dimethylpiperazin-2-yl carboxylic acid

Ethyl 1,4-dimethylpiperazin-2-yl carboxylic acid (1.86 g) was dissolved in EtOH (10 mL) and 5M aqueous NaOH (20 mL) added. The mixture was refluxed for 2 hours, allowed to cool, 10M HCl (9.1 mL) added to give pH4 and the mixture evaporated to dryness. The white solid was stirred with MeOH (25 mL), CH₂Cl₂ (10 mL) added and the filtrate evaporated to give, after trituration with Et₂O, the title compound as a grey solid (761 mg, 48%).

The ethyl 1,4-dimethylpiperazin-2-yl carboxylic acid used in the above procedure is commercial available and was purchased from Fluorochem.

The following compounds were made in an analogous fashion.

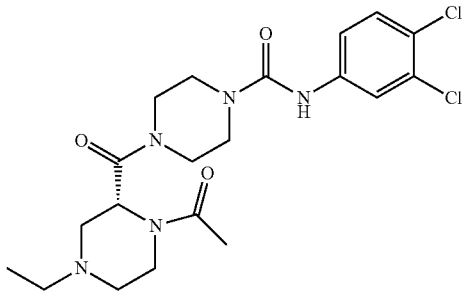 [SMILES: CCN1CCN(C(C)=O)[C@@H](C(=O)N2CCN(C(=O)Nc3ccc(Cl)c(Cl)c3)CC2)C1]

4-{[(2R)-1-Acetyl-4-ethylpiperazin-2-yl]carbonyl}-N-(3,4-dichlorophenyl)piperazine-1-carboxamide N-(3,4-Dichlorophenyl)-4-{[(2R)-4-ethylpiperazin-2-yl]carbonyl}piperazine-1-carboxamide (70 mg) in chloroform (1 ml) was cooled in an ice bath, triethylamine (19 ul) added, followed by acetyl chloride (10 ul) and the mixture stirred for 2 hours at 0° C. The mixture was diluted with CH₂Cl₂, washed with saturated aqueous sodium bicarbonate, the organic phase dried (MgSO₄), evaporated and the residue purified on a 4 g Redisep® SiO₂ column, eluting with 0-50% MeOH/CH₂Cl₂ to give the title compound as a colourless solid (35 mg, 45%).

LCMS M/z(−) 454.22 (M−H⁻), M/z(+) 456.23 (M+H⁺).
¹H NMR (400.132 MHz, CDCl₃) 1.07 (3H, m), 1.64 (3H, m), 2.13 (3H, m), 2.25 (1H, m), 2.37 (1H, m), 2.49 (1H, m), 2.89 (1H, m), 3.05 (1H, m), 3.56 (4H, m), 3.99 (1H, m), 5.30 (1H, m), 6.69 (1H, s), 7.20 (1H, s), 7.22 (2H, s), 7.33 (1H, s), 7.35 (1H, s), 7.59 (1H, m).

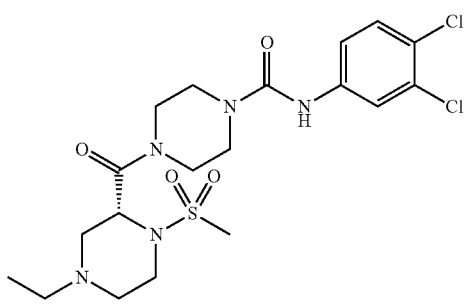 [SMILES: CCN1CCN(S(C)(=O)=O)[C@@H](C(=O)N2CCN(C(=O)Nc3ccc(Cl)c(Cl)c3)CC2)C1]

N-(3,4-Dichlorophenyl)-4-{[(2R)-4-ethyl-1-(methylsulfonyl)piperazin-2-yl]carbonyl}piperazine-1-carboxamide In this way, using methane sulphonylchloride (13 μl), N-(3,4-Dichlorophenyl)-4-{[(2R)-4-ethylpiperazin-2-yl]carbonyl}piperazine-1-carboxamide (70 mg) gave the title compound (53 mg, 64%).

LCMS M/z(−) 490.06 (M−H⁻), M/z(+) 492.12 (M+H⁺).

$^1$H NMR (400.132 MHz, CDCl$_3$) 0.86 (1H, m), 1.05 (3H, m), 2.25 (1H, m), 2.44 (3H, m), 2.84 (1H, m), 2.95 (4H, s), 2.99 (2H, m), 3.59 (6H, m), 3.91 (1H, m), 4.79 (1H, m), 6.42 (1H, m), 7.20 (1H, m), 7.34 (1H, d), 7.58 (1H, s).

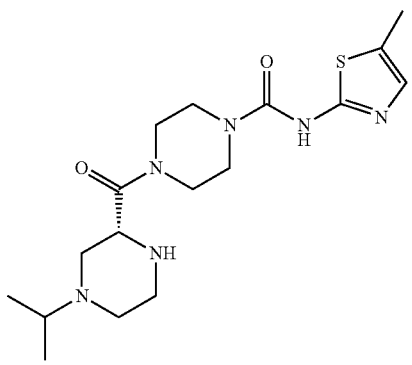 [SMILES: Cc1cnc(NC(=O)N2CCN(C(=O)[C@H]3CN(C(C)C)CCN3)CC2)s1]

N-(5-Chloro-1,3-thiazol-2-yl)-4-{[(2R)-4-isopropylpiperazin-2-yl]carbonyl}piperazine-1-carboxamide LCMS M/z(+) 401 (M+H⁺).

$^1$H NMR (400.132 MHz, DMSO-d$_6$) 0.81 (m, 6H), 2.17 (m, 1H), 2.27 (t, 1H), 2.75-3.06 (m, 4H), 3.12 (d, 1H), 3.40-3.93 (m, 9H), 7.12 (s, 1H).

The starting material, N-(5-chloro-1,3-thiazol-2-yl)piperazine-1-carboxamide used to synthesise N-(5-Chloro-1,3-thiazol-2-yl)-4-{[(2R)-4-isopropylpiperazin-2-yl]carbonyl}piperazine-1-carboxamide was prepared according to the following procedure.

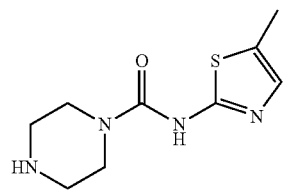

N-(5-Chloro-1,3-thiazol-2-yl)piperazine-1-carboxamide

Phenyl chloroformate (0.305 mL) was added slowly to a stirring solution of 5-chloro-1,3-thiazol-2-amine hydrochloride (400 mg) in THF (5 mL) containing triethylamine (0.98 mL) under an argon atmosphere. After 1 h N-Boc piperazine was added and the reaction was heated to reflux for 1 h. The reaction mixture was taken up in 1M NaOH (10 mL) and DCM (30 mL) and organic layer was separated and washed with 1 MHCl (aq.) (10 mL). The DCM layer was then dried (MgSO$_4$), filtered and evaporated. Purification by column chromatography 1:4 to 1:1 EtOAc:isohexanes afforded the title compound (278 mg) as a white solid which was used without purification $^1$H NMR (400.132 MHz, CDCl$_3$) 1.60 (s, 9H), 3.70 (m, 8H), 7.35 (s, 1H), 9.5 (s, 1H). TFA/DCM (1:1, 10 mL) was added and the reaction stirred under argon for 1 h. The solvent was then removed in vacuo. The residue was then dissolved in MeOH (10 mL) and placed onto SCX-2 column. The column was then washed with 15 mL MeOH before elution of the product with 7M NH3/MeOH (20 mL) and more MeOH (20 mL). The basic fraction was evaporated in vacuo to afford the title compound (220 mg) as an oil which solidified slowly on standing.

LCMS M/z(+) 247 (M+H⁺).

The 5-chloro-1,3-thiazol-2-amine hydrochloride used in Route E1 is commercially available and was purchased from Lancaster Synthesis Ltd., UK. Similarly, the N-[(4-trifluoromethyl)phenylaminocarbonyl]piperazine used in the preparation of examples 337 and 338 was prepared from the N-tert-butoxycarbonyl protected precursor, available commercially from Maybridge, using the sequence described below:—

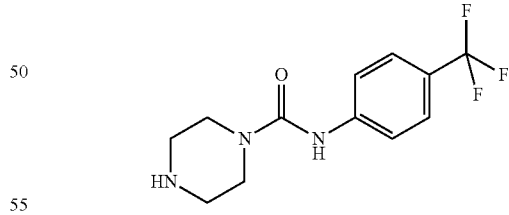

N-[(4-Trifluoromethyl)phenylaminocarbonyl]piperazine 1-tert-Butoxycarbonyl-4-[(4-trifluoromethyl)phenylaminocarbonyl]piperazine (1.516 g, 4.06 mM) was dissolved in CH$_2$Cl$_2$ (20 mL), stirred under argon at RT and TFA (5 ml) added. After 1.5 hours, solvents were removed and the residue dissolved in CH$_2$Cl$_2$ (100 ml) and washed with 0.5 M NaOH (100 ml). The basic aqueous layer was extracted with CH$_2$Cl$_2$ (60 ml) and the combined organic phases washed with 50% brine (1×100 ml), dried (MgSO₄, 12 g) and evaporated to give the product as a white solid (1.118 g, ca. 100%) and the material was used without further purification.

LCMS M/z(+) 274.34 (M+H⁺)

¹H-NMR (CDCl₃) 2.62 (4H, m), 3.30 (4H, m), 7.48 (2H, d), 7.61 (2H, d), 8.72 (1H, s) (piperazine N—H obscured).

As an additional variation of Route E1 the following compounds were prepared as detailed below.

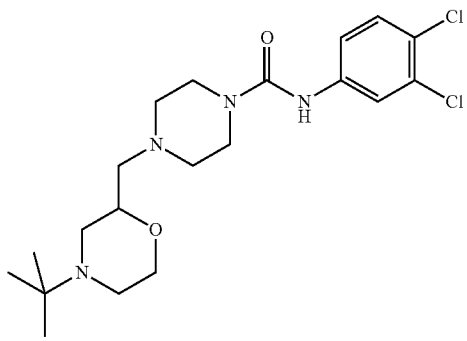 [SMILES: CC(C)(C)N1CCOC(CN2CCN(C(=O)Nc3ccc(Cl)c(Cl)c3)CC2)C1]

4-[(4-tert-Butylmorpholin-2-yl)methyl]-N-(3,4-dichlorophenyl)piperazine-1-carboxamide A solution of 4-tert-butylmorpholine-2-carbaldehyde (154 mg) and N-(3,4-dichlorophenyl)piperazine-1-carboxamide (247 mg) in dichloromethane (20 mL) was stirred at room temperature under argon. Sodium triacetoxyborohydride (381 mg) was added and the mixture was stirred overnight. The reaction was quenched with water and partitioned between water and dichloromethane. The organic layer was washed with saturated aqueous sodium hydrogen carbonate and then brine, dried (Na₂SO₄), filtered and concentrated. The residue was purified on the Isco™ Companion (12 g column: 0-11% MeOH in DCM) to give the title compound as a white solid (75 mg).

LCMS M/z(+) 428.96 (M+H⁺).

¹H NMR (400.132 MHz, CDCl₃) 1.07 (s, 9H), 1.93-2.04 (m, 1H), 2.28-2.35 (m, 2H), 2.48-2.61 (m, 5H), 2.70-2.89 (m, 2H), 3.44-3.57 (m, 4H), 3.57-3.75 (m, 2H), 3.92 (d, 1H), 6.31 (s, 1H), 7.19 (dd, 1H), 7.32 (d, 1H), 7.59 (d, 1H).

The 4-tert-butylmorpholine-2-carbaldehyde used in the above variant of Route E1 was prepared according to the following procedures.

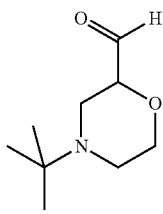

4-tert-Butylmorpholine-2-carbaldehyde

A solution of oxalyl chloride (0.097 mL) in dichloromethane (10 mL) was cooled to −78° C. under argon. A solution of dimethylsulfoxide (0.201 mL) in dichloromethane (5 mL) was added dropwise and the mixture was stirred for 5 minutes. A solution of (4-tert-butylmorpholin-2-yl)methanol (175 mg) in dichloromethane (3 mL) was added and the mixture was stirred for 15 minutes. Triethylamine (0.845 mL) was added and the mixture was warmed to room temperature. The reaction was quenched with water and partitioned between water and dichloromethane. The organic layer was dried (Na₂SO₄), filtered and concentrated to give an orange oil (165 mg). This material was used immediately in the next stage without further purification or analysis.

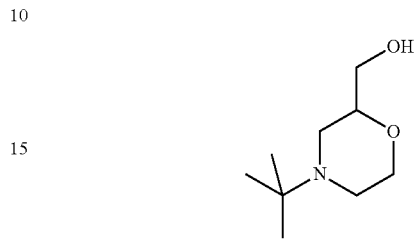

(4-tert-Butylmorpholin-2-yl)methanol

A mixture of 2-[(benzyloxy)methyl]-4-tert-butylmorpholine (268 mg) and 10% palladium on carbon (200 mg) in ethanol (10 mL) was evacuated and purged with hydrogen three times and the left under an atmosphere of hydrogen over the weekend at room temperature. The mixture was filtered through a short pad of celite and the cake was washed with ethanol (10 mL). To the filtrate was added 10% palladium on carbon (200 mg) and the mixture was evacuated and purged with hydrogen three times and the left under an atmosphere of hydrogen for 48 hours. The mixture was filtered through a short pad of celite and the cake was washed with ethanol. The filtrate was concentrated at reduced pressure to give the title compound as a colourless oil (180 mg).

¹H NMR (400.132 MHz, CDCl₃) 1.06 (s, 9H), 2.12-2.20 (m, 1H), 2.33 (td, 1H), 2.65-2.82 (m, 3H), 3.56-3.71 (m, 4H), 3.94 (dt, 1H).

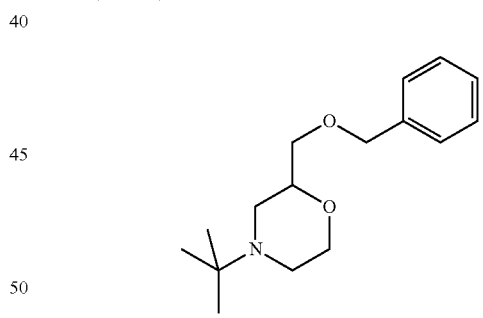

2-[(Benzyloxy)methyl]-4-tert-butylmorpholine

A solution of 1-(benzyloxy)-3-[tert-butyl(2-hydroxyethyl)amino]propan-2-ol (100 mg) in THF (20 mL) was stirred at room temperature under argon. Sodium hydride (60%, 35 mg) was added and the mixture was stirred for 2 hours. The mixture was cooled to ice bath temperature and para-toluenesulfonyl imidazole (79 mg) was added. After 30 minutes the mixture was warmed to room temperature and stirred overnight. The reaction was quenched with saturated aqueous ammonium chloride and then partitioned between 1:1 brine/saturated aqueous sodium hydrogen carbonate and ethyl acetate. The organic layer was washed with 1:1 brine/saturated aqueous sodium hydrogen carbonate, dried (MgSO₄), filtered and concentrated at reduced pressure. The residue was purified on the Isco™ Companion (12 g column: 0-10% MeOH in DCM) to give the title compound as a colourless oil (85 mg).

LCMS M/z(+) 264.12 (M+H$^+$).

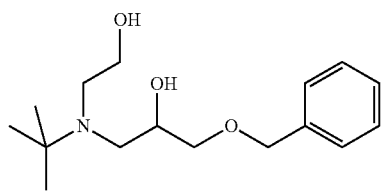 [SMILES: CC(C)(C)N(CCO)CC(O)COCc1ccccc1]

1-(Benzyloxy)-3-[tert-butyl(2-hydroxyethyl)amino]propan-2-ol

A solution of 2-[(benzyloxy)methyl]oxirane (350 mg) and 2-(tert-butylamino)ethanol (500 mg) in ethanol (20 mL) was heated to reflux temperature and left at this temperature overnight. The solution was concentrated at reduced pressure. The residue was purified by filtration through a short pad of silica eluting with 20% methanol in dichloromethane. This gave the title compound as a colourless oil (501 mg)

LCMS M/z(+) 282.00 (M+H$^+$).

2-[(Benzyloxy)methyl]oxirane and 2-(tert-butylamino) are commercially available and were purchased from Aldrich Chemical Company, Inc. and Fluka Chemie AG respectively.

4-[(4-tert-Butylmorpholin-2-yl)methyl]-N-(3,4-dichlorophenyl)piperazine-1-carboxamide was subjected to HPLC purification (Gilson, ChiralPak AS-V, eluent acetonitrile/methanol (90:10), flow 60 mL/min, wavelength 254 nM, 280 nm, resulting in enantiomer separation.

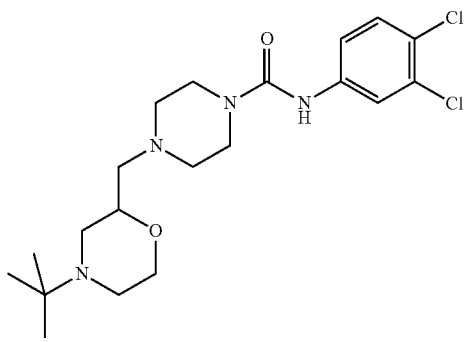 [SMILES: CC(C)(C)N1CCOC(CN2CCN(C(=O)Nc3ccc(Cl)c(Cl)c3)CC2)C1]

4-{[(2S)-4-tert-Butylmorpholin-2-yl]methyl}-N-(3,4-dichlorophenyl)piperazine-1-carboxamide LCMS M/z(+) 428.96 (M+H$^+$).

$^1$H NMR (400.132 MHz, CDCl$_3$) 1.07 (s, 9H), 1.93-2.04 (m, 1H), 2.28-2.35 (m, 2H), 2.48-2.61 (m, 5H), 2.70-2.89 (m, 2H), 3.44-3.57 (m, 4H), 3.57-3.75 (m, 2H), 3.92 (d, 1H), 6.31 (s, 1H), 7.19 (dd, 1H), 7.32 (d, 1H), 7.59 (d, 1H).

4-[(4-tert-Butylpiperazin-2-yl)carbonyl]-N-(3,4-dichlorophenyl)piperazine-1-carboxamide was prepared from 1-(tert-butoxycarbonyl)-4-tert-butylpiperazine-2-carboxylic acid using an identical HATU coupling TFA deprotection sequence as previously described for N-(3,4-dichlorophenyl)-4-{[(2R)-4-isopropylpiperazin-2-yl]carbonyl}piperazine-1-carboxamide (Route E1).

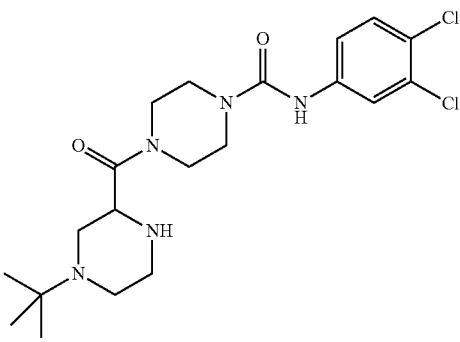 [SMILES: CC(C)(C)N1CCNC(C(=O)N2CCN(C(=O)Nc3ccc(Cl)c(Cl)c3)CC2)C1]

4-[(4-tert-Butylpiperazin-2-yl)carbonyl]-N-(3,4-dichlorophenyl)piperazine-1-carboxamide LCMS M/z(+) 442.10 (M+H$^+$).

$^1$H NMR (400.132 MHz, CDCl$_3$) 1.08 (s, 9H), 2.04-2.18 (m, 2H), 2.84-2.95 (m, 2H), 2.99-3.13 (m, 2H), 3.36-3.91 (m, 10H), 6.49 (s, 1H), 7.21 (dd, 1H), 7.33 (d, 1H), 7.59 (d, 1H).

The 1-(tert-butoxycarbonyl)-4-tert-butylpiperazine-2-carboxylic acid used for the preparation of 4-[(4-tert-Butylpiperazin-2-yl)carbonyl]-N-(3,4-dichlorophenyl)piperazine-1-carboxamide was prepared according to the following procedures.

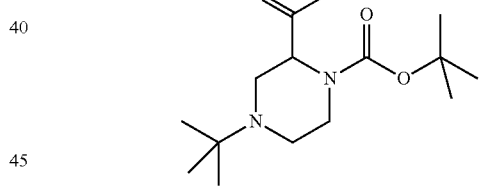

1-(tert-Butoxycarbonyl)-4-tert-butylpiperazine-2-carboxylic acid

A solution of tert-butyl 4-tert-butylpiperazine-1-carboxylate (500 mg) and N,N,N',N'-tetramethylethylenediamine (0.467 mL) in ether (4 mL) was stirred at −78° C. under argon. A 1.4M solution of sec-butyl lithium in cyclohexane (2.2 mL) was added dropwise and the mixture was stirred at −78° C. for 3.5 hours. Carbon dioxide was then bubbled through the reaction mixture via an argon purged syringe for 15 minutes at −78° C. and then whilst warming to 0° C. The reaction was quenched by the addition of water and then diluted with dichloromethane, dried (Na$_2$SO$_4$), filtered and concentrated at reduced pressure. The residue was purified on the Isco™ Companion (40 g column: 0-20% MeOH in DCM) to give the title compound as a white solid (370 mg).

LCMS M/z(+) 286.99 (M+H$^+$).

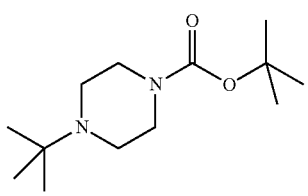 [SMILES: CC(C)(C)OC(=O)N1CCN(C(C)(C)C)CC1]

tert-Butyl 4-tert-butylpiperazine-1-carboxylate

A mixture of 1-benzyl-4-tert-butylpiperazine (740 mg), di-tert-butyl dicarbonate (1.48 g) and 10% palladium on carbon (200 mg) in ethanol (10 mL) was evacuated and purged with hydrogen three times and the left under an atmosphere of hydrogen overnight at room temperature. The mixture was filtered through a short pad of celite and concentrated at reduced pressure. The residue was purified on the Isco™ Companion (40 g column: 0-10% MeOH in DCM) to give the title compound as a white solid (667 mg). LCMS M/z(+) 243.09 (M+H$^+$).

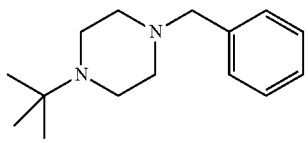 [SMILES: CC(C)(C)N1CCN(Cc2ccccc2)CC1]

1-Benzyl-4-tert-butylpiperazine

A solution of 1-acetyl-4-benzylpiperazine (1.2 g) in tetrahydrofuran was stirred at −10° C. under argon. A 1M solution of titanium (v) chloride (1.2 mL) was then added and the mixture was stirred for 30 minutes. A 3M solution of methylmagnesium bromide in ether (11.3 mL) was then added dropwise and the black reaction mixture was warmed to ambient temperature and stirred overnight. The reaction was quenched with 30% aqueous sodium hydroxide solution and then partitioned between water and dichloromethane. The layers were separated and the organic layer washed with brine, dried (Na$_2$SO$_4$), filtered and concentrated. The residue was purified on the Isco™ Companion (40 g column: 0-10% MeOH in DCM) to give the title compound as a white solid (770 mg). LCMS M/z(+) 233.09 (M+H$^+$).

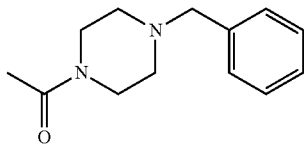 [SMILES: CC(=O)N1CCN(Cc2ccccc2)CC1]

1-Acetyl-4-benzylpiperazine

A solution of 1-benzylpiperazine (1 g) and triethylamine (1.19 mL) in tetrahydrofuran (20 mL) was stirred at room temperature under argon. Acetyl chloride (0.424 mL) was added and the mixture was stirred for 10 minutes. The reaction was filtered and the white solid washed with ether. The filtrate was concentrated at reduced pressure to give the title compound as a colourless oil (1.2 g).

LCMS M/z(+) 219.07 (M+H$^+$).

Pharmaceutical Compositions

This Example illustrates, but is not intended to limit, representative pharmaceutical dosage forms of the invention as defined herein (the active ingredient being termed "Compound X"), for therapeutic or prophylactic use in humans:

EXAMPLE A (a)

| Tablet I | mg/tablet |
|---|---|
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |

(b)

| Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

(c)

| Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

(d)

| Capsule | mg/capsule |
|---|---|
| Compound X | 10 |
| Lactose Ph.Eur | 488.5 |
| Magnesium | 1.5 |

(e)

| Injection I | (50 mg/ml) |
|---|---|
| Compound X | 5.0% w/v |
| 1M Sodium hydroxide solution | 15.0% v/v |
| 0.1M Hydrochloric acid | to adjust pH to 7.6 |
| Polyethylene glycol 400 | 4.5% w/v |
| Water for injection | to 100% |

(f)

| Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection | to 100% |

(g)

| Injection III | (1mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

EXAMPLE A-continued (h)

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

(i)

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j)

| Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

(k)

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l)

| Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note:
Compound X in the above formulations may comprise a compound as illustrated in herein.

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A compound of formula (I)

Q-L-W—C(=X)—Z—P      (I)

wherein
Q is a secondary or tertiary amine of the formula —N($R^1$)($R^2$), wherein $R^1$ and $R^2$ are independently selected from any one of, or combination of, hydrogen, methyl, ethyl, propyl, propenyl, propynyl, isopropyl, cyclopropylmethyl, cyclopropylethyl, butyl, t-butyl, cyclopentylmethyl, cyclopentylethyl, cyclohexyl, cyclohexylmethyl, cyclohexylethyl, benzyl, phenethyl, phenylpropyl, thienylethyl, thienylmethyl, furanylethyl, furanylmethyl, pyrrolidinyl, pyrrolidinylmethyl, pyrrolidinylethyl, pyrrolylethyl, pyrrolylmethyl, pyridylethyl, pyridylmethyl, thiazolylethyl, thiazolylmethyl, benzimidazole, isoxazole, isoxazolylethyl, imidazolylethyl, imidazolylmethyl, pyrazolylethyl, pyrazolylmethyl, indolylmethyl, indolylethyl, indolinylmethyl, piperidinylmethyl, piperazinylmethyl, morpholinyl, morpholinylmethyl, pyridazinyl, pyridazinylmethyl, pyrimidinyl, and pyrimidinylmethyl;

and wherein each chain or ring is independently optionally substituted by one or two of fluorine, hydroxy, hydroxymethyl, methyl, methoxy, ethyl, ethoxy, propenyl, carboxy, methoxycarbonyl, ethoxycarbonyl, cyano, or methylsulfonyl each selected independently;

L taken together with the nitrogen atom of the amine Q and with $R^2$, represents 3-piperazinylcarbonyl; and wherein each ring is independently optionally substituted by hydroxy, halogen and $C_{1-4}$alkyl;

W is piperazine, unsubstituted or monosubstituted by hydroxy, =O or halogen;

X is O;

Z is $NR^3$, wherein $R^3$ is hydrogen or methyl, or when W is attached to C(=X) through a ring N, then Z can also be O;

P is phenyl or naphthyl, or an up to 10 ring membered heteroaryl group comprising 1 or 2 heteroatoms independently selected from N, O or S such as thiophene, isoxazole, benzisoxazole, thiazole, thiadiazole, pyridine, pyrazole, benzthiazole; all of which are optionally substituted by 1, 2 or 3 substituents each independently selected from chlorine, fluorine, bromine, methyl, ethyl, cyano, trifluoromethyl, methoxy, trifluoromethoxy, phenyl, phenoxy, benzoxy, thiomethyl, thioethyl, trifluoromethylthio, methoxycarbonyl, ethoxycarbonyl, and $NO_2$, or a pharmaceutically acceptable salt or solvate thereof.

2. A compound according to claim 1 wherein $R^1$ is t-butyl.

3. A compound according to claim 1 wherein the compound of Formula I has 2R stereochemistry.

4. A pharmaceutical composition comprising a compound, or pharmaceutically acceptable salt thereof, according to claim 1, and a pharmaceutically acceptable diluent or carrier.

5. A compound of formula (IA), or a pharmaceutically acceptable salt thereof

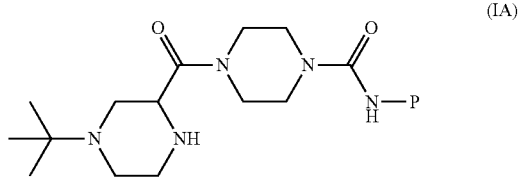

(IA)

wherein P is phenyl or naphthyl, or an up to 10 ring membered heteroaryl group comprising 1 or 2 heteroatoms independently selected from N, O or S such as thiophene, isoxazole, benzisoxazole, thiazole, thiadiazole, pyridine, pyrazole, benzthiazole; all of which are optionally substituted by 1, 2 or 3 substituents each independently selected from chlorine, fluorine, bromine, methyl, ethyl, cyano, trifluoromethyl, methoxy, trifluoromethoxy, phenyl, phenoxy, benzoxy, thiomethyl, thioethyl, trifluoromethylthio, methoxycarbonyl, ethoxycarbonyl, and $NO_2$.

6. A compound according to claim 5 wherein P is phenyl substituted by 1 or 2 substituents independently selected from chlorine, fluorine, bromine, methyl, ethyl, cyano, trifluoromethyl, methoxy, trifluoromethoxy, phenyl, phenoxy, benzoxy, thiomethyl, thioethyl, trifluoromethylthio, methoxycarbonyl, ethoxycarbonyl, and $NO_2$.

7. A compound according to claim 5 wherein P is phenyl substituted by 1 or 2 substituents independently selected from chlorine and fluorine.

8. A pharmaceutical composition comprising a compound, or pharmaceutically acceptable salt thereof, according to claim 5, and a pharmaceutically acceptable diluent or carrier.

* * * * *